United States Patent
Dubost et al.

(10) Patent No.: US 10,039,283 B2
(45) Date of Patent: Aug. 7, 2018

(54) SUBSTITUTED PYRAZOLYL-NICOTIN(THIO)AMIDE DERIVATIVES AND THEIR USE AS FUNGICIDES

(71) Applicant: BAYER CROPSCIENCE AKTIENGESELLSCHAFT, Duesseldorf (DE)

(72) Inventors: Christophe Dubost, La Tour de Salvagny (FR); Cyril Montagne, Monheim am Rhein (DE); Ulrike Wachendorff-Neumann, Neuwied (DE); Phillipp Winter, Deusseldorf (DE); Strphane Brunet, St Andre de Corcy (FR); Jean-Pierre Vors, St Andre de Corcy (FR); Pierre-Yves Coqueron, Lyons (FR); Joerg Greul, Leverkusen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 110 days.

(21) Appl. No.: 15/300,227

(22) PCT Filed: Mar. 31, 2015

(86) PCT No.: PCT/EP2015/056946
§ 371 (c)(1),
(2) Date: Sep. 28, 2016

(87) PCT Pub. No.: WO2015/150352
PCT Pub. Date: Oct. 8, 2015

(65) Prior Publication Data
US 2017/0142969 A1    May 25, 2017

(30) Foreign Application Priority Data

Apr. 2, 2014 (EP) ................................. 14163193

(51) Int. Cl.
*C07D 401/12* (2006.01)
*A01N 43/56* (2006.01)

(52) U.S. Cl.
CPC ........... *A01N 43/56* (2013.01); *C07D 401/12* (2013.01)

(58) Field of Classification Search
None
See application file for complete search history.

(56) References Cited

U.S. PATENT DOCUMENTS 7,176,311 B2 *  2/2007  Bunnage ............ A61K 31/519
                                                  544/118

FOREIGN PATENT DOCUMENTS

| DE | 19854081 A1 | 5/2000 |
|----|-------------|--------|
| EP | 1 329 160 A2 | 7/2003 |
| EP | 2 674 423 A1 | 12/2013 |
| JP | 2010202649 | 9/2010 |
| JP | 2012056944 A | 3/2012 |

OTHER PUBLICATIONS

Cecchi L. et al. "Synthesis of 1,5-Diaryl-3-Methyl-1 H-Pyrazolo not 4,5-3/4 Isoquinolines and Studies of Binding to Specific Peripheral Benzodiazepine Binding Sites", J. Pharm. Sciences, 1989, 78, 6, p. 437-442.

* cited by examiner

*Primary Examiner* — Kamal Saeed
(74) *Attorney, Agent, or Firm* — McBee Moore Woodward & Vanik IP, LLC

(57) ABSTRACT

The present invention relates to novel substituted pyrazolyl-nicotin(thio)amide derivatives, to processes for preparing these compounds, to compositions comprising these compounds, and to the use thereof as biologically active compounds, especially for control of harmful microorganisms, in crop protection and in the protection of materials.

10 Claims, No Drawings

SUBSTITUTED PYRAZOLYL-NICOTIN(THIO)AMIDE DERIVATIVES AND THEIR USE AS FUNGICIDES

CROSS REFERENCE TO RELATED APPLICATIONS

This application is a § 371 National State Application of PCT/EP2015/056946, filed Mar. 31, 2015, which claims priority to European Application No. 14163193.7 filed Apr. 2, 2014.

BACKGROUND OF THE INVENTION

Field of the Invention

The present invention relates to novel substituted pyrazolyl-nicotin(thio)amide derivatives, to processes for preparing these compounds, to compositions comprising these compounds, and to the use thereof as biologically active compounds, especially for control of harmful microorganisms in crop protection and in the protection of materials.

Description of Related Art

Since the ecological and economical demands made on modern crop protection agents are increasing constantly, for example with respect to activity spectrum, toxicity, selectivity, application rate, formation of residues and favourable manufacture, and there can furthermore be problems, for example, with resistances, there is a constant need to develop novel crop protection compositions, in particular fungicides, which, at least in some areas, have advantages over the known ones.

JP2012056944, JP2010202649 JP201205694 and EP1329160 disclose pyrazolyl-carboxamides with fungicidal properties.

*Journal of Pharmaceutical Sciences* Vol. 78, No. 6, 1989, p. 437 discloses pyrazolyl-nicotinamide derivatives binding to specific peripheral benzodiazepine binding sites.

SUMMARY

It has now been found that, surprisingly, the present substituted pyrazolyl-nicotin(thio)amide derivatives achieve at least some aspects of the objects mentioned and are suitable for use as crop protection compositions, especially as fungicides.

The present invention relates to compounds of the general formula (I)

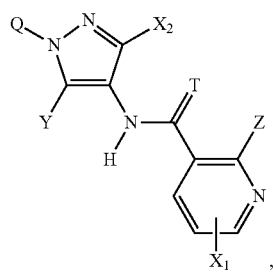

(I)

wherein
Z is selected from halogen, CN, $NH_2$, $NO_2$, $C_1$-$C_6$-alkyl, $C_1$-$C_6$-haloalkyl, $C_3$-$C_8$-cycloalkyl, $C_3$-$C_7$-halocycloalkyl, $C_1$-$C_6$-alkyloxy, $C_1$-$C_6$-haloalkyloxy, $C_1$-$C_6$-alkylsulfanyl, $C_1$-$C_6$-haloalkylsulfanyl, $C_1$-$C_6$-alkylsulfonyl, $C_1$-$C_6$-haloalkylsulfonyl, $C_1$-$C_8$-alkylamino, di-$C_1$-$C_8$-alkylamino, $C_2$-$C_6$-alkenyl, $C_2$-$C_6$-haloalkenyl, $C_2$-$C_6$-alkynyl;

$X_1$ is selected from H, halogen, CN, $NH_2$, $NO_2$, $C_1$-$C_6$-alkyl, $C_1$-$C_6$-haloalkyl, $C_3$-$C_8$-cycloalkyl, $C_3$-$C_7$-halocycloalkyl, $C_1$-$C_6$-alkyloxy, $C_1$-$C_6$-haloalkyloxy, tri($C_1$-$C_8$)alkylsilyl, $C_1$-$C_6$-alkylsulfanyl, $C_1$-$C_6$-haloalkylsulfanyl, $C_1$-$C_6$-alkylsulfonyl, $C_1$-$C_6$-haloalkylsulfonyl, $C_1$-$C_8$-alkylamino, di-$C_1$-$C_8$-alkylamino, $C_2$-$C_6$-alkenyl, $C_2$-$C_6$-haloalkenyl, $C_2$-$C_6$-alkynyl;

$X_2$ is selected from H, halogen, CN, $NH_2$, $NO_2$, $C_1$-$C_6$-alkyl, $C_1$-$C_6$-haloalkyl, $C_3$-$C_8$-cycloalkyl, $C_3$-$C_7$-halocycloalkyl, $C_1$-$C_6$-alkyloxy, $C_1$-$C_6$-haloalkyloxy, $C_1$-$C_6$-alkylsulfanyl, $C_1$-$C_6$-haloalkylsulfanyl, $C_1$-$C_6$-alkylsulfonyl, $C_1$-$C_6$-haloalkylsulfonyl, $C_2$-$C_6$-alkenyl, $C_2$-$C_6$-haloalkenyl, $C_2$-$C_6$-alkynyl;

Y is selected from halogen, CN, $NH_2$, $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkylsulfanyl, $C_1$-$C_6$-haloalkylsulfanyl, $C_1$-$C_6$-alkylsulfonyl, $C_1$-$C_6$-haloalkylsulfonyl, $C_1$-$C_8$-alkylamino, di-$C_1$-$C_8$-alkylamino, $C_2$-$C_6$-alkenyl, $C_2$-$C_6$-haloalkenyl, $C_2$-$C_6$-alkynyl, phenyl or thiophene which may be substituted by one or more $R^a$ group;

Q is a phenyl or a thiophene which may be substituted by one or more $R^a$ groups, a linear or branched carbon chain having 1 to 9 carbon atoms, wherein 1 to 3 non adjacent —$CH_2$— groups may be independently from each other replaced by a group selected from O, $NR^5$, S, SO, $SO_2$, CO, and wherein 1 to 5 hydrogen atoms may be independently from each other replaced by $C_3$-$C_7$-cycloalkyl, halogen or wherein 1 to 5 hydrogen atoms may be independently from each other replaced phenyl or thiophene which may be substituted by one or more $R^a$ groups;

$R^a$ represents hydrogen, halogen, nitro, $NH_2$, cyano, $C_1$-$C_6$-alkyl, $C_1$-$C_6$-haloalkyl, $C_3$-$C_7$-cycloalkyl; $C_1$-$C_6$-alkoxy, $C_1$-$C_6$-haloalkoxy, $C_3$-$C_7$-cycloalkyloxy, $C_1$-$C_6$-alkylsulfanyl, $C_1$-$C_6$-haloalkylsulfanyl, $C_3$-$C_7$-cycloalkylsulfanyl, $C_1$-$C_6$-alkylsulfonyl, $C_1$-$C_6$-haloalkylsulfonyl, $C_3$-$C_7$-cycloalkylsulfonyl, $C_2$-$C_6$-alkenyl, $C_2$-$C_6$-haloalkenyl, $C_2$-$C_6$-alkynyl, tri($C_1$-$C_8$)alkylsilyl, $C_2$-$C_8$-alkynyloxy, aryloxy, $C_1$-$C_6$-alkylamino, di-$C_1$-$C_6$-alkylamino or
two vicinal substituents $R^a$ together with the consecutive carbon atoms to which they are linked form a 5- or 6-membered, saturated or unsaturated, carbo- or heterocycle comprising up to 3 heteroatoms;

T is O or S;

$R^5$ represents hydrogen, $C_1$-$C_6$-alkyl, $C_1$-$C_6$-haloalkyl and $C_3$-$C_7$-cycloalkyl;

provided that

Q does not represent methyl and

Y and $X_2$ represent methyl simultaneously only when Z represents a $C_1$-$C_6$-haloalkyl and provided that formula (I) does not represent 2-chloro-N-[1-(3-chlorophenyl)-3-methyl-5-phenyl-1H-pyrazol-4-yl]-3-pyridine carboxamide or 2-chloro-N-[3-methyl-1-(3-methylphenyl)-5-phenyl-1H-pyrazol-4-yl]-3-pyridine carboxamide and salts, solvates, N-oxides, solvates of the salts and N-oxides thereof.

DETAILED DESCRIPTION OF A PREFERRED EMBODIMENT

Salts for the purposes of the present invention are preferably agrochemically active salts of the compounds according to the invention.

Agrochemically active salts include acid addition salts of inorganic and organic acids well as salts of customary bases. Examples of inorganic acids are hydrohalic acids, such as hydrogen fluoride, hydrogen chloride, hydrogen bromide and hydrogen iodide, sulfuric acid, phosphoric acid and nitric acid, and acidic salts, such as sodium bisulfate and potassium bisulfate. Useful organic acids include, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated fatty acids having 6 to 20 carbon atoms, alkylsulphuric monoesters, alkylsulphonic acids (sulphonic acids having straight-chain or branched alkyl radicals having 1 to 20 carbon atoms), arylsulphonic acids or aryldisulphonic acids (aromatic radicals, such as phenyl and naphthyl, which bear one or two sulphonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulphonic acid, salicylic acid, p-aminosalicylic acid, 2-phenoxybenzoic acid, 2-acetoxybenzoic acid, etc.

Solvates of the compounds of the invention or their salts are stoichiometric compositions of the compounds with solvents.

The definitions of residues indicated specifically in the respective combinations or preferred combinations of residues are also replaced as desired by definitions of residues of other combinations, irrespective of the particular combinations indicated for the residues. Combinations of two or more of the abovementioned preferred ranges are particularly preferred.

Optionally substituted groups may be mono- or polysubstituted, where the substituents in the case of poly substitutions may be identical or different.

Not included are combinations which are against natural laws and which the person skilled in the art would therefore exclude based on his/her expert knowledge. Ring structures having three or more adjacent oxygen atoms, for example, are excluded.

Useful metal ions are especially the ions of the elements of the second main group, especially calcium and magnesium, of the third and fourth main group, especially aluminium, tin and lead, and also of the first to eighth transition groups, especially chromium, manganese, iron, cobalt, nickel, copper, zinc and others. Particular preference is given to the metal ions of the elements of the fourth period. Here, the metals can be present in the various valencies that they can assume.

The compounds of this invention may, either by nature of asymmetric centers or by restricted rotation, be present in the form of isomers (enantiomers, diastereomers). Any isomer may be present in which the asymmetric center is in the (R)-, (S)-, or (R,S) configuration.

It will also be appreciated that when two or more asymmetric centers are present in the compounds of the invention, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the invention.

Any of the compounds of the present invention can also exist in one or more geometric isomer forms depending on the number of double bonds in the compound. Geometric isomers by nature of substituents about a double bond or a ring may be present in cis (=Z-) or trans (=E-) form. The invention thus relates equally to all geometric isomers and to all possible mixtures, in all proportions. The geometric isomers can be separated according to general methods, which are known per se by the man ordinary skilled in the art.

Unless otherwise stated, the following definitions apply for the substituents and residues used throughout this specification and claims:

Halogen represents radicals of fluorine, chlorine, bromine and iodine. Preference is given to the radicals of fluorine and chlorine.

Alkyl represents a straight-chain or branched saturated hydrocarbon radical having 1 to 8 carbon atoms. Non-limiting examples include methyl, ethyl, propyl, 1-methylethyl (iso-propyl), n-butyl, 1-methylpropyl (iso-butyl), 2-methylpropyl (sec-butyl), 1,1-dimethylethyl (tert.-butyl), n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, n-heptyl, 1-methylhexyl, 1-ethylpentyl, 2-ethylpentyl, 1-propylbutyl, octyl, 1-methylheptyl, 2-methylheptyl, 1-ethylhexyl, 2-ethylhexyl, 1-propylpentyl and 2-propylpentyl, in particular propyl, 1-methylethyl, butyl, 1-methylbutyl, 2-methylbutyl, 3-methylbutyl, 1,1-dimethylethyl, 1,2-dimethylbutyl, 1,3-dimethylbutyl, pentyl, 1-methylbutyl, 1-ethylpropyl, hexyl, 3-methylpentyl, heptyl, 1-methylhexyl, 1-ethyl-3-methylbutyl, 1-methylheptyl, 1,2-dimethylhexyl, 1,3-dimethyloctyl, 4-methyloctyl, 1,2,2,3-tetramethylbutyl, 1,3,3-trimethylbutyl, 1,2,3-trimethylbutyl, 1,3-dimethylpentyl, 1,3-dimethylhexyl, 5-methyl-3-hexyl, 2-methyl-4-heptyl and 1-methyl-2-cyclopropylethyl. Preference is given to $(C_1-C_4)$-alkyl representing a straight-chain or branched saturated hydrocarbon radical having 1 to 4 carbon atoms, such as methyl, ethyl, n-propyl, isopropyl, n-butyl, iso-butyl, sec-butyl, tert.-butyl.

Haloalkyl represents in general an alkyl-radical having 1 to 4 carbon atoms, in which 1 up to all hydrogen atoms are replaced by halogen atoms. Non-limiting examples include chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoromethylbutyl.

Cycloalkyl represents a monocyclic saturated hydrocarbon radical having 3 to 8, preferably 3 to 6 carbon atoms. Non-limiting examples include cyclopropyl, cyclobutyl, cyclopentyl, cyclohexyl, cycloheptyl and cyclooctyl.

Carbocyclic ring represent a monocyclic saturated or partially unsaturated hydrocarbon radical having 3 to 8, preferably 3 to 6 carbon atoms. Non-limiting examples include cyclopropyl, cyclobutyl, cyclopentyl, cyclohexyl, cycloheptyl, cyclooctyl, cyclopentenyl, cyclohexenyl, and cyclohexadienyl.

Halocycloalkyl and halocarbocyclic ring represent in general a monocyclic saturated hydrocarbon radical having 3 to 8, preferably 3 to 6 carbon atoms, in which 1 up to 7 hydrogen atoms are replaced by halogen atoms. Non-limiting examples include chlorocyclopropyl, dichlorocyclopropyl, dibromocyclopropyl, fluorocyclopropyl, chlorocyclopentyl and chlorocyclohexyl.

Alkenyl represents an unsaturated, straight-chain or branched hydrocarbon radical having 2 to 8, preferably 2 to 6, carbon atoms and one or two double bonds in any position. Non-limiting examples include ethenyl, prop-1-enyl, prop-2-enyl, 1-methylethenyl, but-1-enyl, but-2-enyl, but-3-enyl, 1-methylprop-1-enyl, 2-methylprop-1-enyl, 1-methylprop-2-enyl, 2-methylprop-2-enyl, pent-1-enyl, pent-2-enyl, pent-3-enyl, pent-4-enyl, 1-methylbut-1-enyl, 2-methylbut-1-enyl, 3-methylbut-1-enyl, 1-methylbut-2-enyl, 2-methylbut-2-enyl, 3-methylbut-2-enyl, 1-methylbut-3-enyl, 2-methylbut-3-enyl, 3-methylbut-3-enyl, 1,1-dimethylprop-2-enyl, 1,2-dimethylprop-1-enyl, 1,2-dimethylprop-2-enyl, 1-ethylprop-1-enyl, 1-ethylprop-2-enyl, hex-1-enyl, hex-2-enyl, hex-3-enyl, hex-4-enyl, hex-5-enyl, 1-methylpent-1-enyl, 2-methylpent-1-enyl, 3-methylpent-1-enyl, 4-methylpent-1-enyl, 1-methylpent-2-enyl, 2-methylpent-2-enyl, 3-methylpent-2-enyl, 4-methylpent-2-enyl, 1-methylpent-3-enyl, 2-methylpent-3-enyl, 3-methylpent-3-enyl, 4-methylpent-3-enyl, 1-methylpent-4-enyl, 2-methylent-4-enyl, 3-methylpent-4-enyl, 4-methylpent-4-enyl, 1,1-dimethylbut-2-enyl, 1,1,-dimethylbut-3-enyl, 1,2-dimethylbut-1-enyl, 1,2-dimethylbut-2-enyl, 1,2-dimethylbut-3-enyl, 1,3-dimethylbut-1-enyl, 1,3-dimethylbut-2-enyl, 1,3-dimethylbut-3-enyl, 2,2-dimethylbut-3-enyl, 2,3-dimethylbut-1-enyl, 2,3-dimethylbut-2-enyl, 2,3-dimethylbut-3-enyl, 3,3-dimethylbut-1-enyl, 3,3-dimethylbut-2-enyl, 1-ethylbut-1-enyl, 1-ethylbut-2-enyl, 1-ethylbut-3-enyl, 2-ethylbut-1-enyl, 2-ethylbut-2-enyl, 2-ethylbut-3-enyl, 1,1,2-trimethylprop-2-enyl, 1-ethyl-1-methylprop-2-enyl, 1-ethyl-2-methylprop-1-enyl and 1-ethyl-2-methylprop-2-enyl.

Cycloalkenyl represents a monocyclic or bicyclic partially unsaturated hydrocarbon radical having 5 to 10 carbon atoms and one to three double bonds. Non-limiting examples include cycloopentenyl, cyclohexenyl, cyclohexadienyl, cycloheptenyl, cyclooctenyl, cyclooctadienyl, indanyl and tetrahydronaphthalenyl.

Alkynyl represents a straight-chain or branched hydrocarbyl groups having 2 to 8, preferably 2 to 6, carbon atoms and one triple bond in any position. Non-limiting examples include ethynyl, prop-1-ynyl, prop-2-ynyl, but-1-ynyl, but-2-ynyl, but-3-ynyl, 1-methylprop-2-ynyl, pent-1-ynyl, pent-2-ynyl, pent-3-ynyl, pent-4-ynyl, 1-methylbut-2-ynyl, 1-methylbut-3-ynyl, 2-methylbut-3-ynyl, 3-methylbut-1-ynyl, 1,1-dimethylprop-2-ynyl, 1-ethylprop-2-ynyl, hex-1-ynyl, hex-2-ynyl, hex-3-ynyl, hex-4-ynyl, hex-5-ynyl, 1-methylpent-2-ynyl, 1-methylpent-3-ynyl, 1-methylpent-4-ynyl, 2-methylpent-3-ynyl, 2-methylpent-4-ynyl, 3-methylpent-1-ynyl, 3-methylpent-4-ynyl, 4-methylpent-1-ynyl, 4-methylpent-2-ynyl, 1,1-dimethylbut-2-ynyl, 1,1-dimethylbut-3-ynyl, 1,2-dimethylbut-3-ynyl, 2,2-dimethylbut-3-ynyl, 3,3-dimethylbut-1-ynyl, 1-ethylbut-2-ynyl, 1-ethylbut-3-ynyl, 2-ethylbut-3-ynyl and 1-ethyl-1-methylprop-2-ynyl.

Haloalkenyl represents in general an alkenyl-radical having 2 to 8 carbon atoms, in which 1 up to all hydrogen atoms are replaced by halogen atoms. Non-limiting examples include 3-bromo-2-propenyl, 2-bromo-2-propenyl, 3-chloro-2-propenyl and 2-chloro-2-propenyl.

Haloalkynyl represents in general an alkynyl-radical having 2 to 8 carbon atoms, in which 1 up to all hydrogen atoms are replaced by halogen atoms. Non-limiting examples include 2-iodopropynyl and 2-bromopropynyl.

Alkoxy represents a saturated, straight-chain or branched alkoxy radical having 1 to 4 atoms. Non-limiting examples include methoxy, ethoxy, propoxy, 1-methylethoxy, butoxy, 1-methylpropoxy, 2-methylpropoxy, 1,1-dimethylethoxy.

Haloalkoxy represents a saturated, straight-chain or branched alkoxy radical having 1 to 4 atoms, in which one up to all hydrogen atoms are replaced by halogen atoms. Non-limiting examples include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy.

Monoalkylamino represents an amino radical having one alkyl residue with 1 to 4 carbon atoms attached to the nitrogen atom. Non-limiting examples include methylamino, ethylamino, n-propylamino, isopropylamino, n-butylamino, tert.-butylamino Dialkylamino represents an amino radical having two independently selected alkyl residues with 1 to 4 carbon atoms each attached to the nitrogen atom. Non-limiting examples include N,N-dimethylamino, N,N-diethylamino, N,N-diisopropylamino, N-ethyl-N-methylamino, N-methyl-N-n-propylamino, N-isopropyl-N-n-propylamino, N-tert.-butyl-N-methylamino Alkylthio represents a thiol radical with an saturated, straight-chain or branched alkyl residue having 1 to 4 carbon atoms. Non-limiting examples include methylthio, ethylthio, n-propylthio, iso-propylthio, 1-methylethylthio, n-butylthio and tert.-butylthio.

Alkylsulphonyl represents a sulphone radical with an saturated, straight-chain or branched alkyl residue having 1 to 8 carbon atoms. Non-limiting examples include methylsulphonyl, ethylsulphonyl, propylsulphonyl, 1-methylethylsulphonyl, butylsulphonyl, 1-methylpropylsulphonyl, 2-methylpropylsulphonyl, 1,1-dimethylethylsulphonyl, pentylsulphonyl, 1-methylbutylsulphonyl, 2-methylbutylsulphonyl, 3-methylbutylsulphonyl, 2,2-dimethylpropylsulphonyl, 1-ethylpropylsulphonyl, hexylsulphonyl, 1,1-dimethylpropylsulphonyl, 1,2-dimethylpropylsulphonyl, 1-methylpentylsulphonyl, 2-methylpentylsulphonyl, 3-methylpentylsulphonyl, 4-methylpentylsulphonyl, 1,1-dimethylbutylsulphonyl, 1,2-dimethylbutylsulphonyl, 1,3-dimethylbutylsulphonyl, 2,2-dimethyl-butylsulphonyl, 2,3-dimethylbutylsulphonyl, 3,3-dimethylbutylsulphonyl, 1-ethylbutylsulphonyl, 2-ethylbutylsulphonyl, 1,1,2-trimethylpropylsulphonyl, 1,2,2-trimethylpropylsulphonyl, 1-ethyl-1-methylpropylsulphonyl and 1-ethyl-2-methylpropylsulphonyl.

Heterocycle and heterocyclic ring represent a monocyclic, saturated or partially unsaturated heterocyclic radical having a total number of 3 to 7, including 2 to 6 carbon atoms and 1 up to 3 heteroatoms and/or hetero-groups independently selected from the group consisting of N, O, S, SO, $SO_2$ and Di-($C_1$-$C_4$)-alkylsilyl, which ring system can be bonded via a ring carbon atom or, if possible, via a ring nitrogen atom. Non-limiting examples include oxiranyl, aziridinyl, oxetan-2-yl, oxetan-3-yl, azetidin-2-yl, azetidin-3-yl, tetrahydrofuran-2-yl, tetrahydrofuran-3-yl, tetrahydrothien-2-yl, tetrahydrothien-3-yl, pyrrolidin-2-yl, pyrrolidin-3-yl, thiolan-2-yl, thiolan-3-yl, sulfolan-2yl, sulfolan-3-yl, isoxazolidin-3-yl, isoxazolidin-4-yl, isoxazolidin-5-yl, isothiazolidin-3-yl, isothiazolidin-4-yl, isothiazolidin-5-yl, pyrazolidin-3-yl, pyrazolidin-4-yl, pyrazolidin-5-yl, oxazolidin-2-yl, oxazolidin-4-yl, oxazolidin-5-yl, thiazolidin-2-yl, thiazolidin-4-yl, thiazolidin-5-yl, imidazolidin-2-yl, imidazolidin-4-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, piperidin-2-yl, piperidin-3-yl, piperidin-4-yl, 1,3-dioxan-5-yl, tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, hexahydropyridazin-3-yl, hexahydropyridazin-4-yl, hexahydropyrimidin-2-yl, hexahydropyrimidin-4-yl, hexahydropyrimidin-5-yl, piperazin-2-yl, morpholin-2-yl, morpholin-3-yl, thiomorpholin-2-yl, thiomorpholin-3-yl, 1,1-dioxidothiomorpholin-2-yl, 1,1-dioxidothiomorpholin-3-yl, 1,3,5-hexahydrotriazin-2-yl and 1,2,4-hexahydrotriazin-3-yl.

Heteroaryl and heteroaryl ring in general represents a mono-cyclic, aromatic heterocyclic radical having a total number of 5 or 6 ring atoms, including 1 to 5 carbon atoms and up to 4 heteroatoms independently selected from the group consisting of N, O and S, which ring system can be bonded via a ring carbon atom or, if possible, via a ring nitrogen atom. Non-limiting examples include furyl, pyrrolyl, thienyl, pyrazolyl, imidazolyl, thiazolyl, oxazolyl, isoxazolyl, isothiazolyl, triazolyl, oxadiazolyl, thiadiazolyl, tetrazolyl, pyridyl, pyrimidinyl, pyridazinyl, pyrazinyl, triazinyl. Preferred are furyl, thienyl, pyrazolyl, imidazolyl, thiazolyl, oxazolyl, isoxazolyl, triazolyl, oxadiazolyl, thiadiazolyl, pyridyl and pyrimidinyl.

Oxo represents a doubly bonded oxygen atom.

Thiooxo represents a doubly bonded sulfur atom.

Preferred are compounds of the general formula (I), wherein

Z is selected from bromine, iodine, fluorine, chlorine, cyclopropyl, cyclobutyl, cyclopentyl, cyclohexyl, cycloheptyl, cyclooctyl, methyl, ethyl, propyl, 1-methylethyl (iso-propyl), n-butyl, 1-methylpropyl (iso-butyl), 2-methylpropyl (sec-butyl), 1,1-dimethylethyl (tert.-butyl), n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoromethylbutyl;

$X_1$ is selected from H, bromine, iodine, fluorine, chlorine, cyclopropyl, cyclobutyl, cyclopentyl, cyclohexyl, cycloheptyl, cyclooctyl, methyl, ethyl, propyl, 1-methylethyl (iso-propyl), n-butyl, 1-methylpropyl (iso-butyl), 2-methylpropyl (sec-butyl), 1,1-dimethylethyl (tert.-butyl), n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoromethylbutyl, CN, $NO_2$, methyloxy, Ethyloxy, methylsulfanyl, ethylsulfanyl, trifluoromethoxy, difluoromethoxy;

$X_2$ is selected from H, bromine, iodine, fluorine, chlorine, cyclopropyl, cyclobutyl, cyclopentyl, cyclohexyl, cycloheptyl, cyclooctyl, methyl, ethyl, propyl, 1-methylethyl (iso-propyl), n-butyl, 1-methylpropyl (iso-butyl), 2-methylpropyl (sec-butyl), 1,1-dimethylethyl (tert.-butyl), n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoromethylbutyl, CN, $NO_2$;

Y is selected from halogen, $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, phenyl which may be substituted by one or more Ra group;

Q is selected from phenyl or thiophene which may be substituted by one or more $R^a$ groups; $C_2$-$C_9$-alkyl, $C_1$-$C_9$-haloalkyl, $C_3$-$C_9$-cycloalkyl, ($C_3$-$C_8$-cycloalkyl)-$C_1$-$C_9$-alkyl, ($C_3$-$C_8$-cycloalkyl)-$C_1$-$C_9$-alkyloxy, ($C_1$-$C_8$-alkyl)-$C_1$-$C_9$-alkyloxy, $C_1$-$C_6$-alkylphenyl which may be substituted by one or more $R^a$ groups.

$R^a$ represents hydrogen, halogen, cyano, $C_1$-$C_6$-alkyl; $C_1$-$C_6$-haloalkyl; $C_3$-$C_7$-cycloalkyl; $C_1$-$C_6$-alkoxy; $C_1$-$C_6$-haloalkoxy; $C_3$-$C_7$-cycloalkyloxy; $C_1$-$C_6$-alkylsulfanyl; $C_1$-$C_6$-haloalkylsulfanyl; $C_3$-$C_7$-cycloalkylsulfanyl; $C_1$-$C_6$-alkylsulfonyl; $C_1$-$C_6$-haloalkylsulfonyl; $C_3$-$C_7$-cycloalkylsulfonyl; $C_2$-$C_8$-alkynyloxy;

T is O or S;

provided that

Y and $X_2$ represent methyl simultaneously only when Z represents a $C_1$-$C_6$-haloalkyl and provided that formula (I) does not represent 2-chloro-N-[1-(3-chlorophenyl)-3-methyl-5-phenyl-1H-pyrazol-4-yl]-3-pyridine carboxamide or 2-chloro-N-[3-methyl-1-(3-methylphenyl)-5-phenyl-1H-pyrazol-4-yl]-3-pyridine carboxamide and salts, solvates, N-oxides, solvates of the salts and N-oxides thereof.

More preferred are compounds of the general formula (I), wherein

Z is selected from fluorine, chlorine, cyclopropyl, cyclobutyl, cyclopentyl, cyclohexyl, methyl, ethyl, propyl, 1-methylethyl (iso-propyl), n-butyl, 1-methylpropyl (iso-butyl), 2-methylpropyl (sec-butyl), 1,1-dimethylethyl (tert.-butyl), n-pentyl, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl;

$X_1$ is selected from H, bromine, iodine, fluorine, chlorine, cyclopropyl, methyl, ethyl, propyl, 1-methylethyl (iso-propyl), n-butyl, 1-methylpropyl (iso-butyl), 2-methylpropyl (sec-butyl), 1,1-dimethylethyl (tert.-butyl), n-pentyl, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, CN, $NO_2$, methyloxy, ethyloxy;

$X_2$ is selected from H, bromine, iodine, fluorine, chlorine, cyclopropyl, methyl, ethyl, propyl, 1-methylethyl (iso-propyl), n-butyl, 1-methylpropyl (iso-butyl), 2-methylpropyl (sec-butyl), 1,1-dimethylethyl (tert.-butyl), n-pentyl, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, CN;

Y is selected from halogen, $C_1$-$C_6$-alkyl, $C_1$-$C_6$-haloalkyl, $C_3$-$C_8$-cycloalkyl, $C_3$-$C_8$-halocycloalkyl, phenyl which may be substituted by one or more $R^a$ group;

Q is selected from phenyl which may be substituted by one or more $R^a$ groups $R^a$ is selected from hydrogen, halogen, nitro, cyano, $C_1$-$C_6$-alkyl; $C_1$-$C_6$-haloalkyl; $C_1$-$C_6$-alkoxy; $C_1$-$C_6$-haloalkoxy;

T is O;

provided that

Y and $X_2$ represent methyl simultaneously only when Z represents a $C_1$-$C_6$-haloalkyl and provided that formula (I) does not represent 2-chloro-N-[1-(3-chlorophenyl)-3-methyl-5-phenyl-1H-pyrazol-4-yl]-3-pyridine carboxamides or 2-chloro-N-[3-methyl-1-(3-methylphenyl)-5-phenyl-1H-pyrazol-4-yl]-3-pyridine carboxamide and salts, solvates, N-oxides, solvates of the salts and N-oxides thereof.

Moreover more preferred are compounds of the general formula (I), wherein

Z is selected from fluorine, chlorine, cyclopropyl, cyclobutyl, cyclopentyl, cyclohexyl, methyl, ethyl, propyl, 1-methylethyl (iso-propyl), n-butyl, 1-methylpropyl (iso-butyl), 2-methylpropyl (sec-butyl), 1,1-dimethylethyl (tert.-butyl), n-pentyl, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl;

$X_1$ is selected from H, bromine, iodine, fluorine, chlorine, cyclopropyl, methyl, ethyl, propyl, 1-methylethyl (iso-propyl), n-butyl, 1-methylpropyl (iso-butyl), 2-methylpropyl (sec-butyl), 1,1-dimethylethyl (tert.-butyl), n-pentyl, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, CN, $NO_2$, methyloxy, ethyloxy;

$X_2$ is selected from H, bromine, iodine, fluorine, chlorine, cyclopropyl, methyl, ethyl, propyl, 1-methylethyl (iso-propyl), n-butyl, 1-methylpropyl (iso-butyl), 2-methylpropyl (sec-butyl), 1,1-dimethylethyl (tert.-butyl), n-pentyl, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, CN;

Y is selected from halogen, $C_1$-$C_6$-alkyl, $C_1$-$C_6$-haloalkyl, $C_3$-$C_8$-cycloalkyl, $C_3$-$C_8$-halocycloalkyl, phenyl which may be substituted by one or more Ra group;

Q is selected from ethyl, propyl, 1-methylethyl (iso-propyl), n-butyl, 1-methylpropyl (iso-butyl), 2-methylpropyl (sec-butyl), 1,1-dimethylethyl (tert.-butyl), n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, n-heptyl, 1-methylhexyl, 1-ethylpentyl, 2-ethylpentyl, 1-propylbutyl, octyl, 1-methylheptyl, 2-methylheptyl, 1-ethylhexyl, 2-ethylhexyl, 1-propylpentyl and 2-propylpentyl, in particular propyl, 1-methylethyl, butyl, 1-methylbutyl, 2-methylbutyl, 3-methylbutyl, 1,1-dimethylethyl, 1,2-dimethylbutyl, 1,3-dimethylbutyl, pentyl, 1-methylbutyl, 1-ethylpropyl, hexyl, 3-methylpentyl, heptyl, 1-methylhexyl, 1-ethyl-3-methylbutyl, 1-methylheptyl, 1,2-dimethylhexyl, 1,3-dimethyloctyl, 4-methyloctyl, 1,2,2,3-tetramethylbutyl, 1,3,3-trimethylbutyl, 1,2,3-trimethylbutyl, 1,3-dimethylpentyl, 1,3-dimethylhexyl, 5-methyl-3-hexyl, 2-methyl-4-heptyl or Q is selected from cyclopropyl, cyclobutyl, cyclopentyl, cyclohexyl, cycloheptyl, cyclooctyl;

T is O;

provided that

Y and $X_2$ represent methyl simultaneously only when Z represents a $C_1$-$C_6$-haloalkyl and provided that formula (I) does not represent 2-chloro-N-[1-(3-chlorophenyl)-3-methyl-5-phenyl-1H-pyrazol-4-yl]-3-pyridine carboxamides or 2-chloro-N-[3-methyl-1-(3-methylphenyl)-5-phenyl-1H-pyrazol-4-yl]-3-pyridine carboxamide
and salts, solvates, N-oxides, solvates of the salts and N-oxides thereof.

Especially preferred are compounds of the general formula (I), wherein
Z is selected from difluoromethyl, trifluoromethyl, methyl, ethyl, bromine;
$X_1$ is H, F, Cl, methyl;
$X_2$ is H;
Y is selected from chlorine, bromine, trifluoromethyl, difluoromethyl, ethyl, isopropyl, methyl, phenyl, 2-chlorophenyl, 3-chlorophenyl, 4-chlorophenyl, 2-fluorophenyl, 3-fluorophenyl, 4-fluorophenyl, 2-methylphenyl, 3-methylphenyl, 4-methylphenyl, 2-trifluoromethylphenyl, 3-trifluoromethylphenyl, 4-trifluoromethylphenyl;
Q is selected from phenyl, 2-chlorophenyl, 3-chlorophenyl, 4-chlorophenyl, 2-fluorophenyl, 3-fluorophenyl, 4-fluorophenyl, 2-methylphenyl, 3-methylphenyl, 4-methylphenyl, 2-trifluoromethylphenyl, 3-trifluoromethylphenyl, 4-trifluoromethylphenyl, 2-difluoromethylphenyl, 3-difluoromethylphenyl, 4-difluoromethylphenyl, 2,3-difluorophenyl, 2,4-difluorophenyl, 2,5-difluorophenyl, 2,6-difluorophenyl, 3,4-difluorophenyl, 3,5-difluorophenyl, 2,3-dichlorophenyl, 2,4-dichlorophenyl, 2,5-dichlorophenyl, 2,6-dichlorophenyl, 3,4-dichlorophenyl, 3,5-dichlorophenyl;
T is O;
and salts, solvates, N-oxides, solvates of the salts and N-oxides thereof.

Furthermore preferred are compounds of the general formula (IV),

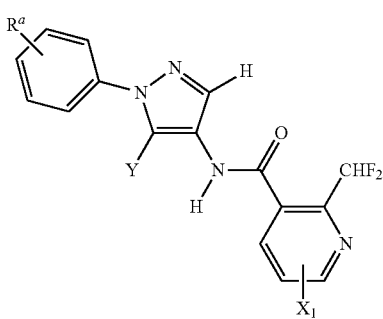

(IV)

wherein $R^a$, Y and $X_1$ have the above mentioned preferred definitions.

Elucidation of the Preparation Processes and Intermediates

Carboxamides of the formula (I-a), i.e. carboxamides of formula (I) wherein T represents oxygen, are obtained when carbonyl halides or acids of formula (II) are reacted with amines of formula (III) optionally in the presence of a coupling agent, optionally in the presence of an acid binder and optionally in the presence of a diluent [Process (a)]:

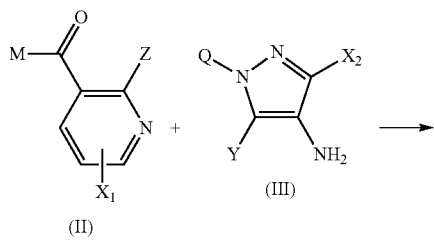

(II)  (III)

-continued

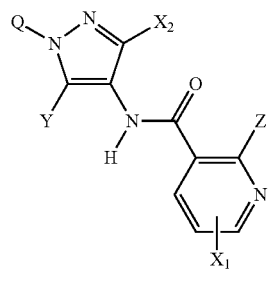

(I-a)

The formula (II) provides a general definition of the carbonyl halides or acids required as starting materials for carrying out the Process (a) according to the invention.

In this formula (II), Z and $X_1$ have generally and preferably those meanings which have already been mentioned for these radicals in connection with the description of the compounds of the formula (I). M represents halogen, hydroxyl or an activated hydroxyl group. M preferably represents fluorine, chlorine or hydroxyl, particularly preferably chlorine or hydroxyl.

An activated hydroxyl group shall mean that the hydroxyl forms together with the adjacent carbonyl an ester which spontaneously reacts with an amino group. Common activated esters include p-nitrophenyl, pentafluorophenyl, succinimido esters or phosphorous anhydrides.

The formula (III) provides a general definition of the amines required as starting materials for carrying out the Process (a) according to the invention.

In this formula (III) Q, Y, and $X_2$ have generally, preferably, particularly preferably, very particularly preferably those meanings which have already been mentioned for these radicals in connection with the description of the compounds of the formula (I).

The carbonyl halides or acids of the formula (II) can be prepared using similar procedures to the ones described in Chem. Commun., 2008, 4207-4209

The amines of the formula (III) can be prepared using similar procedures to the ones described in JP2010202648.

Thiocarboxamides of the formula (I-b), i.e. carboxamides of formula (I) wherein T represents sulfur, are obtained when carboxamides of the formula (I-a) are reacted with a thionating agent, optionally in the presence of a diluent, and optionally in the presence of a catalytic or stoichiometric or more quantity of a base [Process (b)]:

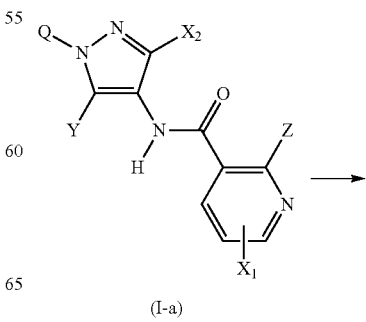

(I-a)

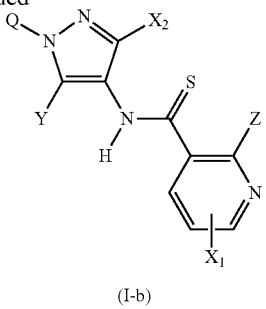

(I-b)

Suitable diluents for carrying out the processes (a) and (b) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, dichloromethane, chloroform, carbon tetrachloride, dichloroethane or tri-chloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisol; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; their mixtures with water or pure water.

The Process (a) according to the invention is, if appropriate, carried out in the presence of a suitable acid acceptor when M represents halogen. Suitable acid acceptors are all customary inorganic or organic bases. These preferably include alkaline earth metal or alkali metal hydrides, hydroxides, amides, alkoholates, acetates, carbonates or bicarbonates, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU). The Process (a) according to the invention is, if appropriate, carried out in the presence of a suitable coupling agent when M represents hydroxyl. Suitable coupling agents are all customary carbonyl activators. These preferably include N-[3-(dimethylamino)propyl]-N'-ethyl-carbodiimide-hydrochloride, N,N'-di-sec-butylcarbodiimide, N,N'-dicyclohexylcarbodiimide, N,N'-diisopropylcarbodiimide, 1-(3-(dimethylamino)propyl)-3-ethylcarbodiimide methiodide, 2-bromo-3-ethyl-4-methylthiazolium tetrafluoroborate, N,N-bis[2-oxo-3-oxazolidinyl]phosphorodiamidic chloride, chlorotripyrrolidinophosphonium hexafluorophosphate, bromtripyrrolidinophosphonium hexafluorophosphate, O-(1H-benzotriazol-1-yloxy)tris(dimethylamino) phosphonium hexafluorophosphate, O-(1H-benzotriazol-1-yl)-N,N,N',N'-tetramethyluronium hexafluorophosphate, O-(1H-benzotriazol-1-yl)-N,N,N',N'-bis(tetramethylene) uronium hexafluorophosphate, O-(1H-benzotriazol-1-yl)-N,N,N',N'-bis(tetramethylene)uronium tetrafluoroborate, N,N, N',N'-bis(tetramethylene)chlorouronium tetrafluoroborate, O-(7-aza-benzotriazol-1-yl)-N,N,N,N-tetramethyluronium hexafluorophosphate and 1-hydroxybenzotriazole. These reagents can be employed separately, but also in combination.

For carrying out the Process (a) according to the invention for preparing the compounds of the formula (I-a) in general from 0.2 to 5 mol, preferably from 0.5 to 2 mol, of amine of the formula (III) are employed per mole of the carbonyl halide or acid of the formula (II). Work-up is carried out by customary methods.

For carrying out the Process (b) according to the invention for preparing the compounds of the formula (I-b) starting amide derivatives of formula (I-a) can be prepared according to Process (a).

Suitable thionating agents for carrying out Process (b) according to the invention can be sulfur (S), sulfhydric acid ($H_2S$), sodium sulfide ($Na_2S$), sodium hydrosulfide (NaHS), boron trisulfide ($B_2S_3$), bis(diethylaluminium) sulfide (($AlEt_2)_2S$), ammonium sulfide (($NH_4)_2S$), phosphorous pentasulfide ($P_2S_5$), Lawesson's reagent (2,4-bis(4-methoxyphenyl)-1,2,3,4-dithiadiphosphetane 2,4-disulfide) or a polymer-supported thionating reagent such as described in J. Chem. Soc., Perkin 1 2001, 358.

The processes (a) and (b) are generally carried out under atmospheric pressure. However, it is also possible to operate under elevated or reduced pressure-in general between 0.1 bar and 100 bar.

When carrying out the Process (a) and (b) according to the invention, the reaction temperatures can be varied within a relatively wide range. In general, the process is carried out at temperatures of from 0° C. to 150° C., preferably at temperatures of from 20° C. to 110° C.

The compounds of formula (I) have potent microbicidal activity and can be used for control of unwanted microorganisms, such as fungi and bacteria, in crop protection and in the protection of materials.

The inventive compounds of formula (I) have very good fungicidal properties and can be used in crop protection, for example for control of Plasmodiophoromycetes, Oomycetes, Chytridiomycetes, Zygomycetes, Ascomycetes, Basidiomycetes and Deuteromycetes.

The invention further relates to a method for controlling unwanted microorganisms, characterized in that the compounds of formula (I) are applied to the microorganisms and/or in their habitat.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Plant parts are understood to mean all parts and organs of plants above and below the ground, such as shoot, leaf, flower and root, examples of which include leaves, needles, stalks, stems, flowers, fruit bodies, fruits and seeds, and also roots, tubers and rhizomes. The plant parts also include harvested material and vegetative and generative propagation material, for example cuttings, tubers, rhizomes, slips and seeds.

Composition/Formulation

The present invention further relates to a crop protection composition for controlling harmful microorganisms, especially unwanted fungi and bacteria, comprising an effective and non-phytotoxic amount of the inventive compounds of formula (I). These are preferably fungicidal compositions which comprise agriculturally suitable auxiliaries, solvents, carriers, surfactants or extenders.

The inventive fungicidal compositions can be used for curative or protective control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

The inventive compositions for controlling phytopathogenic fungi in crop protection comprise an effective but non-phytotoxic amount of the inventive active ingredients. An "effective but non-phytotoxic amount" means an amount of the inventive composition which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions.

In the context of the present invention, "control of harmful microorganisms" means a reduction in infestation by harmful microorganisms, compared with the untreated plant measured as fungicidal efficacy, preferably a reduction by 25-50%, compared with the untreated plant (100%), more preferably a reduction by 40-79%, compared with the untreated plant (100%); even more preferably, the infection by harmful microorganisms is entirely suppressed (by 70-100%). The control may be curative, i.e. for treatment of already infected plants, or protective, for protection of plants which have not yet been infected.

An "effective but non-phytotoxic amount" means an amount of the inventive composition which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions.

Suitable organic solvents include all polar and non-polar organic solvents usually employed for formulation purposes. Preferable the solvents are selected from ketones, e.g. methyl-isobutyl-ketone and cyclohexanone, amides, e.g. dimethyl formamide and alkanecarboxylic acid amides, e.g. N,N-dimethyl decaneamide and N,N-dimethyl octanamide, furthermore cyclic solvents, e.g. N-methyl-pyrrolidone, N-octyl-pyrrolidone, N-dodecyl-pyrrolidone, N-octyl-caprolactame, N-dodecyl-caprolactame and butyrolactone, furthermore strong polar solvents, e.g. dimethylsulfoxide, and aromatic hydrocarbons, e.g. xylol, Solvesso™, mineral oils, e.g. white spirit, petroleum, alkyl benzenes and spindle oil, also esters, e.g. propyleneglycol-monomethylether acetate, adipic acid dibutylester, acetic acid hexylester, acetic acid heptylester, citric acid tri-n-butylester and phthalic acid di-n-butylester, and also alcohols, e.g. benzyl alcohol and 1-methoxy-2-propanol.

According to the invention, a carrier is a natural or synthetic, organic or inorganic substance with which the active ingredients are mixed or combined for better applicability, in particular for application to plants or plant parts or seed. The carrier, which may be solid or liquid, is generally inert and should be suitable for use in agriculture.

Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. Mixtures of such carriers can likewise be used.

Suitable solid filler and carrier include inorganic particles, e.g. carbonates, silicates, sulphates and oxides with an average particle size of between 0.005 and 20 µm, preferably of between 0.02 to 10 µm, for example ammonium sulphate, ammonium phosphate, urea, calcium carbonate, calcium sulphate, magnesium sulphate, magnesium oxide, aluminium oxide, silicium dioxide, so-called fine-particle silica, silica gels, natural or synthetic silicates, and alumosilicates and plant products like cereal flour, wood powder/sawdust and cellulose powder.

Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks.

Useful liquefied gaseous extenders or carriers are those liquids which are gaseous at standard temperature and under standard pressure, for example aerosol propellants such as halohydrocarbons, and also butane, propane, nitrogen and carbon dioxide.

In the formulations, it is possible to use tackifiers such as carboxymethylcellulose, and natural and synthetic polymers in the form of powders, granules or latices, such as gum arabic, polyvinyl alcohol and polyvinyl acetate, or else natural phospholipids, such as cephalins and lecithins, and synthetic phospholipids. Further additives may be mineral and vegetable oils.

If the extender used is water, it is also possible to employ, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

The inventive compositions may additionally comprise further components, for example surfactants. Useful surfactants are emulsifiers and/or foam formers, dispersants or wetting agents having ionic or nonionic properties, or mixtures of these surfactants. Suitable surfactants (adjuvants, emulsifiers, dispersants, protective colloids, wetting agent and adhesive) include all common ionic and non-ionic substances, for example ethoxylated nonylphenols, polyalkylene glycolether of linear or branched alcohols, reaction products of alkyl phenols with ethylene oxide and/or propylene oxide, reaction products of fatty acid amines with ethylene oxide and/or propylene oxide, furthermore fattic acid esters, alkyl sulfonates, alkyl sulphates, alkyl ethersulphates, alkyl etherphosphates, arylsulphate, ethoxylated arylalkylphenols, e.g. tristyryl-phenol-ethoxylates, furthermore ethoxylated and propoxylated arylalkylphenols like sulphated or phosphated arylalkylphenol-ethoxylates and -ethoxy- and -propoxylates. Further examples are natural and synthetic, water soluble polymers, e.g. lignosulphonates, gelatine, gum arabic, phospholipides, starch, hydrophobic modified starch and cellulose derivatives, in particular cellulose ester and cellulose ether, further polyvinyl alcohol, polyvinyl acetate, polyvinyl pyrrolidone, polyacrylic acid, polymethacrylic acid and co-polymerisates of (meth)acrylic acid and (meth)acrylic acid esters, and further co-polymerisates of methacrylic acid and methacrylic acid esters which are neutralized with alkalimetal hydroxide and also condensation products of optionally substituted naphthalene sulfonic acid salts with formaldehyde. The presence of a surfactant is necessary if one of the active ingredients and/or one of the inert carriers is insoluble in water and when application is effected in water. The proportion of surfactants is between 5 and 40 percent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Antifoams which may be present in the formulations include e.g. silicone emulsions, longchain alcohols, fatty acids and their salts as well as fluoroorganic substances and mixtures thereof.

Examples of thickeners are polysaccharides, e.g. xanthan gum or veegum, silicates, e.g. attapulgite, bentonite as well as fine-particle silica.

If appropriate, it is also possible for other additional components to be present, for example protective colloids, binders, adhesives, thickeners, thixotropic substances, penetrants, stabilizers, sequestrants, complexing agents. In general, the active ingredients can be combined with any solid or liquid additive commonly used for formulation purposes.

The inventive active ingredients or compositions can be used as such or, depending on their particular physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, gas (under pressure), gas generating product, foams, pastes, pesticide coated seed, suspension concentrates, suspoemulsion concentrates, soluble concentrates, suspensions, wettable powders, soluble powders, dusts and granules, water-soluble and water-dispersible granules or tablets, water-soluble and water-dispersible powders for the treatment of seed, wettable powders, natural products and synthetic substances impregnated with active ingredient, and also microencapsulations in polymeric substances and in coating materials for seed, and also ULV cold-fogging and warm-fogging formulations.

The inventive compositions include not only formulations which are already ready for use and can be applied with a suitable apparatus to the plant or the seed, but also commercial concentrates which have to be diluted with water prior to use. Customary applications are for example dilution in water and subsequent spraying of the resulting spray liquor, application after dilution in oil, direct application without dilution, seed treatment or soil application of granules.

The inventive compositions and formulations generally contain between 0.05 and 99% by weight, 0.01 and 98% by weight, preferably between 0.1 and 95% by weight, more preferably between 0.5 and 90% of active ingredient, most preferably between 10 and 70% by weight. For special applications, e.g. for protection of wood and derived timber products the inventive compositions and formulations generally contain between 0.0001 and 95% by weight, preferably 0.001 to 60% by weight of active ingredient.

The contents of active ingredient in the application forms prepared from the commercial formulations may vary in a broad range. The concentration of the active ingredients in the application forms is generally between 0.000001 to 95% by weight, preferably between 0.0001 and 2% by weight.

The formulations mentioned can be prepared in a manner known per se, for example by mixing the active ingredients with at least one customary extender, solvent or diluent, adjuvant, emulsifier, dispersant, and/or binder or fixative, wetting agent, water repellent, if appropriate desiccants and UV stabilizers and, if appropriate, dyes and pigments, antifoams, preservatives, inorganic and organic thickeners, adhesives, gibberellins and also further processing auxiliaries and also water. Depending on the formulation type to be prepared further processing steps are necessary, e.g. wet grinding, dry grinding and granulation.

The inventive active ingredients may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The inventive treatment of the plants and plant parts with the active ingredients or compositions is effected directly or by action on their surroundings, habitat or storage space by the customary treatment methods, for example by dipping, spraying, atomizing, irrigating, evaporating, dusting, fogging, broadcasting, foaming, painting, spreading-on, watering (drenching), drip irrigating and, in the case of propagation material, especially in the case of seeds, also by dry seed treatment, wet seed treatment, slurry treatment, incrustation, coating with one or more coats, etc. It is also possible to deploy the active ingredients by the ultra-low volume method or to inject the active ingredient preparation or the active ingredient itself into the soil.

Plant/Crop Protection

The inventive active ingredients or compositions have potent microbicidal activity and can be used for control of unwanted microorganisms, such as fungi and bacteria, in crop protection and in the protection of materials.

The invention also relates to a method for controlling unwanted microorganisms, characterized in that the inventive active ingredients are applied to the phytopathogenic fungi, phytopathogenic bacteria and/or their habitat.

Fungicides can be used in crop protection for control of phytopathogenic fungi. They are characterized by an outstanding efficacy against a broad spectrum of phytopathogenic fungi, including soilborne pathogens, which are in particular members of the classes Plasmodiophoromycetes, Peronosporomycetes (Syn. Oomycetes), Chytridiomycetes, Zygomycetes, Ascomycetes, Basidiomycetes and Deuteromycetes (Syn. Fungi imperfecta). Some fungicides are systemically active and ca be used in plant protection as foliar, seed dressing or soil fungicide. Furthermore, they are suitable for combating fungi, which inter alia infest wood or roots of plant.

Bactericides can be used in crop protection for control of Pseudomonadaceae, Rhizobiaceae, Enterobacteriaceae, Corynebacteriaceae and Streptomycetaceae.

Non-limiting examples of pathogens of fungal diseases which can be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* and *Phakopsora meibomiae*; *Puccinia* species, for example *Puccinia recondite, P. triticina, P. graminis* or *P. striiformis*; *Uromyces* species, for example *Uromyces appendiculatus*;

diseases caused by pathogens from the group of the Oomycetes, for example *Albugo* species, for example *Algubo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara vificola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Alternaria* species, for example *Alternaria solani*; *Cercospora* species, for example *Cercospora beficola*; *Cladiosporium* species, for example *Cladiosporium cucumerinum*; *Cochliobolus* species, for example *Cochliobolus sativus* (conidia form: *Drechslera*, Syn: *Helminthosporium*), *Cochliobolus miyabeanus*; *Colletotrichum* species, for example *Colletotrichum lindemuthanium*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeficolor*; *Glomerella* species, for example *Glomerella cingulata*; *Guignardia* species, for example *Guignardia bidwelli*; *Leptosphaeria* species, for example *Leptosphaeria macularis, Leptosphaeria nodorum*; *Magnaporthe* species, for example *Magnaporthe grisea*; *Microdochium* species, for example *Microdochium nivale*; *Mycosphaerella* species, for example *Mycosphaerella graminicola, M. arachidicola* and *M. fijiensis*; *Phaeosphaeria* species, for example *Phaeosphaeria nodorum*; *Pyrenophora* species, for example *Pyrenophora teres, Pyrenophora tritici repentis*; *Ramularia* species, for example *Ramularia collo-cygni, Ramularia areola*; *Rhynchosporium* species, for example *Rhynchosporium secalis*; *Septoria* species, for example *Septoria apii, Septoria lycopersii*; *Typhula* species, for example *Typhula incarnata*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, such as, for example *Rhizoctonia solani*; *Sarocladium* diseases caused for example by *Sarocladium oryzae*; *Sclerotium* diseases caused for example by *Sclerotium oryzae*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Septoria* species, for example *Septoria nodorum*;

diseases caused by smut fungi, for example *Sphacelotheca* species, for example *Sphacelotheca reiliana*; *Tilletia* species, for example *Tilletia caries, T. controversa*; *Urocystis* species, for example *Urocystis occulta*; *Ustilago* species, for example *Ustilago nuda, U. nuda tritici*;

fruit rot caused, for example, by *Aspergillus* species, for example *Aspergillus flavus*; *Botrytis* species, for example *Botrytis cinerea*; *Penicillium* species, for example *Penicillium expansum* and *P. purpurogenum*; *Sclerotinia* species, for example *Sclerotinia sclerotiorum*; *Verticilium* species, for example *Verticilium alboatrum*;

seed and soilborne decay, mould, wilt, rot and damping-off diseases caused, for example, by *Alternaria* species, caused for example by *Alternaria brassicicola*; *Aphanomyces* species, caused for example by *Aphanomyces euteiches*; *Ascochyta* species, caused for example by *Ascochyta lentis*; *Aspergillus* species, caused for example by *Aspergillus flavus*; *Cladosporium* species, caused for example by *Cladosporium herbarum*; *Cochliobolus* species, caused for example by *Cochliobolus sativus*; (Conidiaform: *Drechslera, Bipolaris* Syn: *Helminthosporium*); *Colletotrichum* species, caused for example by *Colletotrichum coccodes*; *Fusarium* species, caused for example by *Fusarium culmorum*; *Gibberella* species, caused for example by *Gibberella zeae*; *Macrophomina* species, caused for example by *Macrophomina phaseolina*; *Monographella* species, caused for example by *Monographella nivalis*; *Penicillium* species, caused for example by *Penicillium expansum*; *Phoma* species, caused for example by *Phoma lingam*; *Phomopsis* species, caused for example by *Phomopsis sojae*; *Phytophthora* species, caused for example by *Phytophthora cactorum*; *Pyrenophora* species, caused for example by *Pyrenophora graminea*; *Pyricularia* species, caused for example by *Pyricularia oryzae*; *Pythium* species, caused for example by *Pythium ultimum*; *Rhizoctonia* species, caused for example by *Rhizoctonia solani*; *Rhizopus* species, caused for example by *Rhizopus oryzae*; *Sclerotium* species, caused for example by *Sclerotium rolfsii*; *Septoria* species, caused for example by *Septoria nodorum*; *Typhula* species, caused for example by *Typhula incarnata*; *Verticillium* species, caused for example by *Verticillium dahliae*;

cancers, galls and witches' broom caused, for example, by *Nectria* species, for example *Nectria galligena*;

wilt diseases caused, for example, by *Monilinia* species, for example *Monilinia laxa*;

leaf blister or leaf curl diseases caused, for example, by *Exobasidium* species, for example *Exobasidium vexans*; *Taphrina* species, for example *Taphrina deformans*;

decline diseases of wooden plants caused, for example, by Esca disease, caused for example by *Phaemoniella clamydospora, Phaeoacremonium aleophilum* and *Fomifiporia mediterranea*;

*Eutypa* dyeback, caused for example by *Eutypa lata*; *Ganoderma* diseases caused for example by *Ganoderma boninense*; *Rigidoporus* diseases caused for example by *Rigidoporus lignosus*;

diseases of flowers and seeds caused, for example, by *Botrytis* species, for example *Botrytis cinerea*;

diseases of plant tubers caused, for example, by *Rhizoctonia* species, for example *Rhizoctonia solani*; *Helminthosporium* species, for example *Helminthosporium solani*;

Club root caused, for example, by *Plasmodiophora* species, for example *Plasmodiophora brassicae*;

diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

The following diseases of soya beans can be controlled with preference:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerofiorum*), sclerotinia southern blight (*Sclerotinia rolfsii*), thielaviopsis root rot (*Thielaviopsis basicola*).

The inventive fungicidal compositions can be used for curative or protective/preventive control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

The fact that the active ingredients are well tolerated by plants at the concentrations required for controlling plant diseases allows the treatment of above-ground parts of plants, of propagation stock and seeds, and of the soil.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

The inventive active ingredients, when they are well tolerated by plants, have favourable homeotherm toxicity and are well tolerated by the environment, are suitable for protecting plants and plant organs, for enhancing harvest yields, for improving the quality of the harvested material. They can preferably be used as crop protection compositions. They are active against normally sensitive and resistant species and against all or some stages of development.

Plants which can be treated in accordance with the invention include the following main crop plants: maize, soya bean, alfalfa, cotton, sunflower, *Brassica* oil seeds such as *Brassica napus* (e.g. canola, rapeseed), *Brassica rapa, B. juncea* (e.g. (field) mustard) and *Brassica carinata, Arecaceae* sp. (e.g. oilpalm, coconut), rice, wheat, sugar beet, sugar cane, oats, rye, barley, millet and sorghum, triticale, flax, nuts, grapes and vine and various fruit and vegetables from various botanic taxa, e.g. *Rosaceae* sp. (e.g. pome fruits such as apples and pears, but also stone fruits such as apricots, cherries, almonds, plums and peaches, and berry fruits such as strawberries, raspberries, red and black currant and gooseberry), *Ribesioidae* sp., *Juglandaceae* sp., *Betulaceae* sp., *Anacardiaceae* sp., *Fagaceae* sp., *Moraceae* sp., *Oleaceae* sp. (e.g. olive tree), *Actinidaceae* sp., *Lauraceae* sp. (e.g. avocado, cinnamon, camphor), *Musaceae* sp. (e.g. banana trees and plantations), *Rubiaceae* sp. (e.g. coffee), *Theaceae* sp. (e.g. tea), *Sterculiceae* sp., *Rutaceae* sp. (e.g. lemons, oranges, mandarins and grapefruit); *Solanaceae* sp. (e.g. tomatoes, potatoes, peppers, capsicum, aubergines, tobacco), *Liliaceae* sp., *Compositae* sp. (e.g. lettuce, artichokes and chicory—including root chicory, endive or common chicory), *Umbelliferae* sp. (e.g. carrots, parsley, celery and celeriac), *Cucurbitaceae* sp. (e.g. cucumbers—including gherkins, pumpkins, watermelons, calabashes and melons), *Alliaceae* sp. (e.g. leeks and onions), *Cruciferae* sp. (e.g. white cabbage, red cabbage, broccoli, cauliflower, Brussels sprouts, pak choi, kohlrabi, radishes, horseradish, cress and chinese cabbage), *Leguminosae* sp. (e.g. peanuts, peas, lentils and beans—e.g. common beans and broad beans), *Chenopodiaceae* sp. (e.g. Swiss chard, fodder beet, spinach, beetroot), *Linaceae* sp. (e.g. hemp), *Cannabeacea* sp. (e.g. *cannabis*), *Malvaceae* sp. (e.g. okra, cocoa), *Papaveraceae* (e.g. poppy), *Asparagaceae* (e.g. asparagus); useful plants and ornamental plants in the garden and woods including turf, lawn, grass and *Stevia rebaudiana*; and in each case genetically modified types of these plants.

Plant Growth Regulation

In some cases, the inventive compounds can, at particular concentrations or application rates, also be used as herbicides, safeners, growth regulators or agents to improve plant properties, or as microbicides, for example as fungicides, antimycotics, bactericides, viricides (including compositions against viroids) or as compositions against MLO (*Mycoplasma*-like organisms) and RLO (*Rickettsia*-like organisms). If appropriate, they can also be used as intermediates or precursors for the synthesis of other active ingredients.

The inventive active ingredients intervene in the metabolism of the plants and can therefore also be used as growth regulators.

Plant growth regulators may exert various effects on plants. The effect of the substances depends essentially on the time of application in relation to the developmental stage of the plant, and also on the amounts of active ingredient applied to the plants or their environment and on the type of application. In each case, growth regulators should have a particular desired effect on the crop plants.

Plant growth-regulating compounds can be used, for example, to inhibit the vegetative growth of the plants. Such inhibition of growth is of economic interest, for example, in the case of grasses, since it is thus possible to reduce the frequency of grass cutting in ornamental gardens, parks and sport facilities, on roadsides, at airports or in fruit crops. Also of significance is the inhibition of the growth of herbaceous and woody plants on roadsides and in the vicinity of pipelines or overhead cables, or quite generally in areas where vigorous plant growth is unwanted.

Also important is the use of growth regulators for inhibition of the longitudinal growth of cereal. This reduces or completely eliminates the risk of lodging of the plants prior to harvest. In addition, growth regulators in the case of cereals can strengthen the culm, which also counteracts lodging. The employment of growth regulators for shortening and strengthening culms allows the deployment of higher fertilizer volumes to increase the yield, without any risk of lodging of the cereal crop.

In many crop plants, inhibition of vegetative growth allows denser planting, and it is thus possible to achieve higher yields based on the soil surface. Another advantage of the smaller plants obtained in this way is that the crop is easier to cultivate and harvest.

Inhibition of the vegetative plant growth may also lead to enhanced yields because the nutrients and assimilates are of more benefit to flower and fruit formation than to the vegetative parts of the plants.

Frequently, growth regulators can also be used to promote vegetative growth. This is of great benefit when harvesting the vegetative plant parts. However, promoting vegetative growth may also promote generative growth in that more assimilates are formed, resulting in more or larger fruits.

In some cases, yield increases may be achieved by manipulating the metabolism of the plant, without any detectable changes in vegetative growth. In addition, growth regulators can be used to alter the composition of the plants, which in turn may result in an improvement in quality of the harvested products. For example, it is possible to increase the sugar content in sugar beet, sugar cane, pineapples and in citrus fruit, or to increase the protein content in soya or cereals. It is also possible, for example, to use growth regulators to inhibit the degradation of desirable ingredients, for example sugar in sugar beet or sugar cane, before or after harvest. It is also possible to positively influence the production or the elimination of secondary plant ingredients. One example is the stimulation of the flow of latex in rubber trees.

Under the influence of growth regulators, parthenocarpic fruits may be formed. In addition, it is possible to influence the sex of the flowers. It is also possible to produce sterile pollen, which is of great importance in the breeding and production of hybrid seed.

Use of growth regulators can control the branching of the plants. On the one hand, by breaking apical dominance, it is possible to promote the development of side shoots, which may be highly desirable particularly in the cultivation of ornamental plants, also in combination with an inhibition of growth. On the other hand, however, it is also possible to inhibit the growth of the side shoots. This effect is of particular interest, for example, in the cultivation of tobacco or in the cultivation of tomatoes.

Under the influence of growth regulators, the amount of leaves on the plants can be controlled such that defoliation of the plants is achieved at a desired time. Such defoliation plays a major role in the mechanical harvesting of cotton, but is also of interest for facilitating harvesting in other crops, for example in viticulture. Defoliation of the plants can also be undertaken to lower the transpiration of the plants before they are transplanted.

Growth regulators can likewise be used to regulate fruit dehiscence. On the one hand, it is possible to prevent premature fruit dehiscence. On the other hand, it is also possible to promote fruit dehiscence or even flower abortion to achieve a desired mass ("thinning"), in order to eliminate alternation. Alternation is understood to mean the characteristic of some fruit species, for endogenous reasons, to deliver very different yields from year to year. Finally, it is possible to use growth regulators at the time of harvest to reduce the forces required to detach the fruits, in order to allow mechanical harvesting or to facilitate manual harvesting.

Growth regulators can also be used to achieve faster or else delayed ripening of the harvested material before or after harvest. This is particularly advantageous as it allows optimal adjustment to the requirements of the market. Moreover, growth regulators in some cases can improve the fruit colour. In addition, growth regulators can also be used to concentrate maturation within a certain period of time. This establishes the prerequisites for complete mechanical or manual harvesting in a single operation, for example in the case of tobacco, tomatoes or coffee.

By using growth regulators, it is additionally possible to influence the resting of seed or buds of the plants, such that plants such as pineapple or ornamental plants in nurseries, for example, germinate, sprout or flower at a time when they are normally not inclined to do so. In areas where there is a risk of frost, it may be desirable to delay budding or germination of seeds with the aid of growth regulators, in order to avoid damage resulting from late frosts.

Finally, growth regulators can induce resistance of the plants to frost, drought or high salinity of the soil. This allows the cultivation of plants in regions which are normally unsuitable for this purpose.

Resistance Induction/Plant Health and Other Effects

The active compounds according to the invention also exhibit a potent strengthening effect in plants. Accordingly, they can be used for mobilizing the defences of the plant against attack by undesirable microorganisms.

Plant-strengthening (resistance-inducing) substances are to be understood as meaning, in the present context, those substances which are capable of stimulating the defence system of plants in such a way that the treated plants, when subsequently inoculated with undesirable microorganisms, develop a high degree of resistance to these microorganisms.

The active compounds according to the invention are also suitable for increasing the yield of crops. In addition, they show reduced toxicity and are well tolerated by plants.

Further, in context with the present invention plant physiology effects comprise the following:

Abiotic stress tolerance, comprising temperature tolerance, drought tolerance and recovery after drought stress, water use efficiency (correlating to reduced water consumption), flood tolerance, ozone stress and UV tolerance, tolerance towards chemicals like heavy metals, salts, pesticides (safener) etc.

Biotic stress tolerance, comprising increased fungal resistance and increased resistance against nematodes, viruses and bacteria. In context with the present invention, biotic stress tolerance preferably comprises increased fungal resistance and increased resistance against nematodes Increased plant vigor, comprising plant health/plant quality and seed vigor, reduced stand failure, improved appearance, increased recovery, improved greening effect and improved photosynthetic efficiency.

Effects on plant hormones and/or functional enzymes.

Effects on growth regulators (promoters), comprising earlier germination, better emergence, more developed root system and/or improved root growth, increased ability of tillering, more productive tillers, earlier flowering, increased plant height and/or biomass, shorting of stems, improvements in shoot growth, number of kernels/ear, number of ears/m$^2$, number of stolons and/or number of flowers, enhanced harvest index, bigger leaves, less dead basal leaves, improved phyllotaxy, earlier maturation/earlier fruit finish, homogenous riping, increased duration of grain filling, better fruit finish, bigger fruit/vegetable size, sprouting resistance and reduced lodging.

Increased yield, referring to total biomass per hectare, yield per hectare, kernel/fruit weight, seed size and/or hectoliter weight as well as to increased product quality, comprising:
improved processability relating to size distribution (kernel, fruit, etc.), homogenous riping, grain moisture, better milling, better vinification, better brewing, increased juice yield, harvestability, digestibility, sedimentation value, falling number, pod stability, storage stability, improved fiber length/strength/uniformity, increase of milk and/or meet quality of silage fed animals, adaption to cooking and frying; further comprising improved marketability relating to improved fruit/grain quality, size distribution (kernel, fruit, etc.), increased storage/shelf-life, firmness/softness, taste (aroma, texture, etc.), grade (size, shape, number of berries, etc.), number of berries/fruits per bunch, crispness, freshness, coverage with wax, frequency of physiological disorders, colour, etc.;
further comprising increased desired ingredients such as e.g. protein content, fatty acids, oil content, oil quality, amino-acid composition, sugar content, acid content (pH), sugar/acid ratio (Brix), polyphenols, starch content, nutritional quality, gluten content/index, energy content, taste, etc.,
and further comprising decreased undesired ingredients such as e.g. less mycotoxines, less aflatoxines, geosmin level, phenolic aromas, lacchase, polyphenol oxidases and peroxidases, nitrate content etc.

Sustainable agriculture, comprising nutrient use efficiency, especially nitrogen (N)-use efficiency, phosphorus (P)-use efficiency, water use efficiency, improved transpiration, respiration and/or $CO_2$ assimilation rate, better nodulation, improved Ca-metabolism etc.

Delayed senescence, comprising improvement of plant physiology which is manifested, for example, in a longer grain filling phase, leading to higher yield, a longer duration of green leaf colouration of the plant and thus comprising colour (greening), water content, dryness etc. Accordingly, in the context of the present invention, it has been found that the specific inventive application of the active compound combination makes it possible to prolong the green leaf area duration, which delays the maturation (senescence) of the plant. The main advantage to the farmer is a longer grain filling phase leading to higher yield. There is also an advantage to the farmer on the basis of greater flexibility in the harvesting time.

Therein "sedimentation value" is a measure for protein quality and describes according to Zeleny (Zeleny value) the degree of sedimentation of flour suspended in a lactic acid solution during a standard time interval. This is taken as a measure of the baking quality. Swelling of the gluten fraction of flour in lactic acid solution affects the rate of sedimentation of a flour suspension. Both a higher gluten content and a better gluten quality give rise to slower sedimentation and higher Zeleny test values. The sedimentation value of flour depends on the wheat protein composition and is mostly correlated to the protein content, the wheat hardness, and the volume of pan and hearth loaves. A stronger correlation between loaf volume and Zeleny sedimentation volume compared to SDS sedimentation volume could be due to the protein content influencing both the volume and Zeleny value (*Czech J. Food Sci. Vol.* 21, *No.* 3: 91-96, 2000).

Further the "falling number" as mentioned herein is a measure for the baking quality of cereals, especially of wheat. The falling number test indicates that sprout damage may have occurred. It means that changes to the physical properties of the starch portion of the wheat kernel has already happened. Therein, the falling number instrument analyzes viscosity by measuring the resistance of a flour and water paste to a falling plunger. The time (in seconds) for this to happen is known as the falling number. The falling number results are recorded as an index of enzyme activity in a wheat or flour sample and results are expressed in time as seconds. A high falling number (for example, above 300 seconds) indicates minimal enzyme activity and sound quality wheat or flour. A low falling number (for example, below 250 seconds) indicates substantial enzyme activity and sprout-damaged wheat or flour.

The term "more developed root system"/"improved root growth" refers to longer root system, deeper root growth, faster root growth, higher root dry/fresh weight, higher root volume, larger root surface area, bigger root diameter, higher root stability, more root branching, higher number of root hairs, and/or more root tips and can be measured by analyzing the root architecture with suitable methodologies and Image analysis programmes (e.g. WinRhizo).

The term "crop water use efficiency" refers technically to the mass of agriculture produce per unit water consumed and economically to the value of product(s) produced per unit water volume consumed and can e.g. be measured in terms of yield per ha, biomass of the plants, thousand-kernel mass, and the number of ears per m$^2$.

The term "nitrogen-use efficiency" refers technically to the mass of agriculture produce per unit nitrogen consumed and economically to the value of product(s) produced per unit nitrogen consumed, reflecting uptake and utilization efficiency.

Improvement in greening/improved colour and improved photosynthetic efficiency as well as the delay of senescence can be measured with well-known techniques such as a HandyPea system (Hansatech). Fv/Fm is a parameter widely used to indicate the maximum quantum efficiency of photosystem II (PSII). This parameter is widely considered to be a selective indication of plant photosynthetic performance with healthy samples typically achieving a maximum Fv/Fm value of approx. 0.85. Values lower than this will be observed if a sample has been exposed to some type of biotic or abiotic stress factor which has reduced the capacity for photochemical quenching of energy within PSII. Fv/Fm is presented as a ratio of variable fluorescence (Fv) over the maximum fluorescence value (Fm). The Performance Index is essentially an indicator of sample vitality. (See e.g. *Advanced Techniques in Soil Microbiology*, 2007, 11, 319-341; *Applied Soil Ecology*, 2000, 15, 169-182.)

The improvement in greening/improved colour and improved photosynthetic efficiency as well as the delay of senescence can also be assessed by measurement of the net photosynthetic rate (Pn), measurement of the chlorophyll content, e.g. by the pigment extraction method of Ziegler and Ehle, measurement of the photochemical efficiency (Fv/Fm ratio), determination of shoot growth and final root and/or canopy biomass, determination of tiller density as well as of root mortality.

Within the context of the present invention preference is given to improving plant physiology effects which are selected from the group comprising: enhanced root growth/ more developed root system, improved greening, improved water use efficiency (correlating to reduced water consumption), improved nutrient use efficiency, comprising especially improved nitrogen (N)-use efficiency, delayed senescence and enhanced yield.

Within the enhancement of yield preference is given as to an improvement in the sedimentation value and the falling number as well as to the improvement of the protein and sugar content—especially with plants selected from the group of cereals (preferably wheat).

Preferably the novel use of the fungicidal compositions of the present invention relates to a combined use of a) preventively and/or curatively controlling pathogenic fungi and/or nematodes, with or without resistance management, and b) at least one of enhanced root growth, improved greening, improved water use efficiency, delayed senescence and enhanced yield. From group b) enhancement of root system, water use efficiency and N-use efficiency is particularly preferred.

Seed Treatment

The invention further relates to seed which has been treated with at least one compound of formula (I).

The invention finally provides a method for protecting seed against unwanted microorganisms by using seed treated with at least one compound of formula (I) according to the present invention.

The invention further comprises a method for treating seed.

The invention further relates to seed which has been treated by one of the methods described in the previous paragraph. The inventive seeds are employed in methods for the protection of seed from harmful microorganisms. In these methods, seed treated with at least one inventive active ingredient is used.

The inventive active ingredients or compositions are also suitable for treating seed. A large part of the damage to crop plants caused by harmful organisms is triggered by the infection of the seed during storage or after sowing, and also during and after germination of the plant. This phase is particularly critical since the roots and shoots of the growing plant are particularly sensitive, and even minor damage may result in the death of the plant. There is therefore a great interest in protecting the seed and the germinating plant by using appropriate compositions.

The control of phytopathogenic fungi by treating the seed of plants has been known for a long time and is the subject of constant improvements. However, the treatment of seed entails a series of problems which cannot always be solved in a satisfactory manner. For instance, it is desirable to develop methods for protecting the seed and the germinating plant, which dispense with, or at least significantly reduce, the additional deployment of crop protection compositions after planting or after emergence of the plants. It is also desirable to optimize the amount of the active ingredient used so as to provide the best possible protection for the seed and the germinating plant from attack by phytopathogenic fungi, but without damaging the plant itself by the active ingredient employed. In particular, methods for the treatment of seed should also take account of the intrinsic fungicidal properties of transgenic plants in order to achieve optimal protection of the seed and the germinating plant with a minimum expenditure of crop protection compositions.

The present invention therefore also relates to a method for protection of seed and germinating plants from attack by phytopathogenic fungi, by treating the seed with an inventive composition. The invention likewise relates to the use of the inventive compositions for treatment of seed to protect the seed and the germinating plant from phytopathogenic fungi. The invention further relates to seed which has been treated with an inventive composition for protection from phytopathogenic fungi.

The control of phytopathogenic fungi which damage plants post-emergence is effected primarily by treating the soil and the above-ground parts of plants with crop protection compositions. Owing to the concerns regarding a possible influence of the crop protection compositions on the environment and the health of humans and animals, there are efforts to reduce the amount of active ingredients deployed.

One of the advantages of the present invention is that the particular systemic properties of the inventive active ingredients and compositions mean that treatment of the seed with these active ingredients and compositions not only protects the seed itself, but also the resulting plants after emergence, from phytopathogenic fungi. In this way, the immediate treatment of the crop at the time of sowing or shortly thereafter can be dispensed with.

It is likewise considered to be advantageous that the inventive active ingredients or compositions can especially also be used with transgenic seed, in which case the plant growing from this seed is capable of expressing a protein which acts against pests. By virtue of the treatment of such seed with the inventive active ingredients or compositions, merely the expression of the protein, for example an insecticidal protein, can control certain pests. Surprisingly, a further synergistic effect can be observed in this case, which additionally increases the effectiveness for protection against attack by pests.

The inventive compositions are suitable for protecting seed of any plant variety which is used in agriculture, in greenhouses, in forests or in horticulture and viticulture. In particular, this is the seed of cereals (such as wheat, barley, rye, triticale, sorghum/millet and oats), maize, cotton, soya beans, rice, potatoes, sunflower, bean, coffee, beet (for example sugar beet and fodder beet), peanut, oilseed rape, poppy, olive, coconut, cocoa, sugar cane, tobacco, vegetables (such as tomato, cucumbers, onions and lettuce), turf and ornamentals (see also below). The treatment of the seed of cereals (such as wheat, barley, rye, triticale and oats), maize and rice is of particular significance.

As also described below, the treatment of transgenic seed with the inventive active ingredients or compositions is of particular significance. This relates to the seed of plants containing at least one heterologous gene. Definition and examples of suitable heterologous genes are given below.

In the context of the present invention, the inventive composition is applied to the seed alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

When treating the seed, care must generally be taken that the amount of the inventive composition applied to the seed and/or the amount of further additives is selected such that the germination of the seed is not impaired, or that the resulting plant is not damaged. This has to be borne in mind in particular in the case of active ingredients which can have phytotoxic effects at certain application rates.

The inventive compositions can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. No. 4,272,417, U.S. Pat. No. 4,245,432, U.S. Pat. No. 4,808,430, U.S. Pat. No. 5,876,739, US 2003/0176428 A1, WO 2002/080674, WO 2002/028186.

The active ingredients usable in accordance with the invention can be converted to the customary seed dressing formulations, such as solutions, emulsions, suspensions, powders, foams, slurries or other coating compositions for seed, and also ULV formulations.

These formulations are prepared in a known manner, by mixing the active ingredients with customary additives, for example customary extenders and also solvents or diluents, dyes, wetting agents, dispersants, emulsifiers, antifoams, preservatives, secondary thickeners, adhesives, gibberellins and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Preference is given to using alkyl naphthalenesulphonates, such as diisopropyl or diisobutyl naphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The gibberellins which may be present in the seed dressing formulations usable in accordance with the invention may preferably be gibberellins A1, A3 (=gibberellic acid), A4 and A7; particular preference is given to using gibberellic acid. The gibberellins are known (cf. R. Wegler "Chemie der Pflanzenschutz- and Schädlingsbekampfungsmittel" [Chemistry of the Crop Protection Compositions and Pesticides], vol. 2, Springer Verlag, 1970, p. 401-412).

The seed dressing formulations usable in accordance with the invention can be used, either directly or after previously having been diluted with water, for the treatment of a wide range of different seed, including the seed of transgenic plants. In this case, additional synergistic effects may also occur in interaction with the substances formed by expression.

For treatment of seed with the seed dressing formulations usable in accordance with the invention, or the preparations prepared therefrom by adding water, all mixing units usable customarily for the seed dressing are useful. Specifically, the procedure in the seed dressing is to place the seed into a mixer, to add the particular desired amount of seed dressing formulations, either as such or after prior dilution with water, and to mix everything until the formulation is distributed homogeneously on the seed. If appropriate, this is followed by a drying process.

Mycotoxins

In addition, the inventive treatment can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fusiformis, C. paspali, C. africana, Stachybotrys* spec. and others.

Material Protection

The inventive active ingredients or compositions can also be used in the protection of materials, for protection of industrial materials against attack and destruction by harmful microorganisms, for example fungi and insects.

In addition, the inventive compounds can be used as antifouling compositions, alone or in combinations with other active ingredients.

Industrial materials in the present context are understood to mean inanimate materials which have been prepared for use in industry. For example, industrial materials which are to be protected by inventive active ingredients from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The inventive active ingredients or compositions may prevent adverse effects, such as rotting, decay, discoloration, decoloration or formation of mould.

In the case of treatment of wood the compounds/compositions according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention or a composition according to the invention; this includes for example direct application, spraying, dipping, injection or any other suitable means.

In addition, the inventive compounds can be used to protect objects which come into contact with saltwater or brackish water, especially hulls, screens, nets, buildings, moorings and signalling systems, from fouling.

The inventive method for controlling unwanted fungi can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive active ingredients may prevent adverse effects, such as rotting, decay, discoloration, decoloration or formation of mould.

Microorganisms capable of degrading or altering the industrial materials include, for example, bacteria, fungi, yeasts, algae and slime organisms. The inventive active ingredients preferably act against fungi, especially moulds, wood-discoloring and wood-destroying fungi (Ascomycetes, Basidiomycetes, Deuteromycetes and Zygomycetes), and against slime organisms and algae. Examples include microorganisms of the following genera: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pi tyophila*; *Trichoderma*, such as *Trichoderma viride*; *Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli*; *Pseudomonas*, such as *Pseudomonas aeruginosa*; *Staphylococcus*, such as *Staphylococcus aureus*, *Candida* spp. and *Saccharomyces* spp., such as *Saccharomyces cerevisae*.

Antimycotic Activity

In addition, the inventive active ingredients also have very good antimycotic activity. They have a very broad antimycotic activity spectrum, especially against dermatophytes and yeasts, moulds and diphasic fungi (for example against *Candida* species, such as *C. albicans*, *C. glabrata*), and *Epidermophyton floccosum*, *Aspergillus* species, such as *A. niger* and *A. fumigants*, *Trichophyton* species, such as *T. mentagrophytes*, *Microsporon* species such as *M. canis* and *M. audouinii*. The list of these fungi by no means constitutes a restriction of the mycotic spectrum covered, and is merely of illustrative character.

The inventive active ingredients can therefore be used both in medical and in non-medical applications.

GMO

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts" or "parts of plants" or "plant parts" have been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference-RNAi-technology or microRNA-miRNA-technology). A heterologous gene that is located in the genome is also called a transgene. A transgene that is defined by its particular location in the plant genome is called a transformation or transgenic event.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content and composition for example cotton or starch, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance.

Plants or plant cultivars (obtained by plant biotechnology methods such as genetic engineering) which may also be treated according to the invention show altered quantity, quality and/or storage-stability of the harvested product and/or altered properties of specific ingredients of the harvested product.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics.

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Plants or plant cultivars (that can be obtained by plant biotechnology methods such as genetic engineering) which may also be treated according to the invention are plants, such as Tobacco plants, with altered post-translational protein modification patterns.

Application Rates and Timing

When using the inventive active ingredients as fungicides, the application rates can be varied within a relatively wide range, depending on the kind of application. The application rate of the inventive active ingredients is
in the case of treatment of plant parts, for example leaves: from 0.1 to 10 000 g/ha, preferably from 10 to 1000 g/ha, more preferably from 10 to 800 g/ha, even more preferably from 50 to 300 g/ha (in the case of application by watering or dripping, it is even possible to reduce the application rate, especially when inert substrates such as rockwool or perlite are used);
in the case of seed treatment: from 2 to 200 g per 100 kg of seed, preferably from 3 to 150 g per 100 kg of seed, more preferably from 2.5 to 25 g per 100 kg of seed, even more preferably from 2.5 to 12.5 g per 100 kg of seed;
in the case of soil treatment: from 0.1 to 10 000 g/ha, preferably from 1 to 5000 g/ha.

These application rates are merely by way of example and are not limiting for the purposes of the invention.

The inventive active ingredients or compositions comprising a compound according to formula (I) can thus be used to protect plants from attack by the pathogens mentioned for a certain period of time after treatment. The period for which protection is provided extends generally for 1 to 28 days, preferably for 1 to 14 days, more preferably for 1 to 10 days, most preferably for 1 to 7 days, after the treatment of the plants with the active ingredients, or for up to 200 days after a seed treatment.

The plants listed can particularly advantageously be treated in accordance with the invention with the compounds of the general formula (I) and the inventive compositions. The preferred ranges stated above for the active ingredients or compositions also apply to the treatment of these plants. Particular emphasis is given to the treatment of plants with the compounds or compositions specifically mentioned in the present text.

PREPARATION EXAMPLES

In analogy to the examples above and according to the general description of the processes of preparing the compounds according to the invention the compounds according to formula (I) in the following Table 1 may be obtained.

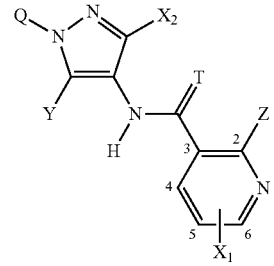

(I)

| Ex n° | Z | $X_1$ | T | $X_2$ | Q | Y | LogP |
|---|---|---|---|---|---|---|---|
| 1 | difluoromethyl | 6-chloro | O | H | phenyl | trifluoromethyl | 2.80[a] |
| 2 | difluoromethyl | H | O | H | 3-methylbutyl | methyl | 2.01[a] |
| 3 | difluoromethyl | H | O | H | 3-isopropylphenyl | trifluoromethyl | 3.51[a] |
| 4 | difluoromethyl | 5-methyl | O | H | phenyl | trifluoromethyl | 2.44[a] |
| 5 | difluoromethyl | H | O | H | 3-chlorophenyl | methyl | 2.25[a] |
| 6 | difluoromethyl | H | O | H | tert-butyl | methyl | 1.63[a] |
| 7 | difluoromethyl | H | O | H | butyl | methyl | 1.69[a] |
| 8 | difluoromethyl | H | O | H | pentan-3-yl | methyl | 1.89[a] |
| 9 | difluoromethyl | H | O | H | phenyl | trifluoromethyl | 2.53[a] |
| 10 | difluoromethyl | H | O | H | 4-chlorophenyl | trifluoromethyl | 3.02[a] |
| 11 | difluoromethyl | H | O | H | cyclopentyl | methyl | 1.83[a] |
| 12 | difluoromethyl | H | O | H | phenyl | methyl | 1.78[a] |
| 13 | difluoromethyl | H | O | H | 2,5-dimethylphenyl | methyl | 2.25[a] |
| 14 | difluoromethyl | H | O | H | isopropyl | cyclopropyl | 1.68[a] |
| 15 | difluoromethyl | H | O | methyl | 3-fluorophenyl | methyl | 1.99[a] |
| 16 | trifluoromethyl | H | O | methyl | 3-fluorophenyl | methyl | 2.27[a] |
| 17 | difluoromethyl | H | O | methyl | phenyl | methyl | 1.81[a] |
| 18 | trifluoromethyl | H | O | methyl | phenyl | methyl | 2.07[a] |
| 19 | trifluoromethyl | H | O | H | 2,6-difluorophenyl | trifluoromethyl | 2.79[a]; 2.72[b] |
| 20 | trifluoromethyl | H | O | H | 2-chlorophenyl | trifluoromethyl | 2.87[a]; 2.80[b] |
| 21 | difluoromethyl | H | O | H | 2,6-difluorophenyl | trifluoromethyl | 2.50[a]; 2.43[b] |
| 22 | difluoromethyl | H | O | H | 2-fluorophenyl | methyl | 1.71[a]; 1.68[b] |
| 23 | difluoromethyl | H | O | H | 4-chlorophenyl | difluoromethyl | 2.69[a] |
| 24 | difluoromethyl | H | O | H | 3-chlorophenyl | difluoromethyl | 2.69[a] |
| 25 | difluoromethyl | H | O | H | 3-fluorophenyl | difluoromethyl | 2.37[a] |
| 26 | difluoromethyl | H | O | H | 3-(difluoromethyl)phenyl | difluoromethyl | 2.48[a] |
| 27 | difluoromethyl | H | O | H | 2-methylphenyl | difluoromethyl | 2.37[a] |
| 28 | difluoromethyl | H | O | H | 4-bromophenyl | difluoromethyl | 2.80[a] |
| 29 | difluoromethyl | H | O | H | 3,5-difluorophenyl | difluoromethyl | 2.62[a] |
| 30 | difluoromethyl | H | O | H | 3-(trifluoromethyl)phenyl | difluoromethyl | 2.88[a] |
| 31 | difluoromethyl | H | O | H | 2-(trifluoromethyl)phenyl | difluoromethyl | 2.51[a] |
| 32 | difluoromethyl | H | O | H | 4-fluorophenyl | difluoromethyl | 2.20[a] |
| 33 | difluoromethyl | H | O | H | 2-fluorophenyl | difluoromethyl | 2.32[a] |
| 34 | difluoromethyl | H | S | H | 3-(difluoromethyl)phenyl | difluoromethyl | 2.90[a] |
| 35 | difluoromethyl | H | O | methyl | phenyl | bromo | 2.07[a] |
| 36 | difluoromethyl | 5-methyl | O | H | tert-butyl | methyl | 1.90[a] |
| 37 | difluoromethyl | 6-chloro | O | H | tert-butyl | methyl | 2.25[a] |
| 38 | difluoromethyl | 5-methyl | O | H | pentan-3-yl | methyl | 2.12[a] |
| 39 | difluoromethyl | 6-chloro | O | H | pentan-3-yl | methyl | 2.51[a] |
| 40 | difluoromethyl | 5-methyl | O | H | cyclopentyl | methyl | 2.09[a] |
| 41 | difluoromethyl | 6-chloro | O | H | cyclopentyl | methyl | 2.46[a] |
| 42 | difluoromethyl | 5-methyl | O | H | isopropyl | cyclopropyl | 1.95[a] |
| 43 | difluoromethyl | 6-chloro | O | H | isopropyl | cyclopropyl | 2.33[a] |
| 44 | difluoromethyl | 5-methyl | O | H | 2,5-dimethylphenyl | methyl | 2.48[a] |
| 45 | difluoromethyl | 6-chloro | O | H | 2,5-dimethylphenyl | methyl | 2.88[a] |
| 46 | difluoromethyl | H | O | H | 4-chlorophenyl | methyl | 2.25[a] |
| 47 | difluoromethyl | H | O | H | 2-chlorophenyl | methyl | 1.94[a] |
| 48 | difluoromethyl | H | O | H | 3-methylphenyl | methyl | 2.11[a] |
| 49 | difluoromethyl | H | O | H | 2-(trifluoromethyl)phenyl | trifluoromethyl | 2.82[a] |
| 50 | difluoromethyl | H | O | H | 4-(trifluoromethyl)phenyl | trifluoromethyl | 3.21[a] |
| 53 | difluoromethyl | H | O | H | 3-(trifluoromethyl)phenyl | 3-chlorophenyl | 3.48[a] |

-continued

| Ex n° | Z | X$_1$ | T | X$_2$ | Q | Y | LogP |
|---|---|---|---|---|---|---|---|
| 54 | difluoromethyl | H | O | H | 3-chlorophenyl | 3-chlorophenyl | 3.31[a] |
| 55 | difluoromethyl | H | O | H | 4-(trifluoromethyl)phenyl | 3-chlorophenyl | 3.58[a] |
| 56 | difluoromethyl | H | O | H | 4-chlorophenyl | 3-chlorophenyl | 3.35[a] |
| 57 | difluoromethyl | H | O | H | 2-fluorophenyl | 3-chlorophenyl | 2.75[a] |
| 58 | difluoromethyl | H | O | H | 3-fluorophenyl | 3-chlorophenyl | 2.98[a] |
| 60 | difluoromethyl | H | O | H | 3-bromophenyl | trifluoromethyl | 3.09[a] |
| 61 | difluoromethyl | H | O | H | 3,5-difluorophenyl | trifluoromethyl | 2.88[a] |
| 62 | difluoromethyl | H | O | H | 3-fluorophenyl | trifluoromethyl | 2.66[a] |
| 63 | difluoromethyl | H | O | H | 4-bromophenyl | trifluoromethyl | 3.13[a] |
| 64 | difluoromethyl | H | O | H | 3-(difluoromethyl)phenyl | trifluoromethyl | 2.71[a] |
| 65 | difluoromethyl | 5-methyl | O | H | 3-chlorophenyl | methyl | 2.51[a] |
| 66 | difluoromethyl | 6-chloro | O | H | 3-chlorophenyl | methyl | 2.88[a] |
| 67 | difluoromethyl | 5-methyl | O | H | 3-methylphenyl | methyl | 2.35[a] |
| 68 | difluoromethyl | 6-chloro | O | H | 3-methylphenyl | methyl | 2.73[a] |
| 69 | difluoromethyl | 5-methyl | O | H | 2-chlorophenyl | methyl | 2.17[a] |
| 70 | difluoromethyl | 6-chloro | O | H | 2-chlorophenyl | methyl | 2.56[a] |
| 71 | difluoromethyl | 5-methyl | O | H | 4-chlorophenyl | methyl | 2.49[a] |
| 72 | difluoromethyl | 6-chloro | O | H | 4-chlorophenyl | methyl | 2.86[a] |
| 73 | difluoromethyl | H | O | H | 2-methylphenyl | trifluoromethyl | 2.71[a] |
| 74 | difluoromethyl | H | O | H | 2-bromophenyl | trifluoromethyl | 2.71[a] |
| 75 | difluoromethyl | H | O | methyl | phenyl | chloro | 2.08[a] |
| 76 | difluoromethyl | H | O | methyl | phenyl | methoxy | 1.88[a] |
| 77 | difluoromethyl | H | O | H | 2-chlorophenyl | trifluoromethyl | 2.58[a]; 2.53[b] |
| 78 | difluoromethyl | H | O | H | 2-(trifluoromethyl)phenyl | 3-chlorophenyl | 3.06[a] |
| 79 | difluoromethyl | H | O | H | 2-chlorophenyl | phenyl | 2.53[a] |
| 80 | difluoromethyl | H | O | H | 2-chlorophenyl | 4-chlorophenyl | 2.90[a] |
| 81 | difluoromethyl | H | O | H | 2-chlorophenyl | 3-chlorophenyl | 2.88[a] |
| 82 | difluoromethyl | H | O | H | 2-chlorophenyl | 3-fluorophenyl | 2.66[a] |
| 83 | difluoromethyl | H | O | H | 2-chlorophenyl | 4-fluorophenyl | 2.66[a] |
| 84 | difluoromethyl | H | O | H | 3-chlorophenyl | trifluoromethyl | 3.00[a] |
| 85 | difluoromethyl | H | O | H | 3-(trifluoromethyl)phenyl | trifluoromethyl | 3.19[a] |
| 86 | difluoromethyl | H | O | H | 3-methylphenyl | trifluoromethyl | 2.73[a] |
| 87 | difluoromethyl | H | O | H | 4-methylphenyl | trifluoromethyl | 2.86[a] |
| 88 | difluoromethyl | H | O | H | 2-fluorophenyl | trifluoromethyl | 2.55[a] |
| 89 | difluoromethyl | H | O | H | 4-fluorophenyl | trifluoromethyl | 2.64[a] |
| 90 | difluoromethyl | H | O | H | 4-isopropylphenyl | trifluoromethyl | 3.55[a] |
| 91 | difluoromethyl | H | O | H | 2,6-dichlorophenyl | trifluoromethyl | 2.94[a] |
| 92 | difluoromethyl | H | O | H | 3,5-dichlorophenyl | trifluoromethyl | 3.64[a] |
| 93 | difluoromethyl | H | O | H | 2,4-dichlorophenyl | trifluoromethyl | 3.27[a] |
| 94 | difluoromethyl | H | O | H | 2,3-dichlorophenyl | trifluoromethyl | 3.11[a] |
| 95 | difluoromethyl | H | O | H | 2,5-dichlorophenyl | trifluoromethyl | 3.15[a] |
| 96 | difluoromethyl | H | O | H | 3,4-dichlorophenyl | trifluoromethyl | 3.51[a] |
| 97 | difluoromethyl | H | O | H | benzyl | trifluoromethyl | 2.71[a] |
| 98 | difluoromethyl | H | O | H | phenyl | methoxy | 1.82[a] |
| 99 | difluoromethyl | H | O | H | 4-methylphenyl | ethyl | 2.34[a] |
| 100 | difluoromethyl | H | O | H | 3-methylphenyl | ethyl | 2.34[a] |
| 101 | difluoromethyl | 5-methyl | O | H | 4-methylphenyl | trifluoromethyl | 3.13[a] |
| 102 | difluoromethyl | H | O | H | 4-chlorophenyl | isopropyl | 2.62[a] |
| 103 | difluoromethyl | H | O | H | 3-chlorophenyl | isopropyl | 2.60[a] |
| 104 | difluoromethyl | H | O | H | 2-methylphenyl | ethyl | 2.18[a] |
| 105 | difluoromethyl | H | O | H | 4-chlorophenyl | ethyl | 2.48[a] |
| 106 | difluoromethyl | H | O | H | 2-methylphenyl | isopropyl | 2.37[a] |
| 107 | difluoromethyl | H | O | H | 3-chlorophenyl | ethyl | 2.48[a] |
| 108 | difluoromethyl | H | O | H | 4-methylphenyl | isopropyl | 2.48[a] |
| 109 | difluoromethyl | H | O | H | 2-chlorophenyl | isopropyl | 2.35[a] |
| 110 | difluoromethyl | H | O | H | 2-chlorophenyl | ethyl | 2.17[a] |
| 111 | difluoromethyl | H | O | H | 2-(trifluoromethyl)phenyl | methyl | 2.08[a] |
| 112 | difluoromethyl | H | O | H | 4-methylphenyl | methyl | 2.10[a] |
| 113 | difluoromethyl | H | O | H | 3-(trifluoromethyl)phenyl | methyl | 2.48[a] |
| 114 | difluoromethyl | H | O | H | 4-(trifluoromethyl)phenyl | methyl | 2.53[a] |
| 115 | difluoromethyl | H | O | H | 2-methylphenyl | methyl | 1.93[a] |
| 116 | difluoromethyl | H | O | H | 3-methylphenyl | isopropyl | 2.50[a] |
| 117 | difluoromethyl | H | O | H | 3-(trifluoromethyl)phenyl | ethyl | 2.69[a] |
| 118 | difluoromethyl | H | O | H | 4-(trifluoromethyl)phenyl | ethyl | 2.76[a] |
| 119 | difluoromethyl | H | O | H | phenyl | ethyl | 2.01[a] |
| 120 | difluoromethyl | H | O | H | phenyl | isopropyl | 2.15[a] |
| 121 | difluoromethyl | H | O | H | phenyl | propyl | 2.28[a] |
| 122 | difluoromethyl | H | O | H | butyl | ethyl | 2.00[a] |
| 123 | difluoromethyl | H | O | H | butyl | isopropyl | 2.18[a] |
| 124 | difluoromethyl | H | O | H | 3-methylbutyl | ethyl | 2.32[a] |
| 125 | difluoromethyl | H | O | H | 3-methylbutyl | isopropyl | 2.53[a] |
| 126 | difluoromethyl | H | O | H | sec-butyl | methyl | 1.63[a] |
| 127 | difluoromethyl | H | O | H | pentan-3-yl | ethyl | 2.20[a] |
| 128 | difluoromethyl | H | O | H | 4-fluorophenyl | 3-chlorophenyl | 2.92[a] |
| 129 | difluoromethyl | H | O | H | 2-(trifluoromethyl)phenyl | phenyl | 2.70[a] |

-continued

| Ex n° | Z | X$_1$ | T | X$_2$ | Q | Y | LogP |
|---|---|---|---|---|---|---|---|
| 130 | difluoromethyl | H | O | H | 2-(trifluoromethyl)phenyl | 4-fluorophenyl | 2.80[a] |
| 131 | difluoromethyl | H | O | H | 2-(trifluoromethyl)phenyl | 3-fluorophenyl | 2.80[a] |
| 132 | difluoromethyl | H | O | H | 2-(trifluoromethyl)phenyl | 4-chlorophenyl | 3.04[a] |
| 133 | difluoromethyl | 5-methyl | O | H | 4-bromophenyl | methyl | 2.59[a] |
| 134 | difluoromethyl | H | O | H | 4-bromophenyl | methyl | 2.34[a] |
| 135 | difluoromethyl | H | O | H | phenyl | bromo | 2.07[a] |
| 136 | difluoromethyl | 5-methoxy | O | H | 3,4-dichlorophenyl | trifluoromethyl | 3.76[a] |
| 137 | difluoromethyl | H | O | H | phenyl | chloro | 2.07[a] |
| 138 | difluoromethyl | 5-methyl | O | H | 3-chlorophenyl | trifluoromethyl | 3.25[a] |
| 139 | difluoromethyl | 5-methyl | O | H | 3-(trifluoromethyl)phenyl | trifluoromethyl | 3.39[a] |
| 140 | difluoromethyl | 5-methyl | O | H | 2-fluorophenyl | trifluoromethyl | 2.77[a] |
| 141 | difluoromethyl | 5-methyl | O | H | 4-fluorophenyl | trifluoromethyl | 2.86[a] |
| 142 | difluoromethyl | 5-methyl | O | H | 4-isopropylphenyl | trifluoromethyl | 3.78[a] |
| 143 | difluoromethyl | H | O | H | phenyl | cyano | 2.28[a] |
| 144 | difluoromethyl | 6-bromo | O | H | 2,3-dichlorophenyl | trifluoromethyl | 3.80[a] |
| 145 | difluoromethyl | 6-bromo | O | H | 4-chlorophenyl | trifluoromethyl | 3.73[a] |
| 146 | difluoromethyl | H | O | H | 2-fluorophenyl | 3-fluorophenyl | 2.51[a] |
| 147 | difluoromethyl | H | O | H | 2-fluorophenyl | 4-fluorophenyl | 2.51[a] |
| 148 | difluoromethyl | H | O | H | 2-fluorophenyl | phenyl | 2.39[a] |
| 149 | difluoromethyl | H | O | H | 2-fluorophenyl | 4-chlorophenyl | 2.73[a] |
| 150 | difluoromethyl | H | O | H | 4-bromophenyl | bromo | 2.67[a] |
| 151 | difluoromethyl | H | O | H | 4-bromophenyl | chloro | 3.47[a] |
| 152 | difluoromethyl | H | O | H | 4-bromophenyl | methoxy | 2.40[a] |
| 153 | difluoromethyl | H | O | H | 3-chlorophenyl | bromo | 2.54[a] |
| 154 | difluoromethyl | 5-methyl | O | H | 3-methylphenyl | trifluoromethyl | 2.96[a] |
| 155 | difluoromethyl | 6-chloro | O | H | 3-chlorophenyl | trifluoromethyl | 3.62[a] |
| 156 | difluoromethyl | 6-chloro | O | H | 3-methylphenyl | trifluoromethyl | 3.33[a] |
| 157 | difluoromethyl | 6-chloro | O | H | 4-methylphenyl | trifluoromethyl | 3.48[a] |
| 158 | difluoromethyl | 6-chloro | O | H | 2-fluorophenyl | trifluoromethyl | 3.15[a] |
| 159 | difluoromethyl | 6-chloro | O | H | 4-isopropylphenyl | trifluoromethyl | 4.13[a] |
| 160 | difluoromethyl | 6-chloro | O | H | 2,6-dichlorophenyl | trifluoromethyl | 3.53[a] |
| 161 | difluoromethyl | 6-chloro | O | H | 3,5-dichlorophenyl | trifluoromethyl | 4.23[a] |
| 162 | difluoromethyl | 6-chloro | O | H | 2,4-dichlorophenyl | trifluoromethyl | 3.85[a] |
| 163 | difluoromethyl | 6-chloro | O | H | 2,3-dichlorophenyl | trifluoromethyl | 3.71[a] |
| 164 | difluoromethyl | 6-chloro | O | H | phenyl | cyano | 2.90[a] |
| 165 | difluoromethyl | 5-methoxy | O | H | 2,3-dichlorophenyl | trifluoromethyl | 3.37[a] |
| 166 | difluoromethyl | 5-methyl | O | H | phenyl | cyano | 2.51[a] |
| 167 | difluoromethyl | 5-methyl | O | H | 2,3-dichlorophenyl | trifluoromethyl | 3.35[a] |
| 168 | difluoromethyl | 5-methoxy | O | H | 2,4-dichlorophenyl | trifluoromethyl | 3.53[a] |
| 169 | difluoromethyl | 5-methoxy | O | H | 4-chlorophenyl | trifluoromethyl | 3.29[a] |
| 170 | difluoromethyl | 5-methyl | O | H | benzyl | trifluoromethyl | 2.95[a] |
| 171 | difluoromethyl | 5-methyl | O | H | 2,6-dichlorophenyl | trifluoromethyl | 3.16[a] |
| 172 | difluoromethyl | 6-bromo | O | H | 2,4-dichlorophenyl | trifluoromethyl | 3.96[a] |
| 173 | difluoromethyl | 6-chloro | O | H | benzyl | trifluoromethyl | 3.33[a] |
| 174 | difluoromethyl | 5-methyl | O | H | 3,5-dichlorophenyl | trifluoromethyl | 3.89[a] |
| 175 | difluoromethyl | 5-methyl | O | H | 2,5-dichlorophenyl | trifluoromethyl | 3.39[a] |
| 176 | difluoromethyl | 6-chloro | O | H | 2,5-dichlorophenyl | trifluoromethyl | 3.76[a] |
| 177 | difluoromethyl | 5-methoxy | O | H | 2,5-dichlorophenyl | trifluoromethyl | 3.39[a] |
| 178 | difluoromethyl | 6-bromo | O | H | 2,5-dichlorophenyl | trifluoromethyl | 3.85[a] |
| 179 | difluoromethyl | 5-methyl | O | H | 3,4-dichlorophenyl | trifluoromethyl | 3.76[a] |
| 180 | difluoromethyl | 6-chloro | O | H | 3,4-dichlorophenyl | trifluoromethyl | 4.11[a] |
| 181 | difluoromethyl | 6-bromo | O | H | 3,4-dichlorophenyl | trifluoromethyl | 4.19[a] |
| 182 | difluoromethyl | H | O | H | 4-(trifluoromethyl)phenyl | 4-chlorophenyl | 3.55[a] |
| 183 | difluoromethyl | H | O | H | 4-chlorophenyl | chloro | 2.55[a] |
| 184 | difluoromethyl | H | O | H | 4-(trifluoromethyl)phenyl | 4-fluorophenyl | 3.31[a] |
| 185 | difluoromethyl | H | O | H | 4-(trifluoromethyl)phenyl | 3-fluorophenyl | 3.31[a] |
| 186 | difluoromethyl | H | O | H | 4-(trifluoromethyl)phenyl | phenyl | 3.24[a] |
| 187 | difluoromethyl | H | O | H | 4-chlorophenyl | 4-fluorophenyl | 3.10[a] |
| 188 | difluoromethyl | H | O | H | 4-(trifluoromethyl)phenyl | chloro | 2.81[a] |
| 189 | difluoromethyl | H | O | H | 4-methoxyphenyl | chloro | 2.09[a] |
| 190 | difluoromethyl | H | O | H | 4-fluorophenyl | chloro | 2.14[a] |
| 191 | difluoromethyl | H | O | H | 2-chlorophenyl | chloro | 2.17[a] |
| 192 | difluoromethyl | H | O | H | 4-fluorophenyl | bromo | 2.17[a] |
| 193 | difluoromethyl | H | O | H | 4-methoxyphenyl | bromo | 2.09[a] |
| 194 | difluoromethyl | H | O | H | 4-chlorophenyl | 4-chlorophenyl | 3.35[a] |
| 195 | difluoromethyl | H | O | H | 4-bromophenyl | 4-fluorophenyl | 3.20[a] |
| 196 | difluoromethyl | H | O | H | 4-bromophenyl | phenyl | 3.10[a] |
| 197 | difluoromethyl | H | O | H | 4-chlorophenyl | 3-fluorophenyl | 3.07[a] |
| 198 | difluoromethyl | H | O | H | 4-chlorophenyl | phenyl | 2.99[a] |
| 199 | difluoromethyl | H | O | H | 4-bromophenyl | 3-chlorophenyl | 3.46[a] |
| 200 | difluoromethyl | H | O | H | 4-bromophenyl | 4-chlorophenyl | 3.46[a] |
| 201 | difluoromethyl | H | O | H | 4-bromophenyl | 3-fluorophenyl | 3.19[a] |
| 202 | difluoromethyl | H | O | H | 3,5-dichlorophenyl | chloro | 3.19[a] |
| 203 | difluoromethyl | H | O | H | 3,5-dichlorophenyl | bromo | 3.23[a] |
| 204 | difluoromethyl | 5-methyl | O | H | 2-methylphenyl | ethyl | 2.44[a] |
| 205 | difluoromethyl | 5-methyl | O | H | 2-methylphenyl | isopropyl | 2.60[a] |

-continued

| Ex n° | Z | X₁ | T | X₂ | Q | Y | LogP |
|---|---|---|---|---|---|---|---|
| 206 | difluoromethyl | 5-methyl | O | H | 3-methylphenyl | ethyl | 2.57[a] |
| 207 | difluoromethyl | 5-methyl | O | H | 4-methylphenyl | ethyl | 2.57[a] |
| 208 | difluoromethyl | 5-methyl | O | H | 4-methylphenyl | isopropyl | 2.73[a] |
| 209 | difluoromethyl | 5-methyl | O | H | 2-chlorophenyl | isopropyl | 2.59[a] |
| 210 | difluoromethyl | 5-methyl | O | H | 3-chlorophenyl | isopropyl | 2.84[a] |
| 211 | difluoromethyl | 5-methyl | O | H | 4-chlorophenyl | isopropyl | 2.86[a] |
| 212 | difluoromethyl | 5-methyl | O | H | 2-chlorophenyl | ethyl | 2.41[a] |
| 213 | difluoromethyl | 5-methyl | O | H | 3-chlorophenyl | ethyl | 2.71[a] |
| 214 | difluoromethyl | 5-methyl | O | H | 4-chlorophenyl | ethyl | 2.73[a] |
| 215 | difluoromethyl | H | O | H | 2-chlorophenyl | methoxy | 1.85[a] |
| 216 | difluoromethyl | H | O | H | 3,5-dichlorophenyl | methoxy | 3.02[a] |
| 217 | difluoromethyl | H | O | H | 2-chlorophenyl | bromo | 2.18[a] |
| 218 | difluoromethyl | H | O | H | 4-chlorophenyl | methoxy | 2.32[a] |
| 219 | difluoromethyl | H | O | H | 4-(trifluoromethyl)phenyl | methoxy | 2.63[a] |
| 220 | difluoromethyl | H | O | H | 4-chlorophenyl | bromo | 2.50[a] |
| 221 | difluoromethyl | H | O | H | 4-chlorophenyl | 2,2,2-trifluoroethoxy | 2.88[a] |
| 222 | difluoromethyl | H | O | H | 4-chlorophenyl | 2,2-difluoroethoxy | 2.60[a] |
| 223 | difluoromethyl | H | O | H | 4-chlorophenyl | cyano | 2.64[a] |
| 224 | difluoromethyl | H | O | H | 4-chlorophenyl | SCF3 | 3.25[a] |
| 225 | difluoromethyl | H | O | H | 4-chlorophenyl | ethoxy | 2.62[a] |
| 226 | difluoromethyl | H | O | H | 4-chlorophenyl | propan-2-oxy | 2.86[a] |
| 227 | difluoromethyl | H | O | H | 4-chlorophenyl | propan-1-oxy | 2.95[a] |
| 228 | difluoromethyl | H | O | H | 4-bromophenyl | SCF3 | 3.43[a] |
| 229 | difluoromethyl | H | O | H | 4-propylphenyl | trifluoromethyl | 3.59[a] |
| 230 | difluoromethyl | H | O | H | 4-ethoxyphenyl | trifluoromethyl | 2.88[a] |
| 231 | difluoromethyl | H | O | H | 4-tert-butylphenyl | trifluoromethyl | 3.79[a] |
| 232 | difluoromethyl | H | O | H | biphenyl-4-yl | trifluoromethyl | 3.59[a] |
| 233 | difluoromethyl | H | O | H | 4-phenoxyphenyl | trifluoromethyl | 3.59[a] |
| 234 | difluoromethyl | H | O | H | 4-iodophenyl | trifluoromethyl | 3.25[a] |
| 235 | difluoromethyl | H | O | H | 4-bromophenyl | 2,2-difluoroethoxy | 2.68[a] |
| 236 | fluoromethyl | H | O | H | 4-chlorophenyl | trifluoromethyl | 2.67[a] |
| 237 | methyl | H | O | H | 4-chlorophenyl | trifluoromethyl | 2.12[a] |
| 238 | difluoromethyl | 5-methyl | O | H | 3-methylphenyl | isopropyl | 2.75[a] |
| 239 | difluoromethyl | 5-methyl | O | H | 3-(trifluoromethyl)phenyl | ethyl | 2.94[a] |
| 240 | difluoromethyl | 5-methyl | O | H | 4-(trifluoromethyl)phenyl | ethyl | 3.00[a] |
| 241 | difluoromethyl | 5-methyl | O | H | 4-(trifluoromethoxy)phenyl | methyl | 2.86[a] |
| 242 | difluoromethyl | H | O | H | 4-(trifluoromethoxy)phenyl | methyl | 2.64[a] |
| 243 | difluoromethyl | H | O | H | 4-[(trifluoromethyl)sulfanyl]phenyl | trifluoromethyl | 3.68[a] |
| 244 | difluoromethyl | H | O | H | 4-(4-chlorophenoxy)phenyl | trifluoromethyl | 4.11[a] |
| 245 | difluoromethyl | H | O | H | 4-(4-methylphenoxy)phenyl | trifluoromethyl | 4.03[a] |
| 246 | difluoromethyl | H | O | H | 4-(methylsulfanyl)phenyl | trifluoromethyl | 2.94[a] |
| 247 | difluoromethyl | H | O | H | 4-(1,1,2,2-tetrafluoroethoxy)phenyl | trifluoromethyl | 3.19[a] |
| 248 | fluoromethyl | H | O | H | 4-bromophenyl | trifluoromethyl | 2.80[a] |
| 249 | methyl | H | O | H | 4-bromophenyl | trifluoromethyl | 2.28[a] |
| 250 | difluoromethyl | 5-methyl | O | H | 4-bromophenyl | methoxymethyl | 2.80[a] |
| 251 | difluoromethyl | H | O | H | 4-bromophenyl | methoxymethyl | 2.58[a] |
| 252 | difluoromethyl | H | O | H | 3,4-dichlorophenyl | chloro | 3.06[a] |
| 253 | difluoromethyl | H | O | H | 3,4,5-trifluorophenyl | chloro | 2.66[a] |
| 254 | difluoromethyl | H | O | H | 4-(cyclohexyloxy)phenyl | trifluoromethyl | 4.11[a] |
| 255 | difluoromethyl | H | O | H | 4-ethylphenyl | trifluoromethyl | 3.19[a] |

Measurement of Log P values was performed according to EEC directive 79/831 Annex V.A8 by HPLC (High Performance Liquid Chromatography) on reversed phase columns with the following methods:

[a] Log P value is determined by measurement of LC-UV, in an acidic range, with 0.1% formic acid in water and acetonitrile as eluent (linear gradient from 10% acetonitrile to 95% acetonitrile).

[b] Log P value is determined by measurement of LC-UV, in a neutral range, with 0.001 molar ammonium acetate solution in water and acetonitrile as eluent (linear gradient from 10% acetonitrile to 95% acetonitrile).

Calibration was done with straight-chain alkan2-ones (with 3 to 16 carbon atoms) with known Log P values (measurement of Log P values using retention times with linear interpolation between successive alkanones). Lambda-max-values were determined using UV-spectra from 200 nm to 400 nm and the peak values of the chromatographic signals.

NMR-Peak Lists

1H-NMR data of selected examples are written in form of 1H-NMR-peak lists. To each signal peak are listed the δ-value in ppm and the signal intensity in round brackets. Between the δ-value—signal intensity pairs are semicolons as delimiters.

The peak list of an example has therefore the form:

$\delta_1$ (intensity$_1$); $\delta_2$ (intensity$_2$); ... ; $\delta_i$ (intensity$_i$); ... ; $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contains therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Example 1: $^1$H-NMR (400.1 MHz, $d_6$-DMSO):
δ = 10.685 (7.3); 8.248 (5.4); 8.227 (6.1); 8.134 (11.3); 7.935 (6.2); 7.914 (5.5); 7.633 (0.7); 7.621 (1.7); 7.611 (6.3); 7.606 (6.4); 7.597 (13.3); 7.593 (16.0); 7.586 (3.4); 7.582 (2.3); 7.572 (0.8); 7.562 (0.7); 7.549 (7.7); 7.542 (5.4); 7.530 (4.6); 7.525 (3.5); 7.357 (3.3); 7.223 (7.7); 7.089 (3.7); 3.410 (0.4); 3.360 (1.0); 3.310 (219.5); 3.261 (1.0); 2.682 (0.9); 2.677 (1.3); 2.672 (0.9); 2.668 (0.5); 2.608 (0.4); 2.562 (0.8); 2.558 (1.0); 2.553 (0.8); 2.530 (3.2); 2.517 (75.4); 2.512 (153.8); 2.508 (208.6); 2.503 (146.3); 2.499 (67.9); 2.468 (0.8); 2.463 (1.0); 2.458 (1.2); 2.454 (1.0); 2.339 (0.9); 2.335 (1.3); 2.330 (0.9); 2.326 (0.5)
Example 2: $^1$H-NMR (300.2 MHz, $d_6$-DMSO):
δ = 10.134 (0.3); 10.036 (2.8); 8.812 (1.8); 8.808 (1.9); 8.796 (2.0); 8.792 (1.9); 8.159 (1.5); 8.134 (1.8); 8.010 (0.7); 7.722 (1.3); 7.706 (1.4); 7.696 (1.3); 7.680 (1.2); 7.596 (5.2); 7.361 (1.3); 7.180 (2.9); 7.158 (0.4); 7.000 (1.4); 4.064 (1.1); 4.050 (2.0); 4.041 (3.9); 4.027 (3.4); 4.017 (4.1); 4.003 (2.4); 3.993 (1.5); 3.324 (9.9); 2.507 (4.2); 2.501 (5.6); 2.495 (4.2); 2.227 (16.0); 2.148 (2.0); 1.989 (13.4); 1.903 (0.5); 1.648 (0.3); 1.628 (0.8); 1.608 (1.9); 1.584 (2.6); 1.562 (2.0); 1.541 (0.9); 1.520 (0.7); 1.497 (0.5); 1.198 (3.5); 1.174 (6.9); 1.151 (3.5); 0.927 (13.8); 0.906 (13.4); 0.892 (2.8); 0.773 (0.3); 0.000 (4.3)
Example 3: $^1$H-NMR (300.2 MHz, $CDCl_3$):
δ = 8.829 (1.0); 8.824 (1.0); 8.813 (1.1); 8.808 (1.0); 8.557 (2.6); 8.135 (1.0); 8.130 (0.9); 8.109 (1.1); 8.104 (1.0); 7.997 (0.8); 7.613 (0.8); 7.597 (0.9); 7.587 (0.8); 7.571 (0.8); 7.439 (0.5); 7.413 (1.6); 7.387 (1.7); 7.373 (0.9); 7.369 (1.7); 7.364 (1.3); 7.348 (0.4); 7.343 (0.8); 7.337 (0.7); 7.325 (1.6); 7.291 (1.0); 7.263 (11.6); 7.152 (1.1); 6.970 (2.3); 6.788 (1.1); 5.301 (0.3); 3.008 (0.7); 2.985 (1.0); 2.962 (0.7); 1.568 (7.3); 1.295 (16.0); 1.272 (15.7); 0.000 (8.1); −0.011 (0.3)
Example 4: $^1$H-NMR (400.1 MHz, $d_6$-DMSO):
δ = 10.598 (7.4); 8.701 (6.0); 8.697 (6.2); 8.098 (11.0); 7.976 (6.0); 7.974 (6.1); 7.634 (0.7); 7.629 (0.6); 7.623 (1.6); 7.619 (1.4); 7.611 (6.0); 7.605 (5.3); 7.597 (12.5); 7.593 (16.0); 7.588 (4.3); 7.586 (4.7); 7.582 (3.1); 7.571 (1.5); 7.566 (1.4); 7.552 (7.9); 7.545 (5.7); 7.533 (4.9); 7.528 (3.8); 7.292 (3.2); 7.157 (7.6); 7.021 (3.7); 3.360 (0.6); 3.310 (99.7); 3.260 (0.6); 2.682 (0.6); 2.677 (0.9); 2.673 (0.7); 2.668 (0.4); 2.613 (0.4); 2.608 (0.4); 2.563 (0.7); 2.558 (1.1); 2.554 (0.8); 2.549 (0.6); 2.531 (2.7); 2.526 (4.3); 2.517 (50.3); 2.513 (104.3); 2.508 (144.9); 2.504 (104.8); 2.499 (52.7); 2.458 (24.5); 2.340 (0.7); 2.335 (1.0); 2.330 (0.7); 2.075 (0.5); 1.996 (1.1); 1.183 (0.7); 1.165 (0.3)
Example 5: $^1$H-NMR (400.1 MHz, $d_6$-DMSO):
δ = 10.273 (2.9); 8.836 (2.2); 8.826 (2.3); 8.207 (1.4); 8.188 (1.5); 7.970 (5.7); 7.747 (0.9); 7.731 (1.3); 7.719 (1.0); 7.671 (2.5); 7.667 (4.0); 7.603 (0.6); 7.583 (2.3); 7.567 (6.6); 7.554 (1.5); 7.549 (1.4); 7.532 (2.3); 7.527 (2.6); 7.521 (1.9); 7.516 (1.7); 7.510 (1.9); 7.504 (1.3); 7.345 (1.6); 7.210 (3.6); 7.075 (1.7); 4.064 (1.0); 4.047 (2.9); 4.029 (3.0); 4.011 (1.1); 3.318 (5.5); 2.677 (0.3); 2.517 (25.2); 2.513 (49.9); 2.508 (68.0); 2.504 (52.3); 2.463 (2.2); 2.459 (2.1); 2.413 (0.5); 2.377 (0.6); 2.351 (16.0); 2.302 (0.6); 2.289 (0.6); 2.276 (0.4); 2.257 (0.5); 2.231 (0.4); 2.191 (0.4); 1.995 (13.3); 1.916 (5.6); 1.364 (1.5); 1.243 (0.4); 1.200 (3.5); 1.183 (7.0); 1.165 (3.6)
Example 6: $^1$H-NMR (400.1 MHz, $d_6$-DMSO):
δ = 9.928 (0.5); 8.817 (0.4); 8.813 (0.4); 8.805 (0.4); 8.801 (0.4); 8.162 (0.3); 8.145 (0.4); 8.143 (0.4); 7.546 (1.2); 7.317 (0.3); 7.182 (0.7); 7.047 (0.4); 3.309 (4.2); 2.531 (0.5); 2.526 (0.8); 2.517 (6.6); 2.513 (13.2); 2.508 (17.8); 2.504 (12.8); 2.499 (6.4); 2.463 (0.4); 2.458 (0.3); 2.363 (4.1); 1.996 (0.8); 1.584 (16.0); 1.183 (0.4)
Example 7: $^1$H-NMR (300.2 MHz, $d_6$-DMSO):
δ = 10.035 (2.4); 8.813 (1.7); 8.808 (1.7); 8.797 (1.8); 8.792 (1.7); 8.160 (1.3); 8.136 (1.6); 8.133 (1.6); 8.000 (0.5); 7.722 (1.2); 7.706 (1.2); 7.696 (1.1); 7.680 (1.1); 7.600 (5.0); 7.362 (1.3); 7.181 (2.9); 7.001 (1.4); 4.065 (0.9); 4.041 (3.2); 4.034 (2.2); 4.017 (3.7); 4.010 (4.2); 3.993 (1.6); 3.986 (2.3); 3.332 (13.8); 2.513 (1.7); 2.507 (3.6); 2.501 (4.9); 2.495 (3.6); 2.490 (1.8); 2.223 (16.0); 2.150 (1.5); 1.989 (12.5); 1.909 (0.6); 1.737 (0.6); 1.713 (1.6); 1.689 (2.2); 1.665 (1.6); 1.639 (0.6); 1.309 (1.1); 1.284 (1.9); 1.258 (2.0); 1.234 (1.4); 1.210 (0.5); 1.198 (3.4); 1.174 (6.6); 1.151 (3.3); 0.922 (4.3); 0.898 (8.5); 0.873 (3.3); 0.000 (3.8)
Example 8: $^1$H-NMR (400.1 MHz, $d_6$-DMSO):
δ = 10.020 (2.2); 8.815 (1.4); 8.812 (1.6); 8.804 (1.6); 8.800 (1.6); 8.179 (1.2); 8.160 (1.3); 7.720 (1.0); 7.707 (1.3); 7.699 (5.5); 7.688 (1.0); 7.336 (1.3); 7.201 (2.9); 7.065 (1.4); 5.760 (0.4); 4.001 (0.5); 3.989 (0.8); 3.978 (1.0); 3.966 (0.8); 3.954 (0.5); 3.315 (0.9); 2.531 (0.7); 2.517 (14.0); 2.513 (28.9); 2.508 (39.7); 2.504 (29.6); 2.499 (15.4); 2.458 (0.5); 2.230 (15.3); 2.029 (0.4); 1.996 (0.5); 1.879 (0.7); 1.861 (0.9); 1.856 (0.8); 1.845 (1.4); 1.838 (1.0); 1.827 (1.4); 1.822 (1.5); 1.804 (1.3); 1.792 (0.5); 1.785 (0.6); 1.780 (0.6); 1.773 (1.3); 1.761 (1.4); 1.755 (1.5); 1.743 (1.6); 1.739 (1.2); 1.727 (1.0); 1.721 (0.9); 1.709 (0.7); 1.703 (0.4); 0.702 (7.3); 0.683 (16.0); 0.665 (7.3); 0.395 (0.4)

-continued

Example 9: $^1$H-NMR (300.2 MHz, d$_6$-DMSO):
δ = 10.665 (8.2); 8.867 (3.9); 8.862 (4.4); 8.851 (4.5); 8.846 (4.4); 8.164 (3.5); 8.141 (3.9); 8.138 (4.1); 8.121 (10.7); 8.119 (10.8); 7.780 (3.0); 7.764 (3.1); 7.754 (2.9); 7.738 (2.8); 7.640 (0.5); 7.634 (0.3); 7.624 (1.3); 7.611 (5.0); 7.604 (5.6); 7.591 (11.4); 7.586 (16.0); 7.578 (4.7); 7.573 (3.8); 7.552 (8.3); 7.541 (5.3); 7.526 (4.1); 7.520 (3.1); 7.383 (3.6); 7.203 (8.2); 7.023 (4.0); 5.762 (3.1); 3.334 (24.1); 2.515 (5.1); 2.509 (11.5); 2.502 (16.3); 2.496 (12.2); 2.490 (6.0); 2.068 (0.3); 1.236 (0.5); 1.213 (0.4); 0.011 (0.7); 0.008 (0.4); 0.000 (21.3); −0.011 (0.9)

Example 10: $^1$H-NMR (300.2 MHz, d$_6$-DMSO):
δ = 10.693 (7.4); 8.866 (3.7); 8.861 (4.1); 8.850 (4.1); 8.845 (4.0); 8.159 (3.5); 8.151 (10.1); 8.149 (10.2); 8.138 (3.9); 8.135 (4.0); 7.779 (2.8); 7.763 (2.8); 7.753 (2.7); 7.737 (2.6); 7.703 (0.9); 7.694 (8.0); 7.687 (3.2); 7.672 (4.0); 7.664 (16.0); 7.655 (2.6); 7.603 (11.6); 7.574 (6.3); 7.380 (3.1); 7.200 (7.3); 7.020 (3.5); 5.762 (0.5); 3.333 (23.2); 2.515 (5.5); 2.509 (12.3); 2.503 (17.3); 2.496 (12.8); 2.490 (6.2); 0.011 (0.8); 0.000 (26.5); −0.011 (1.1)

Example 11: $^1$H-NMR (400.1 MHz, d$_6$-DMSO):
δ = 10.007 (2.3); 8.816 (1.5); 8.812 (1.6); 8.804 (1.6); 8.800 (1.5); 8.153 (1.3); 8.136 (1.3); 8.134 (1.4); 7.722 (1.1); 7.710 (1.1); 7.703 (1.0); 7.691 (1.0); 7.619 (4.5); 7.317 (1.2); 7.181 (2.8); 7.046 (1.4); 4.686 (0.7); 4.667 (1.2); 4.650 (0.8); 3.310 (7.0); 2.530 (0.5); 2.517 (9.8); 2.512 (19.7); 2.508 (26.5); 2.503 (18.7); 2.499 (8.7); 2.244 (16.0); 2.040 (0.5); 2.028 (0.9); 2.008 (1.2); 1.996 (1.5); 1.980 (0.6); 1.967 (0.4); 1.964 (0.4); 1.947 (1.0); 1.932 (1.2); 1.929 (1.2); 1.917 (0.9); 1.913 (0.8); 1.901 (0.6); 1.898 (0.6); 1.886 (0.4); 1.881 (0.4); 1.862 (0.4); 1.844 (0.8); 1.831 (1.1); 1.822 (1.2); 1.811 (0.7); 1.806 (0.8); 1.660 (0.4); 1.651 (0.9); 1.640 (1.0); 1.634 (1.3); 1.623 (1.1); 1.613 (0.7)

Example 12: $^1$H-NMR (300.2 MHz, d$_6$-DMSO):
δ = 10.250 (1.7); 8.836 (1.0); 8.831 (1.0); 8.820 (1.1); 8.815 (1.0); 8.206 (0.8); 8.180 (0.9); 7.920 (3.2); 7.749 (0.7); 7.733 (0.7); 7.723 (0.7); 7.707 (0.7); 7.555 (5.8); 7.541 (7.7); 7.526 (0.5); 7.471 (0.6); 7.457 (0.9); 7.442 (1.0); 7.426 (0.5); 7.392 (0.9); 7.212 (1.9); 7.032 (0.9); 4.065 (1.2); 4.041 (3.6); 4.017 (3.7); 3.993 (1.3); 3.326 (6.8); 2.513 (1.2); 2.507 (2.4); 2.501 (3.3); 2.495 (2.4); 2.490 (1.2); 2.309 (10.0); 1.989 (16.0); 1.909 (1.4); 1.198 (4.2); 1.174 (8.4); 1.151 (4.2); 0.000 (2.7)

Example 13: $^1$H-NMR (499.9 MHz, d$_6$-DMSO):
δ = 10.230 (3.1); 8.835 (1.8); 8.828 (1.8); 8.826 (1.8); 8.212 (1.6); 8.196 (1.8); 7.895 (5.1); 7.745 (1.2); 7.735 (1.3); 7.729 (1.3); 7.720 (1.2); 7.338 (1.2); 7.321 (1.7); 7.305 (2.9); 7.265 (2.0); 7.250 (1.2); 7.230 (2.6); 7.122 (1.4); 7.113 (3.1); 3.323 (16.0); 2.513 (5.0); 2.510 (4.0); 2.349 (12.2); 2.062 (16.0); 2.001 (1.1); 1.961 (12.6); 1.188 (0.6)

Example 14: $^1$H-NMR (400.1 MHz, d$_6$-DMSO):
δ = 9.890 (2.4); 8.830 (1.7); 8.826 (1.8); 8.818 (1.8); 8.814 (1.7); 8.135 (1.4); 8.117 (1.5); 8.115 (1.5); 7.743 (1.2); 7.731 (1.2); 7.723 (1.2); 7.711 (1.1); 7.514 (5.5); 7.342 (1.3); 7.207 (3.0); 7.072 (1.5); 5.760 (0.5); 4.841 (0.4); 4.825 (1.0); 4.809 (1.4); 4.792 (1.0); 4.776 (0.4); 3.310 (10.5); 2.530 (0.9); 2.517 (11.1); 2.513 (21.7); 2.508 (29.0); 2.503 (20.8); 2.499 (10.4); 2.463 (0.6); 2.458 (0.6); 1.733 (0.7); 1.725 (0.7); 1.719 (0.5); 1.712 (1.3); 1.704 (0.5); 1.698 (0.8); 1.691 (0.8); 1.678 (0.4); 1.411 (15.9); 1.394 (16.0); 1.361 (0.4); 0.959 (0.8); 0.949 (2.2); 0.943 (2.4); 0.939 (1.3); 0.933 (1.3); 0.928 (2.3); 0.923 (2.3); 0.913 (1.0); 0.686 (1.0); 0.677 (2.4); 0.671 (2.7); 0.663 (2.6); 0.658 (2.5); 0.648 (0.9)

Example 15: $^1$H-NMR (300.2 MHz, CDCl$_3$):
δ = 8.800 (1.1); 8.795 (1.1); 8.784 (1.2); 8.779 (1.1); 8.127 (1.0); 8.122 (1.1); 8.101 (1.2); 8.096 (1.2); 7.589 (0.9); 7.573 (1.0); 7.563 (0.9); 7.547 (0.9); 7.473 (0.4); 7.452 (0.6); 7.448 (0.6); 7.445 (1.0); 7.425 (1.2); 7.419 (0.7); 7.417 (0.7); 7.398 (0.8); 7.292 (1.0); 7.277 (1.2); 7.274 (1.4); 7.270 (1.7); 7.264 (10.5); 7.255 (0.5); 7.245 (2.3); 7.241 (2.1); 7.234 (0.7); 7.216 (0.8); 7.209 (1.2); 7.201 (0.7); 7.171 (1.3); 7.116 (0.5); 7.113 (0.6); 7.108 (0.5); 7.105 (0.5); 7.088 (1.0); 7.085 (0.9); 7.081 (0.8); 7.077 (0.8); 7.061 (0.5); 7.057 (0.5); 7.052 (0.5); 7.049 (0.5); 6.988 (2.6); 6.805 (1.3); 5.301 (6.8); 2.328 (13.1); 2.291 (14.9); 2.043 (0.4); 1.607 (16.0); 0.000 (6.9)

Example 16: $^1$H-NMR (300.2 MHz, CDCl$_3$):
δ = 8.792 (1.5); 8.776 (1.6); 8.001 (1.4); 7.976 (1.6); 7.619 (1.4); 7.603 (1.4); 7.593 (1.3); 7.577 (1.2); 7.522 (2.0); 7.459 (0.5); 7.437 (0.8); 7.430 (1.2); 7.410 (1.5); 7.383 (0.9); 7.273 (2.1); 7.223 (1.6); 7.221 (1.6); 7.198 (2.5); 7.194 (2.7); 7.171 (0.9); 7.163 (1.4); 7.156 (0.9); 7.106 (0.7); 7.098 (0.6); 7.081 (1.1); 7.077 (1.1); 7.070 (1.0); 7.051 (0.6); 7.045 (0.5); 7.043 (0.5); 2.721 (12.7); 2.275 (15.2); 2.221 (16.0); 2.129 (0.6); 1.773 (4.6); 0.000 (1.2)

Example 17: $^1$H-NMR (300.2 MHz, CDCl$_3$):
δ = 8.747 (1.4); 8.742 (1.4); 8.731 (1.5); 8.726 (1.4); 8.041 (1.3); 8.037 (1.3); 8.015 (1.4); 8.011 (1.4); 7.807 (1.6); 7.516 (1.1); 7.499 (1.1); 7.490 (1.1); 7.473 (1.8); 7.452 (1.7); 7.448 (2.3); 7.443 (1.8); 7.432 (1.1); 7.424 (3.5); 7.404 (2.8); 7.398 (5.3); 7.387 (1.9); 7.381 (1.8); 7.375 (2.3); 7.370 (1.5); 7.359 (1.7); 7.349 (0.5); 7.342 (0.4); 7.336 (0.6); 7.275 (1.7); 7.185 (1.4); 7.002 (2.8); 6.819 (1.4); 4.113 (0.5); 4.090 (0.6); 2.739 (2.4); 2.232 (14.9); 2.211 (16.0); 2.028 (2.6); 1.902 (5.7); 1.273 (0.6); 1.249 (1.3); 1.225 (0.6); 0.000 (1.0)

Example 18: $^1$H-NMR (300.2 MHz, CDCl$_3$):
δ = 8.852 (0.7); 8.841 (0.7); 8.090 (0.6); 8.067 (0.7); 7.673 (0.6); 7.657 (0.7); 7.647 (0.6); 7.631 (0.6); 7.482 (1.2); 7.460 (4.0); 7.442 (0.5); 7.436 (0.7); 7.412 (0.5); 7.406 (0.5); 7.394 (0.5); 7.384 (0.6); 7.372 (0.4); 7.262 (39.4); 7.240 (0.5); 6.949 (0.7); 5.301 (0.3); 2.311 (16.0); 1.563 (23.2); 0.010 (1.1); 0.000 (28.4); −0.011 (1.3)

Example 19: $^1$H-NMR (400.0 MHz, d$_6$-DMSO):
δ = 10.733 (12.0); 8.897 (6.4); 8.885 (6.4); 8.316 (0.8); 8.295 (16.0); 8.225 (6.0); 8.206 (6.6); 7.901 (5.5); 7.890 (5.6); 7.882 (5.2); 7.870 (4.9); 7.840 (4.5); 7.824 (2.8); 7.818 (2.7); 7.807 (2.0); 7.802 (5.6); 7.797 (2.3); 7.786 (2.8); 7.780 (3.4); 7.764 (1.5); 7.506 (8.5); 7.484 (14.0); 7.464 (7.0); 4.768 (0.4); 4.021 (0.3); 3.324 (110.6); 2.944 (1.0); 2.785 (0.8); 2.675 (1.2); 2.671 (1.7); 2.667 (1.3); 2.524 (4.2); 2.511 (98.8); 2.507 (197.8); 2.502 (260.8); 2.498 (192.8); 2.494 (97.2); 2.338 (0.6); 2.334 (1.2); 2.329 (1.7); 2.325 (1.2); 1.989 (1.4); 1.957 (0.8); 1.398 (2.1); 1.193 (0.4); 1.175 (0.7); 1.157 (0.4); 0.914 (2.7); 0.146 (2.3); 0.095 (2.1); 0.033 (0.4); 0.008 (19.2); 0.000 (470.5); −0.008 (22.4); −0.042 (0.5); −0.150 (2.3)

Example 20: $^1$H-NMR (400.0 MHz, d$_6$-DMSO):
δ = 10.670 (9.2); 8.891 (4.7); 8.879 (4.7); 8.206 (16.0); 8.190 (4.9); 8.188 (4.9); 7.893 (4.1); 7.882 (4.1); 7.874 (3.8); 7.862 (3.6); 7.770 (4.3); 7.767 (4.7); 7.750 (6.9); 7.747 (6.9); 7.735 (3.8); 7.732 (4.3); 7.716 (4.8); 7.712 (5.4); 7.689 (3.1); 7.685 (3.2); 7.670 (5.5); 7.666 (4.8); 7.650 (3.3); 7.646 (2.8); 7.598 (4.0); 7.594 (4.1); 7.578 (5.5); 7.575 (5.5); 7.559 (2.3); 7.556 (2.2); 5.758 (1.1); 4.104 (0.7); 4.091 (0.7); 3.329 (24.9); 3.176 (3.1); 3.163 (3.0); 2.672 (0.4); 2.525 (1.1); 2.512 (23.9); 2.507 (48.6); 2.503 (64.1); 2.498 (46.8); 2.494 (22.9); 2.330 (0.4); 1.259 (0.3); 1.235 (0.8); 0.000 (8.0)

Example 21: $^1$H-NMR (400.0 MHz, d$_6$-DMSO):
δ = 10.699 (5.2); 8.868 (6.3); 8.864 (6.8); 8.856 (6.8); 8.852 (6.7); 8.284 (16.0); 8.185 (5.8); 8.166 (6.3); 8.109 (0.6); 8.093 (0.6); 7.842 (1.3); 7.826 (2.8); 7.821 (2.6); 7.810 (2.0); 7.805 (5.4); 7.799 (2.1); 7.788 (2.8); 7.783 (3.7); 7.776 (5.0); 7.765 (5.4); 7.757 (4.5); 7.745 (4.2); 7.507 (8.2); 7.486 (13.5); 7.466 (6.9); 7.350 (5.0); 7.215 (11.4); 7.080 (5.6); 6.605 (0.7); 6.602 (0.6); 6.593 (0.5); 6.589 (0.7); 5.758 (11.0); 4.057 (0.4); 4.039 (1.0); 4.022 (1.1); 4.004 (0.4); 3.334 (56.6); 2.954 (9.9); 2.678 (0.4); 2.673 (0.5); 2.669 (0.4); 2.526 (1.3); 2.513 (28.6); 2.509 (58.2); 2.504 (77.0); 2.499 (56.2); 2.495 (27.5); 2.335 (0.3); 2.331 (0.5); 2.326 (0.4); 2.081 (0.4); 1.990 (4.6); 1.398 (0.4); 1.235 (0.4); 1.193 (1.3); 1.176 (2.5); 1.158 (1.2); 0.146 (0.5); 0.008 (3.9); 0.000 (103.0); −0.009 (4.0); −0.150 (0.5)

Example 22: $^1$H-NMR (400.0 MHz, d$_6$-DMSO):
δ = 10.269 (4.7); 8.833 (2.6); 8.830 (2.8); 8.821 (2.7); 8.818 (2.7); 8.206 (2.4); 8.187 (2.6); 7.959 (8.4); 7.745 (1.9); 7.733 (1.9); 7.725 (1.9); 7.713 (1.8); 7.619 (0.5); 7.614 (0.6); 7.606 (0.6); 7.601 (1.1); 7.595 (1.3); 7.586 (2.3); 7.582 (2.5); 7.576 (1.5); 7.567 (3.6); 7.563 (3.3); 7.547 (1.8); 7.543 (1.3); 7.524 (1.7); 7.521 (1.8); 7.499 (2.0); 7.495 (1.9); 7.477 (1.2); 7.475 (1.1); 7.424 (1.8); 7.422 (1.8); 7.404 (2.8); 7.386 (1.2); 7.383 (1.2); 7.350 (2.1); 7.215 (4.7); 7.080 (2.3); 3.326 (87.8); 2.675 (0.6); 2.671 (0.8); 2.667 (0.6); 2.524 (1.9); 2.510 (43.3); 2.506 (86.6); 2.502 (113.9); 2.497 (83.7); 2.333 (0.5); 2.329 (0.7); 2.324 (0.6); 2.148 (15.7); 2.146 (16.0); 0.146 (0.6); 0.008 (4.3); 0.000 (119.0); −0.009 (4.6); −0.149 (0.6)

Example 23: $^1$H-NMR (400.1 MHz, d$_6$-DMSO):
δ = 10.692 (5.0); 8.864 (3.6); 8.860 (3.9); 8.852 (4.0); 8.848 (3.9); 8.270 (3.1); 8.251 (3.4); 8.123 (8.8); 7.774 (2.6); 7.762 (2.6); 7.754 (2.6); 7.742 (2.5); 7.668 (0.9); 7.662 (6.8); 7.656 (3.0); 7.645 (4.0); 7.640 (16.0); 7.633 (3.2); 7.606 (12.8); 7.601 (3.9); 7.589 (2.7); 7.584 (5.9); 7.560 (0.5); 7.440 (2.3); 7.364 (2.8); 7.311 (5.3); 7.229 (6.6); 7.182 (2.6); 7.094 (3.2); 3.423 (1.0); 3.373 (3.6); 3.323 (532.0); 3.273 (3.9); 3.223 (0.7); 3.201 (0.5); 2.682 (0.4); 2.677 (0.6); 2.673 (0.4); 2.562 (0.5); 2.558 (0.8); 2.554 (0.7); 2.531 (2.7); 2.526 (3.9); 2.517 (33.8); 2.513 (68.1); 2.508 (92.6); 2.504 (66.8); 2.499 (33.5); 2.463 (1.7); 2.458 (1.6); 2.340 (0.5); 2.335 (0.6); 2.330 (0.5); 2.071 (0.6); 1.995 (0.3)

Example 24: $^1$H-NMR (400.1 MHz, d$_6$-DMSO):
δ = 10.714 (8.1); 8.867 (5.3); 8.863 (5.9); 8.855 (5.9); 8.851 (5.9); 8.276 (4.7); 8.257 (5.2); 8.145 (13.0); 7.777 (3.8); 7.765 (4.0); 7.757 (4.0); 7.745 (3.7); 7.663 (8.3); 7.640 (0.9); 7.631 (1.1); 7.621 (10.0); 7.618 (6.8); 7.612 (11.0); 7.608 (16.0); 7.598 (2.5); 7.590 (2.9); 7.587 (2.9); 7.582 (5.0); 7.577 (4.5); 7.570 (4.4); 7.566 (3.6); 7.558 (2.2); 7.554 (1.9); 7.470 (3.3); 7.368 (4.2); 7.341 (7.8); 7.233 (9.6); 7.212 (3.9); 7.098 (4.7); 3.368 (0.8); 3.318 (114.0); 3.268 (0.7); 2.677 (0.4); 2.563 (0.4); 2.558 (0.5); 2.554 (0.4); 2.531 (1.3); 2.517 (21.7); 2.513 (44.0); 2.508 (60.2); 2.504 (44.5); 2.499 (22.9); 2.459 (0.9); 2.335 (0.4); 2.075 (0.8); 1.995 (1.1); 1.200 (0.3); 1.182 (0.7); 1.165 (0.4)

Example 25: $^1$H-NMR (400.1 MHz, d$_6$-DMSO):
δ = 10.702 (10.0); 8.866 (6.7); 8.862 (7.1); 8.854 (7.1); 8.850 (6.8); 8.272 (6.0); 8.253 (6.4); 8.136 (16.0); 7.776 (4.8); 7.764 (4.9); 7.757 (4.7); 7.745 (4.3); 7.658 (2.5); 7.642 (2.5); 7.637 (6.2); 7.621 (5.4); 7.617 (4.3); 7.608 (1.0); 7.600 (3.5); 7.484 (3.0); 7.479 (5.4); 7.473 (4.8); 7.465 (6.2); 7.459 (11.7); 7.449 (4.2); 7.440 (5.7); 7.425 (3.2); 7.419 (2.7); 7.403 (5.3); 7.398 (4.7); 7.382 (2.7); 7.376 (2.4); 7.366 (5.5); 7.336 (9.7); 7.231 (11.5); 7.207 (4.9); 7.096 (5.6); 3.413 (0.6); 3.362 (2.1); 3.313 (287.1); 3.262 (1.3); 2.681 (0.9); 2.677 (1.2); 2.673 (0.9); 2.608 (0.4); 2.558 (1.8); 2.553 (1.8); 2.548 (1.5); 2.517 (83.0); 2.512 (161.0); 2.508 (213.0); 2.504 (151.4); 2.499 (72.0); 2.467 (0.4); 2.462 (0.7); 2.457 (1.2); 2.452 (1.2); 2.408 (0.4); 2.339 (1.0); 2.335 (1.3); 2.330 (1.0); 2.074 (1.0); 1.995 (0.9); 1.256 (0.7); 1.183 (0.5); 0.866 (0.9); 0.849 (0.3)

Example 26: $^1$H-NMR (400.1 MHz, d$_6$-DMSO):
δ = 10.719 (7.1); 8.869 (4.5); 8.865 (4.9); 8.857 (4.9); 8.853 (4.9); 8.285 (4.0); 8.265 (4.3); 8.154 (10.7); 7.779 (6.9); 7.770 (11.7); 7.760 (8.1); 7.744 (15.8); 7.742 (16.0); 7.734 (6.1); 7.728 (5.7); 7.713 (1.3); 7.470 (2.7); 7.374 (3.5); 7.341 (6.4); 7.307 (3.8); 7.239 (8.0); 7.212 (3.2); 7.168 (8.0); 7.149 (0.4); 7.104 (3.9); 7.029 (3.9); 3.365 (0.6); 3.315 (96.0); 3.265 (1.0); 2.682 (0.4); 2.677 (0.5); 2.673 (0.4); 2.563 (0.4); 2.558 (0.6); 2.554 (0.6); 2.517 (28.4); 2.513 (56.3); 2.508 (76.1); 2.504 (55.7); 2.499 (28.5); 2.463 (1.6); 2.458 (1.5); 2.340 (0.4); 2.335 (0.5); 2.330 (0.4); 2.079 (0.6); 1.995 (1.3); 1.200 (0.4); 1.183 (0.7); 1.165 (0.4)

Example 27: $^1$H-NMR (400.1 MHz, d$_6$-DMSO):
δ = 10.658 (2.8); 8.863 (1.8); 8.859 (2.0); 8.851 (2.0); 8.847 (2.0); 8.285 (1.6); 8.266 (1.8); 8.086 (4.2); 7.772 (1.3); 7.760 (1.4); 7.752 (1.3); 7.740 (1.3); 7.500 (0.5); 7.493 (0.7); 7.486 (0.6); 7.481 (1.3); 7.472 (1.3); 7.469 (1.2); 7.460 (1.7); 7.437 (2.5); 7.419 (1.3); 7.395 (0.5); 7.380 (1.9); 7.375 (2.4); 7.371 (3.1); 7.369 (3.1); 7.362 (4.1); 7.322 (1.3); 7.245 (3.2); 7.193 (2.5); 7.111 (1.6); 7.064 (1.3); 4.047 (0.6); 4.029 (0.6); 3.315 (62.0); 3.265 (0.6); 2.531 (1.1); 2.517 (13.0); 2.513 (26.0); 2.508 (35.2); 2.504 (25.9); 2.499 (13.3); 2.463 (0.8); 2.459 (0.7); 1.998 (16.0); 1.950 (0.4); 1.256 (0.5); 1.201 (0.7); 1.183 (1.4); 1.165 (0.7); 0.867 (0.6)

Example 28: $^1$H-NMR (400.1 MHz, d$_6$-DMSO):
δ = 10.692 (7.0); 8.864 (4.3); 8.860 (4.6); 8.852 (4.6); 8.848 (4.4); 8.271 (3.8); 8.251 (4.1); 8.126 (10.4); 7.801 (1.5); 7.793 (12.0); 7.788 (4.3); 7.776 (6.7); 7.771 (16.0); 7.764 (4.3); 7.755 (3.2); 7.743 (3.1); 7.542 (11.5); 7.520 (9.8); 7.442 (2.6); 7.364 (3.2); 7.312 (6.1); 7.230 (7.3); 7.183 (3.0); 7.095 (3.6); 3.412 (0.4); 3.362 (1.0); 3.312 (222.8); 3.262 (1.3); 2.682 (0.8); 2.677 (1.1); 2.672 (0.8); 2.608 (0.4); 2.563 (0.7); 2.558 (0.9); 2.553 (0.7); 2.548 (0.6); 2.517 (65.7); 2.513 (130.7); 2.508 (174.8); 2.504 (124.6); 2.499 (59.5); 2.463 (1.2); 2.458 (1.3); 2.454 (0.9); 2.340 (0.8); 2.335 (1.1); 2.330 (0.8); 2.070 (0.4); 1.996 (0.4)

Example 29: $^1$H-NMR (400.1 MHz, $d_6$-DMSO):
δ = 10.740 (8.6); 8.867 (5.1); 8.864 (5.7); 8.855 (5.7); 8.852 (5.6); 8.272 (4.6); 8.253 (5.1); 8.170 (12.5); 8.134 (0.4); 7.778 (3.8); 7.766 (3.9); 7.759 (3.8); 7.747 (3.7); 7.511 (5.1); 7.504 (2.0); 7.492 (2.9); 7.487 (5.2); 7.481 (3.3); 7.469 (1.8); 7.463 (2.8); 7.458 (1.7); 7.432 (0.7); 7.425 (1.3); 7.413 (7.0); 7.408 (7.3); 7.394 (8.3); 7.388 (7.4); 7.382 (9.8); 7.363 (4.8); 7.333 (0.5); 7.253 (3.8); 7.229 (9.2); 7.094 (4.4); 4.029 (0.3); 3.412 (0.7); 3.363 (1.2); 3.312 (374.8); 3.262 (3.6); 3.212 (0.5); 2.682 (1.2); 2.677 (1.7); 2.673 (1.2); 2.609 (0.6); 2.564 (1.0); 2.560 (0.8); 2.554 (0.3); 2.531 (7.1); 2.517 (94.7); 2.513 (189.6); 2.508 (257.3); 2.504 (187.6); 2.499 (95.8); 2.408 (0.8); 2.390 (0.5); 2.380 (0.3); 2.340 (1.3); 2.335 (1.7); 2.330 (1.2); 2.075 (0.8); 1.995 (1.2); 1.306 (1.1); 1.288 (2.4); 1.256 (10.9); 1.201 (0.7); 1.183 (0.8); 1.165 (0.4); 0.883 (4.9); 0.867 (16.0); 0.849 (6.4)
Example 30: $^1$H-NMR (400.1 MHz, $d_6$-DMSO):
δ = 10.741 (11.9); 8.863 (6.6); 8.859 (7.1); 8.851 (7.0); 8.847 (6.8); 8.280 (6.0); 8.260 (6.4); 8.175 (16.0); 7.920 (13.0); 7.906 (14.6); 7.851 (5.6); 7.830 (5.0); 7.809 (2.0); 7.774 (4.8); 7.762 (4.8); 7.755 (4.6); 7.743 (4.3); 7.493 (4.0); 7.364 (14.4); 7.235 (5.6); 7.229 (12.1); 7.095 (5.7); 3.303 (43.5); 2.674 (0.8); 2.670 (1.0); 2.665 (0.8); 2.601 (0.5); 2.555 (0.6); 2.550 (0.7); 2.541 (0.4); 2.523 (2.9); 2.509 (63.8); 2.505 (128.5); 2.500 (173.2); 2.496 (123.4); 2.492 (58.5); 2.460 (0.9); 2.456 (1.1); 2.451 (1.2); 2.447 (0.8); 2.332 (0.8); 2.327 (1.1); 2.323 (0.8); 2.318 (0.4); 2.074 (1.1); 1.988 (0.6); 1.236 (0.4); 1.175 (0.3); 0.008 (0.6); 0.000 (14.8); −0.009 (0.6)
Example 31: $^1$H-NMR (400.1 MHz, $d_6$-DMSO):
δ = 10.750 (0.5); 10.711 (4.1); 8.857 (2.6); 8.853 (2.7); 8.845 (2.7); 8.842 (2.5); 8.830 (1.1); 8.405 (1.1); 8.289 (2.1); 8.270 (2.2); 8.106 (5.5); 8.092 (0.8); 7.999 (0.3); 7.983 (2.1); 7.967 (2.4); 7.964 (2.4); 7.938 (0.4); 7.934 (0.4); 7.902 (0.8); 7.899 (0.8); 7.884 (2.2); 7.880 (2.0); 7.865 (2.1); 7.861 (1.6); 7.845 (2.2); 7.826 (2.6); 7.808 (1.0); 7.765 (1.7); 7.753 (1.8); 7.746 (1.9); 7.734 (1.8); 7.699 (0.4); 7.677 (2.4); 7.658 (1.8); 7.383 (1.6); 7.374 (1.9); 7.275 (0.5); 7.254 (3.3); 7.239 (4.2); 7.125 (1.7); 7.104 (2.1); 6.289 (0.3); 4.057 (1.2); 4.039 (3.6); 4.021 (3.7); 4.004 (1.2); 3.304 (14.5); 2.550 (0.3); 2.523 (0.8); 2.509 (17.2); 2.505 (34.7); 2.500 (46.8); 2.496 (33.2); 2.492 (15.6); 2.065 (0.4); 1.988 (16.0); 1.280 (0.6); 1.248 (2.7); 1.193 (4.3); 1.175 (8.6); 1.157 (4.2); 0.875 (1.2); 0.858 (3.8); 0.841 (1.5); 0.000 (3.3)
Example 32: $^1$H-NMR (400.1 MHz, $d_6$-DMSO):
δ = 10.728 (0.4); 10.697 (4.8); 8.859 (3.3); 8.855 (3.5); 8.847 (3.7); 8.843 (3.9); 8.455 (1.2); 8.324 (0.3); 8.303 (0.4); 8.273 (2.7); 8.253 (2.9); 8.173 (0.8); 8.115 (6.8); 7.770 (2.2); 7.758 (2.3); 7.750 (2.3); 7.738 (2.2); 7.725 (0.4); 7.713 (0.5); 7.693 (0.4); 7.689 (0.4); 7.667 (0.8); 7.662 (1.0); 7.654 (1.0); 7.648 (1.5); 7.644 (1.8); 7.642 (1.8); 7.628 (3.3); 7.623 (2.6); 7.610 (4.0); 7.590 (1.8); 7.576 (0.4); 7.555 (0.5); 7.535 (0.4); 7.514 (1.9); 7.511 (2.1); 7.493 (2.2); 7.489 (2.8); 7.486 (2.4); 7.468 (1.9); 7.465 (1.8); 7.449 (0.5); 7.430 (0.5); 7.413 (2.2); 7.394 (3.5); 7.383 (2.5); 7.374 (2.3); 7.369 (3.1); 7.354 (0.4); 7.264 (0.8); 7.254 (4.5); 7.234 (5.5); 7.125 (2.3); 7.099 (2.7); 6.555 (0.4); 4.057 (1.2); 4.039 (3.6); 4.021 (3.7); 4.003 (1.3); 3.304 (19.6); 2.669 (0.4); 2.554 (0.5); 2.550 (0.6); 2.545 (0.5); 2.541 (0.3); 2.522 (1.6); 2.509 (22.4); 2.505 (45.8); 2.500 (63.1); 2.496 (46.8); 2.491 (24.2); 2.451 (1.2); 2.331 (0.3); 2.327 (0.4); 2.322 (0.3); 2.063 (0.5); 1.987 (16.0); 1.297 (0.3); 1.280 (0.7); 1.248 (3.1); 1.192 (4.5); 1.175 (8.8); 1.157 (4.4); 0.875 (1.4); 0.858 (4.5); 0.841 (1.8); 0.000 (3.5)
Example 33: $^1$H-NMR (400.1 MHz, $d_6$-DMSO):
δ = 10.661 (8.7); 8.855 (5.4); 8.851 (5.8); 8.843 (5.8); 8.840 (5.7); 8.262 (4.8); 8.242 (5.1); 8.086 (12.7); 7.766 (3.8); 7.754 (4.0); 7.746 (3.9); 7.734 (3.7); 7.615 (6.0); 7.602 (6.8); 7.597 (5.0); 7.592 (8.1); 7.580 (7.7); 7.438 (1.3); 7.430 (9.2); 7.424 (3.3); 7.408 (16.0); 7.391 (3.2); 7.386 (7.6); 7.357 (4.4); 7.281 (7.9); 7.223 (8.9); 7.152 (3.9); 7.088 (4.3); 3.351 (0.5); 3.301 (66.5); 3.251 (0.7); 2.674 (1.1); 2.669 (1.5); 2.664 (1.1); 2.604 (0.6); 2.600 (0.7); 2.550 (2.9); 2.545 (3.1); 2.540 (3.2); 2.522 (7.8); 2.509 (95.7); 2.504 (189.2); 2.500 (254.7); 2.495 (185.7); 2.491 (94.6); 2.455 (5.7); 2.450 (5.5); 2.445 (4.7); 2.353 (0.5); 2.331 (1.4); 2.327 (1.9); 2.322 (1.4); 2.061 (0.9); 1.987 (0.7); 1.175 (0.4); 0.008 (0.5); 0.000 (11.9); −0.008 (0.6)
Example 34: $^1$H-NMR (400.1 MHz, $d_6$-DMSO):
δ = 12.232 (5.8); 8.782 (4.0); 8.778 (4.3); 8.770 (4.4); 8.766 (4.3); 8.364 (9.6); 8.020 (3.0); 8.018 (3.3); 8.001 (3.6); 7.999 (3.8); 7.793 (6.7); 7.779 (4.3); 7.773 (4.5); 7.766 (16.0); 7.759 (4.0); 7.749 (3.1); 7.733 (0.7); 7.711 (3.2); 7.699 (3.1); 7.691 (2.9); 7.679 (2.7); 7.591 (0.3); 7.415 (2.5); 7.321 (0.5); 7.312 (4.4); 7.297 (0.7); 7.286 (6.0); 7.175 (9.4); 7.174 (9.6); 7.157 (3.2); 7.042 (3.5); 7.034 (3.7); 4.047 (0.6); 4.030 (0.6); 3.332 (5.2); 2.677 (0.4); 2.563 (0.5); 2.558 (0.6); 2.554 (0.5); 2.549 (0.4); 2.531 (1.7); 2.526 (2.4); 2.517 (24.3); 2.513 (50.3); 2.508 (69.5); 2.504 (50.3); 2.499 (25.2); 2.464 (1.1); 2.459 (1.0); 2.340 (0.3); 2.335 (0.5); 2.331 (0.4); 1.996 (2.5); 1.256 (1.4); 1.201 (0.8); 1.183 (1.5); 1.165 (0.7); 0.883 (0.6); 0.867 (2.2); 0.849 (0.9)
Example 35: $^1$H-NMR (400.0 MHz, $d_6$-DMSO):
δ = 10.248 (3.8); 8.857 (2.4); 8.849 (2.5); 8.846 (2.5); 8.343 (0.6); 8.324 (0.6); 8.204 (1.9); 8.185 (1.9); 7.779 (1.3); 7.767 (1.4); 7.759 (1.4); 7.747 (1.2); 7.710 (0.5); 7.698 (0.6); 7.691 (0.5); 7.679 (0.5); 7.673 (0.5); 7.578 (9.8); 7.567 (12.0); 7.545 (0.6); 7.537 (1.1); 7.525 (0.5); 7.515 (1.1); 7.504 (1.6); 7.493 (1.7); 7.483 (0.9); 7.471 (0.4); 7.402 (0.5); 7.357 (1.4); 7.221 (2.9); 7.086 (1.4); 3.330 (1.6); 2.507 (17.4); 2.502 (22.6); 2.498 (17.9); 2.274 (0.6); 2.234 (16.0); 1.989 (0.7); 1.235 (1.0); 1.175 (0.4); 1.150 (0.4); 0.987 (0.3); 0.008 (1.6); 0.000 (31.2)
Example 36: $^1$H-NMR (300.2 MHz, $d_6$-DMSO):
δ = 9.903 (0.6); 8.642 (0.5); 8.638 (0.5); 7.974 (0.5); 7.521 (1.2); 7.130 (0.7); 6.949 (0.4); 4.040 (0.6); 4.017 (0.6); 3.327 (25.6); 2.514 (2.9); 2.508 (6.3); 2.501 (8.8); 2.495 (6.4); 2.489 (3.1); 2.427 (1.9); 2.351 (3.9); 1.989 (2.8); 1.573 (16.0); 1.198 (0.8); 1.174 (1.6); 1.150 (0.8); 0.000 (7.2)
Example 37: $^1$H-NMR (400.1 MHz, $d_6$-DMSO):
δ = 9.988 (0.6); 8.259 (0.5); 8.239 (0.5); 7.882 (0.5); 7.861 (0.5); 7.555 (1.2); 7.200 (0.8); 7.066 (0.4); 3.312 (0.9); 2.518 (2.0); 2.513 (4.2); 2.508 (5.8); 2.504 (4.2); 2.499 (2.1); 2.361 (3.9); 1.581 (16.0)
Example 38: $^1$H-NMR (400.1 MHz, $d_6$-DMSO):
δ = 9.977 (2.3); 8.647 (2.1); 8.643 (2.2); 8.001 (2.1); 7.998 (2.2); 7.683 (4.6); 7.290 (1.2); 7.154 (2.8); 7.018 (1.3); 3.999 (0.5); 3.987 (0.7); 3.975 (1.0); 3.963 (0.8); 3.951 (0.5); 3.311 (12.0); 2.531 (0.7); 2.526 (1.1); 2.517 (13.2); 2.513 (27.6); 2.508 (38.5); 2.504 (28.4); 2.499 (14.5); 2.463 (0.9); 2.459 (0.8); 2.432 (8.1); 2.414 (1.1); 2.229 (15.9); 2.213 (0.7); 2.047 (0.4); 1.996 (0.4); 1.878 (0.6);

-continued 1.860 (0.9); 1.854 (0.8); 1.844 (1.3); 1.836 (0.9); 1.826 (1.4); 1.820 (1.5); 1.802 (1.3); 1.791 (0.5); 1.783 (0.6); 1.779 (0.6); 1.772 (1.2); 1.761 (1.4); 1.754 (1.4); 1.742 (1.5); 1.738 (1.2); 1.726 (0.9); 1.720 (0.9); 1.708 (0.7); 1.702 (0.3); 0.700 (7.2); 0.681 (16.0); 0.663 (7.2); 0.632 (0.3); 0.404 (0.4)

Example 39: $^1$H-NMR (400.1 MHz, $d_6$-DMSO):
δ = 10.079 (2.4); 8.278 (1.9); 8.257 (2.1); 7.880 (2.2); 7.860 (2.0); 7.704 (4.6); 7.353 (1.3); 7.219 (3.1); 7.085 (1.5); 5.759 (0.5); 4.001 (0.5); 3.989 (0.7); 3.977 (0.9); 3.966 (0.7); 3.954 (0.5); 3.310 (44.7); 2.682 (0.4); 2.677 (0.5); 2.672 (0.3); 2.562 (0.4); 2.558 (0.5); 2.554 (0.4); 2.531 (1.5); 2.526 (2.4); 2.517 (29.0); 2.513 (59.0); 2.508 (80.3); 2.504 (56.0); 2.499 (25.9); 2.458 (0.3); 2.340 (0.4); 2.335 (0.5); 2.330 (0.4); 2.228 (16.0); 2.021 (0.4); 1.996 (0.7); 1.875 (0.6); 1.857 (0.8); 1.852 (0.7); 1.841 (1.3); 1.834 (0.8); 1.823 (1.3); 1.818 (1.4); 1.800 (1.2); 1.790 (0.4); 1.778 (0.6); 1.771 (1.2); 1.759 (1.3); 1.753 (1.3); 1.741 (1.5); 1.737 (1.0); 1.725 (0.8); 1.719 (0.8); 1.707 (0.6); 1.183 (0.4); 0.696 (7.3); 0.678 (15.9); 0.659 (6.9); 0.395 (0.4)

Example 40: $^1$H-NMR (300.2 MHz, $d_6$-DMSO):
δ = 9.975 (2.5); 8.641 (2.1); 8.637 (2.1); 7.966 (2.1); 7.593 (4.5); 7.309 (1.2); 7.128 (2.9); 6.947 (1.4); 4.681 (0.7); 4.658 (1.1); 4.634 (0.7); 4.611 (0.3); 3.321 (48.5); 3.298 (0.8); 2.513 (11.8); 2.507 (25.8); 2.501 (36.6); 2.495 (27.0); 2.489 (13.0); 2.426 (7.6); 2.233 (16.0); 2.020 (0.8); 2.000 (1.2); 1.982 (1.1); 1.942 (1.2); 1.918 (1.4); 1.903 (0.9); 1.876 (0.8); 1.861 (0.8); 1.838 (0.9); 1.809 (1.1); 1.790 (0.8); 1.677 (0.4); 1.658 (0.5); 1.644 (1.0); 1.633 (1.1); 1.624 (1.3); 1.617 (0.9); 1.608 (1.0); 0.011 (0.9); 0.000 (33.7); −0.011 (1.4)

Example 41: $^1$H-NMR (400.1 MHz, $d_6$-DMSO):
δ = 10.067 (2.4); 8.251 (1.9); 8.231 (2.1); 7.882 (2.1); 7.862 (2.0); 7.625 (4.5); 7.334 (1.3); 7.200 (3.1); 7.065 (1.5); 4.684 (0.7); 4.667 (1.2); 4.648 (0.7); 3.312 (3.9); 2.531 (0.7); 2.526 (0.7); 2.518 (8.6); 2.513 (18.2); 2.508 (25.5); 2.504 (18.6); 2.499 (9.4); 2.468 (0.6); 2.464 (0.6); 2.459 (0.5); 2.455 (0.4); 2.243 (16.0); 2.038 (0.5); 2.026 (0.8); 2.019 (0.7); 2.006 (1.2); 1.996 (1.7); 1.978 (0.6); 1.974 (0.6); 1.963 (0.5); 1.959 (0.5); 1.942 (1.0); 1.927 (1.2); 1.925 (1.2); 1.912 (1.0); 1.908 (0.9); 1.897 (0.7); 1.893 (0.7); 1.881 (0.4); 1.876 (0.5); 1.859 (0.4); 1.841 (0.8); 1.828 (1.1); 1.819 (1.2); 1.809 (0.8); 1.804 (0.8); 1.791 (0.4); 1.785 (0.3); 1.658 (0.4); 1.649 (0.9); 1.639 (1.0); 1.633 (1.3); 1.621 (1.1); 1.620 (1.1); 1.611 (0.8); 1.256 (0.8); 1.183 (0.4); 0.884 (0.4); 0.867 (1.3); 0.849 (0.5)

Example 42: $^1$H-NMR (300.2 MHz, $d_6$-DMSO):
δ = 9.854 (2.7); 8.657 (2.3); 8.652 (2.3); 7.937 (2.3); 7.482 (5.9); 7.334 (1.3); 7.153 (3.0); 6.972 (1.5); 5.758 (0.4); 4.842 (0.4); 4.821 (1.0); 4.798 (1.3); 4.777 (0.9); 4.754 (0.4); 3.321 (74.7); 2.513 (14.0); 2.507 (30.6); 2.501 (42.7); 2.495 (31.1); 2.489 (14.7); 2.438 (8.7); 1.729 (0.6); 1.721 (0.6); 1.702 (1.3); 1.684 (0.7); 1.674 (0.7); 1.657 (0.4); 1.403 (16.0); 1.381 (16.0); 1.186 (0.4); 0.954 (0.7); 0.939 (2.1); 0.932 (2.4); 0.918 (1.2); 0.911 (2.2); 0.904 (2.2); 0.891 (0.9); 0.675 (0.9); 0.662 (2.2); 0.655 (2.6); 0.645 (2.4); 0.638 (2.4); 0.623 (0.8); 0.011 (0.9); 0.000 (29.9); −0.011 (1.2)

Example 43: $^1$H-NMR (300.2 MHz, $d_6$-DMSO):
δ = 9.971 (2.8); 8.214 (2.0); 8.187 (2.4); 7.900 (2.5); 7.872 (2.1); 7.527 (6.0); 7.390 (1.5); 7.211 (3.7); 7.032 (1.8); 4.840 (0.4); 4.819 (1.0); 4.797 (1.4); 4.776 (1.0); 4.754 (0.4); 3.321 (38.8); 2.513 (10.0); 2.507 (22.0); 2.501 (30.4); 2.495 (22.0); 2.489 (10.4); 1.726 (0.6); 1.715 (0.7); 1.698 (1.3); 1.680 (0.8); 1.671 (0.8); 1.653 (0.3); 1.400 (16.0); 1.378 (16.0); 0.956 (0.7); 0.942 (2.1); 0.935 (2.4); 0.921 (1.2); 0.914 (2.3); 0.907 (2.2); 0.894 (0.9); 0.671 (0.9); 0.658 (2.3); 0.651 (2.6); 0.640 (2.5); 0.633 (2.3); 0.619 (0.7); 0.011 (0.7); 0.000 (21.6); −0.011 (0.8)

Example 44: $^1$H-NMR (400.1 MHz, $d_6$-DMSO):
δ = 10.178 (2.7); 8.666 (2.2); 8.662 (2.2); 8.027 (2.2); 8.025 (2.2); 7.870 (5.2); 7.317 (1.5); 7.313 (1.5); 7.298 (2.7); 7.263 (1.6); 7.261 (1.7); 7.244 (0.8); 7.241 (0.9); 7.177 (2.8); 7.108 (2.4); 7.042 (1.4); 5.760 (1.1); 4.047 (0.7); 4.029 (0.7); 3.311 (17.4); 2.531 (0.5); 2.526 (0.8); 2.517 (12.2); 2.513 (25.1); 2.508 (34.2); 2.504 (24.1); 2.499 (11.2); 2.446 (8.1); 2.345 (10.6); 2.054 (16.0); 1.996 (3.2); 1.953 (11.1); 1.201 (0.9); 1.183 (1.8); 1.165 (0.9)

Example 45: $^1$H-NMR (400.1 MHz, $d_6$-DMSO):
δ = 10.276 (2.7); 8.307 (2.0); 8.286 (2.2); 7.904 (2.3); 7.891 (5.4); 7.884 (2.3); 7.378 (1.3); 7.318 (1.3); 7.298 (2.7); 7.264 (1.6); 7.261 (1.7); 7.243 (4.0); 7.109 (2.5); 7.105 (2.5); 3.260 (0.4); 2.677 (0.4); 2.531 (1.2); 2.526 (1.9); 2.517 (21.3); 2.513 (44.5); 2.508 (61.7); 2.504 (44.6); 2.499 (22.3); 2.464 (1.4); 2.459 (1.3); 2.454 (0.9); 2.343 (10.3); 2.301 (0.3); 2.054 (16.0); 1.951 (10.8)

Example 46: $^1$H-NMR (400.1 MHz, $d_6$-DMSO):
δ = 10.254 (1.7); 8.839 (0.9); 8.835 (1.0); 8.827 (1.0); 8.823 (1.0); 8.207 (0.7); 8.205 (0.8); 8.203 (0.8); 8.187 (0.8); 8.185 (0.9); 7.948 (3.1); 7.748 (0.7); 7.736 (0.7); 7.728 (0.7); 7.717 (0.7); 7.605 (16.0); 7.345 (0.8); 7.210 (1.8); 7.075 (0.9); 3.313 (8.8); 2.526 (0.4); 2.518 (5.5); 2.513 (11.4); 2.508 (15.8); 2.504 (11.5); 2.499 (5.7); 2.325 (9.8)

Example 47: $^1$H-NMR (400.1 MHz, $d_6$-DMSO):
δ = 10.262 (2.5); 8.837 (1.5); 8.833 (1.7); 8.825 (1.6); 8.821 (1.6); 8.215 (1.3); 8.197 (1.3); 8.195 (1.4); 7.952 (4.9); 7.745 (1.2); 7.741 (1.4); 7.739 (1.5); 7.737 (1.9); 7.736 (2.0); 7.733 (1.4); 7.725 (1.3); 7.721 (1.8); 7.719 (3.0); 7.716 (2.2); 7.623 (0.8); 7.614 (1.0); 7.609 (1.3); 7.604 (0.6); 7.600 (1.7); 7.593 (0.8); 7.591 (1.2); 7.583 (0.6); 7.580 (1.9); 7.572 (0.7); 7.564 (2.8); 7.560 (4.6); 7.558 (3.4); 7.550 (3.3); 7.548 (3.1); 7.541 (0.5); 7.357 (1.3); 7.222 (2.9); 7.087 (1.5); 5.760 (4.8); 4.065 (0.5); 4.047 (1.7); 4.029 (1.7); 4.012 (0.6); 3.311 (40.5); 3.261 (0.4); 2.677 (0.4); 2.531 (1.0); 2.526 (1.8); 2.518 (21.0); 2.513 (43.8); 2.508 (60.9); 2.504 (44.0); 2.499 (21.9); 2.464 (1.2); 2.459 (1.1); 2.335 (0.4); 2.094 (16.0); 1.996 (7.6); 1.201 (2.1); 1.183 (4.4); 1.165 (2.2)

Example 48: $^1$H-NMR (400.1 MHz, $d_6$-DMSO):
δ = 10.226 (2.5); 8.838 (1.5); 8.834 (1.7); 8.826 (1.6); 8.822 (1.7); 8.207 (1.2); 8.205 (1.3); 8.203 (1.3); 8.187 (1.3); 8.185 (1.4); 7.904 (5.0); 7.747 (1.1); 7.735 (1.1); 7.727 (1.1); 7.715 (1.0); 7.445 (1.0); 7.426 (2.4); 7.406 (1.8); 7.366 (2.2); 7.349 (1.4); 7.338 (1.5); 7.337 (1.5); 7.317 (1.0); 7.271 (1.4); 7.253 (1.2); 7.214 (3.0); 7.078 (1.4); 5.760 (2.1); 4.065 (0.4); 4.047 (1.9); 4.030 (1.9); 4.012 (0.7); 3.311 (28.7); 2.558 (0.4); 2.531 (0.8); 2.526 (1.3); 2.518 (15.5); 2.513 (32.4); 2.508 (45.2); 2.504 (32.9); 2.499 (16.5); 2.467 (0.8); 2.463 (0.8); 2.458 (0.8); 2.454 (0.7); 2.405 (11.5); 2.335 (0.4); 2.305 (16.0); 1.996 (8.7); 1.201 (2.4); 1.183 (5.1); 1.166 (2.4)

Example 49: $^1$H-NMR (400.1 MHz, $d_6$-DMSO):
δ = 10.644 (11.7); 8.863 (6.2); 8.860 (6.7); 8.852 (6.6); 8.848 (6.5); 8.191 (16.0); 8.176 (5.7); 8.156 (6.1); 8.045 (4.6); 8.042 (4.4); 8.027 (6.2); 8.023 (6.0); 7.948 (1.9); 7.933 (5.0); 7.929 (4.8);

7.914 (6.1); 7.909 (7.5); 7.888 (5.1); 7.869 (1.7); 7.769 (4.9); 7.758 (10.3); 7.750 (5.2); 7.738 (8.3); 7.341 (4.9); 7.205 (11.0); 7.070 (5.5); 5.760 (4.9); 4.047 (0.5); 4.029 (0.5); 3.361 (0.5); 3.311 (95.1); 2.682 (0.9); 2.677 (1.2); 2.673 (0.8); 2.608 (0.4); 2.563 (0.9); 2.558 (1.2); 2.554 (0.9); 2.531 (3.0); 2.517 (69.4); 2.513 (142.3); 2.508 (193.5); 2.504 (136.5); 2.499 (63.5); 2.463 (0.8); 2.458 (0.9); 2.454 (0.7); 2.340 (0.9); 2.335 (1.2); 2.331 (0.9); 2.084 (0.5); 1.996 (2.3); 1.201 (0.7); 1.183 (1.3); 1.165 (0.7)

Example 50: $^1$H-NMR (400.1 MHz, $d_6$-DMSO):

δ = 10.740 (12.0); 8.873 (6.3); 8.870 (6.8); 8.862 (6.9); 8.858 (6.7); 8.216 (16.0); 8.171 (5.5); 8.153 (5.8); 8.151 (6.1); 8.016 (11.6); 7.995 (14.2); 7.828 (12.2); 7.807 (10.5); 7.783 (5.0); 7.771 (4.9); 7.763 (4.7); 7.751 (4.4); 7.339 (4.9); 7.204 (11.6); 7.069 (5.6); 5.759 (0.7); 3.361 (0.5); 3.311 (83.3); 3.261 (0.6); 2.682 (0.7); 2.677 (1.0); 2.673 (0.7); 2.563 (0.8); 2.559 (1.0); 2.554 (0.7); 2.531 (4.1); 2.526 (5.9); 2.517 (57.5); 2.513 (118.4); 2.508 (162.9); 2.504 (117.4); 2.499 (58.4); 2.459 (2.6); 2.409 (0.5); 2.344 (0.4); 2.340 (0.8); 2.335 (1.1); 2.330 (0.8)

Example 53: $^1$H-NMR (300.2 MHz, CDCl$_3$):

δ = 8.712 (1.0); 8.707 (1.1); 8.696 (1.1); 8.691 (1.1); 8.369 (4.7); 8.012 (1.0); 8.007 (1.0); 7.986 (1.1); 7.981 (1.1); 7.871 (1.1); 7.850 (0.3); 7.594 (1.7); 7.554 (0.8); 7.528 (1.2); 7.506 (1.0); 7.490 (0.9); 7.480 (0.9); 7.464 (0.8); 7.450 (0.7); 7.423 (1.4); 7.414 (0.6); 7.409 (0.8); 7.403 (0.9); 7.397 (1.1); 7.387 (1.5); 7.381 (2.0); 7.376 (1.5); 7.365 (2.3); 7.360 (1.4); 7.341 (2.1); 7.331 (0.8); 7.315 (0.9); 7.314 (0.9); 7.288 (1.2); 7.283 (2.2); 7.280 (2.0); 7.121 (0.9); 7.116 (1.5); 7.111 (0.9); 7.096 (0.8); 7.092 (1.3); 7.086 (0.8); 7.079 (1.2); 6.896 (2.3); 6.714 (1.1); 5.295 (6.0); 4.122 (1.1); 4.098 (3.4); 4.074 (3.5); 4.050 (1.2); 2.011 (16.0); 2.000 (0.4); 1.983 (0.8); 1.790 (0.8); 1.290 (0.3); 1.267 (5.9); 1.251 (0.7); 1.249 (0.7); 1.243 (9.1); 1.233 (0.4); 1.231 (0.3); 1.219 (4.5); 0.901 (0.5); 0.879 (1.8); 0.856 (0.7); 0.000 (0.7)

Example 54: $^1$H-NMR (300.2 MHz, CDCl$_3$):

δ = 8.715 (3.5); 8.710 (3.8); 8.699 (3.9); 8.694 (3.8); 8.672 (0.6); 8.667 (0.6); 8.656 (0.6); 8.330 (16.0); 8.006 (3.4); 8.001 (3.5); 7.980 (3.8); 7.975 (3.8); 7.805 (3.4); 7.583 (3.8); 7.579 (0.4); 7.556 (0.5); 7.553 (0.5); 7.506 (3.0); 7.489 (3.2); 7.479 (2.9); 7.463 (2.9); 7.403 (1.3); 7.398 (2.5); 7.392 (2.0); 7.381 (5.0); 7.376 (12.0); 7.370 (10.8); 7.365 (6.2); 7.360 (6.3); 7.358 (6.4); 7.335 (6.7); 7.309 (2.6); 7.279 (6.9); 7.273 (11.1); 7.269 (5.4); 7.257 (5.2); 7.252 (5.8); 7.251 (5.9); 7.246 (4.4); 7.228 (5.4); 7.202 (7.6); 7.188 (0.5); 7.175 (3.5); 7.149 (0.6); 7.113 (0.6); 7.108 (5.1); 7.102 (2.9); 7.088 (2.7); 7.084 (4.5); 7.077 (4.9); 7.045 (0.5); 7.039 (0.6); 7.033 (0.4); 7.007 (3.2); 7.002 (4.0); 7.000 (3.8); 6.996 (3.3); 6.981 (2.7); 6.976 (3.2); 6.974 (3.2); 6.970 (2.5); 6.894 (7.9); 6.711 (3.9); 6.525 (0.8); 6.343 (0.4); 4.126 (0.8); 4.102 (2.6); 4.078 (2.6); 4.054 (0.9); 3.661 (0.4); 2.063 (0.4); 2.016 (12.1); 1.739 (4.1); 1.305 (0.5); 1.269 (6.3); 1.245 (7.1); 1.221 (3.4); 0.901 (1.2); 0.879 (4.0); 0.856 (1.5); 0.000 (3.6)

Example 55: $^1$H-NMR (300.2 MHz, CDCl$_3$):

δ = 8.738 (3.6); 8.733 (3.8); 8.722 (4.0); 8.717 (3.8); 8.682 (0.9); 8.677 (0.9); 8.666 (0.9); 8.661 (0.9); 8.437 (16.0); 8.044 (3.5); 8.039 (3.6); 8.017 (4.0); 8.013 (3.6); 7.857 (1.2); 7.680 (3.6); 7.599 (7.4); 7.571 (10.1); 7.553 (1.9); 7.533 (3.3); 7.517 (3.3); 7.507 (3.3); 7.491 (2.9); 7.479 (0.7); 7.476 (0.6); 7.435 (1.5); 7.430 (2.3); 7.424 (2.0); 7.408 (4.6); 7.402 (8.0); 7.397 (8.9); 7.391 (10.6); 7.387 (10.5); 7.362 (13.1); 7.335 (3.2); 7.319 (4.7); 7.314 (7.6); 7.308 (4.4); 7.282 (1.2); 7.267 (6.8); 7.254 (1.0); 7.121 (3.0); 7.116 (5.1); 7.111 (3.0); 7.097 (2.7); 7.092 (4.4); 7.087 (2.5); 7.080 (1.0); 7.074 (1.2); 7.063 (3.9); 6.881 (7.9); 6.826 (0.4); 6.823 (0.6); 6.818 (0.4); 6.801 (0.3); 6.797 (0.4); 6.727 (0.7); 6.698 (3.9); 6.545 (1.4); 6.363 (0.7); 4.139 (0.7); 4.115 (2.0); 4.091 (2.1); 4.067 (0.7); 2.100 (0.5); 2.028 (9.5); 1.659 (7.3); 1.306 (0.7); 1.275 (4.4); 1.267 (4.2); 1.251 (6.3); 1.227 (2.8); 0.902 (1.4); 0.881 (4.8); 0.857 (1.7); 0.000 (6.7)

Example 56: $^1$H-NMR (300.2 MHz, CDCl$_3$):

δ = 8.752 (3.5); 8.748 (3.5); 8.736 (3.8); 8.732 (3.6); 8.405 (14.1); 8.052 (3.4); 8.048 (3.3); 8.026 (3.9); 8.022 (3.7); 7.590 (3.3); 7.543 (3.0); 7.527 (3.0); 7.516 (2.8); 7.500 (2.6); 7.412 (1.2); 7.407 (2.0); 7.401 (1.6); 7.386 (4.1); 7.380 (6.1); 7.374 (4.2); 7.366 (5.3); 7.365 (5.2); 7.340 (6.4); 7.324 (1.4); 7.315 (10.9); 7.308 (3.8); 7.286 (18.8); 7.277 (3.0); 7.264 (12.8); 7.213 (2.3); 7.204 (15.0); 7.197 (4.2); 7.181 (3.6); 7.174 (8.6); 7.165 (1.1); 7.104 (3.0); 7.099 (4.7); 7.094 (2.7); 7.079 (2.9); 7.075 (4.9); 7.070 (5.7); 6.888 (7.3); 6.705 (3.6); 4.125 (0.6); 4.102 (0.7); 2.038 (2.9); 2.003 (16.0); 1.598 (3.6); 1.280 (0.8); 1.256 (1.6); 1.232 (0.8); 0.011 (0.3); 0.000 (9.1); −0.011 (0.4)

Example 57: $^1$H-NMR (300.2 MHz, CDCl$_3$):

δ = 8.702 (3.2); 8.697 (3.5); 8.686 (3.6); 8.681 (3.5); 8.671 (0.6); 8.654 (0.4); 8.263 (13.9); 8.047 (3.9); 7.983 (3.0); 7.979 (3.2); 7.957 (3.4); 7.953 (3.4); 7.826 (0.3); 7.484 (2.6); 7.468 (2.7); 7.458 (2.6); 7.442 (2.4); 7.417 (1.5); 7.412 (2.0); 7.392 (3.5); 7.387 (4.6); 7.378 (1.9); 7.367 (3.6); 7.362 (4.2); 7.352 (2.6); 7.344 (2.0); 7.342 (2.1); 7.336 (1.5); 7.325 (1.7); 7.319 (1.4); 7.314 (1.4); 7.309 (2.0); 7.303 (1.6); 7.287 (3.6); 7.281 (6.1); 7.279 (5.2); 7.276 (4.6); 7.268 (5.0); 7.243 (5.9); 7.216 (7.7); 7.209 (7.3); 7.203 (4.4); 7.192 (4.0); 7.190 (4.1); 7.166 (1.7); 7.164 (1.7); 7.151 (0.4); 7.110 (3.2); 7.079 (2.5); 7.071 (3.4); 7.066 (4.7); 7.061 (2.9); 7.046 (5.6); 7.042 (5.8); 7.018 (2.0); 7.015 (1.8); 6.972 (0.3); 6.928 (6.6); 6.745 (3.4); 6.499 (0.4); 4.116 (1.1); 4.092 (3.5); 4.068 (3.6); 4.044 (1.2); 2.006 (16.0); 1.842 (3.7); 1.305 (0.7); 1.263 (8.2); 1.239 (9.1); 1.215 (4.5); 1.189 (0.3); 1.049 (0.5); 0.901 (1.4); 0.879 (4.6); 0.856 (1.7); 0.000 (1.9)

Example 58: $^1$H-NMR (300.2 MHz, CDCl$_3$):

δ = 8.724 (3.6); 8.719 (4.0); 8.708 (4.0); 8.703 (4.0); 8.675 (0.7); 8.671 (0.8); 8.660 (0.7); 8.655 (0.7); 8.351 (16.0); 8.017 (3.4); 8.012 (3.6); 7.991 (4.0); 7.986 (4.0); 7.817 (0.9); 7.753 (3.7); 7.585 (0.5); 7.581 (0.5); 7.558 (0.7); 7.554 (0.7); 7.515 (3.1); 7.499 (3.2); 7.488 (3.2); 7.472 (2.9); 7.464 (0.7); 7.460 (0.6); 7.457 (0.6); 7.454 (0.5); 7.406 (1.2); 7.400 (2.5); 7.394 (2.0); 7.379 (4.8); 7.373 (7.9); 7.367 (5.7); 7.363 (6.3); 7.362 (6.5); 7.351 (1.4); 7.338 (6.9); 7.324 (0.8); 7.311 (2.7); 7.299 (2.0); 7.277 (9.0); 7.271 (12.8); 7.251 (4.3); 7.245 (3.3); 7.224 (2.7); 7.198 (0.4); 7.127 (3.0); 7.121 (5.2); 7.116 (3.1); 7.102 (2.7); 7.097 (4.4); 7.092 (2.6); 7.075 (4.1); 7.067 (2.2); 7.059 (3.9); 7.052 (3.0); 7.035 (2.5); 7.028 (5.9); 7.020 (4.6); 7.001 (3.7); 6.998 (4.6); 6.992 (3.0); 6.989 (3.0); 6.973 (5.5); 6.970 (5.7); 6.962 (2.4); 6.949 (3.2); 6.947 (3.4); 6.943 (3.3); 6.931 (0.7); 6.923 (0.6); 6.916 (0.4); 6.892 (8.0); 6.852 (0.4); 6.845 (0.6); 6.841 (0.5); 6.836 (0.4); 6.825 (0.4); 6.819 (0.5); 6.710 (4.5); 6.528 (1.1); 6.345 (0.5); 4.132 (0.7); 4.108 (2.2); 4.084 (2.3); 4.060 (0.8); 2.075 (0.5); 2.021 (10.3); 1.713 (6.5); 1.305 (0.4); 1.272 (4.4); 1.248 (6.2); 1.233 (0.8); 1.224 (2.9); 1.210 (0.3); 1.058 (0.4); 0.902 (0.8); 0.880 (2.7); 0.857 (1.0); 0.000 (4.1)

-continued

Example 60: $^1$H-NMR (300.2 MHz, CDCl$_3$):
δ = 8.830 (6.1); 8.825 (6.5); 8.814 (6.6); 8.809 (6.5); 8.594 (16.0); 8.141 (5.9); 8.136 (6.0); 8.115 (6.7); 8.110 (6.6); 8.005 (4.6); 7.672 (11.1); 7.666 (8.8); 7.661 (8.4); 7.656 (8.4); 7.650 (3.7); 7.636 (6.6); 7.631 (9.2); 7.625 (6.0); 7.618 (5.8); 7.602 (5.5); 7.592 (5.1); 7.576 (4.7); 7.450 (3.1); 7.423 (8.8); 7.405 (10.7); 7.378 (11.5); 7.353 (3.8); 7.262 (79.1); 7.135 (7.0); 6.953 (14.3); 6.911 (0.4); 6.771 (7.1); 2.225 (0.6); 2.046 (0.6); 1.558 (94.7); 1.260 (0.8); 1.191 (0.9); 0.882 (0.4); 0.195 (0.4); 0.069 (0.5); 0.011 (2.6); 0.000 (79.4); −0.011 (3.4); −0.199 (0.3)

Example 61: $^1$H-NMR (300.2 MHz, CDCl$_3$):
δ = 8.830 (6.2); 8.825 (6.5); 8.814 (6.7); 8.809 (6.4); 8.617 (16.0); 8.142 (6.0); 8.137 (6.0); 8.115 (6.8); 8.111 (6.5); 8.022 (4.3); 7.977 (0.4); 7.621 (5.2); 7.605 (5.3); 7.595 (4.9); 7.579 (4.6); 7.262 (59.4); 7.125 (8.4); 7.107 (8.1); 7.101 (9.7); 7.084 (9.1); 7.078 (8.9); 7.061 (1.5); 7.011 (2.7); 7.003 (4.1); 6.996 (2.1); 6.982 (5.3); 6.975 (8.3); 6.967 (4.0); 6.953 (3.1); 6.943 (15.9); 6.911 (0.4); 6.761 (7.2); 2.045 (1.4); 1.560 (63.0); 1.283 (0.6); 1.259 (1.3); 1.236 (0.5); 1.190 (0.7); 0.882 (0.7); 0.858 (0.4); 0.011 (2.0); 0.000 (60.6); −0.011 (2.2)

Example 62: $^1$H-NMR (300.2 MHz, CDCl$_3$):
δ = 8.830 (6.2); 8.825 (6.5); 8.814 (6.7); 8.809 (6.5); 8.593 (16.0); 8.139 (6.0); 8.135 (6.0); 8.113 (6.8); 8.109 (6.6); 8.008 (4.4); 7.617 (5.2); 7.601 (5.3); 7.591 (5.1); 7.575 (4.7); 7.521 (2.2); 7.500 (2.8); 7.494 (5.4); 7.492 (5.1); 7.474 (5.1); 7.471 (4.9); 7.465 (4.0); 7.448 (2.7); 7.445 (3.3); 7.311 (6.6); 7.282 (5.2); 7.262 (58.6); 7.254 (10.9); 7.251 (9.4); 7.227 (12.6); 7.224 (11.4); 7.200 (3.5); 7.197 (3.3); 7.192 (2.3); 7.189 (2.0); 7.137 (7.1); 6.955 (14.5); 6.911 (0.4); 6.773 (7.2); 1.562 (60.8); 1.258 (0.8); 1.190 (0.7); 0.882 (0.5); 0.070 (1.0); 0.011 (1.9); 0.000 (53.2); −0.011 (2.3)

Example 63: $^1$H-NMR (300.2 MHz, d$_6$-DMSO):
δ = 10.697 (2.5); 8.853 (5.4); 8.841 (5.5); 8.160 (16.0); 8.140 (5.7); 7.821 (12.5); 7.793 (15.6); 7.770 (4.1); 7.754 (4.2); 7.744 (3.7); 7.728 (3.5); 7.529 (12.7); 7.500 (10.8); 7.409 (3.3); 7.228 (7.0); 7.049 (3.4); 3.327 (43.0); 3.176 (0.3); 2.507 (26.1); 2.502 (34.5); 2.496 (26.3); 1.900 (1.2); 1.355 (0.9); 1.235 (0.8); 0.000 (20.3)

Example 64: $^1$H-NMR (300.2 MHz, CDCl$_3$):
δ = 8.831 (4.9); 8.826 (5.2); 8.815 (5.3); 8.810 (5.1); 8.608 (12.8); 8.145 (4.8); 8.140 (4.8); 8.118 (5.4); 8.114 (5.2); 8.019 (3.6); 7.674 (1.8); 7.658 (10.5); 7.648 (9.6); 7.623 (16.0); 7.620 (13.8); 7.603 (11.0); 7.593 (5.4); 7.577 (4.0); 7.262 (45.1); 7.139 (5.5); 6.957 (11.4); 6.904 (5.1); 6.774 (5.6); 6.717 (10.3); 6.530 (5.0); 5.301 (0.6); 1.563 (65.0); 1.259 (0.4); 1.190 (0.5); 0.070 (0.7); 0.011 (1.5); 0.000 (39.4); −0.011 (1.5)

Example 65: $^1$H-NMR (300.2 MHz, d$_6$-DMSO):
δ = 12.490 (0.6); 10.245 (2.6); 10.021 (0.7); 8.661 (2.2); 8.017 (2.5); 7.948 (5.1); 7.663 (2.6); 7.581 (2.0); 7.572 (1.6); 7.561 (4.9); 7.557 (4.1); 7.546 (1.1); 7.531 (1.5); 7.524 (1.5); 7.503 (0.7); 7.493 (0.7); 7.339 (1.2); 7.158 (3.0); 6.978 (1.5); 5.586 (0.6); 3.325 (145.0); 3.285 (0.9); 3.274 (0.7); 2.726 (1.0); 2.513 (45.6); 2.507 (98.2); 2.501 (134.8); 2.495 (97.7); 2.489 (45.7); 2.443 (8.6); 2.365 (0.7); 2.342 (16.0); 2.271 (1.0); 1.989 (0.9); 1.264 (0.8); 1.246 (1.8); 0.858 (1.9); 0.194 (0.7); 0.011 (3.7); 0.000 (127.7); −0.011 (5.4)

Example 66: $^1$H-NMR (300.2 MHz, d$_6$-DMSO):
δ = 10.340 (2.8); 8.306 (1.9); 8.279 (2.3); 7.968 (5.4); 7.912 (2.3); 7.885 (2.0); 7.669 (1.5); 7.665 (2.4); 7.661 (2.5); 7.656 (1.4); 7.581 (1.4); 7.571 (1.5); 7.560 (4.9); 7.557 (4.2); 7.545 (1.2); 7.539 (0.8); 7.532 (1.8); 7.525 (1.7); 7.521 (1.1); 7.516 (1.0); 7.512 (0.9); 7.504 (0.8); 7.494 (0.5); 7.408 (1.2); 7.229 (3.2); 7.050 (1.5); 3.325 (54.8); 2.722 (0.3); 2.514 (14.2); 2.508 (31.6); 2.501 (44.4); 2.495 (32.6); 2.489 (15.9); 2.341 (16.0); 2.271 (0.4); 0.011 (1.5); 0.000 (50.2); −0.011 (2.0)

Example 67: $^1$H-NMR (300.2 MHz, d$_6$-DMSO):
δ = 10.200 (2.8); 8.663 (2.2); 8.014 (2.1); 7.880 (5.3); 7.445 (0.8); 7.419 (2.2); 7.394 (1.9); 7.360 (2.3); 7.343 (1.7); 7.335 (1.7); 7.310 (0.9); 7.266 (1.5); 7.240 (1.1); 7.162 (2.9); 6.981 (1.3); 4.064 (0.3); 4.040 (0.9); 4.017 (0.8); 3.325 (67.4); 2.533 (0.4); 2.514 (14.2); 2.507 (31.1); 2.501 (43.1); 2.495 (31.3); 2.489 (14.8); 2.443 (8.0); 2.397 (11.9); 2.295 (16.0); 1.989 (3.5); 1.198 (0.9); 1.174 (2.0); 1.150 (1.0); 0.011 (1.2); 0.000 (44.5); −0.011 (1.9)

Example 68: $^1$H-NMR (300.2 MHz, d$_6$-DMSO):
δ = 10.297 (3.2); 8.303 (2.0); 8.275 (2.3); 7.911 (2.7); 7.903 (5.6); 7.883 (2.0); 7.445 (1.0); 7.419 (2.5); 7.408 (1.6); 7.394 (2.0); 7.357 (2.5); 7.333 (1.7); 7.305 (1.0); 7.268 (1.8); 7.243 (1.4); 7.229 (3.3); 7.050 (1.5); 4.041 (0.5); 4.017 (0.4); 3.397 (0.6); 3.330 (382.7); 3.259 (0.6); 2.514 (13.9); 2.508 (29.0); 2.502 (39.5); 2.496 (29.0); 2.490 (14.2); 2.396 (12.8); 2.352 (0.4); 2.295 (16.0); 1.989 (2.1); 1.245 (0.8); 1.198 (0.6); 1.174 (1.2); 1.150 (0.6); 0.879 (0.4); 0.859 (0.7); 0.834 (0.3); 0.000 (25.7); −0.011 (1.3)

Example 69: $^1$H-NMR (300.2 MHz, d$_6$-DMSO):
δ = 10.975 (0.3); 10.238 (2.8); 8.663 (2.4); 8.032 (2.2); 7.931 (5.1); 7.735 (1.5); 7.717 (1.4); 7.712 (2.5); 7.708 (1.5); 7.625 (0.8); 7.607 (1.1); 7.594 (1.8); 7.568 (2.3); 7.556 (5.4); 7.543 (2.9); 7.351 (1.3); 7.171 (2.9); 6.990 (1.5); 5.408 (0.3); 4.633 (0.4); 4.017 (0.4); 3.325 (136.8); 3.303 (1.9); 3.222 (0.3); 2.728 (0.4); 2.513 (21.6); 2.507 (48.1); 2.501 (67.6); 2.495 (50.0); 2.489 (24.3); 2.439 (8.3); 2.391 (0.4); 2.351 (0.4); 2.272 (0.5); 2.083 (16.0); 1.989 (1.4); 1.865 (0.4); 1.198 (0.5); 1.174 (0.8); 0.011 (1.6); 0.000 (54.3); −0.011 (2.4); −0.041 (0.4)

Example 70: $^1$H-NMR (300.2 MHz, d$_6$-DMSO):
δ = 10.333 (3.0); 8.315 (2.0); 8.288 (2.3); 7.949 (5.2); 7.911 (2.3); 7.883 (2.0); 7.735 (1.4); 7.717 (1.4); 7.712 (2.7); 7.708 (1.6); 7.626 (0.7); 7.612 (0.9); 7.608 (1.3); 7.595 (1.8); 7.584 (1.3); 7.569 (2.0); 7.559 (3.7); 7.554 (5.5); 7.541 (3.0); 7.537 (2.2); 7.418 (1.4); 7.239 (3.3); 7.061 (1.6); 5.759 (0.3); 4.064 (0.7); 4.040 (2.3); 4.017 (2.4); 3.993 (0.8); 3.325 (44.3); 2.514 (11.7); 2.508 (25.1); 2.501 (34.5); 2.495 (24.9); 2.489 (11.7); 2.083 (16.0); 1.989 (10.4); 1.246 (2.3); 1.198 (3.0); 1.174 (5.8); 1.151 (2.8); 0.880 (0.7); 0.858 (2.2); 0.835 (0.8); 0.011 (1.0); 0.000 (27.9); −0.011 (1.0)

Example 71: $^1$H-NMR (300.2 MHz, d$_6$-DMSO):
δ = 10.227 (1.7); 8.665 (1.3); 8.015 (1.2); 7.924 (3.0); 7.600 (16.0); 7.339 (0.8); 7.157 (1.6); 6.977 (0.9); 3.325 (68.3); 3.303 (0.9); 2.513 (10.1); 2.507 (22.1); 2.501 (30.8); 2.495 (22.7); 2.489 (11.0); 2.442 (4.8); 2.315 (9.0); 1.989 (1.3); 1.198 (0.4); 1.174 (0.7); 1.151 (0.4); 0.011 (0.7); 0.000 (26.0); −0.011 (1.1)

-continued

Example 72: $^1$H-NMR (300.2 MHz, d$_6$-DMSO):
δ = 10.323 (1.8); 8.303 (1.3); 8.276 (1.3); 7.945 (3.2); 7.912 (1.4); 7.884 (1.3); 7.599 (16.0); 7.570 (0.3); 7.405 (0.8); 7.227 (1.8); 7.048 (1.0); 5.759 (0.3); 4.040 (0.4); 4.016 (0.4); 3.325 (74.9); 2.514 (14.2); 2.507 (31.2); 2.501 (43.6); 2.495 (31.8); 2.489 (15.2); 2.315 (9.8); 2.272 (0.4); 1.989 (1.6); 1.248 (0.5); 1.198 (0.5); 1.174 (0.9); 1.151 (0.5); 0.858 (0.5); 0.011 (1.0); 0.000 (35.5); −0.011 (1.4)

Example 73: $^1$H-NMR (300.2 MHz, CDCl$_3$):
δ = 8.832 (1.5); 8.827 (1.6); 8.816 (1.7); 8.811 (1.6); 8.587 (4.1); 8.143 (1.5); 8.139 (1.5); 8.117 (1.7); 8.112 (1.7); 7.999 (1.1); 7.614 (1.3); 7.598 (1.3); 7.588 (1.2); 7.572 (1.2); 7.462 (0.6); 7.452 (0.7); 7.443 (0.6); 7.435 (1.2); 7.425 (1.1); 7.419 (0.9); 7.407 (1.5); 7.357 (2.2); 7.355 (2.2); 7.332 (1.4); 7.314 (2.2); 7.309 (2.5); 7.305 (2.7); 7.295 (4.0); 7.279 (0.5); 7.262 (13.2); 7.165 (1.7); 6.983 (3.5); 6.801 (1.7); 2.077 (16.0); 1.568 (13.7); 1.255 (0.3); 0.011 (0.4); 0.000 (11.6); −0.011 (0.4)

Example 74: $^1$H-NMR (300.2 MHz, CDCl$_3$):
δ = 8.833 (3.6); 8.828 (3.8); 8.817 (3.9); 8.812 (3.8); 8.633 (9.6); 8.482 (0.3); 8.150 (3.5); 8.145 (3.6); 8.123 (4.0); 8.119 (3.9); 7.999 (2.7); 7.757 (3.0); 7.753 (4.7); 7.749 (2.9); 7.729 (5.5); 7.725 (3.7); 7.710 (0.5); 7.617 (3.1); 7.601 (3.2); 7.590 (3.0); 7.574 (2.8); 7.481 (2.7); 7.476 (6.2); 7.463 (16.0); 7.451 (8.2); 7.436 (2.9); 7.433 (2.9); 7.426 (5.0); 7.418 (1.5); 7.410 (3.4); 7.395 (1.6); 7.262 (40.4); 7.162 (4.2); 6.980 (8.5); 6.798 (4.3); 5.301 (5.9); 4.133 (0.4); 4.109 (0.4); 2.228 (2.0); 2.045 (1.7); 1.566 (47.5); 1.283 (0.7); 1.259 (1.6); 1.255 (1.1); 1.244 (0.5); 1.236 (0.6); 1.191 (0.5); 0.070 (0.5); 0.011 (1.3); 0.000 (36.6); −0.011 (1.3)

Example 75: $^1$H-NMR (400.0 MHz, d$_6$-DMSO):
δ = 10.986 (0.5); 10.283 (3.0); 8.858 (1.5); 8.855 (1.9); 8.846 (1.7); 8.843 (1.9); 8.216 (1.4); 8.197 (1.4); 7.943 (0.6); 7.921 (0.7); 7.773 (1.2); 7.761 (1.3); 7.754 (1.3); 7.742 (1.2); 7.653 (0.8); 7.630 (0.7); 7.607 (0.8); 7.600 (0.6); 7.591 (10.2); 7.585 (4.9); 7.574 (3.8); 7.569 (0.9); 7.559 (0.6); 7.553 (1.0); 7.511 (0.8); 7.505 (1.2); 7.498 (0.8); 7.497 (0.8); 7.492 (0.8); 7.490 (1.1); 7.485 (0.6); 7.482 (0.5); 7.480 (0.4); 7.474 (0.5); 7.468 (0.4); 7.349 (1.3); 7.341 (0.3); 7.214 (2.9); 7.206 (0.7); 7.078 (1.4); 7.071 (0.4); 5.757 (5.7); 3.335 (11.6); 3.332 (11.5); 2.550 (3.1); 2.520 (0.4); 2.512 (5.6); 2.507 (11.6); 2.503 (15.5); 2.498 (11.4); 2.494 (5.7); 2.228 (16.0); 1.989 (0.7); 1.175 (0.4); 0.008 (0.6); 0.000 (17.6); −0.009 (0.7)

Example 76: $^1$H-NMR (400.0 MHz, d$_6$-DMSO):
δ = 10.017 (2.2); 8.844 (1.1); 8.841 (1.2); 8.832 (1.2); 8.829 (1.2); 8.213 (1.0); 8.193 (1.1); 7.763 (0.8); 7.751 (0.8); 7.744 (0.8); 7.732 (0.8); 7.641 (1.6); 7.638 (2.2); 7.619 (2.7); 7.617 (2.5); 7.506 (1.7); 7.501 (0.6); 7.488 (2.6); 7.471 (0.7); 7.467 (1.7); 7.356 (0.9); 7.347 (0.6); 7.344 (1.0); 7.341 (0.6); 7.325 (1.5); 7.310 (0.4); 7.307 (0.6); 7.304 (0.4); 7.220 (2.1); 7.085 (1.0); 5.758 (0.8); 4.038 (0.7); 4.018 (16.0); 3.336 (26.8); 3.333 (35.3); 2.984 (0.5); 2.728 (0.5); 2.525 (2.8); 2.520 (1.2); 2.511 (14.9); 2.507 (30.4); 2.502 (40.1); 2.498 (29.4); 2.493 (14.4); 2.112 (12.4); 1.989 (2.6); 1.298 (0.3); 1.259 (0.5); 1.192 (0.7); 1.175 (1.4); 1.157 (0.8); 0.008 (1.5); 0.000 (42.0); −0.009 (1.5)

Example 77: $^1$H-NMR (400.0 MHz, d$_6$-DMSO):
δ = 10.647 (8.1); 8.860 (6.1); 8.857 (6.7); 8.848 (6.6); 8.845 (6.6); 8.190 (16.0); 8.171 (5.7); 8.151 (6.2); 7.773 (6.6); 7.770 (9.8); 7.754 (11.4); 7.750 (12.8); 7.738 (4.4); 7.717 (5.7); 7.698 (7.7); 7.693 (5.0); 7.688 (4.3); 7.674 (7.8); 7.669 (6.2); 7.654 (4.4); 7.650 (3.5); 7.602 (5.3); 7.598 (5.3); 7.582 (7.2); 7.579 (7.1); 7.563 (2.9); 7.560 (2.8); 7.340 (5.1); 7.205 (11.4); 7.070 (5.6); 6.898 (0.7); 6.722 (0.4); 5.759 (16.0); 4.207 (0.4); 3.975 (0.3); 3.335 (81.9); 3.017 (0.5); 2.677 (0.5); 2.672 (0.7); 2.668 (0.5); 2.541 (0.3); 2.526 (1.6); 2.521 (2.5); 2.512 (38.3); 2.508 (78.0); 2.503 (102.9); 2.499 (75.3); 2.495 (37.5); 2.334 (0.6); 2.330 (0.7); 2.326 (0.5); 2.290 (0.4); 1.352 (6.4); 1.337 (2.6); 1.315 (0.8); 1.299 (1.6); 1.259 (2.7); 1.250 (4.2); 1.229 (7.2); 1.193 (0.4); 1.188 (2.5); 1.175 (0.4); 1.157 (1.0); 1.138 (1.5); 1.121 (1.0); 0.868 (0.8); 0.852 (1.9); 0.841 (1.4); 0.834 (1.4); 0.828 (1.2); 0.823 (1.1); 0.813 (0.8); 0.806 (0.6); 0.146 (0.5); 0.008 (3.9); 0.000 (115.5); −0.009 (4.4); −0.150 (0.5)

Example 78: $^1$H-NMR (300.2 MHz, CDCl$_3$):
δ = 8.746 (2.7); 8.741 (2.9); 8.730 (3.0); 8.725 (3.0); 8.700 (0.3); 8.695 (0.3); 8.390 (12.4); 8.043 (2.6); 8.039 (2.7); 8.017 (3.0); 8.012 (2.9); 7.869 (0.4); 7.798 (2.0); 7.787 (2.3); 7.781 (2.5); 7.778 (1.6); 7.774 (1.5); 7.766 (2.8); 7.755 (0.7); 7.700 (2.7); 7.570 (0.6); 7.557 (6.6); 7.544 (4.1); 7.536 (5.0); 7.532 (4.1); 7.526 (7.2); 7.516 (3.1); 7.509 (2.3); 7.506 (2.7); 7.490 (2.3); 7.308 (0.9); 7.302 (1.7); 7.296 (1.4); 7.281 (3.2); 7.275 (5.8); 7.268 (9.7); 7.265 (4.9); 7.263 (4.8); 7.239 (5.7); 7.233 (3.4); 7.219 (8.0); 7.213 (7.3); 7.202 (2.5); 7.187 (0.6); 7.113 (3.0); 7.063 (3.8); 7.058 (2.2); 7.039 (1.9); 7.034 (3.1); 7.029 (1.8); 6.981 (0.4); 6.931 (6.2); 6.749 (3.1); 4.141 (1.1); 4.117 (3.4); 4.093 (3.5); 4.069 (1.2); 2.031 (16.0); 1.665 (6.6); 1.276 (4.4); 1.267 (0.5); 1.252 (8.9); 1.244 (0.6); 1.228 (4.3); 0.000 (5.1)

Example 79: $^1$H-NMR (300.2 MHz, CDCl$_3$):
δ = 8.752 (3.6); 8.747 (3.9); 8.736 (4.0); 8.731 (3.9); 8.453 (16.0); 8.018 (3.4); 8.013 (3.5); 7.992 (3.8); 7.989 (3.7); 7.987 (3.8); 7.723 (3.5); 7.519 (3.1); 7.503 (3.1); 7.493 (3.0); 7.476 (2.8); 7.423 (2.8); 7.418 (2.5); 7.415 (2.4); 7.399 (4.4); 7.397 (5.4); 7.391 (4.5); 7.383 (1.2); 7.364 (3.2); 7.358 (4.6); 7.351 (3.9); 7.340 (5.4); 7.335 (10.9); 7.332 (20.5); 7.325 (9.0); 7.319 (13.9); 7.310 (20.0); 7.304 (10.1); 7.298 (8.4); 7.289 (2.3); 7.282 (2.7); 7.277 (2.5); 7.274 (3.9); 7.266 (8.8); 7.255 (1.7); 7.250 (1.4); 7.244 (0.7); 7.237 (1.1); 7.232 (1.1); 7.222 (6.9); 7.214 (4.2); 7.210 (7.4); 7.198 (5.4); 7.190 (4.7); 7.178 (0.8); 7.141 (4.1); 6.958 (8.4); 6.776 (4.2); 4.121 (0.9); 4.098 (1.0); 4.074 (0.3); 2.034 (4.3); 1.657 (9.5); 1.278 (1.3); 1.254 (2.6); 1.230 (1.2); 0.000 (5.0)

Example 80: $^1$H-NMR (300.2 MHz, CDCl$_3$):
δ = 8.753 (3.6); 8.748 (3.9); 8.737 (4.0); 8.732 (4.0); 8.404 (16.0); 8.047 (3.4); 8.042 (3.6); 8.021 (3.9); 8.016 (3.9); 7.734 (3.5); 7.537 (3.1); 7.521 (3.1); 7.510 (3.0); 7.494 (2.8); 7.443 (2.6); 7.437 (2.1); 7.430 (1.5); 7.418 (5.3); 7.416 (5.4); 7.410 (4.6); 7.391 (3.3); 7.386 (2.5); 7.379 (4.7); 7.370 (1.8); 7.363 (10.6); 7.359 (10.7); 7.355 (6.5); 7.340 (9.5); 7.332 (7.1); 7.323 (2.7); 7.320 (1.9); 7.308 (4.9); 7.302 (2.3); 7.291 (1.9); 7.286 (4.8); 7.281 (7.8); 7.275 (5.7); 7.267 (14.1); 7.244 (8.6); 7.235 (7.9); 7.229 (4.7); 7.219 (3.2); 7.121 (4.0); 7.091 (3.2); 7.085 (5.3); 7.080 (3.1); 7.066 (2.5); 7.061 (4.2); 7.056 (2.4); 6.938 (8.1); 6.756 (4.1); 4.144 (1.0); 4.120 (3.0); 4.096 (3.1); 4.072 (1.1); 2.034 (14.2); 2.000 (6.4); 1.652 (14.7); 1.277 (3.9); 1.254 (7.8); 1.230 (3.8); 0.000 (7.4)

-continued

Example 81: $^1$H-NMR (300.2 MHz, CDCl$_3$):
δ = 8.734 (3.3); 8.729 (3.4); 8.718 (3.5); 8.713 (3.4); 8.347 (10.0); 8.023 (3.1); 8.019 (3.1); 7.997 (3.5); 7.859 (3.2); 7.517 (2.6); 7.501 (2.7); 7.491 (2.5); 7.475 (2.4); 7.434 (2.2); 7.429 (1.7); 7.418 (1.4); 7.408 (4.4); 7.401 (4.3); 7.386 (2.4); 7.377 (2.6); 7.371 (1.8); 7.364 (4.2); 7.356 (5.9); 7.345 (6.6); 7.339 (6.2); 7.335 (7.3); 7.331 (6.5); 7.325 (5.9); 7.313 (2.1); 7.310 (2.5); 7.304 (2.8); 7.300 (3.0); 7.293 (1.9); 7.283 (1.7); 7.278 (4.5); 7.272 (10.8); 7.266 (5.3); 7.261 (5.2); 7.236 (7.4); 7.227 (7.1); 7.221 (4.1); 7.210 (2.8); 7.122 (3.6); 7.083 (2.9); 7.078 (4.7); 7.072 (2.6); 7.059 (2.3); 7.054 (3.7); 7.049 (2.1); 6.940 (7.2); 6.758 (3.6); 4.132 (1.1); 4.109 (3.5); 4.085 (3.6); 4.061 (1.2); 2.023 (16.0); 1.725 (3.4); 1.272 (4.7); 1.264 (0.7); 1.248 (9.0); 1.240 (0.7); 1.224 (4.5); 0.880 (0.4); 0.000 (4.0)

Example 82: $^1$H-NMR (300.2 MHz, CDCl$_3$):
δ = 8.746 (3.6); 8.741 (3.9); 8.730 (4.0); 8.725 (3.9); 8.693 (0.4); 8.688 (0.4); 8.677 (0.4); 8.393 (16.0); 8.374 (0.5); 8.033 (3.4); 8.028 (3.5); 8.007 (3.9); 8.002 (3.8); 7.865 (0.5); 7.791 (3.6); 7.526 (3.1); 7.510 (3.1); 7.500 (3.0); 7.484 (2.8); 7.437 (2.7); 7.432 (2.1); 7.420 (2.0); 7.417 (2.2); 7.412 (4.8); 7.411 (5.1); 7.405 (5.1); 7.385 (2.9); 7.377 (4.0); 7.369 (3.5); 7.364 (2.8); 7.356 (7.7); 7.350 (9.3); 7.344 (6.1); 7.335 (7.8); 7.331 (7.3); 7.324 (6.2); 7.317 (3.2); 7.314 (3.2); 7.309 (4.7); 7.301 (3.5); 7.287 (4.2); 7.281 (3.7); 7.269 (6.8); 7.261 (2.9); 7.245 (0.5); 7.236 (0.4); 7.224 (0.4); 7.220 (0.5); 7.200 (0.3); 7.117 (4.0); 7.100 (0.4); 7.095 (0.4); 7.046 (1.4); 7.043 (1.8); 7.038 (1.8); 7.035 (2.1); 7.015 (7.4); 7.009 (7.4); 6.988 (5.1); 6.982 (4.6); 6.935 (10.6); 6.922 (2.3); 6.904 (2.7); 6.898 (3.5); 6.891 (2.1); 6.753 (4.1); 1.994 (1.5); 1.688 (5.9); 0.000 (4.4)

Example 83: $^1$H-NMR (300.2 MHz, CDCl$_3$):
δ = 8.756 (3.6); 8.751 (3.9); 8.740 (3.9); 8.735 (3.9); 8.693 (0.4); 8.412 (16.0); 8.042 (3.4); 8.037 (3.5); 8.016 (3.9); 8.011 (3.8); 7.863 (0.4); 7.659 (3.4); 7.534 (3.1); 7.518 (3.1); 7.508 (3.0); 7.492 (2.8); 7.433 (2.9); 7.427 (2.3); 7.418 (1.7); 7.408 (4.6); 7.406 (5.3); 7.400 (4.9); 7.377 (3.0); 7.369 (4.1); 7.363 (3.8); 7.356 (2.4); 7.348 (8.7); 7.343 (10.2); 7.338 (6.2); 7.327 (6.6); 7.323 (7.1); 7.317 (6.5); 7.309 (2.1); 7.303 (2.2); 7.294 (3.0); 7.275 (1.5); 7.267 (11.6); 7.242 (0.4); 7.236 (0.8); 7.226 (5.1); 7.219 (2.6); 7.208 (5.8); 7.204 (3.7); 7.201 (3.6); 7.197 (7.5); 7.186 (3.2); 7.179 (7.0); 7.170 (1.2); 7.116 (4.1); 7.052 (1.1); 7.042 (7.7); 7.035 (2.5); 7.020 (3.0); 7.014 (11.7); 7.007 (3.1); 6.992 (2.4); 6.984 (5.9); 6.975 (1.0); 6.933 (8.4); 6.921 (0.7); 6.909 (0.3); 6.751 (4.1); 6.739 (0.3); 4.148 (0.9); 4.124 (2.6); 4.100 (2.7); 4.076 (0.9); 2.037 (12.3); 2.002 (1.9); 1.646 (15.5); 1.279 (3.5); 1.255 (7.2); 1.232 (3.4); 1.066 (0.5); 0.000 (7.6); −0.011 (0.3)

Example 84: $^1$H-NMR (400.1 MHz, d$_6$-DMSO):
δ = 10.691 (10.4); 8.868 (5.7); 8.865 (5.9); 8.856 (6.0); 8.853 (5.8); 8.169 (16.0); 8.142 (5.5); 7.777 (4.1); 7.765 (4.1); 7.757 (3.9); 7.745 (3.8); 7.699 (12.1); 7.696 (13.5); 7.680 (6.8); 7.677 (8.1); 7.672 (4.5); 7.659 (5.1); 7.640 (7.5); 7.619 (3.4); 7.557 (5.8); 7.538 (3.8); 7.333 (4.3); 7.198 (10.0); 7.063 (4.9); 5.759 (0.5); 3.413 (0.5); 3.363 (1.3); 3.313 (194.5); 3.263 (1.0); 2.682 (0.7); 2.677 (1.0); 2.673 (0.7); 2.607 (0.4); 2.563 (0.8); 2.558 (1.0); 2.554 (0.7); 2.549 (0.4); 2.531 (2.3); 2.517 (57.0); 2.513 (115.8); 2.508 (156.3); 2.504 (110.0); 2.499 (51.0); 2.467 (0.6); 2.463 (0.8); 2.458 (1.0); 2.454 (0.6); 2.340 (0.7); 2.335 (0.9); 2.331 (0.7); 1.243 (0.3)

Example 85: $^1$H-NMR (300.2 MHz, d$_6$-DMSO):
δ = 10.743 (11.6); 8.869 (6.1); 8.865 (6.7); 8.854 (6.8); 8.849 (6.6); 8.204 (16.0); 8.168 (5.6); 8.142 (6.3); 7.999 (4.2); 7.975 (6.6); 7.953 (9.5); 7.924 (3.0); 7.896 (8.0); 7.882 (8.0); 7.858 (6.0); 7.831 (2.0); 7.783 (4.6); 7.767 (4.7); 7.757 (4.4); 7.741 (4.1); 7.383 (5.1); 7.203 (11.6); 7.023 (5.6); 5.761 (12.7); 3.330 (71.2); 2.515 (8.5); 2.509 (18.1); 2.503 (24.7); 2.497 (18.3); 2.491 (9.0); 0.011 (0.6); 0.000 (15.4); −0.011 (0.7)

Example 86: $^1$H-NMR (400.1 MHz, d$_6$-DMSO):
δ = 10.581 (3.3); 8.866 (1.8); 8.862 (2.0); 8.854 (2.0); 8.850 (2.0); 8.172 (1.6); 8.153 (1.8); 8.133 (4.9); 7.773 (1.3); 7.761 (1.4); 7.753 (1.3); 7.741 (1.3); 7.546 (0.5); 7.535 (0.9); 7.527 (1.2); 7.515 (1.5); 7.506 (1.6); 7.495 (0.4); 7.478 (2.6); 7.459 (1.3); 7.410 (4.8); 7.401 (3.6); 7.346 (1.5); 7.211 (3.3); 7.076 (1.6); 5.760 (0.5); 3.314 (57.9); 3.264 (1.4); 2.531 (0.8); 2.526 (1.4); 2.518 (17.3); 2.513 (36.3); 2.509 (50.5); 2.504 (37.3); 2.500 (19.1); 2.468 (1.1); 2.464 (1.2); 2.459 (1.3); 2.454 (1.0); 2.450 (0.6); 2.005 (16.0); 1.956 (0.4)

Example 87: $^1$H-NMR (400.1 MHz, d$_6$-DMSO):
δ = 10.609 (5.5); 8.865 (2.8); 8.862 (3.0); 8.854 (3.0); 8.850 (2.9); 8.158 (2.5); 8.139 (2.7); 8.091 (7.7); 7.774 (2.0); 7.762 (2.1); 7.754 (1.9); 7.742 (1.8); 7.426 (1.4); 7.419 (0.9); 7.404 (16.0); 7.400 (15.7); 7.384 (0.9); 7.378 (1.5); 7.334 (2.2); 7.199 (5.1); 7.064 (5.3); 5.759 (3.4); 3.363 (0.4); 3.313 (110.6); 3.264 (0.9); 2.682 (0.4); 2.677 (0.5); 2.673 (0.4); 2.531 (1.4); 2.517 (32.1); 2.513 (65.3); 2.508 (88.6); 2.504 (62.9); 2.499 (29.5); 2.463 (0.7); 2.459 (0.8); 2.454 (0.5); 2.417 (22.6); 2.340 (0.4); 2.335 (0.6); 2.331 (0.4); 1.996 (0.7); 1.183 (0.4)

Example 88: $^1$H-NMR (400.1 MHz, d$_6$-DMSO):
δ = 10.636 (11.4); 8.867 (6.2); 8.864 (6.8); 8.855 (6.7); 8.852 (6.6); 8.195 (16.0); 8.170 (5.6); 8.151 (6.2); 7.776 (4.5); 7.764 (4.6); 7.757 (4.4); 7.745 (4.1); 7.729 (1.3); 7.725 (2.0); 7.710 (5.6); 7.707 (5.5); 7.692 (10.9); 7.673 (7.2); 7.575 (3.7); 7.573 (3.8); 7.550 (5.5); 7.527 (3.2); 7.462 (4.0); 7.443 (6.6); 7.423 (3.1); 7.340 (4.9); 7.205 (11.0); 7.069 (5.5); 5.760 (0.4); 3.414 (0.5); 3.364 (1.1); 3.313 (214.7); 3.263 (1.1); 2.682 (0.8); 2.677 (1.1); 2.673 (0.8); 2.609 (0.5); 2.568 (0.7); 2.564 (0.9); 2.560 (0.8); 2.531 (2.4); 2.517 (68.8); 2.513 (142.4); 2.508 (194.5); 2.504 (138.7); 2.499 (65.5); 2.463 (1.3); 2.340 (0.9); 2.335 (1.1); 2.331 (0.8); 1.996 (1.0); 1.254 (0.3); 1.200 (0.4); 1.183 (0.6); 1.165 (0.4); 0.866 (0.4)

Example 89: $^1$H-NMR (400.1 MHz, d$_6$-DMSO):
δ = 10.639 (10.6); 8.867 (6.0); 8.863 (6.4); 8.855 (6.5); 8.851 (6.3); 8.160 (5.3); 8.140 (6.0); 8.126 (15.8); 8.076 (0.4); 7.776 (4.4); 7.764 (4.4); 7.756 (4.3); 7.744 (4.0); 7.635 (6.2); 7.623 (6.9); 7.618 (5.2); 7.613 (8.6); 7.601 (8.1); 7.476 (1.3); 7.468 (10.3); 7.462 (3.5); 7.455 (2.2); 7.446 (16.0); 7.441 (4.3); 7.430 (3.3); 7.424 (8.3); 7.415 (1.2); 7.396 (0.5); 7.334 (4.7); 7.199 (10.8); 7.064 (5.3); 3.414 (0.6); 3.363 (0.8); 3.314 (202.5); 3.264 (2.9); 2.682 (0.7); 2.678 (1.0); 2.673 (0.8); 2.613 (0.4); 2.609 (0.5); 2.604 (0.4); 2.557 (0.8); 2.531 (4.9); 2.526 (6.6); 2.518 (61.2); 2.513 (124.7); 2.509 (170.8); 2.504 (123.3); 2.499 (61.3); 2.468 (3.7); 2.463 (4.0); 2.459 (4.3); 2.454 (3.5); 2.340 (0.9); 2.335 (1.1); 2.331 (0.9)

Example 90: $^1$H-NMR (300.2 MHz, d$_6$-DMSO):
δ = 10.636 (2.8); 8.865 (1.4); 8.860 (1.5); 8.849 (1.5); 8.844 (1.5); 8.159 (1.1); 8.134 (1.3); 8.088 (3.7); 7.778 (1.0); 7.762 (1.0); 7.752 (0.9); 7.736 (0.9); 7.481 (0.5); 7.450 (13.1); 7.417 (0.5); 7.378 (1.2); 7.198 (2.8); 7.018 (1.3); 3.356 (1.6); 3.056 (0.3); 3.033 (0.9); 3.010 (1.3); 2.987 (1.0); 2.964 (0.4); 2.514 (2.1); 2.508 (4.7); 2.502 (6.5); 2.496 (4.8); 2.490 (2.3); 1.270 (16.0); 1.247 (15.8); 1.220 (0.5); 0.000 (5.8)
Example 91: $^1$H-NMR (300.2 MHz, d$_6$-DMSO):
δ = 10.696 (4.7); 8.862 (3.1); 8.858 (3.4); 8.846 (3.4); 8.842 (3.3); 8.298 (7.6); 8.296 (7.5); 8.190 (2.8); 8.164 (3.2); 7.816 (5.3); 7.810 (6.5); 7.787 (13.1); 7.786 (13.6); 7.773 (2.9); 7.756 (2.6); 7.746 (2.5); 7.733 (7.8); 7.711 (4.1); 7.702 (3.2); 7.687 (0.7); 7.680 (2.2); 7.393 (2.6); 7.213 (5.7); 7.034 (2.8); 5.760 (2.0); 3.330 (53.6); 2.514 (5.1); 2.508 (10.7); 2.502 (14.7); 2.496 (10.9); 2.490 (5.4); 2.076 (16.0); 0.000 (6.0)
Example 92: $^1$H-NMR (300.2 MHz, d$_6$-DMSO):
δ = 10.753 (4.2); 8.866 (3.7); 8.861 (4.0); 8.850 (4.1); 8.845 (4.0); 8.208 (10.0); 8.158 (3.2); 8.132 (3.7); 7.918 (5.7); 7.912 (11.4); 7.906 (6.5); 7.779 (2.7); 7.763 (2.9); 7.752 (3.4); 7.744 (15.3); 7.738 (16.0); 7.373 (3.1); 7.193 (7.4); 7.013 (3.6); 5.761 (0.5); 3.337 (11.5); 2.515 (5.9); 2.509 (12.9); 2.503 (18.0); 2.496 (13.2); 2.490 (6.3); 2.077 (1.8); 0.011 (0.4); 0.000 (13.9); −0.011 (0.6)
Example 93: $^1$H-NMR (300.2 MHz, d$_6$-DMSO):
δ = 10.669 (11.1); 8.862 (6.1); 8.857 (6.8); 8.846 (6.8); 8.841 (6.6); 8.218 (16.0); 8.216 (15.9); 8.170 (5.3); 8.144 (6.0); 8.012 (13.8); 8.004 (14.5); 7.899 (0.5); 7.806 (7.6); 7.777 (15.9); 7.758 (4.9); 7.748 (4.5); 7.732 (4.1); 7.706 (10.8); 7.698 (10.2); 7.677 (6.5); 7.670 (6.5); 7.603 (0.9); 7.599 (0.7); 7.399 (0.4); 7.379 (5.4); 7.198 (12.3); 7.019 (5.9); 3.340 (19.4); 2.515 (10.6); 2.509 (22.9); 2.502 (31.8); 2.496 (23.5); 2.490 (11.3); 2.077 (0.8); 0.940 (0.4); 0.011 (0.8); 0.000 (23.2); −0.011 (1.0)
Example 94: $^1$H-NMR (300.2 MHz, d$_6$-DMSO):
δ = 10.684 (10.2); 8.862 (6.1); 8.857 (6.8); 8.846 (6.9); 8.841 (6.6); 8.235 (15.9); 8.233 (16.0); 8.176 (5.4); 8.150 (6.0); 7.980 (7.5); 7.975 (8.6); 7.953 (9.3); 7.948 (9.5); 7.774 (9.4); 7.758 (5.6); 7.750 (11.1); 7.732 (4.6); 7.646 (9.9); 7.619 (14.5); 7.592 (6.5); 7.558 (0.3); 7.533 (0.3); 7.416 (0.3); 7.390 (5.0); 7.210 (11.6); 7.030 (5.6); 5.760 (0.5); 3.330 (100.3); 3.281 (0.5); 2.515 (9.9); 2.509 (21.8); 2.502 (30.5); 2.496 (22.4); 2.490 (10.8); 2.076 (4.7); 0.011 (0.4); 0.000 (12.3); −0.011 (0.6)
Example 95: $^1$H-NMR (300.2 MHz, d$_6$-DMSO):
δ = 10.686 (5.9); 8.862 (4.9); 8.857 (5.3); 8.846 (5.4); 8.841 (5.2); 8.234 (12.9); 8.232 (12.7); 8.169 (4.3); 8.143 (4.9); 8.027 (7.8); 8.020 (8.1); 7.831 (2.5); 7.804 (16.0); 7.802 (15.5); 7.797 (14.0); 7.789 (11.8); 7.774 (4.2); 7.768 (2.9); 7.760 (5.1); 7.748 (3.6); 7.732 (3.3); 7.711 (0.6); 7.700 (0.5); 7.693 (0.4); 7.378 (4.2); 7.198 (9.7); 7.018 (4.8); 5.761 (0.5); 3.475 (0.4); 3.452 (1.2); 3.429 (1.3); 3.405 (1.0); 3.350 (4.5); 3.168 (1.2); 2.515 (8.3); 2.509 (18.4); 2.502 (25.7); 2.496 (18.9); 2.490 (9.2); 2.076 (12.4); 1.079 (1.0); 1.055 (2.0); 1.032 (1.0); 0.011 (0.4); 0.000 (13.2); −0.011 (0.6)
Example 96: $^1$H-NMR (300.2 MHz, d$_6$-DMSO):
δ = 10.734 (11.1); 8.866 (5.9); 8.861 (6.4); 8.850 (6.6); 8.846 (6.3); 8.190 (16.0); 8.160 (5.3); 8.134 (5.8); 7.962 (10.3); 7.954 (10.9); 7.924 (0.4); 7.905 (12.6); 7.876 (15.3); 7.779 (4.3); 7.763 (4.4); 7.753 (4.1); 7.737 (3.9); 7.614 (5.5); 7.606 (5.4); 7.586 (4.6); 7.578 (4.5); 7.376 (5.1); 7.196 (11.8); 7.016 (5.6); 3.330 (76.1); 2.515 (9.3); 2.509 (20.3); 2.503 (28.1); 2.497 (20.4); 2.491 (9.6); 2.077 (1.1); 0.011 (0.6); 0.000 (21.2); −0.011 (0.8)
Example 97: $^1$H-NMR (300.2 MHz, d$_6$-DMSO):
δ = 10.434 (6.6); 8.845 (4.1); 8.840 (4.3); 8.829 (4.4); 8.824 (4.2); 8.124 (3.4); 8.098 (3.9); 7.932 (10.7); 7.752 (3.0); 7.736 (3.0); 7.725 (2.7); 7.710 (2.6); 7.403 (1.8); 7.396 (2.3); 7.390 (1.4); 7.374 (8.2); 7.369 (4.1); 7.355 (4.7); 7.350 (11.3); 7.339 (6.0); 7.333 (3.7); 7.326 (1.6); 7.316 (3.6); 7.303 (0.8); 7.297 (0.8); 7.292 (0.9); 7.194 (6.6); 7.189 (7.6); 7.168 (14.1); 6.988 (3.9); 5.500 (16.0); 3.340 (8.7); 2.514 (6.2); 2.508 (13.4); 2.502 (18.6); 2.496 (13.6); 2.490 (6.5); 2.076 (0.4); 0.011 (0.4); 0.000 (13.1); −0.011 (0.5)
Example 98: $^1$H-NMR (400.0 MHz, CDCl$_3$):
δ = 8.795 (1.2); 8.792 (1.3); 8.783 (1.3); 8.780 (1.3); 8.344 (0.3); 8.341 (0.4); 8.122 (1.3); 8.106 (1.3); 8.103 (1.3); 7.943 (4.7); 7.792 (0.6); 7.702 (2.0); 7.699 (2.8); 7.680 (3.0); 7.678 (2.9); 7.666 (0.3); 7.662 (0.4); 7.647 (0.6); 7.643 (0.5); 7.574 (1.8); 7.562 (1.2); 7.554 (1.1); 7.542 (1.0); 7.491 (0.8); 7.486 (1.9); 7.481 (0.9); 7.467 (3.4); 7.446 (2.4); 7.360 (1.2); 7.357 (0.8); 7.341 (1.7); 7.325 (0.6); 7.323 (0.7); 7.264 (5.9); 7.137 (1.2); 7.000 (2.4); 6.863 (1.2); 5.300 (5.1); 3.943 (1.6); 3.864 (16.0); 3.839 (2.3); 1.622 (3.8); 1.254 (0.4); 0.000 (5.5)
Example 99: $^1$H-NMR (400.1 MHz, d$_6$-DMSO):
δ = 10.158 (3.5); 8.828 (2.0); 8.824 (2.2); 8.816 (2.2); 8.812 (2.2); 8.165 (1.7); 8.147 (1.8); 8.145 (1.9); 7.860 (8.0); 7.742 (1.4); 7.730 (1.5); 7.722 (1.5); 7.710 (1.4); 7.382 (1.1); 7.379 (0.9); 7.374 (0.7); 7.367 (1.2); 7.359 (13.1); 7.355 (11.1); 7.340 (0.9); 7.332 (1.3); 7.323 (1.9); 7.188 (3.9); 7.053 (1.9); 3.352 (0.3); 3.302 (54.0); 3.253 (0.5); 2.756 (1.0); 2.737 (3.2); 2.719 (3.3); 2.700 (1.2); 2.673 (0.5); 2.669 (0.7); 2.664 (0.5); 2.554 (0.4); 2.550 (0.6); 2.545 (0.5); 2.522 (1.3); 2.517 (2.2); 2.509 (31.6); 2.504 (67.6); 2.500 (94.8); 2.495 (69.9); 2.491 (35.4); 2.455 (1.8); 2.450 (1.8); 2.445 (1.5); 2.391 (16.0); 2.349 (0.4); 2.336 (0.4); 2.331 (0.6); 2.327 (0.7); 2.322 (0.6); 0.965 (4.4); 0.946 (10.8); 0.928 (4.5); 0.008 (0.9); 0.000 (28.4); −0.009 (1.2)
Example 100: $^1$H-NMR (400.1 MHz, d$_6$-DMSO):
δ = 10.168 (3.5); 8.830 (2.1); 8.826 (2.2); 8.818 (2.2); 8.814 (2.1); 8.169 (1.8); 8.151 (1.8); 8.149 (1.9); 7.873 (7.8); 7.744 (1.5); 7.732 (1.5); 7.724 (1.4); 7.712 (1.3); 7.448 (1.3); 7.429 (3.2); 7.410 (2.0); 7.327 (1.8); 7.309 (3.1); 7.307 (3.1); 7.305 (3.0); 7.300 (2.5); 7.289 (2.0); 7.284 (2.2); 7.282 (2.2); 7.270 (1.3); 7.191 (4.0); 7.056 (1.9); 3.302 (30.7); 2.780 (1.1); 2.762 (3.3); 2.743 (3.4); 2.724 (1.1); 2.669 (0.4); 2.599 (0.4); 2.595 (0.3); 2.554 (0.3); 2.548 (1.4); 2.544 (0.7); 2.540 (0.6); 2.522 (1.3); 2.517 (2.0); 2.509 (26.5); 2.504 (54.1); 2.500 (73.3); 2.495 (51.1); 2.491 (23.2); 2.448 (0.6); 2.445 (0.6); 2.398 (16.0); 2.338 (0.6); 2.331 (0.4); 2.327 (0.5); 2.322 (0.3); 0.976 (4.6); 0.957 (10.9); 0.939 (4.5); 0.008 (0.8); 0.000 (23.4); −0.009 (0.7)

-continued

Example 101: $^1$H-NMR (300.2 MHz, d$_6$-DMSO):
δ = 10.591 (3.1); 8.694 (3.2); 8.689 (3.3); 8.063 (5.8); 7.966 (3.2); 7.428 (1.0); 7.396 (16.0); 7.364 (1.3); 7.333 (1.8); 7.152 (3.9); 6.972 (1.9); 3.568 (1.6); 3.331 (27.0); 2.514 (4.2); 2.508 (8.8); 2.502 (12.0); 2.496 (8.8); 2.490 (4.4); 2.448 (11.7); 2.408 (17.3); 2.363 (0.5); 0.000 (7.1)

Example 102: $^1$H-NMR (400.1 MHz, d$_6$-DMSO):
δ = 9.965 (3.1); 8.847 (1.7); 8.844 (1.8); 8.835 (1.8); 8.832 (1.8); 8.152 (1.4); 8.135 (1.5); 8.133 (1.5); 7.767 (1.3); 7.755 (1.3); 7.748 (1.3); 7.734 (6.5); 7.643 (4.5); 7.638 (1.6); 7.626 (1.9); 7.621 (6.3); 7.614 (0.8); 7.513 (0.8); 7.506 (6.2); 7.500 (1.8); 7.489 (1.6); 7.484 (4.4); 7.477 (0.5); 7.344 (1.3); 7.209 (3.1); 7.074 (1.4); 3.417 (0.4); 3.415 (0.9); 3.367 (0.8); 3.364 (0.6); 3.316 (422.7); 3.266 (5.4); 3.216 (1.1); 3.088 (0.4); 3.070 (1.0); 3.053 (1.3); 3.035 (1.0); 3.018 (0.4); 2.682 (0.6); 2.678 (0.9); 2.673 (0.7); 2.556 (0.4); 2.531 (3.5); 2.526 (5.3); 2.518 (52.5); 2.513 (108.4); 2.509 (149.5); 2.504 (108.1); 2.500 (53.6); 2.468 (2.9); 2.463 (3.1); 2.458 (3.2); 2.454 (2.6); 2.413 (0.6); 2.408 (0.6); 2.340 (0.7); 2.336 (1.0); 2.331 (0.7); 1.228 (16.0); 1.210 (16.0); 1.183 (0.5); 1.177 (0.5); 1.165 (0.4); 1.159 (0.5)

Example 103: $^1$H-NMR (400.1 MHz, d$_6$-DMSO):
δ = 9.968 (3.0); 8.841 (1.6); 8.837 (1.8); 8.829 (1.8); 8.825 (1.8); 8.149 (1.2); 8.147 (1.3); 8.130 (1.4); 8.127 (1.5); 7.761 (1.2); 7.745 (6.3); 7.729 (1.2); 7.611 (0.4); 7.604 (3.8); 7.601 (3.8); 7.595 (2.3); 7.590 (4.0); 7.588 (3.1); 7.580 (0.5); 7.572 (1.7); 7.569 (2.7); 7.567 (2.7); 7.563 (1.8); 7.561 (1.4); 7.459 (1.2); 7.454 (1.2); 7.450 (1.3); 7.444 (1.5); 7.442 (1.1); 7.436 (1.1); 7.431 (1.0); 7.340 (1.3); 7.204 (3.1); 7.069 (1.5); 4.039 (0.7); 4.021 (0.7); 3.304 (19.1); 3.101 (0.3); 3.083 (0.9); 3.066 (1.3); 3.048 (1.0); 3.030 (0.4); 2.523 (0.7); 2.518 (1.0); 2.509 (10.4); 2.505 (21.4); 2.500 (29.6); 2.496 (21.3); 2.491 (10.6); 2.460 (0.6); 2.455 (0.6); 2.450 (0.5); 2.446 (0.4); 1.988 (3.0); 1.234 (16.0); 1.216 (15.9); 1.193 (1.2); 1.184 (0.5); 1.175 (1.9); 1.167 (0.3); 1.157 (0.9); 0.008 (0.4); 0.000 (9.5); −0.009 (0.4)

Example 104: $^1$H-NMR (400.1 MHz, d$_6$-DMSO):
δ = 10.193 (2.9); 8.828 (1.7); 8.824 (1.8); 8.816 (1.8); 8.812 (1.8); 8.178 (1.5); 8.158 (1.6); 7.899 (6.5); 7.740 (1.2); 7.728 (1.2); 7.720 (1.2); 7.708 (1.1); 7.473 (0.3); 7.457 (1.4); 7.453 (1.4); 7.441 (3.8); 7.438 (4.4); 7.424 (0.6); 7.391 (0.7); 7.385 (0.7); 7.372 (1.3); 7.366 (1.1); 7.356 (0.8); 7.350 (0.8); 7.337 (1.5); 7.323 (2.3); 7.304 (1.3); 7.201 (3.2); 7.066 (1.6); 5.751 (8.8); 4.039 (0.9); 4.021 (0.9); 3.303 (26.0); 2.545 (0.9); 2.526 (2.6); 2.509 (20.7); 2.504 (38.9); 2.500 (51.8); 2.495 (36.7); 2.491 (17.6); 2.454 (0.3); 2.450 (0.4); 2.327 (0.4); 1.989 (16.0); 1.192 (1.0); 1.175 (2.0); 1.157 (1.0); 1.056 (0.3); 0.899 (3.7); 0.880 (8.7); 0.861 (3.7); 0.008 (0.5); 0.000 (14.6); −0.009 (0.5)

Example 105: $^1$H-NMR (400.1 MHz, d$_6$-DMSO):
δ = 10.197 (5.5); 8.831 (3.0); 8.828 (3.3); 8.819 (3.2); 8.816 (3.2); 8.170 (2.6); 8.153 (2.7); 8.151 (2.8); 7.919 (11.2); 7.745 (2.2); 7.733 (2.2); 7.726 (2.1); 7.714 (2.0); 7.634 (0.7); 7.627 (6.3); 7.622 (2.5); 7.611 (3.2); 7.605 (13.0); 7.598 (1.7); 7.567 (1.8); 7.561 (12.7); 7.555 (3.3); 7.544 (2.4); 7.538 (6.5); 7.532 (0.7); 7.323 (2.5); 7.188 (5.9); 7.053 (2.8); 3.304 (24.4); 2.800 (1.5); 2.781 (4.8); 2.763 (4.9); 2.744 (1.6); 2.674 (0.3); 2.669 (0.5); 2.665 (0.4); 2.550 (0.4); 2.545 (0.3); 2.523 (1.6); 2.518 (2.3); 2.509 (26.0); 2.505 (54.0); 2.500 (74.7); 2.496 (53.4); 2.491 (25.2); 2.454 (0.4); 2.450 (0.5); 2.446 (0.4); 2.331 (0.3); 2.327 (0.5); 2.322 (0.3); 0.981 (6.7); 0.963 (16.0); 0.944 (6.6); 0.008 (0.9); 0.000 (26.5); −0.009 (0.9)

Example 106: $^1$H-NMR (400.1 MHz, d$_6$-DMSO):
δ = 9.953 (3.4); 8.835 (1.9); 8.831 (2.0); 8.823 (2.0); 8.820 (1.9); 8.156 (1.6); 8.136 (1.8); 7.752 (1.4); 7.740 (1.4); 7.727 (6.9); 7.721 (1.4); 7.482 (0.5); 7.478 (0.5); 7.462 (1.5); 7.459 (1.4); 7.446 (2.1); 7.442 (2.8); 7.434 (2.7); 7.420 (0.9); 7.393 (0.8); 7.388 (0.6); 7.373 (1.5); 7.369 (1.3); 7.357 (1.1); 7.351 (2.4); 7.337 (2.5); 7.334 (2.6); 7.318 (1.1); 7.215 (3.3); 7.080 (1.7); 3.304 (15.9); 2.826 (0.4); 2.808 (1.1); 2.790 (1.5); 2.772 (1.1); 2.754 (0.4); 2.522 (0.6); 2.509 (13.0); 2.505 (26.4); 2.500 (35.7); 2.496 (25.1); 2.491 (11.6); 1.968 (16.0); 1.134 (4.2); 1.121 (4.1); 0.008 (0.4); 0.000 (10.1); −0.008 (0.3)

Example 107: $^1$H-NMR (400.1 MHz, d$_6$-DMSO):
δ = 10.215 (5.0); 8.863 (0.4); 8.859 (0.4); 8.851 (0.4); 8.847 (0.5); 8.833 (2.9); 8.829 (3.2); 8.821 (3.2); 8.817 (3.1); 8.342 (0.3); 8.322 (0.3); 8.175 (2.3); 8.173 (2.4); 8.171 (2.4); 8.155 (2.6); 8.153 (2.7); 7.941 (10.8); 7.747 (2.1); 7.735 (2.2); 7.727 (2.1); 7.715 (2.2); 7.701 (0.4); 7.693 (0.4); 7.657 (0.4); 7.626 (2.9); 7.621 (5.6); 7.617 (3.4); 7.616 (3.3); 7.609 (1.5); 7.590 (4.1); 7.572 (5.3); 7.570 (5.1); 7.567 (3.4); 7.562 (6.1); 7.558 (3.9); 7.547 (1.7); 7.542 (2.0); 7.537 (1.0); 7.529 (3.0); 7.524 (4.5); 7.520 (2.8); 7.511 (1.9); 7.505 (2.5); 7.501 (1.6); 7.325 (2.4); 7.189 (5.7); 7.054 (2.8); 3.305 (15.2); 2.828 (1.5); 2.809 (4.7); 2.790 (4.8); 2.771 (1.7); 2.669 (0.4); 2.555 (0.4); 2.550 (0.5); 2.523 (1.0); 2.518 (1.6); 2.509 (21.8); 2.505 (46.1); 2.500 (64.4); 2.496 (46.9); 2.491 (23.5); 2.327 (0.4); 0.989 (6.5); 0.971 (16.0); 0.952 (6.7); 0.008 (0.7); 0.000 (20.7); −0.009 (0.9)

Example 108: $^1$H-NMR (400.1 MHz, d$_6$-DMSO):
δ = 9.922 (3.1); 8.837 (1.6); 8.833 (1.8); 8.825 (1.8); 8.821 (1.7); 8.142 (1.4); 8.123 (1.5); 7.756 (1.2); 7.744 (1.2); 7.736 (1.1); 7.724 (1.1); 7.669 (5.7); 7.365 (2.0); 7.344 (5.0); 7.339 (2.4); 7.318 (6.3); 7.302 (1.1); 7.297 (2.5); 7.203 (3.0); 7.068 (1.5); 5.751 (0.4); 4.057 (1.2); 4.039 (3.6); 4.021 (3.6); 4.003 (1.2); 3.303 (26.2); 3.058 (0.3); 3.040 (0.9); 3.022 (1.3); 3.004 (1.0); 2.987 (0.4); 2.522 (0.6); 2.518 (1.0); 2.509 (15.4); 2.504 (31.8); 2.500 (43.4); 2.495 (30.6); 2.491 (14.2); 2.450 (0.4); 2.398 (11.5); 1.987 (16.0); 1.201 (15.9); 1.193 (5.6); 1.183 (15.7); 1.175 (9.4); 1.157 (4.3); 0.008 (0.4); 0.000 (12.4); −0.009 (0.4)

Example 109: $^1$H-NMR (400.1 MHz, d$_6$-DMSO):
δ = 9.976 (8.0); 8.835 (4.6); 8.831 (5.0); 8.823 (5.0); 8.819 (4.9); 8.156 (3.7); 8.138 (4.0); 8.136 (4.1); 7.769 (16.0); 7.768 (16.0); 7.751 (3.6); 7.739 (3.5); 7.729 (6.0); 7.725 (3.9); 7.722 (4.2); 7.720 (3.8); 7.708 (7.9); 7.704 (4.4); 7.700 (1.5); 7.629 (2.7); 7.624 (3.4); 7.612 (4.0); 7.610 (5.2); 7.607 (6.5); 7.604 (5.4); 7.589 (11.3); 7.587 (10.8); 7.569 (5.9); 7.565 (5.8); 7.551 (5.0); 7.542 (1.9); 7.532 (1.8); 7.528 (1.6); 7.347 (3.6); 7.211 (8.2); 7.076 (4.1); 3.402 (0.3); 3.352 (0.7); 3.302 (132.0); 3.252 (0.8); 2.828 (0.9); 2.811 (2.5); 2.793 (3.6); 2.776 (2.7); 2.758 (1.1); 2.678 (0.5); 2.673 (1.0); 2.669 (1.4); 2.664 (1.1); 2.660 (0.5); 2.604 (0.4); 2.600 (0.6); 2.595 (0.4); 2.554 (1.0); 2.550 (1.5); 2.545 (1.2); 2.522 (5.2); 2.518 (7.7); 2.509 (81.0); 2.504 (169.2); 2.500 (235.1); 2.495 (169.1); 2.491 (83.7); 2.454 (3.6); 2.450 (3.4); 2.445 (2.7); 2.405 (0.6); 2.400 (0.6); 2.336 (0.6); 2.331 (1.1); 2.327 (1.5); 2.322 (1.1); 1.987 (1.3); 1.209 (8.3); 1.191 (8.7); 1.175 (2.2); 1.157 (1.2); 1.099 (8.4); 1.081 (8.3); 0.050 (0.4); 0.008 (2.6); 0.000 (78.9); −0.009 (3.3); −0.050 (0.5)

Example 110: $^1$H-NMR (400.1 MHz, d$_6$-DMSO):
δ = 10.226 (5.5); 8.829 (3.2); 8.825 (3.4); 8.817 (3.5); 8.813 (3.4); 8.181 (2.8); 8.161 (3.0); 7.939 (11.4); 7.741 (2.5); 7.730 (4.8); 7.722 (2.6); 7.711 (5.4); 7.625 (1.6); 7.618 (2.0); 7.608 (2.3); 7.602 (3.4); 7.593 (1.2); 7.588 (2.7); 7.583 (3.9); 7.574 (6.8); 7.568 (7.2); 7.564 (4.8); 7.551 (2.6); 7.548 (2.6); 7.532 (0.9); 7.528 (0.8); 7.335 (2.5); 7.199 (5.7); 7.064 (2.9); 3.352 (0.6); 3.303 (45.5); 3.252 (0.6); 2.673 (0.5); 2.669 (0.7); 2.664 (0.5); 2.600 (0.5); 2.595 (0.4); 2.559 (1.6); 2.554 (2.4); 2.550 (3.0); 2.545 (2.8); 2.540 (2.6); 2.522 (4.3); 2.509 (39.6); 2.504 (79.0); 2.500 (107.3); 2.495 (77.7); 2.491 (39.1); 2.459 (2.0); 2.454 (2.1); 2.450 (2.2); 2.445 (1.8); 2.441 (1.3); 2.400 (0.4); 2.331 (0.6); 2.327 (0.8); 2.322 (0.5); 1.987 (0.5); 0.925 (7.1); 0.906 (16.0); 0.888 (7.1); 0.856 (0.3); 0.050 (0.4); 0.008 (1.0); 0.000 (27.4); −0.009 (1.3); −0.050 (0.4)

Example 111: $^1$H-NMR (400.1 MHz, d$_6$-DMSO):
δ = 10.267 (2.8); 8.835 (1.6); 8.831 (1.8); 8.823 (1.8); 8.820 (1.8); 8.221 (1.4); 8.202 (1.5); 7.995 (1.4); 7.979 (1.6); 7.976 (1.7); 7.942 (5.5); 7.907 (0.7); 7.891 (1.5); 7.872 (1.1); 7.827 (1.1); 7.808 (1.5); 7.789 (0.7); 7.742 (1.2); 7.730 (1.2); 7.722 (1.2); 7.710 (1.1); 7.605 (1.7); 7.585 (1.6); 7.360 (1.3); 7.225 (3.0); 7.089 (1.5); 3.319 (57.2); 3.269 (0.8); 2.531 (0.9); 2.526 (1.3); 2.518 (12.6); 2.513 (25.8); 2.509 (35.6); 2.504 (25.9); 2.499 (13.0); 2.463 (0.8); 2.459 (0.7); 2.071 (16.0); 1.995 (1.0); 1.183 (0.5)

Example 112: $^1$H-NMR (400.1 MHz, d$_6$-DMSO):
δ = 10.216 (2.7); 8.835 (1.6); 8.832 (1.6); 8.823 (1.6); 8.820 (1.6); 8.199 (1.3); 8.180 (1.4); 7.888 (5.2); 7.745 (1.1); 7.733 (1.1); 7.725 (1.0); 7.713 (1.0); 7.429 (2.9); 7.408 (5.3); 7.356 (4.2); 7.346 (1.6); 7.336 (2.4); 7.210 (2.9); 7.075 (1.4); 3.318 (86.1); 3.267 (1.0); 2.531 (0.7); 2.517 (14.2); 2.513 (28.8); 2.508 (38.8); 2.504 (27.4); 2.499 (12.7); 2.458 (0.4); 2.453 (0.3); 2.390 (10.9); 2.283 (16.0)

Example 113: $^1$H-NMR (400.1 MHz, d$_6$-DMSO):
δ = 10.299 (2.8); 8.842 (1.6); 8.839 (1.6); 8.830 (1.6); 8.827 (1.6); 8.212 (1.3); 8.194 (1.4); 8.192 (1.4); 8.008 (5.3); 7.928 (1.1); 7.914 (3.3); 7.832 (0.4); 7.814 (4.4); 7.801 (0.6); 7.794 (1.3); 7.774 (0.3); 7.753 (1.1); 7.741 (1.2); 7.733 (1.1); 7.721 (1.0); 7.348 (1.3); 7.213 (2.9); 7.077 (1.4); 4.065 (0.5); 4.047 (1.5); 4.029 (1.5); 4.011 (0.5); 3.417 (0.4); 3.365 (0.5); 3.317 (180.1); 3.266 (1.4); 2.677 (0.4); 2.531 (1.1); 2.517 (25.7); 2.513 (52.9); 2.508 (72.1); 2.504 (50.8); 2.499 (23.6); 2.463 (0.5); 2.458 (0.7); 2.454 (0.5); 2.374 (16.0); 2.340 (0.4); 2.335 (0.5); 1.996 (6.6); 1.201 (1.8); 1.183 (3.6); 1.165 (1.8)

Example 114: $^1$H-NMR (400.1 MHz, d$_6$-DMSO):
δ = 10.298 (2.8); 8.843 (1.6); 8.839 (1.7); 8.831 (1.7); 8.828 (1.6); 8.216 (1.4); 8.199 (1.5); 8.197 (1.5); 8.013 (5.2); 7.929 (2.4); 7.908 (3.9); 7.846 (3.7); 7.825 (2.4); 7.754 (1.1); 7.742 (1.2); 7.734 (1.1); 7.722 (1.1); 7.350 (1.2); 7.215 (2.8); 7.080 (1.4); 5.759 (3.8); 3.416 (0.4); 3.366 (1.2); 3.363 (0.7); 3.316 (208.8); 3.266 (2.4); 3.215 (0.4); 2.682 (0.4); 2.677 (0.5); 2.673 (0.4); 2.553 (1.0); 2.530 (2.7); 2.517 (32.7); 2.513 (63.8); 2.508 (84.9); 2.504 (60.6); 2.499 (30.0); 2.463 (1.9); 2.458 (2.0); 2.393 (16.0); 2.340 (0.6); 2.335 (0.7); 2.331 (0.5)

Example 115: $^1$H-NMR (400.1 MHz, d$_6$-DMSO):
δ = 10.233 (2.5); 8.835 (1.5); 8.831 (1.6); 8.823 (1.6); 8.819 (1.6); 8.209 (1.3); 8.190 (1.4); 7.910 (5.2); 7.743 (1.1); 7.731 (1.1); 7.723 (1.0); 7.711 (1.0); 7.454 (1.3); 7.451 (1.7); 7.447 (2.0); 7.440 (4.4); 7.438 (4.6); 7.428 (0.5); 7.394 (0.7); 7.386 (0.8); 7.375 (1.1); 7.366 (1.1); 7.360 (1.8); 7.353 (0.7); 7.304 (2.1); 7.285 (1.4); 7.225 (2.9); 7.089 (1.4); 4.065 (0.6); 4.047 (1.9); 4.029 (1.9); 4.011 (0.6); 3.368 (0.4); 3.318 (67.3); 3.269 (0.4); 2.531 (0.5); 2.517 (11.3); 2.513 (23.0); 2.508 (31.2); 2.504 (22.1); 2.499 (10.4); 2.060 (16.0); 2.014 (14.3); 1.995 (8.3); 1.201 (2.2); 1.183 (4.3); 1.165 (2.1)

Example 116: $^1$H-NMR (300.2 MHz, d$_6$-DMSO):
δ = 9.947 (0.6); 8.837 (0.3); 7.684 (0.9); 7.437 (0.5); 7.411 (0.4); 7.256 (0.5); 7.214 (0.4); 5.759 (16.0); 3.323 (42.2); 2.513 (6.9); 2.507 (15.3); 2.501 (21.5); 2.495 (16.0); 2.489 (7.7); 2.399 (2.4); 1.219 (2.9); 1.195 (2.9); 0.011 (0.5); 0.000 (17.3); −0.011 (0.8)

Example 117: $^1$H-NMR (300.2 MHz, d$_6$-DMSO):
δ = 10.261 (5.2); 8.840 (3.1); 8.835 (3.3); 8.824 (3.3); 8.819 (3.3); 8.185 (2.5); 8.160 (2.9); 7.985 (13.1); 7.871 (8.6); 7.852 (4.2); 7.831 (3.6); 7.805 (2.2); 7.779 (0.8); 7.759 (2.5); 7.743 (2.3); 7.733 (2.2); 7.717 (2.1); 7.378 (2.6); 7.198 (6.1); 7.018 (3.0); 5.759 (8.3); 3.324 (70.5); 2.857 (1.5); 2.832 (4.6); 2.807 (4.8); 2.782 (1.6); 2.727 (0.4); 2.514 (14.4); 2.508 (32.1); 2.502 (44.9); 2.495 (33.1); 2.489 (16.0); 2.367 (0.4); 1.000 (6.3); 0.975 (16.0); 0.950 (6.1); 0.011 (1.1); 0.000 (42.4); −0.011 (1.9)

Example 118: $^1$H-NMR (300.2 MHz, d$_6$-DMSO):
δ = 18.448 (0.4); 17.581 (0.4); 16.993 (0.4); 16.443 (0.4); 15.811 (0.4); 14.500 (0.4); 14.461 (0.4); 12.753 (0.4); 10.259 (4.9); 8.842 (2.7); 8.836 (2.9); 8.826 (2.8); 8.821 (2.8); 8.210 (0.4); 8.190 (2.3); 8.163 (2.5); 8.032 (0.5); 7.991 (9.7); 7.947 (4.1); 7.918 (6.2); 7.887 (0.5); 7.873 (0.4); 7.802 (5.8); 7.774 (4.1); 7.761 (2.2); 7.745 (2.0); 7.734 (2.0); 7.719 (1.6); 7.378 (2.2); 7.198 (5.2); 7.018 (2.5); 5.759 (16.0); 3.618 (0.4); 3.476 (0.4); 3.407 (0.5); 3.369 (0.5); 3.324 (224.4); 3.301 (2.9); 3.202 (0.4); 2.925 (0.4); 2.886 (1.4); 2.860 (3.7); 2.836 (3.9); 2.811 (1.6); 2.728 (0.9); 2.641 (0.4); 2.514 (30.1); 2.508 (65.5); 2.501 (90.9); 2.495 (66.3); 2.489 (31.9); 2.446 (0.9); 2.408 (0.5); 2.265 (0.5); 1.011 (5.2); 0.986 (13.3); 0.961 (5.1); 0.831 (0.4); 0.011 (2.0); 0.000 (70.7); −0.011 (3.3); −0.051 (0.5); −0.174 (0.4); −0.199 (0.5); −1.131 (0.4)

Example 119: $^1$H-NMR (300.2 MHz, d$_6$-DMSO):
δ = 10.201 (5.2); 8.836 (3.0); 8.831 (3.3); 8.820 (3.4); 8.815 (3.3); 8.178 (2.7); 8.152 (3.0); 7.898 (12.1); 7.754 (2.3); 7.738 (2.3); 7.728 (2.2); 7.712 (2.1); 7.592 (1.3); 7.588 (2.0); 7.582 (1.2); 7.563 (4.6); 7.558 (3.6); 7.547 (2.0); 7.539 (7.1); 7.511 (11.1); 7.503 (5.2); 7.493 (3.6); 7.487 (5.1); 7.477 (4.0); 7.467 (1.0); 7.460 (0.9); 7.454 (1.3); 7.378 (2.6); 7.198 (6.0); 7.018 (2.9); 5.759 (11.7); 3.366 (0.4); 3.358 (0.4); 3.325 (90.2); 3.274 (0.4); 2.799 (1.5); 2.774 (4.9); 2.749 (5.2); 2.725 (2.0); 2.513 (13.7); 2.507 (29.9); 2.501 (41.7); 2.495 (31.1); 2.489 (15.7); 0.978 (6.5); 0.953 (16.0); 0.928 (6.4); 0.011 (0.9); 0.000 (30.5); −0.011 (1.6)

Example 120: $^1$H-NMR (300.2 MHz, d$_6$-DMSO):
δ = 9.960 (2.7); 8.844 (1.5); 8.839 (1.6); 8.828 (1.6); 8.823 (1.6); 8.154 (1.2); 8.128 (1.4); 7.769 (1.1); 7.753 (1.1); 7.743 (1.0); 7.727 (1.1); 7.704 (5.3); 7.598 (0.5); 7.591 (0.8); 7.585 (0.5); 7.570 (2.8); 7.565 (1.3); 7.562 (1.5); 7.545 (3.6); 7.533 (2.2); 7.528 (1.5); 7.520 (0.7); 7.511 (1.4); 7.498

(0.4); 7.486 (0.5); 7.459 (2.8); 7.453 (3.4); 7.445 (0.9); 7.437 (1.3); 7.431 (2.7); 7.427 (2.0); 7.394 (1.2); 7.213 (2.8); 7.033 (1.3); 5.759 (16.0); 3.325 (49.3); 3.068 (0.8); 3.044 (1.2); 3.021 (0.9); 2.997 (0.4); 2.514 (6.0); 2.507 (13.3); 2.501 (18.6); 2.495 (13.6); 2.489 (6.6); 2.075 (1.8); 1.989 (0.6); 1.219 (14.5); 1.195 (14.3); 1.174 (0.7); 0.011 (0.4); 0.000 (14.5); −0.011 (0.6)

Example 121: $^1$H-NMR (300.2 MHz, $d_6$-DMSO):
δ = 10.195 (4.2); 8.836 (2.5); 8.831 (2.6); 8.820 (2.7); 8.815 (2.6); 8.158 (2.1); 8.131 (2.3); 7.914 (10.7); 7.758 (1.8); 7.742 (2.0); 7.732 (1.8); 7.716 (1.7); 7.582 (1.7); 7.576 (0.8); 7.557 (3.7); 7.553 (3.2); 7.543 (1.5); 7.534 (5.6); 7.500 (9.0); 7.476 (4.8); 7.471 (4.9); 7.453 (0.8); 7.448 (1.0); 7.443 (0.8); 7.371 (2.1); 7.190 (4.9); 7.009 (2.4); 5.759 (16.0); 3.324 (92.6); 2.760 (2.3); 2.734 (3.4); 2.709 (2.5); 2.514 (14.7); 2.507 (32.8); 2.501 (46.1); 2.495 (33.8); 2.489 (16.4); 2.271 (0.4); 1.400 (0.3); 1.376 (1.3); 1.351 (2.4); 1.326 (2.7); 1.301 (1.6); 1.279 (0.5); 0.757 (6.1); 0.732 (13.7); 0.708 (5.4); 0.011 (1.1); 0.000 (40.0); −0.011 (1.7)

Example 122: $^1$H-NMR (300.2 MHz, $d_6$-DMSO):
δ = 10.000 (4.3); 8.814 (2.7); 8.809 (2.9); 8.798 (3.0); 8.793 (2.9); 8.134 (2.1); 8.132 (2.2); 8.108 (2.5); 8.105 (2.6); 7.727 (2.0); 7.711 (2.1); 7.701 (1.9); 7.685 (1.8); 7.612 (10.0); 7.344 (2.5); 7.164 (5.6); 6.983 (2.7); 5.759 (9.9); 4.041 (0.4); 4.027 (3.6); 4.017 (0.8); 4.003 (6.2); 3.979 (3.7); 3.325 (49.0); 2.727 (1.4); 2.701 (4.1); 2.676 (4.3); 2.651 (1.4); 2.513 (6.8); 2.507 (14.6); 2.501 (20.3); 2.495 (14.7); 2.489 (7.1); 1.989 (0.9); 1.775 (0.9); 1.751 (2.3); 1.726 (3.6); 1.719 (2.0); 1.702 (2.5); 1.677 (1.1); 1.356 (0.5); 1.331 (1.9); 1.306 (3.0); 1.281 (3.2); 1.256 (2.0); 1.233 (0.7); 1.198 (0.3); 1.174 (0.6); 1.150 (0.4); 1.122 (5.6); 1.097 (14.0); 1.072 (5.4); 0.928 (7.7); 0.903 (16.0); 0.879 (6.0); 0.011 (0.5); 0.000 (16.8); −0.011 (0.7)

Example 123: $^1$H-NMR (300.2 MHz, $d_6$-DMSO):
δ = 9.802 (2.7); 8.823 (1.6); 8.818 (1.7); 8.807 (1.7); 8.802 (1.6); 8.113 (1.3); 8.089 (1.4); 8.086 (1.4); 7.741 (1.2); 7.725 (1.2); 7.714 (1.1); 7.699 (1.0); 7.423 (5.6); 7.363 (1.4); 7.182 (3.1); 7.002 (1.5); 5.759 (2.2); 4.055 (1.8); 4.031 (3.0); 4.007 (2.0); 3.325 (22.2); 3.189 (0.8); 3.166 (1.1); 3.142 (0.9); 3.119 (0.4); 2.513 (3.6); 2.507 (7.9); 2.501 (11.0); 2.495 (8.0); 2.489 (3.8); 1.774 (0.5); 1.749 (1.2); 1.725 (1.9); 1.701 (1.3); 1.675 (0.6); 1.349 (1.1); 1.324 (1.8); 1.299 (1.9); 1.277 (0.8); 1.253 (15.2); 1.219 (0.4); 0.933 (4.4); 0.909 (9.2); 0.884 (3.5); 0.000 (9.2); −0.011 (0.4)

Example 124: $^1$H-NMR (300.2 MHz, $d_6$-DMSO):
δ = 10.001 (3.1); 8.814 (1.8); 8.809 (2.0); 8.798 (2.0); 8.793 (1.9); 8.134 (1.4); 8.131 (1.5); 8.108 (1.7); 8.105 (1.7); 7.727 (1.4); 7.711 (1.4); 7.701 (1.3); 7.685 (1.2); 7.608 (6.9); 7.344 (1.7); 7.164 (3.8); 6.983 (1.8); 5.759 (7.0); 4.044 (1.9); 4.041 (1.7); 4.018 (2.8); 3.996 (2.3); 3.326 (21.4); 2.728 (0.9); 2.704 (2.7); 2.678 (2.8); 2.654 (1.0); 2.513 (2.3); 2.507 (5.2); 2.501 (7.2); 2.495 (5.3); 2.489 (2.6); 1.989 (2.4); 1.667 (0.6); 1.648 (1.9); 1.623 (2.6); 1.602 (1.8); 1.585 (1.0); 1.564 (0.6); 1.541 (0.4); 1.198 (0.7); 1.174 (1.4); 1.151 (0.8); 1.129 (3.7); 1.105 (9.3); 1.079 (3.6); 0.934 (16.0); 0.913 (15.5); 0.000 (4.6)

Example 125: $^1$H-NMR (300.2 MHz, $d_6$-DMSO):
δ = 9.802 (3.0); 8.823 (1.7); 8.818 (1.8); 8.807 (1.8); 8.802 (1.8); 8.112 (1.4); 8.089 (1.5); 8.086 (1.6); 7.740 (1.2); 7.724 (1.3); 7.714 (1.1); 7.698 (1.1); 7.421 (6.2); 7.362 (1.4); 7.182 (3.4); 7.001 (1.6); 5.759 (9.8); 4.073 (1.4); 4.048 (2.1); 4.024 (1.7); 3.325 (28.3); 3.210 (0.3); 3.186 (0.9); 3.162 (1.2); 3.138 (1.0); 3.115 (0.4); 2.513 (4.0); 2.507 (8.9); 2.501 (12.6); 2.495 (9.3); 2.489 (4.5); 1.989 (0.4); 1.663 (0.5); 1.646 (1.6); 1.630 (2.3); 1.622 (2.3); 1.606 (1.7); 1.586 (0.6); 1.281 (16.0); 1.258 (15.9); 0.938 (12.1); 0.917 (11.9); 0.011 (0.3); 0.000 (10.9); −0.011 (0.5)

Example 126: $^1$H-NMR (300.2 MHz, $d_6$-DMSO):
δ = 10.024 (2.2); 8.813 (1.5); 8.808 (1.6); 8.797 (1.7); 8.792 (1.5); 8.162 (1.3); 8.138 (1.4); 8.136 (1.4); 7.722 (1.1); 7.706 (1.1); 7.696 (1.1); 7.680 (1.1); 7.660 (4.4); 7.365 (1.3); 7.184 (3.1); 7.004 (1.5); 5.759 (10.8); 4.255 (0.4); 4.236 (0.6); 4.227 (0.6); 4.205 (0.6); 4.186 (0.5); 3.325 (39.3); 3.302 (0.6); 2.514 (7.4); 2.507 (15.7); 2.501 (21.7); 2.495 (15.7); 2.489 (7.5); 2.225 (16.0); 1.989 (0.6); 1.873 (0.5); 1.852 (0.7); 1.827 (0.8); 1.823 (0.8); 1.799 (0.6); 1.742 (0.6); 1.724 (0.7); 1.718 (0.7); 1.700 (0.9); 1.673 (0.5); 1.654 (0.4); 1.360 (7.7); 1.338 (7.7); 1.174 (0.4); 0.732 (3.7); 0.708 (8.1); 0.683 (3.5); 0.011 (0.5); 0.000 (16.8); −0.011 (0.7)

Example 127: $^1$H-NMR (300.2 MHz, $d_6$-DMSO):
δ = 10.000 (2.5); 8.813 (1.7); 8.808 (1.7); 8.797 (1.7); 8.792 (1.6); 8.147 (1.3); 8.121 (1.5); 7.725 (1.3); 7.704 (5.8); 7.683 (1.1); 7.357 (1.5); 7.176 (3.3); 6.996 (1.6); 5.759 (13.5); 4.017 (0.3); 3.997 (0.5); 3.981 (0.6); 3.966 (0.9); 3.950 (0.7); 3.936 (0.5); 3.324 (52.6); 2.742 (0.8); 2.716 (2.3); 2.692 (2.4); 2.667 (0.8); 2.513 (8.6); 2.507 (19.0); 2.501 (26.7); 2.495 (19.6); 2.489 (9.4); 1.989 (1.1); 1.887 (0.5); 1.862 (0.8); 1.857 (0.7); 1.842 (1.3); 1.817 (1.5); 1.812 (1.7); 1.786 (2.1); 1.768 (1.6); 1.760 (1.7); 1.743 (1.6); 1.721 (0.8); 1.698 (0.5); 1.174 (0.7); 1.150 (0.4); 1.121 (2.9); 1.096 (7.7); 1.071 (3.0); 0.713 (7.1); 0.689 (16.0); 0.664 (6.7); 0.011 (0.6); 0.000 (21.1); −0.011 (0.9)

Example 128: $^1$H-NMR (300.2 MHz, CDCl$_3$):
δ = 8.731 (3.6); 8.726 (3.8); 8.715 (4.0); 8.710 (3.8); 8.324 (16.0); 8.023 (3.4); 8.018 (3.5); 7.996 (4.0); 7.992 (3.9); 7.737 (3.5); 7.521 (3.0); 7.505 (3.1); 7.495 (3.0); 7.479 (2.8); 7.386 (1.2); 7.380 (2.1); 7.374 (1.8); 7.359 (4.4); 7.353 (7.1); 7.347 (5.0); 7.342 (5.8); 7.340 (5.9); 7.316 (6.7); 7.290 (2.7); 7.271 (5.8); 7.262 (4.5); 7.257 (7.4); 7.251 (4.5); 7.233 (5.5); 7.226 (2.4); 7.217 (6.0); 7.210 (4.0); 7.203 (7.9); 7.194 (2.9); 7.187 (7.6); 7.176 (1.2); 7.091 (3.2); 7.086 (5.9); 7.081 (6.4); 7.067 (2.9); 7.062 (4.7); 7.057 (3.3); 7.046 (7.7); 7.039 (2.5); 7.030 (1.5); 7.019 (9.3); 7.005 (1.3); 6.996 (2.3); 6.989 (5.7); 6.978 (0.8); 6.899 (8.1); 6.717 (4.0); 4.135 (0.7); 4.112 (2.2); 4.088 (2.2); 4.064 (0.8); 2.026 (10.3); 1.994 (0.6); 1.720 (8.6); 1.274 (2.8); 1.250 (5.6); 1.226 (2.8); 0.000 (3.3)

Example 129: $^1$H-NMR (300.2 MHz, CDCl$_3$):
δ = 8.745 (2.8); 8.740 (3.1); 8.730 (3.1); 8.725 (3.1); 8.435 (12.7); 8.014 (2.6); 8.010 (2.8); 7.988 (3.0); 7.986 (2.9); 7.983 (3.0); 7.781 (2.1); 7.772 (1.8); 7.768 (2.3); 7.762 (1.5); 7.758 (1.7); 7.755 (1.7); 7.749 (2.9); 7.681 (2.8); 7.543 (0.4); 7.537 (0.7); 7.535 (0.7); 7.514 (0.9); 7.500 (8.2); 7.489 (6.6); 7.483 (4.6); 7.473 (2.8); 7.466 (1.3); 7.457 (0.7); 7.340 (1.4); 7.335 (1.4); 7.328 (5.8); 7.324 (5.6); 7.321 (5.1); 7.313 (10.6); 7.305 (13.7); 7.293 (2.0); 7.281 (0.6); 7.267 (6.1); 7.217 (0.9); 7.201 (6.7); 7.188 (7.5); 7.176 (6.4); 7.169 (4.0); 7.157 (0.8); 7.133 (3.2); 6.950 (6.6); 6.768 (3.2); 4.119 (0.8); 4.095 (0.9); 2.032 (3.9); 1.997 (0.5); 1.667 (16.0); 1.276 (1.1); 1.253 (2.2); 1.229 (1.1); 0.000 (4.4)

Example 130: $^1$H-NMR (300.2 MHz, CDCl$_3$):
δ = 8.742 (3.5); 8.737 (3.8); 8.727 (3.8); 8.721 (3.8); 8.370 (16.0); 8.029 (3.3); 8.024 (3.4); 8.003 (3.8); 7.998 (3.7); 7.795 (0.3); 7.784 (2.7); 7.774 (2.5); 7.769 (3.0); 7.762 (1.9); 7.759 (1.9); 7.753 (3.5); 7.742 (0.7); 7.662 (3.5); 7.566 (0.3); 7.558 (0.8); 7.550 (0.7); 7.539 (7.2); 7.531 (3.7); 7.524 (8.6); 7.517 (4.8); 7.508 (9.8); 7.497 (3.7); 7.481 (3.2); 7.427 (0.3); 7.269 (7.0); 7.221 (0.7); 7.211 (3.6); 7.202 (6.3); 7.195 (5.1); 7.189 (3.5); 7.184 (6.5); 7.180 (6.0); 7.172 (7.4); 7.162 (3.2); 7.155 (6.6); 7.146 (1.1); 7.108 (3.9); 7.046 (1.0); 7.037 (7.4); 7.029 (2.4); 7.014 (2.7); 7.008 (11.1); 7.001 (2.9); 6.986 (2.2); 6.979 (5.4); 6.969 (0.9); 6.926 (8.1); 6.907 (0.4); 6.744 (4.0); 4.141 (0.8); 4.117 (2.3); 4.093 (2.4); 4.070 (0.8); 2.030 (10.9); 1.686 (11.3); 1.276 (3.1); 1.267 (0.3); 1.252 (6.1); 1.243 (0.4); 1.228 (2.9); 0.000 (5.7)

Example 131: $^1$H-NMR (300.2 MHz, CDCl$_3$):
δ = 8.722 (3.5); 8.717 (3.8); 8.706 (3.9); 8.701 (3.8); 8.682 (0.3); 8.334 (16.0); 8.009 (3.3); 8.004 (3.5); 7.983 (3.8); 7.978 (3.7); 7.850 (3.9); 7.801 (0.5); 7.789 (2.7); 7.779 (2.4); 7.775 (3.2); 7.766 (2.0); 7.764 (2.0); 7.757 (3.6); 7.747 (0.7); 7.576 (0.4); 7.568 (0.8); 7.567 (0.7); 7.547 (6.3); 7.533 (6.8); 7.524 (4.3); 7.516 (5.9); 7.507 (3.7); 7.499 (1.8); 7.491 (3.6); 7.481 (3.0); 7.465 (2.8); 7.326 (1.6); 7.307 (1.9); 7.299 (3.0); 7.279 (3.2); 7.276 (5.3); 7.253 (2.5); 7.227 (0.6); 7.217 (3.2); 7.208 (1.9); 7.204 (1.8); 7.200 (3.1); 7.195 (2.4); 7.186 (2.7); 7.174 (0.5); 7.110 (3.7); 7.034 (1.4); 7.031 (1.8); 7.025 (1.7); 7.022 (1.9); 7.006 (2.5); 7.003 (3.3); 6.994 (5.5); 6.988 (4.9); 6.978 (1.8); 6.975 (2.0); 6.966 (4.3); 6.963 (4.3); 6.928 (7.8); 6.908 (2.5); 6.902 (2.8); 6.900 (2.8); 6.894 (2.1); 6.877 (2.5); 6.871 (2.9); 6.863 (2.0); 6.746 (3.9); 4.125 (0.6); 4.101 (1.8); 4.077 (1.9); 4.053 (0.7); 2.015 (8.7); 1.985 (9.2); 1.791 (1.9); 1.268 (2.4); 1.244 (4.8); 1.220 (2.4); 0.000 (2.7)

Example 132: $^1$H-NMR (300.2 MHz, CDCl$_3$):
δ = 8.738 (3.6); 8.733 (3.8); 8.722 (3.9); 8.717 (3.8); 8.370 (16.0); 8.034 (3.3); 8.029 (3.4); 8.008 (3.8); 8.003 (3.8); 7.810 (0.4); 7.795 (2.6); 7.784 (3.0); 7.778 (3.3); 7.774 (2.0); 7.771 (1.9); 7.763 (3.8); 7.736 (3.7); 7.571 (0.7); 7.568 (0.8); 7.556 (8.3); 7.543 (5.2); 7.535 (5.2); 7.525 (11.2); 7.509 (4.3); 7.499 (3.4); 7.483 (3.0); 7.305 (1.1); 7.300 (2.2); 7.293 (1.8); 7.278 (4.2); 7.272 (8.1); 7.269 (9.3); 7.267 (6.0); 7.262 (5.9); 7.260 (5.8); 7.249 (0.9); 7.236 (7.1); 7.229 (4.1); 7.215 (10.2); 7.210 (9.3); 7.199 (3.3); 7.183 (0.8); 7.111 (3.9); 7.061 (2.9); 7.056 (4.9); 7.050 (2.8); 7.037 (2.5); 7.032 (4.0); 7.026 (2.3); 6.929 (8.0); 6.747 (4.0); 4.136 (0.8); 4.112 (2.6); 4.088 (2.7); 4.065 (0.9); 2.026 (12.3); 1.692 (12.5); 1.274 (3.4); 1.250 (6.7); 1.226 (3.3); 0.000 (5.0)

Example 133: $^1$H-NMR (300.2 MHz, d$_6$-DMSO):
δ = 10.230 (3.2); 8.664 (2.7); 8.017 (2.6); 7.927 (5.4); 7.749 (4.0); 7.719 (5.4); 7.547 (5.3); 7.518 (4.2); 7.340 (1.3); 7.159 (2.8); 6.978 (1.3); 3.568 (1.1); 3.327 (58.8); 2.507 (28.5); 2.502 (38.7); 2.496 (29.2); 2.442 (9.3); 2.317 (16.0); 2.271 (0.4); 0.000 (25.9)

Example 134: $^1$H-NMR (300.2 MHz, d$_6$-DMSO):
δ = 10.270 (2.9); 8.834 (1.6); 8.830 (1.7); 8.819 (1.7); 8.814 (1.7); 8.203 (1.4); 8.178 (1.5); 7.947 (5.4); 7.749 (5.2); 7.720 (6.4); 7.709 (1.3); 7.557 (0.6); 7.547 (5.5); 7.541 (1.7); 7.525 (1.5); 7.518 (4.2); 7.387 (1.3); 7.207 (3.0); 7.027 (1.4); 3.568 (1.1); 3.328 (28.9); 2.513 (4.6); 2.508 (9.9); 2.502 (13.6); 2.496 (10.2); 2.490 (5.0); 2.319 (16.0); 0.000 (9.0); −0.011 (0.4)

Example 135: $^1$H-NMR (400.0 MHz, CDCl$_3$):
δ = 8.816 (5.2); 8.808 (4.9); 8.804 (5.3); 8.397 (16.0); 8.355 (1.4); 8.150 (5.0); 8.131 (5.3); 7.729 (3.1); 7.595 (4.5); 7.583 (8.6); 7.579 (3.1); 7.561 (14.8); 7.539 (0.4); 7.527 (6.6); 7.522 (2.6); 7.509 (13.0); 7.489 (7.3); 7.471 (3.1); 7.468 (5.4); 7.464 (3.5); 7.456 (2.2); 7.450 (4.7); 7.443 (1.5); 7.432 (1.7); 7.422 (0.5); 7.265 (15.4); 7.147 (4.4); 7.010 (9.0); 6.874 (4.5); 5.300 (0.4); 2.212 (0.6); 2.042 (0.7); 1.637 (10.5); 1.426 (0.4); 1.257 (0.8); 0.008 (0.4); 0.000 (14.6); −0.008 (0.6)

Example 136: $^1$H-NMR (300.2 MHz, CDCl$_3$):
δ = 8.608 (3.8); 8.444 (2.6); 8.435 (2.6); 8.108 (1.2); 7.635 (2.5); 7.628 (2.5); 7.601 (2.5); 7.580 (3.0); 7.572 (5.5); 7.368 (1.5); 7.360 (1.4); 7.339 (1.2); 7.262 (25.2); 7.048 (1.2); 6.865 (2.5); 6.682 (1.2); 3.973 (16.0); 1.554 (35.1); 0.000 (27.1)

Example 137: $^1$H-NMR (400.0 MHz, d$_6$-DMSO):
δ = 10.565 (4.6); 8.846 (2.5); 8.842 (2.6); 8.834 (2.6); 8.830 (2.6); 8.186 (2.2); 8.167 (2.4); 8.144 (11.1); 7.749 (1.9); 7.737 (1.9); 7.729 (1.8); 7.717 (1.7); 7.629 (0.6); 7.623 (1.4); 7.617 (1.0); 7.607 (16.0); 7.602 (7.9); 7.591 (6.3); 7.585 (1.3); 7.576 (1.0); 7.571 (1.5); 7.538 (1.3); 7.533 (2.0); 7.525 (1.4); 7.520 (1.3); 7.517 (1.8); 7.513 (1.0); 7.509 (0.8); 7.507 (0.7); 7.502 (0.7); 7.495 (0.5); 7.339 (2.0); 7.204 (4.7); 7.069 (2.3); 3.331 (28.0); 2.525 (0.7); 2.511 (13.8); 2.507 (27.8); 2.503 (36.7); 2.498 (26.9); 2.494 (13.2); 0.008 (1.4); 0.000 (41.6); −0.009 (1.6)

Example 138: $^1$H-NMR (400.1 MHz, d$_6$-DMSO):
δ = 10.650 (5.8); 8.701 (8.6); 8.697 (8.8); 8.143 (15.4); 7.971 (8.4); 7.698 (12.2); 7.694 (16.0); 7.679 (8.2); 7.676 (9.3); 7.675 (8.1); 7.671 (5.7); 7.659 (6.0); 7.656 (3.9); 7.640 (8.6); 7.622 (2.0); 7.618 (4.1); 7.556 (5.9); 7.537 (3.9); 7.286 (4.3); 7.150 (10.3); 7.015 (4.9); 3.476 (0.4); 3.448 (0.5); 3.429 (1.1); 3.410 (0.9); 3.377 (3.5); 3.328 (310.0); 3.278 (5.4); 3.227 (1.0); 2.898 (0.6); 2.740 (0.5); 2.738 (0.6); 2.682 (0.7); 2.678 (1.1); 2.673 (0.8); 2.669 (0.4); 2.613 (0.4); 2.609 (0.4); 2.604 (0.4); 2.563 (0.7); 2.559 (1.2); 2.554 (1.1); 2.549 (0.8); 2.531 (2.8); 2.526 (4.6); 2.518 (60.8); 2.513 (128.6); 2.509 (180.5); 2.504 (132.6); 2.500 (67.1); 2.457 (32.8); 2.408 (0.9); 2.340 (0.9); 2.336 (1.2); 2.331 (0.9); 2.093 (2.9)

Example 139: $^1$H-NMR (400.1 MHz, d$_6$-DMSO):
δ = 10.682 (7.4); 8.702 (8.8); 8.699 (8.8); 8.182 (16.0); 7.997 (4.4); 7.979 (14.3); 7.948 (8.4); 7.920 (2.7); 7.900 (6.6); 7.883 (6.3); 7.864 (5.9); 7.844 (1.9); 7.291 (4.3); 7.156 (10.0); 7.020 (4.9); 3.424 (1.8); 3.375 (6.5); 3.361 (1.0); 3.325 (1134.4); 3.291 (0.9); 3.275 (4.4); 3.268 (0.6); 3.225 (1.2); 2.898 (1.0); 2.739 (0.8); 2.682 (0.8); 2.678 (1.1); 2.673 (0.8); 2.613 (0.3); 2.608 (0.3); 2.563 (0.9); 2.558 (1.3); 2.554 (1.0); 2.531 (2.9); 2.526 (4.8); 2.517 (66.2); 2.513 (136.5); 2.508 (186.3); 2.504 (130.5); 2.499 (60.1); 2.459 (32.2); 2.409 (0.5); 2.345 (0.5); 2.340 (0.9); 2.335 (1.2); 2.331 (0.8); 2.092 (2.6); 1.203 (0.4)

Example 140: $^1$H-NMR (400.1 MHz, d$_6$-DMSO):
δ = 10.595 (7.6); 8.699 (9.5); 8.696 (9.4); 8.170 (16.0); 7.982 (9.2); 7.728 (1.4); 7.724 (2.0); 7.710 (5.0); 7.706 (7.1); 7.690 (10.0); 7.687 (8.9); 7.672 (6.4); 7.573 (3.6); 7.571 (3.6); 7.551 (3.8); 7.547 (5.1); 7.525 (2.9); 7.461 (4.0); 7.442 (6.5); 7.422 (3.0); 7.290 (4.5); 7.154 (10.3); 7.019 (5.1); 3.430 (1.2); 3.381 (4.4); 3.331 (233.1); 3.234 (0.8); 2.898 (0.8); 2.739 (0.7); 2.682 (0.8); 2.677 (1.0); 2.673 (0.7); 2.613 (0.5); 2.608 (0.4); 2.567 (0.7); 2.563 (1.1); 2.558 (1.5); 2.554 (1.2); 2.531

(3.0); 2.517 (61.4); 2.513 (123.3); 2.508 (166.0); 2.504 (117.7); 2.499 (55.4); 2.455 (34.0); 2.408 (0.4); 2.340 (0.8); 2.335 (1.0); 2.331 (0.7); 2.092 (1.9); 0.941 (0.4)

Example 141: $^1$H-NMR (400.1 MHz, d$_6$-DMSO):
δ = 10.599 (5.2); 8.699 (8.9); 8.695 (8.8); 8.100 (16.0); 7.971 (8.5); 7.659 (0.3); 7.633 (6.2); 7.620 (6.8); 7.615 (4.8); 7.610 (8.2); 7.598 (7.6); 7.590 (7.4); 7.474 (1.3); 7.466 (10.2); 7.460 (3.2); 7.453 (1.9); 7.444 (15.7); 7.428 (2.8); 7.422 (7.7); 7.413 (0.6); 7.286 (4.4); 7.150 (10.2); 7.015 (4.9); 3.426 (2.1); 3.376 (6.6); 3.368 (0.7); 3.357 (1.5); 3.326 (1001.0); 3.293 (1.1); 3.283 (0.7); 3.276 (3.3); 3.269 (0.5); 3.226 (0.8); 2.898 (0.4); 2.682 (0.7); 2.677 (0.9); 2.673 (0.6); 2.613 (0.4); 2.609 (0.4); 2.563 (0.9); 2.558 (1.2); 2.554 (0.8); 2.531 (2.3); 2.517 (56.4); 2.513 (116.8); 2.508 (159.8); 2.504 (112.9); 2.499 (52.7); 2.455 (32.1); 2.408 (0.4); 2.340 (0.8); 2.335 (1.0); 2.331 (0.8); 2.326 (0.4); 2.092 (2.1)

Example 142: $^1$H-NMR (400.1 MHz, d$_6$-DMSO):
δ = 10.575 (2.0); 8.698 (2.1); 8.695 (2.1); 8.067 (3.9); 7.969 (2.0); 7.477 (0.8); 7.470 (0.5); 7.455 (8.2); 7.450 (7.2); 7.434 (0.4); 7.428 (0.7); 7.288 (1.0); 7.153 (2.4); 7.017 (1.2); 3.426 (0.5); 3.376 (0.9); 3.326 (267.6); 3.292 (0.3); 3.276 (2.3); 3.051 (0.3); 3.034 (0.9); 3.017 (1.3); 2.999 (1.0); 2.982 (0.4); 2.531 (0.6); 2.526 (1.0); 2.517 (14.9); 2.513 (30.9); 2.508 (42.2); 2.504 (29.8); 2.499 (13.9); 2.455 (7.7); 2.092 (0.5); 1.275 (16.0); 1.258 (15.8)

Example 143: $^1$H-NMR (400.1 MHz, d$_6$-DMSO):
δ = 11.403 (3.1); 8.872 (3.7); 8.869 (4.0); 8.860 (3.9); 8.857 (3.8); 8.278 (16.0); 8.231 (3.2); 8.212 (3.4); 7.777 (2.7); 7.765 (2.7); 7.758 (2.8); 7.748 (6.3); 7.744 (8.8); 7.740 (2.3); 7.729 (5.0); 7.726 (8.6); 7.724 (9.2); 7.717 (1.1); 7.661 (4.7); 7.656 (1.9); 7.643 (9.3); 7.639 (4.4); 7.627 (2.6); 7.623 (5.4); 7.586 (2.3); 7.583 (4.0); 7.580 (2.3); 7.570 (1.1); 7.564 (4.8); 7.559 (1.1); 7.549 (1.0); 7.546 (1.6); 7.543 (0.9); 7.339 (2.9); 7.204 (6.7); 7.069 (3.3); 3.431 (0.7); 3.332 (110.9); 2.898 (1.8); 2.739 (1.5); 2.682 (0.4); 2.677 (0.5); 2.673 (0.4); 2.562 (0.4); 2.558 (0.5); 2.554 (0.4); 2.531 (1.4); 2.517 (30.8); 2.513 (63.1); 2.508 (85.8); 2.504 (60.2); 2.499 (27.7); 2.463 (0.4); 2.458 (0.5); 2.454 (0.4); 2.340 (0.4); 2.335 (0.5); 2.331 (0.4); 2.092 (1.1)

Example 144: $^1$H-NMR (300.2 MHz, d$_6$-DMSO):
δ = 10.718 (10.8); 8.244 (16.0); 8.142 (5.7); 8.115 (11.2); 8.062 (11.3); 8.034 (5.8); 7.979 (6.9); 7.974 (7.6); 7.952 (8.4); 7.947 (8.5); 7.911 (0.4); 7.770 (5.3); 7.747 (7.8); 7.644 (8.7); 7.617 (12.8); 7.590 (5.5); 7.398 (4.4); 7.219 (9.9); 7.040 (4.8); 5.759 (5.9); 4.065 (0.9); 4.041 (2.7); 4.017 (2.8); 3.994 (0.9); 3.326 (115.8); 3.272 (0.5); 2.514 (13.9); 2.508 (29.2); 2.502 (40.2); 2.496 (29.9); 2.490 (14.9); 1.989 (12.0); 1.236 (0.5); 1.198 (3.2); 1.175 (6.3); 1.151 (3.2); 0.000 (24.3)

Example 145: $^1$H-NMR (300.2 MHz, d$_6$-DMSO):
δ = 10.727 (8.5); 8.159 (11.3); 8.125 (3.3); 8.098 (8.2); 8.065 (8.3); 8.038 (3.5); 7.691 (8.4); 7.684 (3.3); 7.669 (5.0); 7.662 (16.0); 7.599 (13.0); 7.570 (7.1); 7.386 (3.2); 7.207 (7.2); 7.029 (3.5); 5.760 (2.4); 3.328 (57.5); 2.508 (16.2); 2.502 (21.7); 2.497 (16.3); 0.000 (13.5)

Example 146: $^1$H-NMR (300.2 MHz, CDCl$_3$):
δ = 8.728 (3.9); 8.724 (4.2); 8.713 (4.3); 8.708 (4.2); 8.345 (16.0); 8.006 (3.9); 7.983 (4.3); 7.980 (4.3); 7.887 (4.3); 7.510 (3.2); 7.494 (3.3); 7.484 (3.1); 7.468 (2.9); 7.442 (1.9); 7.437 (2.2); 7.417 (3.8); 7.411 (4.5); 7.397 (1.6); 7.392 (3.3); 7.386 (3.2); 7.372 (2.5); 7.367 (2.1); 7.356 (2.6); 7.350 (3.9); 7.339 (1.9); 7.329 (3.7); 7.323 (4.8); 7.303 (3.5); 7.297 (2.9); 7.277 (2.8); 7.272 (3.3); 7.223 (3.2); 7.198 (4.6); 7.174 (1.9); 7.104 (3.8); 7.084 (2.8); 7.080 (2.7); 7.062 (2.3); 7.056 (4.5); 7.052 (5.2); 7.047 (3.4); 7.034 (3.5); 7.025 (4.4); 7.019 (2.9); 7.005 (6.1); 6.979 (4.3); 6.922 (10.9); 6.898 (2.8); 6.892 (3.2); 6.885 (2.3); 6.740 (3.9); 1.988 (2.9); 1.751 (5.8); 0.000 (2.7)

Example 147: $^1$H-NMR (300.2 MHz, CDCl$_3$):
δ = 8.729 (5.2); 8.713 (5.4); 8.351 (16.0); 8.006 (4.9); 7.980 (5.5); 7.784 (5.4); 7.511 (3.7); 7.495 (3.8); 7.485 (3.8); 7.469 (3.5); 7.426 (2.5); 7.401 (5.3); 7.381 (7.5); 7.375 (3.9); 7.362 (3.1); 7.345 (3.0); 7.337 (3.0); 7.320 (2.1); 7.314 (1.8); 7.271 (3.1); 7.215 (9.0); 7.188 (13.9); 7.169 (8.8); 7.101 (4.1); 7.073 (3.5); 7.064 (1.8); 7.054 (8.3); 7.044 (6.8); 7.025 (13.4); 7.016 (5.2); 6.997 (6.2); 6.919 (8.2); 6.736 (4.1); 5.297 (0.6); 2.026 (0.4); 1.992 (3.3); 1.727 (7.0); 1.258 (0.3); 1.250 (0.3); 0.000 (2.9)

Example 148: $^1$H-NMR (300.2 MHz, CDCl$_3$):
δ = 8.727 (3.9); 8.722 (4.1); 8.711 (4.3); 8.706 (4.2); 8.385 (16.0); 7.982 (3.7); 7.959 (4.2); 7.854 (4.3); 7.494 (3.1); 7.478 (3.3); 7.468 (3.1); 7.452 (3.0); 7.426 (2.0); 7.420 (2.3); 7.400 (3.9); 7.395 (4.5); 7.375 (2.7); 7.369 (3.9); 7.363 (1.9); 7.352 (3.9); 7.346 (11.9); 7.335 (14.1); 7.328 (10.3); 7.324 (15.9); 7.311 (3.9); 7.300 (2.4); 7.294 (1.9); 7.271 (2.8); 7.227 (1.2); 7.214 (6.6); 7.209 (4.7); 7.204 (6.5); 7.196 (7.6); 7.192 (7.6); 7.182 (5.0); 7.169 (5.2); 7.145 (2.1); 7.123 (4.0); 7.064 (2.7); 7.060 (2.6); 7.036 (2.7); 7.031 (4.3); 7.026 (3.0); 7.003 (2.4); 6.999 (2.2); 6.941 (8.0); 6.759 (4.0); 5.291 (3.4); 1.986 (3.6); 1.755 (4.6); 1.236 (0.4); 1.059 (0.3); 0.000 (2.5)

Example 149: $^1$H-NMR (300.2 MHz, CDCl$_3$):
δ = 8.706 (4.2); 8.703 (4.5); 8.691 (4.5); 8.687 (4.5); 8.276 (16.0); 8.003 (5.3); 7.989 (5.1); 7.962 (4.7); 7.492 (3.3); 7.476 (3.4); 7.466 (3.2); 7.450 (3.0); 7.420 (1.8); 7.414 (2.3); 7.394 (4.4); 7.390 (5.5); 7.381 (2.0); 7.370 (4.5); 7.364 (5.0); 7.354 (3.1); 7.345 (2.6); 7.338 (1.8); 7.328 (2.1); 7.320 (2.1); 7.313 (2.5); 7.308 (1.9); 7.292 (4.3); 7.286 (7.1); 7.281 (5.2); 7.274 (6.7); 7.248 (7.2); 7.221 (6.6); 7.216 (7.4); 7.210 (8.8); 7.194 (5.4); 7.168 (2.2); 7.109 (3.8); 7.073 (4.0); 7.068 (5.6); 7.063 (3.6); 7.048 (6.9); 7.044 (7.1); 7.020 (2.6); 6.927 (7.7); 6.745 (3.8); 4.094 (0.6); 4.070 (0.6); 2.009 (2.8); 1.979 (6.1); 1.813 (4.6); 1.265 (0.8); 1.241 (1.5); 1.217 (0.8); 0.000 (1.5)

Example 150: $^1$H-NMR (400.0 MHz, CDCl$_3$):
δ = 8.814 (4.2); 8.802 (4.5); 8.799 (4.3); 8.786 (0.7); 8.608 (1.7); 8.404 (3.4); 8.363 (11.0); 8.148 (4.1); 8.128 (4.4); 8.079 (0.5); 8.059 (0.5); 7.717 (2.5); 7.700 (2.7); 7.671 (0.4); 7.655 (1.5); 7.648 (11.5); 7.643 (4.7); 7.631 (4.8); 7.626 (16.0); 7.619 (2.6); 7.608 (0.9); 7.602 (3.0); 7.591 (4.6); 7.582 (3.5); 7.574 (3.2); 7.562 (2.9); 7.541 (0.6); 7.535 (0.5); 7.523 (0.5); 7.504 (1.7); 7.497 (11.7); 7.492 (4.1); 7.480 (6.7); 7.475 (10.2); 7.468 (1.4); 7.463 (1.5); 7.459 (3.1); 7.330 (0.3); 7.265 (15.9); 7.142 (0.4); 7.127 (1.3); 7.121 (3.3); 7.005 (0.7); 6.990 (2.5); 6.984 (6.7); 6.869 (0.4); 6.853 (1.3); 6.848 (3.4); 4.125 (0.6); 4.107 (0.7); 2.042 (2.8); 1.625 (7.1); 1.425 (1.0); 1.318 (0.3); 1.275 (0.8); 1.257 (1.8); 1.251 (1.0); 1.239 (0.8); 0.008 (0.5); 0.000 (14.5); −0.009 (0.6)

Example 151: $^1$H-NMR (400.0 MHz, d$_6$-DMSO):
δ = 10.442 (7.7); 8.121 (15.4); 7.811 (1.3); 7.804 (10.3); 7.799 (4.0); 7.787 (7.4); 7.782 (16.0); 7.774 (5.3); 7.765 (6.6); 7.749 (0.5); 7.735 (0.7); 7.730 (1.4); 7.717 (4.8); 7.712 (5.7); 7.703 (5.9);

7.694 (4.3); 7.677 (0.6); 7.614 (1.4); 7.607 (12.7); 7.602 (3.9); 7.590 (3.4); 7.585 (10.5); 7.578 (1.2); 7.572 (0.5); 7.474 (2.6); 7.335 (6.0); 7.196 (2.9); 6.937 (0.5); 6.457 (0.4); 6.438 (0.4); 6.378 (0.4); 6.360 (0.4); 4.920 (0.6); 3.330 (103.7); 2.676 (0.5); 2.671 (0.7); 2.667 (0.6); 2.525 (1.9); 2.520 (2.8); 2.511 (38.9); 2.507 (80.3); 2.502 (107.6); 2.498 (79.4); 2.493 (39.3); 2.334 (0.5); 2.329 (0.7); 2.324 (0.5); 1.989 (0.4); 1.398 (5.3); 1.370 (1.6); 1.355 (1.6); 1.300 (2.4); 1.234 (0.7); 1.149 (0.4); 0.992 (0.3); 0.000 (3.1)

Example 152: $^1$H-NMR (400.0 MHz, d$_6$-DMSO):
δ = 10.267 (2.6); 8.838 (1.3); 8.835 (1.4); 8.826 (1.4); 8.823 (1.4); 8.198 (1.2); 8.179 (1.3); 7.797 (5.1); 7.746 (1.0); 7.734 (1.1); 7.725 (3.3); 7.719 (1.3); 7.715 (1.1); 7.708 (1.5); 7.702 (5.3); 7.696 (0.8); 7.659 (0.7); 7.653 (5.0); 7.648 (1.5); 7.636 (1.0); 7.631 (2.7); 7.624 (0.4); 7.577 (0.3); 7.355 (1.0); 7.219 (2.2); 7.084 (1.1); 3.979 (16.0); 3.330 (22.0); 2.511 (11.8); 2.507 (23.5); 2.503 (30.9); 2.498 (23.4); 1.989 (0.5); 0.000 (0.4)

Example 153: $^1$H-NMR (400.0 MHz, CDCl$_3$):
δ = 8.819 (6.8); 8.807 (7.0); 8.421 (16.0); 8.381 (3.0); 8.262 (0.6); 8.156 (6.6); 8.136 (7.0); 7.714 (4.2); 7.642 (1.9); 7.622 (9.3); 7.602 (4.5); 7.590 (5.0); 7.583 (5.2); 7.570 (4.2); 7.530 (1.1); 7.512 (4.6); 7.508 (4.0); 7.504 (4.0); 7.497 (6.3); 7.492 (4.8); 7.478 (1.0); 7.465 (3.3); 7.445 (11.2); 7.438 (7.1); 7.428 (14.8); 7.419 (3.7); 7.404 (1.4); 7.265 (18.4); 7.132 (4.6); 6.995 (9.4); 6.858 (4.7); 3.482 (2.0); 2.218 (2.4); 2.043 (0.7); 1.619 (15.2); 1.425 (0.8); 1.258 (0.6); 0.000 (17.7)

Example 154: $^1$H-NMR (400.1 MHz, d$_6$-DMSO):
δ = 10.538 (2.5); 8.696 (2.8); 8.693 (2.8); 8.107 (5.0); 7.985 (2.7); 7.544 (0.6); 7.534 (1.0); 7.525 (1.3); 7.514 (1.5); 7.504 (1.5); 7.476 (2.5); 7.458 (1.3); 7.408 (4.8); 7.399 (3.8); 7.299 (1.4); 7.163 (3.1); 7.028 (1.5); 3.437 (0.8); 3.387 (2.6); 3.364 (0.9); 3.337 (435.5); 3.307 (0.6); 3.287 (2.2); 3.237 (0.5); 2.531 (0.7); 2.517 (15.9); 2.513 (32.2); 2.508 (43.3); 2.504 (30.6); 2.499 (14.4); 2.453 (10.2); 2.001 (16.0)

Example 155: $^1$H-NMR (400.1 MHz, d$_6$-DMSO):
δ = 10.738 (8.8); 8.948 (0.5); 8.942 (0.5); 8.362 (0.4); 8.356 (0.4); 8.245 (7.0); 8.224 (8.1); 8.177 (15.2); 7.933 (8.1); 7.913 (7.3); 7.698 (12.3); 7.694 (16.0); 7.689 (5.9); 7.680 (8.0); 7.677 (9.1); 7.672 (5.3); 7.658 (6.2); 7.654 (3.0); 7.639 (9.1); 7.622 (1.7); 7.617 (4.5); 7.554 (6.0); 7.534 (3.9); 7.347 (4.4); 7.213 (10.5); 7.197 (0.6); 7.079 (5.0); 3.433 (2.5); 3.398 (0.4); 3.390 (0.4); 3.383 (7.3); 3.333 (1178.3); 3.285 (4.6); 3.282 (7.8); 3.233 (1.4); 3.211 (0.5); 3.208 (0.4); 3.201 (0.4); 2.682 (0.6); 2.678 (0.8); 2.673 (0.6); 2.564 (0.5); 2.559 (0.8); 2.554 (0.6); 2.531 (2.8); 2.526 (4.2); 2.518 (47.0); 2.513 (98.7); 2.509 (137.6); 2.504 (100.6); 2.500 (50.9); 2.463 (1.7); 2.458 (1.6); 2.454 (1.2); 2.340 (0.7); 2.336 (0.9); 2.331 (0.7); 2.092 (0.9)

Example 156: $^1$H-NMR (400.1 MHz, d$_6$-DMSO):
δ = 10.632 (2.4); 8.255 (2.2); 8.235 (2.6); 8.146 (5.0); 7.929 (2.6); 7.908 (2.4); 7.545 (0.5); 7.534 (1.0); 7.526 (1.3); 7.515 (1.7); 7.505 (1.6); 7.494 (0.4); 7.476 (2.6); 7.457 (1.4); 7.407 (4.8); 7.398 (4.1); 7.378 (0.3); 7.363 (1.5); 7.229 (3.2); 7.095 (1.6); 3.433 (1.0); 3.384 (2.7); 3.370 (0.4); 3.334 (421.0); 3.284 (3.9); 3.233 (0.6); 2.531 (1.0); 2.518 (15.7); 2.513 (32.4); 2.509 (44.6); 2.504 (32.5); 2.500 (16.4); 2.464 (0.8); 2.459 (0.8); 1.999 (16.0)

Example 157: $^1$H-NMR (400.1 MHz, d$_6$-DMSO):
δ = 10.660 (2.5); 8.241 (2.5); 8.220 (2.8); 8.102 (5.7); 7.929 (2.8); 7.908 (2.5); 7.422 (0.9); 7.399 (16.0); 7.383 (0.5); 7.375 (0.8); 7.351 (1.5); 7.217 (3.3); 7.083 (1.6); 3.432 (1.2); 3.382 (2.7); 3.333 (504.9); 3.311 (1.3); 3.284 (2.7); 3.233 (0.9); 2.677 (0.3); 2.531 (0.9); 2.517 (22.3); 2.513 (45.1); 2.508 (60.8); 2.504 (43.4); 2.500 (20.7); 2.459 (0.5); 2.414 (16.7); 2.335 (0.4); 2.077 (0.5)

Example 158: $^1$H-NMR (400.1 MHz, d$_6$-DMSO):
δ = 10.687 (9.3); 8.946 (0.5); 8.940 (0.4); 8.375 (0.5); 8.254 (7.5); 8.233 (8.5); 8.206 (16.0); 7.932 (8.6); 7.912 (7.6); 7.728 (1.4); 7.724 (1.9); 7.705 (8.0); 7.690 (9.2); 7.687 (9.5); 7.671 (5.4); 7.572 (3.5); 7.569 (3.5); 7.550 (3.9); 7.546 (5.1); 7.524 (3.0); 7.460 (4.1); 7.441 (6.6); 7.422 (3.0); 7.355 (4.5); 7.221 (10.2); 7.204 (0.4); 7.087 (5.0); 3.458 (0.4); 3.454 (0.4); 3.434 (4.0); 3.415 (0.5); 3.403 (0.7); 3.384 (9.2); 3.370 (1.4); 3.334 (1664.3); 3.301 (2.5); 3.293 (1.9); 3.283 (6.5); 3.278 (0.8); 3.270 (0.8); 3.262 (0.3); 3.233 (1.6); 2.682 (0.8); 2.677 (1.1); 2.673 (0.8); 2.609 (0.5); 2.564 (0.8); 2.559 (1.0); 2.555 (0.7); 2.531 (2.8); 2.517 (66.9); 2.513 (136.3); 2.508 (184.7); 2.504 (131.4); 2.500 (62.1); 2.463 (1.0); 2.459 (1.0); 2.340 (0.9); 2.335 (1.2); 2.331 (0.8); 2.092 (0.8); 2.077 (0.6)

Example 159: $^1$H-NMR (400.1 MHz, d$_6$-DMSO):
δ = 10.666 (1.8); 8.242 (1.7); 8.221 (1.9); 8.102 (3.9); 7.931 (2.0); 7.910 (1.7); 7.476 (0.9); 7.469 (0.6); 7.453 (7.7); 7.447 (6.6); 7.431 (0.5); 7.425 (0.8); 7.350 (1.0); 7.216 (2.5); 7.082 (1.2); 3.433 (0.8); 3.383 (2.3); 3.333 (378.2); 3.293 (0.4); 3.283 (2.9); 3.234 (0.4); 3.050 (0.4); 3.033 (0.9); 3.015 (1.3); 2.998 (1.0); 2.981 (0.4); 2.531 (0.9); 2.517 (15.2); 2.513 (30.6); 2.508 (41.3); 2.504 (29.1); 2.499 (13.6); 1.273 (16.0); 1.256 (15.7)

Example 160: $^1$H-NMR (400.1 MHz, d$_6$-DMSO):
δ = 10.726 (6.0); 8.942 (0.4); 8.936 (0.4); 8.406 (0.3); 8.311 (9.0); 8.310 (9.2); 8.276 (4.7); 8.256 (5.2); 7.928 (5.2); 7.907 (4.8); 7.811 (7.6); 7.808 (8.7); 7.789 (16.0); 7.732 (7.2); 7.714 (4.9); 7.709 (4.2); 7.692 (3.0); 7.368 (2.5); 7.234 (5.8); 7.216 (0.4); 7.100 (2.8); 3.457 (0.6); 3.434 (2.7); 3.404 (0.3); 3.384 (9.7); 3.373 (0.9); 3.366 (1.2); 3.334 (1106.6); 3.284 (8.6); 3.234 (1.6); 3.203 (0.4); 3.194 (0.4); 3.084 (0.3); 2.682 (0.5); 2.678 (0.7); 2.673 (0.5); 2.568 (0.3); 2.564 (0.6); 2.559 (0.9); 2.554 (0.6); 2.531 (1.8); 2.518 (38.4); 2.513 (80.5); 2.509 (112.3); 2.504 (83.1); 2.500 (42.7); 2.464 (2.1); 2.459 (1.9); 2.408 (0.4); 2.340 (0.6); 2.336 (0.8); 2.331 (0.6); 2.092 (0.6); 2.078 (4.8)

Example 161: $^1$H-NMR (400.1 MHz, d$_6$-DMSO):
δ = 10.777 (5.1); 8.946 (0.3); 8.941 (0.3); 8.242 (5.1); 8.217 (12.1); 7.931 (5.9); 7.912 (10.1); 7.908 (13.4); 7.903 (6.8); 7.738 (16.0); 7.733 (15.0); 7.344 (3.0); 7.210 (7.0); 7.194 (0.5); 7.076 (3.4); 3.433 (3.0); 3.383 (8.5); 3.333 (1185.3); 3.284 (9.7); 3.234 (2.2); 3.213 (0.9); 3.208 (0.6); 3.200 (0.6); 3.192 (0.5); 3.183 (0.4); 2.682 (0.6); 2.678 (0.8); 2.673 (0.6); 2.609 (0.4); 2.563 (0.8); 2.558 (1.0); 2.554 (1.0); 2.531 (3.7); 2.518 (47.6); 2.513 (96.3); 2.509 (131.0); 2.504 (95.0); 2.500 (47.7); 2.459 (2.3); 2.340 (0.7); 2.335 (0.9); 2.331 (0.7); 2.092 (0.6)

Example 162: $^1$H-NMR (400.1 MHz, d$_6$-DMSO):
δ = 10.697 (9.2); 8.941 (0.5); 8.936 (0.5); 8.380 (0.4); 8.255 (6.9); 8.230 (16.0); 8.003 (12.1); 7.997 (12.1); 7.928 (7.7); 7.907 (6.8); 7.796 (7.0); 7.774 (10.7); 7.703 (8.4); 7.697 (7.8); 7.681 (5.4); 7.676 (5.3); 7.352 (3.9); 7.218 (9.0); 7.201 (0.4); 7.084 (4.4); 3.455 (0.7); 3.433 (4.6); 3.384

(2.3); 3.381 (9.8); 3.366 (3.1); 3.333 (1824.6); 3.283 (12.0); 3.268 (1.4); 3.235 (1.0); 3.232 (1.3); 3.208 (0.4); 3.204 (0.4); 2.682 (0.8); 2.678 (1.1); 2.673 (0.8); 2.609 (0.5); 2.557 (1.1); 2.552 (1.2); 2.547 (1.1); 2.531 (3.3); 2.517 (73.0); 2.513 (148.1); 2.508 (200.0); 2.504 (140.7); 2.500 (65.4); 2.458 (1.6); 2.454 (1.4); 2.407 (0.3); 2.340 (0.9); 2.335 (1.3); 2.331 (0.8); 2.092 (0.9); 2.077 (2.9)

Example 163: $^1$H-NMR (400.1 MHz, $d_6$-DMSO):
δ = 10.713 (4.6); 8.260 (3.7); 8.243 (8.4); 7.977 (3.7); 7.973 (4.1); 7.957 (4.3); 7.953 (4.4); 7.930 (4.1); 7.909 (3.7); 7.768 (2.4); 7.766 (2.6); 7.749 (3.5); 7.746 (3.3); 7.644 (4.3); 7.624 (6.5); 7.604 (3.1); 7.356 (2.1); 7.222 (5.0); 7.088 (2.4); 3.460 (0.5); 3.437 (1.0); 3.386 (3.2); 3.372 (1.4); 3.337 (1022.0); 3.287 (16.0); 3.237 (2.7); 2.682 (0.4); 2.678 (0.6); 2.673 (0.4); 2.558 (0.4); 2.553 (0.4); 2.548 (0.4); 2.531 (1.8); 2.526 (2.8); 2.518 (32.2); 2.513 (66.7); 2.509 (92.5); 2.504 (67.5); 2.500 (34.2); 2.468 (1.7); 2.464 (1.9); 2.459 (2.0); 2.455 (1.5); 2.414 (0.3); 2.409 (0.4); 2.405 (0.3); 2.340 (0.4); 2.336 (0.6); 2.331 (0.4); 2.092 (0.4); 2.077 (16.0)

Example 164: $^1$H-NMR (400.1 MHz, $d_6$-DMSO):
δ = 11.449 (4.1); 8.323 (4.7); 8.303 (5.4); 8.296 (1.6); 8.287 (16.0); 7.940 (5.2); 7.919 (4.8); 7.745 (5.0); 7.741 (7.1); 7.721 (9.7); 7.661 (4.9); 7.656 (1.9); 7.642 (9.5); 7.639 (4.4); 7.622 (5.5); 7.583 (4.1); 7.580 (2.3); 7.570 (1.7); 7.565 (4.9); 7.559 (1.1); 7.547 (1.5); 7.359 (2.7); 7.225 (6.1); 7.092 (2.9); 3.535 (0.4); 3.454 (0.4); 3.434 (2.8); 3.379 (3.8); 3.334 (1553.6); 3.283 (29.6); 3.234 (3.1); 2.682 (0.8); 2.678 (1.2); 2.673 (0.8); 2.531 (3.5); 2.517 (72.4); 2.513 (147.2); 2.509 (199.7); 2.504 (141.9); 2.500 (66.6); 2.463 (2.7); 2.458 (3.7); 2.454 (2.7); 2.409 (0.5); 2.340 (0.9); 2.335 (1.2); 2.331 (0.9); 2.092 (0.9)

Example 165: $^1$H-NMR (300.2 MHz, $d_6$-DMSO):
δ = 10.642 (2.8); 8.553 (2.8); 8.544 (2.9); 8.226 (3.7); 7.982 (1.6); 7.977 (1.7); 7.955 (1.9); 7.950 (1.9); 7.772 (1.2); 7.750 (1.8); 7.719 (2.1); 7.710 (2.1); 7.648 (2.0); 7.621 (3.0); 7.594 (1.3); 7.301 (1.0); 7.121 (2.3); 6.940 (1.1); 5.760 (0.6); 3.970 (16.0); 3.329 (18.2); 2.514 (2.7); 2.508 (5.7); 2.502 (7.8); 2.496 (5.7); 2.490 (2.8); 0.000 (5.5)

Example 166: $^1$H-NMR (300.2 MHz, $d_6$-DMSO):
δ = 11.341 (0.6); 8.654 (4.6); 8.213 (2.4); 8.003 (3.3); 7.696 (3.9); 7.670 (6.4); 7.616 (2.9); 7.591 (5.3); 7.565 (3.3); 7.534 (2.5); 7.511 (2.4); 7.487 (0.9); 7.292 (1.4); 7.112 (2.9); 6.932 (1.4); 5.712 (16.0); 3.411 (6.7); 3.123 (0.9); 2.456 (10.2); 2.405 (12.0); 2.340 (0.4); 1.415 (0.7); 1.188 (0.5); 1.153 (0.4); 1.128 (0.3); 0.881 (1.1)

Example 167: $^1$H-NMR (300.2 MHz, $d_6$-DMSO):
δ = 10.640 (10.7); 8.693 (9.5); 8.689 (9.9); 8.207 (16.0); 7.986 (10.3); 7.980 (11.9); 7.975 (9.2); 7.953 (8.4); 7.948 (8.7); 7.772 (5.3); 7.749 (7.7); 7.645 (8.6); 7.618 (12.9); 7.592 (5.6); 7.339 (4.8); 7.159 (10.5); 6.978 (5.2); 5.760 (5.5); 4.018 (0.4); 3.328 (89.4); 2.508 (23.6); 2.502 (33.2); 2.496 (25.3); 2.446 (34.7); 2.272 (0.4); 2.080 (0.4); 1.990 (1.4); 1.248 (0.4); 1.199 (0.4); 1.175 (0.7); 1.151 (0.4); 0.858 (0.5); 0.011 (0.7); 0.000 (21.1)

Example 168: $^1$H-NMR (300.2 MHz, $d_6$-DMSO):
δ = 10.625 (3.1); 8.552 (2.9); 8.542 (2.9); 8.211 (4.0); 8.012 (3.0); 8.004 (3.0); 7.804 (1.8); 7.776 (3.0); 7.714 (2.5); 7.706 (4.4); 7.699 (2.6); 7.678 (1.4); 7.671 (1.3); 7.297 (1.0); 7.117 (2.3); 6.936 (1.2); 3.969 (16.0); 3.329 (26.1); 2.508 (6.9); 2.502 (9.0); 2.496 (6.6); 0.000 (5.3)

Example 169: $^1$H-NMR (300.2 MHz, $d_6$-DMSO):
δ = 10.649 (2.7); 8.558 (2.8); 8.549 (2.9); 8.145 (3.8); 7.693 (4.3); 7.682 (2.4); 7.672 (1.7); 7.665 (5.8); 7.656 (0.9); 7.601 (4.4); 7.572 (2.4); 7.293 (1.0); 7.113 (2.4); 6.932 (1.2); 5.760 (1.3); 3.973 (16.0); 3.329 (27.5); 2.514 (2.1); 2.508 (4.5); 2.502 (6.3); 2.496 (4.7); 2.490 (2.3); 0.000 (2.9)

Example 170: $^1$H-NMR (300.2 MHz, $d_6$-DMSO):
δ = 10.344 (4.7); 8.622 (4.7); 7.885 (5.0); 7.860 (6.9); 7.347 (1.8); 7.325 (5.3); 7.300 (6.5); 7.290 (4.4); 7.267 (2.9); 7.253 (2.6); 7.140 (5.8); 7.117 (4.9); 7.072 (4.1); 6.892 (1.9); 5.708 (0.5); 5.447 (11.3); 5.391 (0.4); 3.371 (0.3); 3.290 (79.3); 2.452 (5.7); 2.379 (16.0); 1.967 (0.6); −0.051 (0.3)

Example 171: $^1$H-NMR (300.2 MHz, $d_6$-DMSO):
δ = 10.647 (6.3); 8.692 (5.4); 8.687 (5.6); 8.273 (8.8); 8.271 (8.7); 8.006 (5.5); 7.815 (6.2); 7.809 (7.5); 7.784 (16.0); 7.732 (7.6); 7.709 (4.7); 7.701 (3.6); 7.678 (2.6); 7.348 (2.7); 7.168 (6.1); 6.987 (3.0); 5.759 (2.4); 3.327 (71.1); 2.514 (6.6); 2.508 (14.2); 2.502 (19.8); 2.496 (14.7); 2.490 (7.2); 2.444 (20.0); 1.989 (0.9); 1.175 (0.6); 0.011 (0.6); 0.000 (15.7); −0.011 (0.7)

Example 172: $^1$H-NMR (300.2 MHz, $d_6$-DMSO):
δ = 10.702 (11.0); 8.228 (16.0); 8.137 (5.5); 8.109 (11.0); 8.060 (11.2); 8.033 (5.8); 8.008 (12.3); 8.001 (13.0); 7.899 (0.4); 7.802 (7.3); 7.774 (12.5); 7.741 (0.4); 7.703 (9.2); 7.696 (8.6); 7.675 (5.5); 7.667 (5.4); 7.391 (4.3); 7.212 (9.6); 7.034 (4.6); 5.759 (1.9); 4.041 (0.6); 4.017 (0.7); 3.327 (115.6); 3.271 (0.4); 2.508 (26.5); 2.502 (36.6); 2.496 (27.7); 1.990 (2.5); 1.236 (0.7); 1.198 (0.8); 1.175 (1.5); 1.151 (0.8); 0.000 (20.4)

Example 173: $^1$H-NMR (300.2 MHz, $d_6$-DMSO):
δ = 10.482 (6.2); 8.209 (4.7); 8.182 (5.7); 7.947 (10.6); 7.910 (5.8); 7.882 (4.9); 7.401 (1.5); 7.393 (2.2); 7.371 (9.3); 7.348 (9.0); 7.337 (5.7); 7.324 (1.6); 7.314 (3.5); 7.301 (0.7); 7.290 (0.9); 7.190 (12.4); 7.161 (6.4); 7.012 (3.3); 5.759 (0.4); 5.498 (16.0); 3.327 (41.9); 2.508 (11.7); 2.502 (16.0); 2.496 (12.1); 1.236 (0.4); 0.011 (0.4); 0.000 (9.3)

Example 174: $^1$H-NMR (300.2 MHz, CDCl$_3$):
δ = 8.614 (8.5); 8.017 (2.0); 7.915 (4.1); 7.607 (0.3); 7.507 (2.7); 7.502 (5.8); 7.496 (3.8); 7.429 (9.7); 7.423 (8.9); 7.262 (64.7); 7.213 (0.5); 7.080 (2.4); 6.911 (0.4); 6.897 (4.9); 6.715 (2.4); 2.491 (16.0); 2.010 (1.9); 1.621 (0.5); 1.610 (0.4); 1.558 (139.5); 1.475 (0.3); 1.254 (0.6); 0.000 (56.5)

Example 175: $^1$H-NMR (300.2 MHz, CDCl$_3$):
δ = 8.649 (6.4); 8.626 (4.1); 8.000 (2.1); 7.926 (4.1); 7.608 (0.4); 7.526 (0.4); 7.492 (16.0); 7.262 (73.4); 7.101 (2.7); 6.919 (5.3); 6.736 (2.6); 2.490 (15.7); 2.010 (0.4); 1.620 (0.3); 1.561 (154.0); 1.470 (0.4); 1.255 (1.9); 0.881 (0.4); 0.011 (1.9); 0.000 (61.5); −0.011 (3.4)

Example 176: $^1$H-NMR (300.2 MHz, CDCl$_3$):
δ = 8.631 (6.4); 8.132 (4.2); 8.105 (4.5); 8.012 (2.0); 7.633 (3.7); 7.606 (3.5); 7.496 (15.0); 7.485 (6.4); 7.262 (53.2); 7.054 (2.6); 6.911 (0.5); 6.872 (5.2); 6.691 (2.6); 2.009 (16.0); 1.551 (68.6); 1.498 (0.4); 0.011 (2.0); 0.000 (57.0); −0.011 (2.4)

-continued

Example 177: $^1$H-NMR (300.2 MHz, CDCl$_3$):
δ = 8.657 (3.0); 8.448 (2.2); 8.439 (2.3); 8.097 (0.9); 7.593 (2.1); 7.584 (2.1); 7.493 (7.0); 7.262 (26.1); 7.064 (1.2); 6.881 (2.5); 6.698 (1.3); 3.974 (16.0); 1.553 (36.5); 0.011 (1.0); 0.000 (28.0); −0.011 (1.3)
Example 178: $^1$H-NMR (300.2 MHz, CDCl$_3$):
δ = 8.627 (6.8); 8.013 (5.8); 7.986 (5.2); 7.794 (4.2); 7.766 (3.4); 7.495 (15.1); 7.484 (6.5); 7.262 (35.2); 7.050 (2.6); 6.868 (5.3); 6.687 (2.7); 2.009 (16.0); 1.558 (61.8); 1.263 (0.8); 0.000 (36.2); −0.011 (1.9)
Example 179: $^1$H-NMR (300.2 MHz, CDCl$_3$):
δ = 8.617 (4.1); 8.601 (6.5); 8.004 (2.0); 7.966 (0.4); 7.917 (4.2); 7.635 (4.4); 7.627 (4.8); 7.600 (5.6); 7.572 (7.1); 7.368 (2.6); 7.360 (2.4); 7.340 (2.0); 7.332 (2.0); 7.314 (0.4); 7.285 (0.4); 7.261 (127.0); 7.212 (0.4); 7.080 (2.7); 6.910 (0.8); 6.897 (5.3); 6.715 (2.6); 2.489 (16.0); 2.010 (1.3); 1.547 (148.4); 1.483 (0.4); 0.195 (0.6); 0.043 (0.5); 0.011 (4.9); 0.000 (142.3); −0.011 (6.1); −0.063 (0.4); −0.199 (0.6); −0.429 (0.3)
Example 180: $^1$H-NMR (300.2 MHz, CDCl$_3$):
δ = 19.622 (0.4); 16.427 (0.3); 13.343 (0.3); 12.563 (0.4); 8.740 (0.5); 8.582 (12.6); 8.137 (0.4); 8.121 (8.4); 8.093 (8.8); 8.023 (4.0); 7.631 (14.7); 7.622 (10.1); 7.603 (16.0); 7.574 (13.5); 7.363 (5.1); 7.355 (4.9); 7.334 (4.1); 7.327 (4.0); 7.262 (115.4); 7.035 (6.9); 6.911 (0.8); 6.892 (0.6); 6.854 (10.3); 6.811 (0.4); 6.672 (5.1); 2.009 (0.5); 1.627 (0.3); 1.601 (0.3); 1.554 (216.0); 1.497 (1.1); 1.386 (0.4); 1.280 (0.3); 0.195 (0.5); 0.011 (3.5); 0.000 (114.7); −0.011 (6.8); −0.055 (0.7); −0.200 (0.6); −2.804 (0.3); −3.490 (0.4)
Example 181: $^1$H-NMR (300.2 MHz, CDCl$_3$):
δ = 12.686 (0.7); 8.581 (15.5); 8.556 (0.6); 8.062 (0.6); 8.026 (5.0); 8.004 (10.7); 7.976 (11.7); 7.918 (0.6); 7.793 (9.6); 7.766 (7.6); 7.629 (10.5); 7.621 (11.0); 7.602 (13.1); 7.573 (16.0); 7.362 (6.1); 7.354 (5.8); 7.334 (5.1); 7.325 (4.6); 7.261 (204.2); 7.031 (5.9); 6.910 (1.1); 6.850 (12.7); 6.669 (6.0); 2.488 (0.6); 2.010 (3.0); 1.599 (0.8); 1.549 (286.1); 1.471 (0.9); 1.253 (6.3); 1.224 (0.6); 0.194 (0.9); 0.011 (9.1); 0.000 (219.8); −0.011 (8.7); −0.053 (0.8); −0.198 (0.8); −2.848 (0.6)
Example 182: $^1$H-NMR (300.2 MHz, CDCl$_3$):
δ = 8.717 (4.2); 8.713 (4.3); 8.702 (4.5); 8.698 (4.4); 8.670 (0.4); 8.654 (0.3); 8.396 (16.0); 8.208 (0.4); 8.019 (4.0); 8.015 (4.0); 7.993 (4.5); 7.989 (4.4); 7.853 (0.4); 7.791 (4.6); 7.594 (8.2); 7.566 (10.9); 7.516 (3.4); 7.500 (3.4); 7.490 (3.4); 7.474 (3.1); 7.427 (1.5); 7.422 (2.4); 7.416 (2.0); 7.400 (4.8); 7.394 (7.6); 7.389 (6.7); 7.379 (15.8); 7.354 (13.8); 7.328 (3.4); 7.306 (8.3); 7.274 (2.9); 7.249 (0.6); 7.111 (5.2); 7.106 (3.2); 7.086 (4.5); 7.082 (2.8); 7.066 (4.1); 6.884 (7.7); 6.701 (3.8); 6.540 (0.4); 4.125 (0.7); 4.101 (2.2); 4.078 (2.2); 4.054 (0.8); 3.662 (0.6); 2.073 (1.2); 2.016 (9.7); 1.988 (1.0); 1.757 (7.2); 1.269 (2.6); 1.246 (5.2); 1.222 (2.6); 0.000 (2.4)
Example 183: $^1$H-NMR (400.0 MHz, d$_6$-DMSO):
δ = 10.593 (2.2); 8.846 (1.1); 8.842 (1.2); 8.834 (1.1); 8.831 (1.1); 8.182 (1.1); 8.171 (4.2); 8.163 (1.2); 7.749 (0.8); 7.737 (0.8); 7.730 (0.8); 7.718 (0.7); 7.663 (16.0); 7.334 (0.8); 7.199 (1.8); 7.064 (0.9); 3.334 (11.6); 2.508 (11.0); 2.503 (14.4); 2.499 (10.8); 0.000 (0.5)
Example 184: $^1$H-NMR (300.2 MHz, CDCl$_3$):
δ = 8.737 (4.6); 8.734 (4.7); 8.722 (4.9); 8.428 (16.0); 8.032 (4.5); 8.006 (5.1); 7.652 (4.7); 7.587 (9.0); 7.558 (11.6); 7.530 (3.7); 7.514 (3.7); 7.504 (3.5); 7.488 (3.2); 7.375 (11.0); 7.347 (8.6); 7.303 (0.3); 7.276 (5.1); 7.270 (5.7); 7.258 (5.9); 7.247 (8.4); 7.236 (3.9); 7.230 (7.8); 7.163 (8.1); 7.157 (2.7); 7.135 (12.6); 7.107 (5.2); 7.060 (4.0); 6.878 (8.0); 6.696 (4.0); 4.139 (0.5); 4.115 (1.4); 4.091 (1.4); 4.067 (0.5); 2.086 (0.3); 2.029 (6.1); 1.692 (7.6); 1.276 (1.8); 1.252 (3.3); 1.228 (1.6); 0.880 (0.4); 0.000 (3.1)
Example 185: $^1$H-NMR (300.2 MHz, CDCl$_3$):
δ = 8.712 (4.2); 8.709 (4.5); 8.697 (4.5); 8.693 (4.4); 8.385 (16.0); 8.194 (0.6); 8.005 (4.0); 8.001 (4.1); 7.979 (4.5); 7.975 (4.5); 7.849 (4.8); 7.587 (8.2); 7.559 (10.8); 7.532 (0.7); 7.507 (3.4); 7.491 (3.4); 7.481 (3.3); 7.465 (3.0); 7.448 (2.0); 7.428 (2.4); 7.421 (3.7); 7.401 (3.7); 7.394 (3.1); 7.375 (12.3); 7.347 (8.0); 7.328 (0.8); 7.297 (0.5); 7.278 (2.1); 7.157 (1.9); 7.151 (2.0); 7.131 (3.1); 7.129 (3.4); 7.123 (3.6); 7.120 (3.5); 7.103 (1.6); 7.100 (1.7); 7.095 (1.9); 7.092 (1.9); 7.077 (0.5); 7.064 (4.0); 7.048 (5.2); 7.023 (4.5); 6.998 (3.0); 6.991 (3.4); 6.968 (3.0); 6.963 (3.3); 6.882 (7.8); 6.699 (3.8); 4.096 (1.0); 4.072 (1.0); 4.048 (0.4); 2.058 (1.8); 2.011 (4.5); 1.983 (11.1); 1.966 (0.4); 1.267 (1.4); 1.243 (2.5); 1.219 (1.4); 0.000 (1.5)
Example 186: $^1$H-NMR (300.2 MHz, CDCl$_3$):
δ = 8.723 (4.6); 8.720 (4.6); 8.708 (4.9); 8.450 (16.0); 7.995 (4.4); 7.969 (5.0); 7.750 (5.1); 7.562 (8.8); 7.533 (11.7); 7.505 (3.8); 7.488 (3.8); 7.479 (3.6); 7.462 (4.3); 7.447 (11.1); 7.436 (13.9); 7.427 (14.5); 7.414 (2.4); 7.379 (11.2); 7.351 (8.4); 7.268 (7.3); 7.256 (7.5); 7.245 (6.2); 7.236 (5.2); 7.078 (3.9); 6.896 (7.9); 6.714 (4.0); 4.108 (0.6); 4.085 (0.7); 2.067 (0.3); 2.022 (2.8); 1.991 (3.6); 1.754 (5.2); 1.272 (0.8); 1.248 (1.5); 1.225 (0.7); 0.000 (2.0)
Example 187: $^1$H-NMR (300.2 MHz, CDCl$_3$):
δ = 8.712 (5.7); 8.697 (5.7); 8.302 (16.0); 7.988 (5.3); 7.962 (5.9); 7.782 (6.2); 7.501 (3.9); 7.485 (4.2); 7.475 (3.8); 7.459 (3.5); 7.287 (10.5); 7.280 (5.5); 7.278 (5.2); 7.258 (16.6); 7.235 (5.4); 7.216 (6.8); 7.207 (9.1); 7.189 (8.2); 7.157 (16.3); 7.126 (13.5); 7.094 (12.9); 7.072 (6.6); 7.066 (6.1); 7.023 (0.4); 6.890 (8.1); 6.708 (4.0); 4.126 (0.6); 4.102 (1.9); 4.079 (1.9); 4.055 (0.7); 2.018 (7.9); 1.989 (0.6); 1.819 (6.5); 1.270 (2.2); 1.247 (4.2); 1.223 (2.3); 0.000 (1.8)
Example 188: $^1$H-NMR (400.0 MHz, d$_6$-DMSO):
δ = 10.643 (6.9); 8.851 (4.0); 8.848 (4.4); 8.840 (4.4); 8.836 (4.3); 8.241 (16.0); 8.193 (3.8); 8.173 (4.2); 7.990 (6.2); 7.969 (11.2); 7.919 (10.5); 7.897 (6.0); 7.756 (3.0); 7.744 (3.1); 7.736 (2.9); 7.724 (2.8); 7.341 (3.1); 7.206 (7.0); 7.071 (3.5); 3.335 (52.2); 2.673 (0.4); 2.508 (44.5); 2.504 (57.9); 2.500 (43.3); 2.331 (0.4); 2.075 (0.4); 1.234 (0.8); 0.000 (1.9)
Example 189: $^1$H-NMR (400.0 MHz, d$_6$-DMSO):
δ = 10.525 (3.6); 9.661 (0.8); 8.840 (1.9); 8.829 (2.0); 8.178 (1.7); 8.159 (1.9); 8.085 (5.0); 7.968 (1.4); 7.745 (1.2); 7.733 (1.3); 7.726 (1.3); 7.714 (1.1); 7.509 (3.9); 7.487 (4.5); 7.470 (1.3); 7.447 (1.3); 7.334 (1.1); 7.199 (2.4); 7.127 (4.3); 7.105 (4.8); 7.080 (1.3); 7.064 (1.3); 3.837 (16.0); 3.825 (5.7); 3.332 (17.4); 2.503 (31.3); 2.053 (4.1); 1.397 (0.6); 0.000 (0.7)

Example 190: $^1$H-NMR (400.0 MHz, d$_6$-DMSO):
δ = 10.575 (2.4); 8.845 (1.2); 8.841 (1.3); 8.833 (1.2); 8.829 (1.3); 8.181 (1.1); 8.161 (1.2); 8.143 (4.6); 7.976 (0.3); 7.748 (0.9); 7.736 (0.9); 7.728 (0.9); 7.716 (0.9); 7.681 (1.6); 7.676 (0.7); 7.669 (1.7); 7.663 (1.1); 7.658 (2.1); 7.652 (0.8); 7.646 (2.0); 7.465 (0.4); 7.457 (2.0); 7.451 (0.7); 7.435 (3.2); 7.419 (0.6); 7.413 (1.7); 7.334 (0.9); 7.199 (2.1); 7.064 (1.0); 3.333 (13.3); 2.690 (16.0); 2.507 (13.3); 2.503 (17.5); 2.499 (13.1); 2.063 (0.4); 2.056 (0.4); 0.146 (0.4); 0.008 (3.4); 0.000 (64.9); −0.009 (3.4); −0.150 (0.4)

Example 191: $^1$H-NMR (400.0 MHz, d$_6$-DMSO):
δ = 10.602 (7.1); 8.914 (0.4); 8.903 (0.3); 8.838 (3.9); 8.829 (3.9); 8.826 (3.8); 8.404 (0.3); 8.384 (0.4); 8.197 (3.5); 8.178 (16.0); 7.772 (3.8); 7.761 (1.3); 7.753 (4.6); 7.748 (4.2); 7.743 (3.5); 7.731 (2.8); 7.723 (2.7); 7.711 (2.5); 7.671 (1.7); 7.666 (2.3); 7.659 (2.8); 7.654 (4.5); 7.649 (4.9); 7.640 (5.3); 7.636 (5.6); 7.631 (4.8); 7.604 (3.7); 7.601 (3.9); 7.583 (3.5); 7.567 (1.3); 7.564 (1.3); 7.500 (0.4); 7.365 (0.6); 7.345 (2.6); 7.230 (0.3); 7.209 (5.7); 7.074 (2.9); 5.758 (1.4); 4.038 (0.3); 4.020 (0.3); 3.334 (91.3); 2.672 (0.5); 2.662 (0.4); 2.507 (53.9); 2.503 (68.5); 2.499 (52.5); 2.330 (0.4); 2.062 (4.1); 2.056 (3.9); 1.989 (1.4); 1.336 (0.5); 1.299 (0.4); 1.264 (0.7); 1.259 (0.8); 1.248 (0.9); 1.235 (1.4); 1.204 (0.4); 1.192 (0.6); 1.186 (0.8); 1.175 (0.9); 1.168 (0.7); 1.157 (0.5); 1.093 (0.7); 1.076 (0.7); 0.000 (27.8)

Example 192: $^1$H-NMR (400.0 MHz, d$_6$-DMSO):
δ = 10.458 (10.3); 8.914 (0.4); 8.903 (0.4); 8.843 (5.8); 8.832 (5.7); 8.808 (0.6); 8.797 (0.6); 8.403 (0.3); 8.384 (0.4); 8.290 (0.5); 8.271 (0.5); 8.172 (5.1); 8.153 (5.5); 8.103 (16.0); 7.982 (0.7); 7.774 (0.3); 7.752 (3.9); 7.740 (4.1); 7.733 (4.0); 7.721 (3.6); 7.695 (0.4); 7.656 (6.0); 7.644 (7.0); 7.639 (5.7); 7.634 (8.4); 7.622 (7.6); 7.453 (7.7); 7.431 (12.8); 7.409 (6.2); 7.381 (0.4); 7.365 (0.7); 7.340 (3.5); 7.239 (0.4); 7.230 (0.4); 7.205 (7.6); 7.105 (0.7); 7.069 (3.8); 6.970 (0.3); 3.335 (108.7); 2.689 (6.3); 2.672 (0.8); 2.503 (100.7); 2.330 (0.6); 2.062 (3.5); 2.056 (3.5); 1.264 (0.4); 1.248 (0.4); 1.235 (0.4); 1.205 (0.3); 1.187 (0.5); 1.166 (0.4); 1.092 (0.5); 1.076 (0.5); 0.000 (33.3)

Example 193: $^1$H-NMR (400.0 MHz, d$_6$-DMSO):
δ = 10.412 (2.7); 8.844 (1.4); 8.841 (1.4); 8.832 (1.4); 8.829 (1.4); 8.170 (1.2); 8.150 (1.3); 8.047 (5.3); 7.750 (1.0); 7.738 (1.0); 7.730 (0.9); 7.718 (0.9); 7.492 (0.4); 7.484 (3.7); 7.479 (1.3); 7.467 (1.3); 7.462 (4.2); 7.453 (0.4); 7.341 (1.0); 7.206 (2.4); 7.130 (0.5); 7.121 (4.1); 7.116 (1.4); 7.104 (1.3); 7.099 (3.7); 7.090 (0.4); 7.070 (1.2); 3.839 (16.0); 3.827 (0.3); 3.332 (17.7); 2.525 (0.4); 2.511 (9.2); 2.507 (18.3); 2.502 (23.7); 2.498 (17.4); 0.000 (2.6)

Example 194: $^1$H-NMR (300.2 MHz, CDCl$_3$):
δ = 8.708 (2.9); 8.703 (3.0); 8.692 (3.1); 8.687 (3.0); 8.298 (12.1); 7.995 (2.7); 7.991 (2.7); 7.969 (3.1); 7.965 (3.0); 7.865 (3.3); 7.500 (2.3); 7.484 (2.4); 7.474 (2.3); 7.458 (2.1); 7.391 (1.0); 7.386 (1.7); 7.380 (1.4); 7.364 (3.2); 7.358 (5.2); 7.352 (3.7); 7.346 (4.5); 7.321 (5.1); 7.308 (1.1); 7.298 (7.9); 7.277 (5.3); 7.269 (15.5); 7.260 (5.2); 7.235 (0.5); 7.227 (0.4); 7.180 (1.6); 7.171 (11.7); 7.164 (3.5); 7.148 (2.8); 7.142 (7.4); 7.132 (1.1); 7.085 (2.5); 7.080 (4.8); 7.077 (4.5); 7.061 (2.2); 7.056 (3.3); 7.051 (1.9); 7.037 (0.3); 6.895 (5.7); 6.712 (2.8); 5.296 (0.9); 4.122 (1.2); 4.098 (3.6); 4.075 (3.6); 4.051 (1.2); 2.014 (16.0); 1.816 (5.4); 1.268 (4.8); 1.244 (8.4); 1.221 (4.3); 0.879 (0.7); 0.000 (1.4)

Example 195: $^1$H-NMR (300.2 MHz, CDCl$_3$):
δ = 8.716 (2.7); 8.711 (2.8); 8.700 (3.0); 8.695 (2.8); 8.308 (10.6); 7.991 (2.6); 7.987 (2.6); 7.965 (3.0); 7.780 (3.1); 7.501 (2.2); 7.485 (2.2); 7.475 (2.1); 7.459 (2.1); 7.448 (1.1); 7.439 (8.0); 7.432 (2.9); 7.416 (3.4); 7.409 (9.5); 7.400 (1.4); 7.278 (1.6); 7.238 (3.0); 7.231 (1.5); 7.220 (3.6); 7.209 (5.3); 7.198 (2.3); 7.191 (4.8); 7.182 (0.9); 7.135 (0.9); 7.126 (5.5); 7.119 (1.8); 7.099 (16.0); 7.070 (12.2); 7.060 (1.7); 6.889 (5.1); 6.707 (2.6); 5.297 (0.5); 4.127 (0.9); 4.104 (2.7); 4.080 (2.8); 4.056 (1.0); 2.019 (12.2); 1.817 (4.6); 1.271 (4.1); 1.247 (6.7); 1.223 (3.3); 0.901 (0.4); 0.879 (1.1); 0.856 (0.5); 0.000 (1.3)

Example 196: $^1$H-NMR (300.2 MHz, CDCl$_3$):
δ = 8.716 (3.1); 8.711 (3.3); 8.700 (3.3); 8.695 (3.3); 8.370 (12.7); 7.975 (2.9); 7.971 (3.0); 7.949 (3.3); 7.945 (3.3); 7.775 (3.5); 7.490 (2.5); 7.474 (2.6); 7.464 (2.5); 7.448 (2.4); 7.427 (2.6); 7.418 (16.0); 7.412 (8.5); 7.405 (10.9); 7.396 (15.2); 7.389 (13.8); 7.350 (0.5); 7.273 (1.9); 7.251 (0.6); 7.249 (0.6); 7.237 (4.8); 7.225 (5.7); 7.213 (4.5); 7.205 (4.0); 7.194 (0.8); 7.126 (1.3); 7.116 (11.0); 7.110 (3.7); 7.093 (3.3); 7.087 (10.8); 7.078 (1.6); 7.046 (0.3); 6.902 (6.2); 6.720 (3.1); 5.294 (0.8); 4.107 (0.6); 4.083 (0.6); 2.021 (2.7); 1.990 (5.5); 1.782 (4.9); 1.271 (0.8); 1.247 (1.5); 1.223 (0.7); 0.000 (1.5)

Example 197: $^1$H-NMR (300.2 MHz, CDCl$_3$):
δ = 8.733 (4.2); 8.729 (4.3); 8.718 (4.5); 8.713 (4.2); 8.366 (16.0); 8.022 (4.1); 8.018 (4.0); 7.996 (4.6); 7.992 (4.3); 7.727 (4.4); 7.522 (3.3); 7.506 (3.5); 7.496 (3.2); 7.480 (3.0); 7.427 (1.9); 7.407 (2.4); 7.400 (3.6); 7.381 (3.8); 7.374 (2.9); 7.354 (2.6); 7.303 (9.9); 7.297 (3.9); 7.281 (5.5); 7.274 (17.5); 7.265 (3.1); 7.246 (0.7); 7.219 (0.5); 7.188 (16.4); 7.181 (4.8); 7.165 (4.2); 7.159 (9.8); 7.149 (1.5); 7.135 (2.1); 7.129 (2.1); 7.127 (2.0); 7.107 (3.4); 7.101 (3.4); 7.079 (1.9); 7.070 (5.4); 7.029 (5.2); 7.003 (4.5); 6.972 (2.9); 6.965 (3.2); 6.959 (2.3); 6.941 (2.9); 6.936 (3.2); 6.929 (2.2); 6.888 (8.1); 6.705 (4.0); 5.298 (1.6); 2.028 (0.8); 1.996 (6.7); 1.746 (0.4); 1.717 (4.4); 1.261 (0.4); 1.251 (0.6); 1.238 (0.4); 1.061 (0.3); 0.995 (0.5); 0.000 (2.7)

Example 198: $^1$H-NMR (300.2 MHz, CDCl$_3$):
δ = 8.698 (3.9); 8.694 (4.5); 8.682 (4.3); 8.678 (4.5); 8.649 (0.3); 8.327 (16.0); 7.952 (4.1); 7.926 (4.5); 7.855 (5.0); 7.473 (3.3); 7.457 (3.4); 7.447 (3.4); 7.431 (3.3); 7.407 (9.6); 7.395 (12.9); 7.386 (14.8); 7.373 (2.6); 7.277 (1.9); 7.270 (1.3); 7.261 (8.8); 7.254 (4.1); 7.239 (5.2); 7.231 (19.6); 7.216 (8.1); 7.204 (6.3); 7.196 (5.6); 7.170 (2.6); 7.161 (16.3); 7.154 (5.5); 7.139 (3.6); 7.132 (9.4); 7.084 (3.8); 6.902 (7.7); 6.720 (3.8); 4.095 (0.3); 4.072 (0.3); 2.010 (1.5); 1.980 (1.8); 1.852 (4.0); 1.266 (0.5); 1.242 (0.9); 1.223 (0.4); 1.218 (0.5); 1.054 (0.4); 0.000 (1.4)

Example 199: $^1$H-NMR (300.2 MHz, CDCl$_3$):
δ = 8.686 (3.9); 8.682 (4.0); 8.671 (4.2); 8.666 (4.0); 8.258 (16.0); 7.970 (4.1); 7.966 (4.3); 7.945 (7.6); 7.481 (3.1); 7.464 (3.2); 7.454 (3.4); 7.440 (13.7); 7.418 (4.9); 7.411 (13.7); 7.402 (2.1); 7.384 (1.5); 7.379 (2.3); 7.373 (2.0); 7.357 (4.3); 7.352 (6.9); 7.346 (5.1); 7.340 (6.0); 7.315 (6.6); 7.288 (2.7); 7.282 (1.9); 7.259 (7.6); 7.253 (4.5); 7.107 (1.7); 7.098 (13.5); 7.091 (4.4); 7.069

-continued (14.7); 7.059 (2.4); 7.052 (3.4); 7.047 (4.7); 7.042 (2.7); 6.998 (0.3); 6.891 (7.3); 6.709 (3.6); 4.110 (0.5); 4.086 (1.4); 4.062 (1.4); 4.038 (0.5); 2.003 (6.3); 1.978 (7.4); 1.888 (5.8); 1.262 (1.7); 1.238 (3.3); 1.215 (1.7); 1.209 (0.4); 0.000 (1.4)

Example 200: $^1$H-NMR (300.2 MHz, CDCl$_3$):
δ = 8.716 (4.7); 8.704 (4.6); 8.700 (4.7); 8.330 (16.0); 8.004 (4.4); 7.978 (4.8); 7.806 (0.4); 7.772 (5.0); 7.732 (0.4); 7.550 (0.4); 7.511 (3.5); 7.495 (3.6); 7.485 (3.6); 7.469 (3.5); 7.453 (12.1); 7.424 (14.8); 7.395 (2.8); 7.389 (2.3); 7.372 (4.6); 7.367 (7.5); 7.362 (5.5); 7.354 (6.5); 7.329 (7.3); 7.302 (2.9); 7.275 (9.3); 7.273 (9.2); 7.147 (0.3); 7.130 (1.9); 7.120 (14.0); 7.091 (14.0); 7.084 (7.6); 7.073 (5.4); 7.060 (5.0); 7.025 (0.4); 7.009 (0.4); 6.890 (7.8); 6.708 (4.0); 5.297 (1.3); 2.332 (0.5); 2.022 (1.2); 1.992 (14.5); 1.743 (10.4); 1.272 (0.4); 1.255 (0.4); 1.248 (0.8); 1.231 (0.4); 1.224 (0.4); 1.057 (0.3); 0.000 (2.8)

Example 201: $^1$H-NMR (300.2 MHz, CDCl$_3$):
δ = 8.712 (4.5); 8.700 (4.6); 8.696 (4.6); 8.329 (16.0); 7.996 (4.2); 7.972 (4.6); 7.970 (4.7); 7.804 (4.9); 7.505 (3.4); 7.489 (3.5); 7.479 (3.4); 7.463 (3.5); 7.447 (12.0); 7.441 (4.8); 7.418 (15.1); 7.409 (2.9); 7.403 (3.0); 7.396 (4.2); 7.376 (3.9); 7.369 (3.1); 7.350 (2.6); 7.275 (2.4); 7.125 (3.6); 7.116 (14.6); 7.110 (5.8); 7.106 (4.8); 7.103 (4.5); 7.094 (7.7); 7.087 (12.7); 7.077 (3.4); 7.067 (5.9); 7.021 (5.2); 6.996 (4.7); 6.965 (2.9); 6.959 (3.4); 6.935 (2.9); 6.929 (3.4); 6.885 (8.0); 6.702 (4.0); 5.296 (1.9); 4.102 (0.4); 4.079 (0.4); 2.018 (1.9); 1.989 (5.6); 1.782 (9.1); 1.270 (0.6); 1.246 (1.1); 1.222 (0.6); 0.000 (2.0)

Example 202: $^1$H-NMR (400.0 MHz, d$_6$-DMSO):
δ = 10.660 (7.0); 8.846 (3.5); 8.843 (3.6); 8.834 (3.7); 8.831 (3.5); 8.234 (12.3); 8.178 (3.2); 8.158 (3.5); 7.811 (3.3); 7.807 (6.3); 7.802 (4.8); 7.781 (16.0); 7.777 (11.6); 7.749 (2.5); 7.737 (2.7); 7.730 (2.5); 7.717 (2.3); 7.327 (2.5); 7.192 (5.6); 7.056 (2.8); 3.333 (31.7); 2.508 (36.8); 2.504 (45.7); 2.500 (33.8); 1.234 (0.8); 0.000 (8.3)

Example 203: $^1$H-NMR (400.0 MHz, d$_6$-DMSO):
δ = 10.536 (6.0); 8.846 (3.1); 8.842 (3.4); 8.834 (3.3); 8.831 (3.3); 8.191 (14.1); 8.166 (2.8); 8.147 (3.1); 7.824 (3.3); 7.819 (6.9); 7.814 (4.6); 7.771 (16.0); 7.766 (13.9); 7.752 (2.3); 7.740 (2.3); 7.732 (2.2); 7.720 (2.0); 7.331 (2.4); 7.195 (5.5); 7.060 (2.7); 3.332 (159.3); 2.676 (0.6); 2.672 (0.8); 2.667 (0.6); 2.525 (1.9); 2.511 (43.9); 2.507 (88.6); 2.503 (116.1); 2.498 (86.4); 2.494 (43.7); 2.334 (0.6); 2.329 (0.8); 2.325 (0.6); 1.989 (1.1); 1.193 (0.3); 1.175 (0.6); 0.146 (0.4); 0.008 (3.6); 0.000 (94.2); −0.008 (4.1); −0.150 (0.4)

Example 204: $^1$H-NMR (300.2 MHz, d$_6$-DMSO):
δ = 10.179 (3.2); 8.663 (2.7); 7.996 (2.6); 7.884 (6.1); 7.486 (0.4); 7.462 (1.3); 7.457 (1.6); 7.438 (5.2); 7.421 (1.0); 7.401 (0.8); 7.391 (0.8); 7.375 (1.5); 7.365 (1.5); 7.355 (1.0); 7.346 (1.2); 7.333 (2.8); 7.304 (1.2); 7.157 (3.1); 6.976 (1.5); 3.328 (58.9); 2.552 (0.9); 2.527 (2.9); 2.513 (10.2); 2.507 (21.5); 2.502 (30.4); 2.496 (21.8); 2.490 (10.9); 2.443 (9.7); 2.024 (0.4); 1.985 (16.0); 1.942 (0.4); 1.909 (1.6); 1.355 (0.6); 1.235 (0.3); 1.198 (0.4); 1.174 (0.5); 0.897 (3.5); 0.873 (8.3); 0.848 (3.5); 0.011 (0.6); 0.000 (17.4); −0.011 (0.9)

Example 205: $^1$H-NMR (300.2 MHz, d$_6$-DMSO):
δ = 9.933 (3.6); 8.669 (2.8); 7.966 (2.8); 7.708 (6.0); 7.665 (0.4); 7.486 (0.5); 7.467 (1.3); 7.461 (1.3); 7.441 (4.2); 7.418 (1.2); 7.401 (0.9); 7.375 (1.7); 7.368 (1.5); 7.346 (4.2); 7.318 (1.0); 7.167 (3.0); 6.986 (1.4); 4.040 (0.3); 3.383 (0.4); 3.328 (78.8); 2.834 (0.5); 2.811 (1.0); 2.787 (1.4); 2.763 (1.1); 2.739 (0.6); 2.725 (0.4); 2.554 (0.4); 2.507 (24.8); 2.501 (33.6); 2.495 (25.1); 2.449 (10.1); 2.011 (0.5); 1.989 (1.1); 1.963 (16.0); 1.922 (0.5); 1.909 (0.8); 1.354 (0.6); 1.235 (0.5); 1.196 (0.8); 1.174 (1.4); 1.129 (5.1); 1.111 (5.1); 0.000 (18.3)

Example 206: $^1$H-NMR (300.2 MHz, d$_6$-DMSO):
δ = 10.155 (3.7); 8.665 (2.9); 8.659 (3.0); 7.984 (2.9); 7.856 (8.0); 7.457 (1.2); 7.431 (2.8); 7.406 (2.0); 7.327 (1.9); 7.304 (4.3); 7.298 (3.3); 7.273 (2.2); 7.146 (3.8); 6.966 (1.8); 4.040 (0.4); 4.016 (0.4); 3.329 (83.0); 2.789 (1.0); 2.764 (3.0); 2.739 (3.2); 2.714 (1.1); 2.514 (8.2); 2.508 (18.1); 2.502 (25.3); 2.496 (18.8); 2.490 (9.1); 2.446 (10.9); 2.398 (16.0); 1.989 (1.7); 1.198 (0.5); 1.174 (0.9); 1.150 (0.5); 0.975 (4.0); 0.950 (10.2); 0.925 (4.1); 0.011 (0.5); 0.000 (15.6); −0.011 (0.7)

Example 207: $^1$H-NMR (300.2 MHz, d$_6$-DMSO):
δ = 10.143 (4.1); 8.658 (3.1); 7.982 (3.3); 7.843 (6.8); 7.390 (1.1); 7.359 (15.5); 7.324 (2.4); 7.143 (3.4); 6.962 (1.7); 3.328 (66.2); 2.765 (1.0); 2.740 (3.3); 2.715 (3.2); 2.690 (1.2); 2.508 (29.9); 2.502 (42.3); 2.496 (33.2); 2.444 (11.7); 2.391 (16.0); 2.271 (0.4); 2.022 (0.3); 1.989 (0.6); 1.174 (1.6); 1.152 (0.3); 0.964 (4.1); 0.939 (9.5); 0.914 (4.1); 0.011 (0.9); 0.000 (29.6)

Example 208: $^1$H-NMR (300.2 MHz, d$_6$-DMSO):
δ = 18.513 (0.4); 9.905 (3.4); 8.665 (2.7); 7.951 (2.7); 7.650 (6.2); 7.371 (1.9); 7.343 (6.5); 7.322 (7.6); 7.293 (2.3); 7.154 (3.2); 6.972 (1.3); 3.445 (0.4); 3.328 (116.2); 3.244 (0.4); 3.064 (0.4); 3.038 (1.1); 3.016 (1.5); 2.992 (1.1); 2.966 (0.6); 2.727 (0.6); 2.513 (26.9); 2.507 (57.0); 2.501 (78.4); 2.495 (57.8); 2.490 (28.0); 2.452 (10.4); 2.398 (13.1); 2.275 (0.6); 2.007 (0.5); 1.989 (0.6); 1.354 (0.8); 1.290 (0.4); 1.270 (0.7); 1.248 (0.8); 1.223 (0.8); 1.197 (16.0); 1.174 (15.6); 1.135 (0.9); 0.000 (59.8); −0.011 (2.8); −0.033 (0.6); −1.515 (0.4)

Example 209: $^1$H-NMR (300.2 MHz, d$_6$-DMSO):
δ = 9.960 (4.1); 8.665 (3.3); 7.968 (3.1); 7.751 (7.1); 7.737 (2.1); 7.723 (0.8); 7.711 (2.8); 7.705 (2.1); 7.639 (1.0); 7.632 (1.3); 7.610 (3.0); 7.596 (3.3); 7.588 (4.3); 7.575 (2.8); 7.569 (2.8); 7.552 (1.7); 7.548 (1.8); 7.526 (0.7); 7.521 (0.7); 7.346 (1.6); 7.165 (3.6); 6.984 (1.7); 4.064 (1.2); 4.040 (3.8); 4.017 (3.8); 3.993 (1.4); 3.331 (51.3); 2.840 (0.5); 2.816 (1.0); 2.793 (1.6); 2.769 (1.2); 2.745 (0.5); 2.508 (13.1); 2.502 (18.4); 2.496 (14.0); 2.448 (11.5); 2.014 (0.5); 1.989 (16.0); 1.904 (2.8); 1.355 (0.7); 1.235 (0.8); 1.204 (5.5); 1.198 (7.0); 1.181 (5.7); 1.174 (11.1); 1.151 (5.0); 1.095 (5.3); 1.071 (5.1); 0.890 (0.3); 0.868 (0.3); 0.000 (7.9)

Example 210: $^1$H-NMR (300.2 MHz, d$_6$-DMSO):
δ = 9.949 (3.6); 8.669 (3.1); 7.952 (3.1); 7.725 (6.4); 7.604 (4.4); 7.590 (4.3); 7.573 (3.8); 7.463 (1.2); 7.454 (1.4); 7.445 (1.5); 7.429 (0.9); 7.336 (1.3); 7.155 (2.9); 6.974 (1.5); 3.329 (52.5); 3.106 (0.4); 3.082 (1.1); 3.057 (1.5); 3.034 (1.2); 3.010 (0.6); 2.506 (18.2); 2.501 (25.1); 2.496 (20.3); 2.454 (11.0); 1.989 (0.5); 1.258 (0.5); 1.230 (16.0); 1.207 (15.9); 1.173 (0.7); 0.000 (12.3)

Example 211: $^1$H-NMR (300.2 MHz, d$_6$-DMSO):
δ = 9.940 (3.5); 8.674 (2.7); 8.669 (2.7); 7.952 (2.6); 7.708 (6.3); 7.641 (4.2); 7.635 (1.6); 7.612 (6.7); 7.603 (1.0); 7.586 (0.3); 7.504 (6.4); 7.497 (1.9); 7.482 (1.6); 7.475 (4.4); 7.334 (1.4); 7.153

(3.1); 6.972 (1.5); 4.040 (0.6); 4.017 (0.5); 3.330 (61.9); 3.086 (0.4); 3.062 (1.0); 3.039 (1.4); 3.016 (1.1); 2.992 (0.4); 2.514 (6.7); 2.508 (14.5); 2.502 (20.2); 2.496 (15.0); 2.490 (7.4); 2.454 (9.7); 1.989 (2.2); 1.354 (0.6); 1.218 (16.0); 1.194 (15.9); 1.174 (1.9); 1.155 (0.8); 1.151 (1.0); 0.011 (0.4); 0.000 (13.0)

Example 212: $^1$H-NMR (300.2 MHz, $d_6$-DMSO):

δ = 10.215 (6.2); 8.664 (4.7); 8.659 (4.9); 8.004 (4.7); 8.001 (4.7); 7.927 (12.1); 7.788 (0.6); 7.744 (2.0); 7.740 (2.5); 7.739 (2.5); 7.735 (1.9); 7.719 (2.8); 7.716 (4.8); 7.711 (3.3); 7.702 (0.8); 7.635 (1.6); 7.626 (2.0); 7.614 (2.4); 7.611 (1.8); 7.605 (4.1); 7.598 (2.3); 7.595 (2.9); 7.581 (10.7); 7.578 (8.7); 7.573 (7.4); 7.568 (5.9); 7.553 (3.4); 7.548 (2.2); 7.535 (0.9); 7.526 (0.9); 7.521 (0.8); 7.338 (2.6); 7.157 (6.0); 6.976 (3.0); 3.333 (46.3); 2.553 (1.9); 2.529 (2.1); 2.514 (4.8); 2.508 (8.7); 2.502 (11.6); 2.496 (8.7); 2.490 (4.5); 2.443 (17.4); 2.028 (0.7); 1.990 (0.6); 1.909 (1.3); 1.355 (1.1); 1.235 (0.7); 1.195 (0.5); 1.174 (0.5); 0.968 (0.4); 0.943 (1.0); 0.925 (6.8); 0.900 (16.0); 0.875 (6.7); 0.839 (0.5); 0.000 (5.4)

Example 213: $^1$H-NMR (300.2 MHz, $d_6$-DMSO):

δ = 17.062 (0.4); 10.200 (6.1); 8.684 (0.4); 8.667 (5.0); 8.662 (5.2); 7.989 (5.1); 7.923 (12.4); 7.633 (3.1); 7.626 (6.2); 7.594 (3.6); 7.571 (7.6); 7.566 (8.7); 7.560 (5.4); 7.547 (1.9); 7.536 (3.7); 7.529 (4.5); 7.523 (2.5); 7.513 (1.8); 7.505 (2.5); 7.499 (1.5); 7.325 (2.7); 7.144 (5.7); 6.963 (3.0); 4.039 (0.5); 4.016 (0.4); 3.383 (0.4); 3.376 (0.4); 3.329 (150.4); 3.276 (0.6); 3.021 (0.3); 2.835 (1.6); 2.811 (5.0); 2.786 (5.2); 2.760 (1.9); 2.732 (0.6); 2.544 (0.5); 2.508 (42.4); 2.502 (60.8); 2.496 (46.8); 2.447 (18.6); 2.343 (0.5); 2.272 (0.6); 2.251 (0.4); 2.028 (0.4); 1.989 (1.8); 1.234 (0.5); 1.198 (0.8); 1.174 (1.2); 1.151 (0.5); 0.987 (6.6); 0.962 (16.0); 0.937 (6.7); 0.885 (0.3); 0.011 (1.1); 0.000 (38.0); −0.058 (0.4)

Example 214: $^1$H-NMR (300.2 MHz, $d_6$-DMSO):

δ = 10.183 (6.1); 8.666 (4.4); 8.660 (4.7); 7.985 (4.5); 7.951 (0.5); 7.902 (11.0); 7.789 (0.5); 7.774 (0.6); 7.635 (5.0); 7.628 (2.4); 7.613 (3.2); 7.606 (13.7); 7.598 (3.0); 7.589 (1.5); 7.575 (2.8); 7.567 (13.4); 7.559 (3.7); 7.545 (2.7); 7.537 (6.4); 7.528 (1.8); 7.520 (1.4); 7.499 (1.0); 7.454 (0.9); 7.425 (0.6); 7.323 (2.6); 7.171 (0.6); 7.143 (5.7); 6.962 (2.7); 4.042 (0.3); 3.330 (94.1); 2.810 (1.5); 2.784 (4.7); 2.759 (4.8); 2.735 (1.9); 2.713 (0.6); 2.689 (0.5); 2.656 (0.6); 2.631 (0.6); 2.514 (10.7); 2.508 (22.7); 2.502 (31.5); 2.496 (23.5); 2.490 (11.5); 2.446 (16.4); 2.028 (1.1); 1.989 (0.5); 1.355 (1.2); 1.235 (1.3); 1.195 (0.7); 1.174 (0.7); 1.116 (0.3); 1.038 (0.6); 1.013 (1.0); 0.980 (6.9); 0.955 (16.0); 0.930 (6.7); 0.919 (1.3); 0.894 (0.5); 0.011 (0.7); 0.000 (17.9); −0.011 (0.8)

Example 215: $^1$H-NMR (400.0 MHz, $d_6$-DMSO):

δ = 10.225 (2.5); 8.833 (1.3); 8.829 (1.4); 8.821 (1.4); 8.818 (1.4); 8.202 (1.2); 8.182 (1.3); 7.759 (5.1); 7.740 (1.0); 7.728 (1.0); 7.721 (1.0); 7.709 (0.9); 7.702 (1.4); 7.690 (0.5); 7.682 (1.4); 7.678 (1.2); 7.588 (0.5); 7.582 (0.7); 7.577 (0.7); 7.571 (1.4); 7.565 (1.8); 7.562 (1.2); 7.557 (2.2); 7.553 (2.3); 7.549 (2.4); 7.544 (2.0); 7.539 (1.9); 7.527 (0.8); 7.523 (0.9); 7.507 (0.4); 7.503 (0.3); 7.368 (1.0); 7.233 (2.2); 7.098 (1.1); 5.758 (1.8); 3.957 (0.3); 3.893 (16.0); 3.330 (37.8); 3.015 (0.4); 2.891 (0.7); 2.762 (0.4); 2.731 (0.6); 2.689 (12.6); 2.676 (0.4); 2.671 (0.4); 2.507 (39.9); 2.502 (52.0); 2.498 (39.5); 2.329 (0.3); 0.008 (1.5); 0.000 (37.7)

Example 216: $^1$H-NMR (400.0 MHz, $d_6$-DMSO):

δ = 10.303 (2.5); 8.842 (1.2); 8.838 (1.3); 8.830 (1.3); 8.826 (1.3); 8.204 (1.1); 8.185 (1.2); 7.845 (5.1); 7.756 (5.9); 7.751 (7.0); 7.738 (0.9); 7.730 (0.9); 7.718 (0.8); 7.633 (1.6); 7.628 (2.8); 7.623 (1.4); 7.355 (0.9); 7.220 (2.2); 7.085 (1.1); 4.055 (16.0); 3.332 (56.5); 2.690 (5.2); 2.672 (0.3); 2.525 (0.8); 2.512 (17.0); 2.507 (35.0); 2.503 (46.4); 2.498 (34.1); 2.494 (16.9); 1.234 (0.5); 1.167 (0.3); 0.000 (3.5)

Example 217: $^1$H-NMR (400.0 MHz, $d_6$-DMSO):

δ = 10.487 (7.8); 8.842 (4.0); 8.839 (4.3); 8.830 (4.3); 8.827 (4.2); 8.187 (3.6); 8.167 (4.0); 8.136 (16.0); 7.765 (3.7); 7.762 (3.6); 7.745 (8.1); 7.733 (3.1); 7.725 (2.9); 7.713 (2.7); 7.663 (2.1); 7.658 (2.5); 7.646 (3.1); 7.641 (4.3); 7.629 (2.0); 7.624 (3.7); 7.621 (4.3); 7.610 (7.8); 7.605 (4.4); 7.597 (5.0); 7.594 (5.0); 7.580 (3.1); 7.577 (3.6); 7.561 (1.2); 7.557 (1.1); 7.349 (3.1); 7.214 (6.9); 7.079 (3.5); 5.757 (11.3); 4.038 (0.7); 4.020 (0.7); 3.335 (57.8); 2.525 (0.9); 2.511 (18.5); 2.507 (37.1); 2.502 (48.5); 2.498 (36.0); 2.494 (18.1); 1.989 (3.0); 1.235 (0.9); 1.193 (0.8); 1.175 (1.6); 1.157 (0.8); 0.008 (0.9); 0.000 (24.5); −0.008 (1.1)

Example 218: $^1$H-NMR (400.0 MHz, $d_6$-DMSO):

δ = 10.269 (2.6); 8.839 (1.3); 8.836 (1.4); 8.827 (1.4); 8.824 (1.4); 8.200 (1.2); 8.181 (1.3); 7.795 (5.2); 7.747 (0.9); 7.735 (1.0); 7.728 (1.0); 7.716 (4.0); 7.711 (1.3); 7.699 (1.4); 7.694 (4.6); 7.686 (0.6); 7.600 (0.6); 7.592 (4.6); 7.587 (1.4); 7.575 (1.2); 7.570 (3.2); 7.563 (0.4); 7.357 (1.0); 7.222 (2.2); 7.087 (1.1); 3.981 (16.0); 3.334 (14.5); 2.690 (0.4); 2.512 (6.6); 2.508 (13.1); 2.503 (16.9); 2.499 (12.5); 2.495 (6.3); 0.008 (0.4); 0.000 (10.3); −0.008 (0.5)

Example 219: $^1$H-NMR (400.0 MHz, $d_6$-DMSO):

δ = 10.312 (2.9); 8.845 (1.4); 8.842 (1.5); 8.833 (1.5); 8.830 (1.5); 8.212 (1.3); 8.193 (1.4); 7.960 (1.8); 7.938 (4.0); 7.902 (4.1); 7.880 (2.0); 7.866 (5.2); 7.754 (1.0); 7.742 (1.1); 7.735 (1.0); 7.723 (1.0); 7.364 (1.0); 7.229 (2.3); 7.094 (1.1); 4.026 (16.0); 3.334 (14.7); 2.508 (17.3); 2.504 (22.3); 2.499 (16.9); 0.008 (0.4); 0.000 (9.0)

Example 220: $^1$H-NMR (400.0 MHz, $d_6$-DMSO):

δ = 11.034 (2.1); 8.851 (1.2); 8.848 (1.3); 8.839 (1.3); 8.836 (1.3); 8.722 (3.6); 8.215 (1.1); 8.196 (1.1); 7.913 (0.4); 7.906 (3.0); 7.901 (1.1); 7.884 (7.2); 7.759 (0.8); 7.748 (0.9); 7.740 (0.8); 7.728 (0.8); 7.571 (0.5); 7.564 (3.5); 7.559 (1.2); 7.546 (1.1); 7.541 (3.1); 7.534 (0.4); 7.385 (0.8); 7.250 (1.9); 7.115 (0.9); 5.759 (2.7); 3.338 (6.9); 2.690 (16.0); 2.509 (10.7); 2.504 (13.6); 2.500 (10.0); 1.991 (0.3); 0.000 (2.9)

Example 221: $^1$H-NMR (400.0 MHz, $d_6$-DMSO):

δ = 10.338 (8.2); 8.850 (4.0); 8.847 (4.4); 8.838 (4.3); 8.835 (4.3); 8.247 (3.8); 8.228 (4.1); 7.873 (15.9); 7.771 (2.9); 7.759 (3.0); 7.751 (3.0); 7.739 (2.7); 7.675 (6.9); 7.670 (3.1); 7.658 (4.1); 7.653 (16.0); 7.618 (15.9); 7.613 (4.7); 7.601 (2.9); 7.596 (7.0); 7.359 (2.9); 7.224 (6.6); 7.089 (3.3); 4.931 (2.8); 4.909 (8.9); 4.887 (9.3); 4.865 (3.2); 3.331 (49.4); 2.672 (0.6); 2.667 (0.5); 2.660 (0.5); 2.507 (71.8); 2.503 (93.0); 2.498 (70.5); 2.329 (0.6); 2.325 (0.5); 1.989 (0.8); 1.265 (0.5); 1.259 (0.4); 1.248 (0.5); 1.235 (0.4); 1.205 (0.5); 1.187 (1.0); 1.175 (0.6); 1.167 (0.8); 1.157 (0.4); 1.093 (0.7); 1.076 (0.6); 0.008 (1.1); 0.000 (26.6)

Example 222: $^1$H-NMR (400.0 MHz, d$_6$-DMSO):
δ = 10.285 (10.8); 8.846 (6.0); 8.835 (6.1); 8.227 (5.4); 8.208 (5.7); 7.873 (0.4); 7.829 (16.0); 7.766 (3.9); 7.754 (4.3); 7.747 (4.1); 7.735 (3.8); 7.713 (11.1); 7.691 (15.8); 7.652 (0.7); 7.602 (15.7); 7.580 (10.6); 7.513 (0.3); 7.357 (3.5); 7.222 (7.6); 7.087 (3.8); 6.440 (1.2); 6.433 (2.0); 6.426 (1.1); 6.305 (2.3); 6.298 (4.2); 6.291 (2.2); 6.171 (1.2); 6.163 (2.1); 6.156 (1.1); 4.560 (3.9); 4.553 (4.1); 4.523 (8.2); 4.515 (8.0); 4.485 (4.2); 4.478 (4.0); 3.332 (44.1); 2.891 (0.9); 2.731 (0.8); 2.689 (0.9); 2.671 (0.8); 2.662 (0.6); 2.502 (116.2); 2.329 (0.8); 1.264 (0.5); 1.248 (0.6); 1.235 (0.7); 1.204 (0.5); 1.186 (1.1); 1.168 (0.9); 1.093 (0.8); 1.077 (0.8); 0.000 (26.1)
Example 223: $^1$H-NMR (400.0 MHz, d$_6$-DMSO):
δ = 11.451 (8.0); 9.318 (0.3); 8.868 (3.7); 8.864 (4.0); 8.856 (3.9); 8.852 (4.0); 8.295 (15.9); 8.223 (3.4); 8.203 (3.7); 7.797 (0.8); 7.790 (7.8); 7.784 (3.1); 7.774 (6.1); 7.768 (16.0); 7.762 (4.6); 7.755 (3.1); 7.743 (2.7); 7.728 (2.1); 7.722 (16.0); 7.716 (4.2); 7.705 (3.0); 7.699 (8.2); 7.692 (0.9); 7.330 (3.0); 7.195 (6.9); 7.060 (3.4); 5.757 (1.1); 3.329 (58.0); 2.677 (0.4); 2.672 (0.5); 2.667 (0.4); 2.525 (1.2); 2.521 (1.9); 2.512 (28.0); 2.507 (57.6); 2.503 (77.0); 2.498 (57.4); 2.494 (28.8); 2.334 (0.4); 2.330 (0.5); 2.325 (0.4); 1.299 (0.4); 1.259 (0.6); 1.249 (0.4); 1.235 (1.3); 0.000 (5.5)
Example 224: $^1$H-NMR (400.0 MHz, d$_6$-DMSO):
δ = 10.905 (7.4); 8.846 (3.4); 8.842 (3.7); 8.834 (3.7); 8.830 (3.6); 8.451 (14.0); 8.077 (3.2); 8.058 (3.5); 7.759 (2.6); 7.747 (2.6); 7.740 (2.5); 7.728 (2.3); 7.706 (4.7); 7.701 (2.1); 7.690 (3.1); 7.684 (15.7); 7.664 (16.0); 7.658 (3.3); 7.648 (2.1); 7.642 (4.9); 7.274 (2.9); 7.139 (6.5); 7.003 (3.2); 4.038 (0.4); 4.020 (0.4); 3.328 (25.2); 2.676 (0.4); 2.672 (0.5); 2.668 (0.4); 2.525 (1.3); 2.512 (27.3); 2.507 (55.0); 2.503 (72.6); 2.498 (53.5); 2.494 (26.6); 2.334 (0.3); 2.330 (0.5); 2.325 (0.3); 1.989 (1.7); 1.235 (0.9); 1.193 (0.5); 1.175 (0.9); 1.158 (0.5); 0.146 (0.5); 0.008 (3.6); 0.000 (96.8); −0.008 (3.9); −0.150 (0.5)
Example 225: $^1$H-NMR (400.0 MHz, d$_6$-DMSO):
δ = 10.246 (3.0); 8.838 (1.4); 8.834 (1.5); 8.826 (1.5); 8.822 (1.5); 8.177 (1.3); 8.158 (1.4); 7.814 (5.7); 7.749 (1.1); 7.734 (4.2); 7.729 (2.3); 7.717 (2.3); 7.712 (5.1); 7.704 (0.6); 7.604 (0.6); 7.596 (4.9); 7.591 (1.5); 7.579 (1.2); 7.574 (3.7); 7.567 (0.4); 7.349 (1.1); 7.214 (2.5); 7.078 (1.2); 5.758 (1.5); 4.265 (1.3); 4.248 (4.1); 4.230 (4.1); 4.213 (1.3); 3.332 (10.0); 2.891 (1.8); 2.732 (1.6); 2.690 (16.0); 2.512 (6.3); 2.508 (12.6); 2.503 (16.6); 2.499 (12.4); 1.273 (4.3); 1.256 (8.5); 1.238 (4.2); 0.008 (0.4); 0.000 (9.7); −0.008 (0.4)
Example 226: $^1$H-NMR (400.0 MHz, d$_6$-DMSO):
δ = 10.237 (3.1); 8.837 (1.5); 8.833 (1.6); 8.825 (1.6); 8.821 (1.6); 8.147 (1.4); 8.128 (1.5); 7.838 (6.0); 7.750 (1.2); 7.735 (4.5); 7.730 (2.4); 7.718 (2.5); 7.713 (5.4); 7.706 (0.7); 7.604 (0.6); 7.596 (5.3); 7.591 (1.6); 7.579 (1.3); 7.574 (3.8); 7.567 (0.4); 7.342 (1.1); 7.206 (2.6); 7.071 (1.3); 5.757 (4.2); 4.573 (0.4); 4.558 (1.1); 4.542 (1.6); 4.527 (1.2); 4.512 (0.5); 3.331 (28.4); 2.525 (0.5); 2.512 (10.6); 2.507 (20.9); 2.503 (27.3); 2.498 (20.3); 1.234 (0.4); 1.209 (16.0); 1.194 (15.9); 1.167 (0.4); 0.008 (0.5); 0.000 (14.8); −0.008 (0.7)
Example 227: $^1$H-NMR (400.0 MHz, d$_6$-DMSO):
δ = 10.211 (4.3); 8.840 (2.0); 8.836 (2.3); 8.828 (2.2); 8.824 (2.2); 8.175 (1.8); 8.155 (2.0); 7.777 (8.8); 7.755 (1.5); 7.743 (1.5); 7.736 (1.5); 7.721 (5.9); 7.716 (2.0); 7.704 (2.0); 7.699 (7.8); 7.691 (0.9); 7.605 (0.9); 7.597 (7.7); 7.592 (2.2); 7.580 (1.7); 7.575 (5.4); 7.568 (0.5); 7.353 (1.6); 7.217 (3.8); 7.082 (1.8); 5.757 (0.7); 4.174 (3.9); 4.157 (8.2); 4.141 (4.0); 3.329 (26.8); 3.016 (0.4); 2.891 (0.7); 2.763 (0.4); 2.732 (0.6); 2.690 (16.0); 2.672 (0.3); 2.525 (0.7); 2.520 (1.1); 2.512 (17.2); 2.507 (36.0); 2.503 (48.3); 2.498 (35.8); 2.494 (17.9); 2.329 (0.3); 1.692 (0.5); 1.674 (1.9); 1.657 (3.7); 1.639 (3.8); 1.622 (1.9); 1.604 (0.5); 1.235 (0.5); 1.187 (0.4); 0.872 (6.6); 0.854 (13.4); 0.835 (6.1); 0.008 (0.8); 0.000 (27.3); −0.009 (1.0)
Example 228: $^1$H-NMR (400.0 MHz, d$_6$-DMSO):
δ = 10.907 (9.7); 8.845 (4.6); 8.843 (4.9); 8.834 (4.9); 8.831 (4.8); 8.452 (16.0); 8.353 (0.3); 8.077 (4.3); 8.058 (4.8); 7.953 (0.3); 7.801 (11.6); 7.779 (15.1); 7.773 (2.4); 7.759 (3.6); 7.747 (3.6); 7.740 (3.3); 7.728 (3.1); 7.637 (14.2); 7.616 (11.2); 7.599 (0.6); 7.582 (0.4); 7.578 (0.4); 7.274 (3.6); 7.139 (7.9); 7.003 (3.9); 3.332 (66.9); 2.891 (2.0); 2.732 (1.7); 2.672 (0.6); 2.507 (74.8); 2.503 (95.8); 2.499 (71.7); 2.330 (0.6); 2.136 (1.0); 1.235 (1.0); 0.007 (1.7); 0.000 (41.2); −0.008 (1.9)
Example 229: $^1$H-NMR (400.1 MHz, d$_6$-DMSO):
δ = 10.612 (6.0); 8.865 (3.1); 8.862 (3.3); 8.853 (3.3); 8.850 (3.2); 8.158 (2.8); 8.138 (3.0); 8.092 (8.5); 7.773 (2.2); 7.761 (2.3); 7.753 (2.1); 7.742 (1.9); 7.443 (2.6); 7.422 (12.4); 7.411 (12.8); 7.390 (2.6); 7.333 (2.3); 7.198 (5.1); 7.063 (2.5); 3.416 (0.4); 3.366 (0.9); 3.316 (174.4); 3.266 (0.8); 2.686 (3.8); 2.668 (5.6); 2.648 (3.9); 2.557 (0.7); 2.516 (35.9); 2.512 (70.9); 2.508 (94.1); 2.503 (67.7); 2.462 (0.4); 2.458 (0.5); 2.335 (0.6); 2.330 (0.4); 1.704 (0.6); 1.685 (2.4); 1.666 (4.2); 1.648 (4.2); 1.629 (2.5); 1.611 (0.6); 1.350 (0.8); 0.949 (7.9); 0.931 (16.0); 0.912 (7.1); −0.054 (1.4)
Example 230: $^1$H-NMR (400.1 MHz, d$_6$-DMSO):
δ = 10.579 (6.1); 8.863 (3.0); 8.859 (3.2); 8.851 (3.2); 8.847 (3.1); 8.154 (2.6); 8.134 (2.8); 8.064 (8.3); 7.771 (2.2); 7.759 (2.1); 7.751 (2.0); 7.739 (1.9); 7.441 (6.1); 7.419 (7.0); 7.331 (2.2); 7.195 (5.3); 7.113 (1.1); 7.105 (8.8); 7.099 (2.8); 7.087 (2.7); 7.082 (7.7); 7.074 (0.9); 7.060 (2.7); 7.048 (0.3); 4.147 (2.3); 4.129 (7.5); 4.112 (7.6); 4.095 (2.3); 3.415 (0.4); 3.366 (1.4); 3.315 (188.6); 3.266 (1.1); 2.681 (0.4); 2.676 (0.6); 2.672 (0.4); 2.562 (0.7); 2.558 (0.8); 2.553 (0.6); 2.530 (2.0); 2.516 (36.5); 2.512 (72.5); 2.507 (96.7); 2.503 (67.7); 2.499 (31.5); 2.463 (0.6); 2.459 (0.6); 2.339 (0.4); 2.334 (0.6); 2.330 (0.4); 1.994 (0.4); 1.390 (7.6); 1.373 (16.0); 1.355 (7.5); 1.335 (0.4); −0.054 (1.0)
Example 231: $^1$H-NMR (400.1 MHz, d$_6$-DMSO):
δ = 10.618 (1.0); 8.867 (0.5); 8.863 (0.5); 8.855 (0.5); 8.852 (0.5); 8.160 (0.5); 8.141 (0.5); 8.092 (1.4); 7.776 (0.4); 7.764 (0.4); 7.756 (0.3); 7.744 (0.3); 7.620 (1.2); 7.598 (1.6); 7.465 (1.3); 7.444 (1.0); 7.334 (0.4); 7.199 (0.9); 7.064 (0.5); 3.315 (36.1); 2.530 (0.3); 2.517 (7.1); 2.513 (14.4); 2.508 (19.5); 2.504 (14.0); 2.499 (6.7); 1.351 (16.0); 1.321 (0.8); 1.255 (0.4); 0.866 (0.5)
Example 232: $^1$H-NMR (400.1 MHz, d$_6$-DMSO):
δ = 10.669 (8.7); 8.874 (4.4); 8.870 (4.6); 8.862 (4.6); 8.859 (4.4); 8.175 (3.9); 8.156 (16.0); 7.906 (10.9); 7.901 (4.0); 7.889 (4.6); 7.884 (12.9); 7.789 (7.0); 7.786 (10.4); 7.768 (11.6); 7.752 (2.9); 7.645 (10.3); 7.624 (8.8); 7.548 (4.7); 7.530 (10.4); 7.510 (6.5); 7.460 (4.2); 7.441 (5.5); 7.423 (1.8); 7.349 (3.2); 7.213 (7.4); 7.078 (3.7); 3.417 (0.6); 3.366 (1.4); 3.355 (0.4); 3.332 (2.0);

3.317 (245.7); 3.266 (2.3); 2.682 (0.5); 2.678 (0.7); 2.673 (0.5); 2.557 (0.8); 2.553 (0.9); 2.548 (0.8); 2.531 (2.6); 2.517 (46.3); 2.513 (92.6); 2.508 (123.9); 2.504 (87.2); 2.499 (40.6); 2.462 (0.7); 2.458 (1.2); 2.453 (1.0); 2.340 (0.5); 2.335 (0.7); 2.331 (0.5)

Example 233: $^1$H-NMR (400.1 MHz, d$_6$-DMSO):
δ = 10.619 (6.4); 8.866 (3.3); 8.862 (3.6); 8.854 (3.5); 8.851 (3.4); 8.160 (3.0); 8.140 (3.3); 8.101 (8.8); 7.774 (2.3); 7.762 (2.5); 7.755 (2.3); 7.743 (2.1); 7.550 (7.0); 7.528 (7.9); 7.499 (4.1); 7.494 (1.9); 7.480 (7.0); 7.478 (7.0); 7.459 (5.5); 7.334 (2.4); 7.265 (2.7); 7.246 (4.4); 7.228 (2.0); 7.199 (5.4); 7.165 (16.0); 7.143 (15.0); 7.064 (2.6); 3.416 (0.4); 3.366 (1.4); 3.316 (159.6); 2.682 (0.4); 2.677 (0.5); 2.673 (0.4); 2.558 (0.9); 2.554 (0.8); 2.513 (67.7); 2.508 (88.9); 2.504 (65.0); 2.340 (0.4); 2.335 (0.6); 2.331 (0.4); 1.995 (0.7); 1.251 (0.4); 1.183 (0.4); 0.866 (0.5)

Example 234: $^1$H-NMR (400.1 MHz, d$_6$-DMSO):
δ = 10.665 (9.3); 8.866 (5.3); 8.862 (5.7); 8.854 (5.7); 8.851 (5.7); 8.157 (5.3); 8.144 (15.5); 8.009 (0.4); 7.980 (14.5); 7.963 (6.1); 7.958 (16.0); 7.898 (0.3); 7.774 (3.8); 7.762 (4.0); 7.755 (3.9); 7.743 (3.6); 7.367 (12.2); 7.346 (11.9); 7.331 (4.5); 7.196 (8.5); 7.061 (4.1); 5.758 (0.5); 3.439 (0.4); 3.417 (0.5); 3.365 (3.9); 3.315 (337.0); 3.259 (1.5); 3.216 (1.5); 2.682 (0.9); 2.678 (1.2); 2.673 (0.9); 2.638 (0.4); 2.563 (2.1); 2.559 (2.4); 2.554 (1.9); 2.549 (1.5); 2.517 (70.4); 2.513 (137.3); 2.509 (183.8); 2.504 (137.1); 2.500 (72.0); 2.415 (1.9); 2.340 (1.1); 2.335 (1.4); 2.331 (1.1); 1.244 (0.4)

Example 235: $^1$H-NMR (400.0 MHz, d$_6$-DMSO):
δ = 10.284 (7.0); 8.848 (3.4); 8.844 (3.7); 8.836 (3.6); 8.832 (3.6); 8.317 (0.4); 8.225 (2.9); 8.208 (3.0); 8.206 (3.1); 7.831 (16.0); 7.766 (2.5); 7.754 (2.5); 7.746 (2.5); 7.741 (1.2); 7.734 (10.3); 7.728 (3.1); 7.717 (3.5); 7.711 (14.1); 7.704 (1.9); 7.690 (0.4); 7.683 (0.4); 7.677 (0.3); 7.671 (0.3); 7.663 (0.6); 7.656 (1.8); 7.650 (13.8); 7.644 (3.6); 7.633 (2.8); 7.627 (8.3); 7.620 (0.8); 7.613 (0.5); 7.355 (2.6); 7.220 (6.3); 7.085 (3.0); 6.441 (0.7); 6.433 (1.5); 6.425 (0.7); 6.306 (1.6); 6.298 (3.3); 6.290 (1.6); 6.171 (0.7); 6.164 (1.6); 6.156 (0.8); 4.559 (2.6); 4.551 (2.8); 4.521 (6.0); 4.514 (5.8); 4.484 (3.0); 4.476 (2.8); 4.038 (0.4); 4.020 (0.4); 3.330 (87.2); 2.680 (1.5); 2.676 (0.7); 2.671 (0.8); 2.667 (0.6); 2.525 (1.8); 2.520 (2.6); 2.511 (38.8); 2.507 (81.0); 2.502 (108.1); 2.498 (77.9); 2.493 (37.7); 2.334 (0.5); 2.329 (0.7); 2.325 (0.5); 2.022 (0.9); 1.989 (1.9); 1.235 (0.5); 1.193 (0.6); 1.175 (1.1); 1.157 (0.5); 0.008 (0.5); 0.000 (16.4); −0.009 (0.6)

Example 236: $^1$H-NMR (400.0 MHz, d$_6$-DMSO):
δ = 10.580 (8.6); 8.763 (4.1); 8.760 (4.3); 8.751 (4.3); 8.748 (4.3); 8.123 (11.2); 8.069 (4.0); 8.050 (4.4); 7.693 (1.0); 7.686 (9.6); 7.681 (3.7); 7.669 (4.4); 7.664 (16.0); 7.657 (2.3); 7.626 (2.7); 7.624 (2.7); 7.611 (3.2); 7.604 (4.5); 7.598 (13.5); 7.576 (7.8); 5.696 (13.5); 5.579 (13.6); 5.446 (0.9); 3.333 (75.4); 2.690 (0.8); 2.677 (0.4); 2.672 (0.6); 2.668 (0.4); 2.526 (1.6); 2.508 (65.4); 2.503 (85.2); 2.499 (62.7); 2.334 (0.4); 2.330 (0.5); 2.325 (0.4); 1.397 (0.4); 1.235 (0.6); 0.146 (0.7); 0.008 (5.7); 0.000 (146.2); −0.009 (6.3); −0.150 (0.7)

Example 237: $^1$H-NMR (400.0 MHz, d$_6$-DMSO):
δ = 10.441 (0.6); 8.593 (0.3); 8.589 (0.4); 8.581 (0.4); 8.577 (0.4); 8.124 (0.9); 7.953 (2.0); 7.871 (0.3); 7.856 (0.4); 7.852 (0.4); 7.684 (0.8); 7.668 (0.3); 7.662 (1.2); 7.594 (1.0); 7.572 (0.6); 3.339 (24.4); 2.892 (13.2); 2.733 (11.5); 2.690 (16.0); 2.586 (3.1); 2.508 (8.4); 2.504 (11.0); 2.499 (8.3); 0.008 (0.8); 0.000 (19.1); −0.008 (0.8)

Example 238: $^1$H-NMR (300.2 MHz, d$_6$-DMSO):
δ = 9.931 (3.5); 8.696 (2.7); 8.692 (2.7); 7.977 (2.7); 7.683 (6.3); 7.485 (1.1); 7.460 (2.7); 7.434 (2.0); 7.362 (2.9); 7.333 (1.3); 7.280 (2.8); 7.258 (1.7); 7.230 (1.3); 7.181 (3.2); 7.000 (1.5); 3.353 (115.2); 3.309 (0.5); 3.302 (0.5); 3.107 (0.4); 3.083 (1.0); 3.060 (1.4); 3.036 (1.1); 3.013 (0.4); 2.537 (3.7); 2.531 (7.7); 2.525 (10.4); 2.519 (7.8); 2.513 (3.9); 2.477 (9.6); 2.422 (13.4); 1.237 (16.0); 1.213 (15.8); 0.034 (0.3); 0.023 (9.2); 0.012 (0.5)

Example 239: $^1$H-NMR (300.2 MHz, d$_6$-DMSO):
δ = 10.246 (6.2); 8.692 (5.9); 8.018 (6.0); 7.986 (12.2); 7.895 (11.9); 7.874 (5.6); 7.853 (4.5); 7.827 (2.8); 7.801 (0.9); 7.352 (2.6); 7.171 (5.9); 6.990 (2.8); 3.350 (93.7); 3.300 (0.6); 2.879 (1.9); 2.855 (5.5); 2.829 (5.6); 2.805 (2.1); 2.760 (0.4); 2.531 (25.1); 2.525 (32.1); 2.519 (24.3); 2.473 (20.7); 2.392 (1.0); 2.012 (1.0); 1.259 (0.4); 1.198 (0.7); 1.018 (7.1); 0.994 (16.0); 0.969 (7.0); 0.882 (0.4); 0.023 (22.1)

Example 240: $^1$H-NMR (300.2 MHz, d$_6$-DMSO):
δ = 10.244 (5.3); 8.694 (4.4); 8.689 (4.5); 8.020 (4.5); 7.992 (13.6); 7.969 (5.2); 7.941 (7.4); 7.826 (6.8); 7.798 (5.0); 7.355 (2.6); 7.174 (6.0); 6.993 (2.8); 3.351 (136.2); 3.301 (0.7); 2.908 (1.3); 2.884 (4.4); 2.859 (4.6); 2.834 (1.6); 2.537 (8.3); 2.531 (18.6); 2.525 (26.0); 2.519 (19.1); 2.513 (9.3); 2.473 (16.2); 2.410 (0.4); 1.030 (6.2); 1.005 (16.0); 0.980 (6.3); 0.034 (0.7); 0.023 (23.9); 0.012 (1.0)

Example 241: $^1$H-NMR (300.2 MHz, d$_6$-DMSO):
δ = 10.256 (3.6); 8.689 (3.0); 8.043 (3.0); 7.960 (5.4); 7.746 (4.0); 7.716 (5.6); 7.584 (4.0); 7.555 (2.9); 7.365 (1.3); 7.185 (2.8); 7.004 (1.3); 4.041 (0.4); 3.347 (50.8); 3.300 (0.4); 2.530 (8.1); 2.525 (10.1); 2.519 (7.7); 2.467 (10.5); 2.355 (16.0); 2.012 (1.4); 1.270 (0.7); 1.221 (0.4); 1.198 (0.7); 1.174 (0.4); 0.881 (0.5); 0.023 (5.9)

Example 242: $^1$H-NMR (300.2 MHz, d$_6$-DMSO):
δ = 10.297 (3.3); 8.860 (1.7); 8.855 (1.8); 8.844 (1.9); 8.839 (1.7); 8.230 (1.5); 8.204 (1.7); 7.980 (5.3); 7.773 (1.3); 7.757 (1.8); 7.746 (5.1); 7.739 (1.9); 7.731 (1.6); 7.724 (2.1); 7.716 (5.8); 7.706 (0.8); 7.583 (3.5); 7.555 (2.6); 7.412 (1.4); 7.231 (3.1); 7.051 (1.5); 3.351 (65.5); 2.531 (4.4); 2.525 (5.8); 2.519 (4.3); 2.356 (16.0); 2.098 (1.0); 0.023 (4.6)

Example 243: $^1$H-NMR (300.2 MHz, d$_6$-DMSO):
δ = 10.766 (11.4); 8.892 (5.8); 8.887 (6.2); 8.876 (6.3); 8.871 (6.1); 8.847 (0.5); 8.835 (0.4); 8.313 (0.3); 8.222 (15.0); 8.189 (5.1); 8.163 (5.7); 7.992 (12.1); 7.964 (16.0); 7.937 (0.7); 7.805 (4.3); 7.789 (4.6); 7.778 (6.5); 7.770 (16.0); 7.742 (12.2); 7.614 (0.4); 7.587 (0.4); 7.402 (4.8); 7.222 (11.1); 7.086 (0.5); 7.042 (5.3); 3.348 (90.3); 3.289 (0.7); 2.537 (8.9); 2.531 (19.2); 2.525 (26.6); 2.519 (19.5); 2.513 (9.4); 2.012 (0.7); 1.197 (0.4); 0.033 (1.0); 0.022 (32.0); 0.011 (1.4)

Example 244: $^1$H-NMR (300.2 MHz, d$_6$-DMSO):
δ = 10.662 (5.5); 8.887 (2.5); 8.882 (2.7); 8.871 (2.7); 8.866 (2.7); 8.181 (2.1); 8.157 (2.4); 8.154 (2.4); 8.124 (6.7); 7.799 (1.9); 7.783 (1.9); 7.773 (1.7); 7.757 (1.6); 7.587 (5.3); 7.558 (6.9); 7.552 (9.7); 7.544 (3.5); 7.529 (3.3); 7.522 (10.6); 7.510 (1.3); 7.397 (2.2); 7.234 (1.1); 7.223 (9.6); 7.216

(16.0); 7.208 (4.0); 7.201 (3.2); 7.193 (10.3); 7.186 (9.2); 7.174 (1.2); 7.158 (0.3); 7.037 (2.4);
3.349 (116.7); 2.537 (5.9); 2.531 (12.8); 2.525 (17.7); 2.519 (12.8); 2.513 (6.0); 0.034 (0.7); 0.023
(21.1); 0.012 (0.8)
Example 245: $^1$H-NMR (300.2 MHz, d$_6$-DMSO):
δ = 10.648 (4.5); 8.885 (1.9); 8.880 (2.1); 8.870 (2.2); 8.865 (2.1); 8.179 (1.7); 8.152 (1.9); 8.109
(5.3); 7.797 (1.5); 7.781 (1.5); 7.771 (1.4); 7.755 (1.3); 7.544 (4.2); 7.515 (4.8); 7.396 (1.7); 7.308
(3.8); 7.281 (4.8); 7.216 (3.9); 7.144 (0.7); 7.133 (6.5); 7.126 (2.1); 7.111 (1.9); 7.103 (5.8); 7.086
(6.5); 7.079 (2.2); 7.064 (1.9); 7.058 (5.0); 7.036 (2.0); 3.348 (94.9); 2.537 (5.8); 2.531 (12.7);
2.525 (17.6); 2.519 (12.9); 2.513 (6.3); 2.348 (16.0); 0.034 (0.5); 0.023 (14.9); 0.012 (0.6)
Example 246: $^1$H-NMR (300.2 MHz, d$_6$-DMSO):
δ = 10.663 (5.7); 8.887 (2.7); 8.882 (2.9); 8.871 (3.0); 8.866 (2.9); 8.181 (2.3); 8.157 (2.6); 8.155
(2.6); 8.125 (7.1); 7.799 (2.0); 7.783 (2.0); 7.773 (1.9); 7.757 (1.8); 7.507 (1.5); 7.497 (0.9); 7.476
(13.8); 7.469 (16.0); 7.448 (1.3); 7.441 (1.6); 7.438 (1.7); 7.398 (2.3); 7.218 (5.3); 7.038 (2.5);
3.348 (49.8); 2.577 (37.9); 2.537 (4.7); 2.531 (10.0); 2.525 (13.7); 2.519 (10.1); 2.513 (4.9); 0.034
(0.6); 0.023 (19.7); 0.012 (0.9)
Example 247: $^1$H-NMR (300.2 MHz, d$_6$-DMSO):
δ = 10.712 (11.3); 8.890 (5.8); 8.885 (6.2); 8.874 (6.4); 8.869 (6.2); 8.184 (5.6); 8.176 (15.7);
8.163 (6.0); 8.160 (6.1); 7.803 (4.4); 7.787 (4.4); 7.776 (4.1); 7.761 (3.9); 7.715 (11.0); 7.685
(16.0); 7.557 (14.1); 7.527 (10.3); 7.401 (4.9); 7.221 (11.5); 7.083 (1.2); 7.073 (2.3); 7.063 (1.2);
7.041 (5.6); 6.910 (2.3); 6.901 (5.4); 6.890 (2.7); 6.738 (1.1); 6.728 (2.5); 6.718 (1.3); 3.348
(104.4); 3.292 (0.3); 2.914 (0.7); 2.753 (0.7); 2.537 (10.1); 2.531 (22.0); 2.525 (30.6); 2.519 (22.3);
2.513 (10.6); 2.109 (0.5); 0.033 (1.5); 0.022 (47.2); 0.011 (1.8)
Example 248: $^1$H-NMR (400.0 MHz, d$_6$-DMSO):
δ = 10.582 (9.8); 8.943 (0.4); 8.940 (0.4); 8.931 (0.5); 8.928 (0.5); 8.762 (4.8); 8.759 (5.1); 8.751
(5.1); 8.747 (5.0); 8.329 (0.5); 8.325 (0.5); 8.318 (0.4); 8.309 (0.5); 8.306 (0.5); 8.123 (13.2); 8.068
(4.7); 8.049 (5.1); 7.825 (1.6); 7.818 (13.7); 7.813 (5.0); 7.801 (5.1); 7.796 (16.0); 7.789 (1.9);
7.652 (0.4); 7.640 (0.5); 7.625 (3.1); 7.623 (3.2); 7.613 (3.2); 7.611 (3.3); 7.606 (3.4); 7.594 (2.9);
7.592 (2.8); 7.528 (12.7); 7.506 (11.0); 5.695 (15.8); 5.577 (15.9); 5.446 (2.8); 3.331 (137.1); 2.690
(0.7); 2.676 (0.8); 2.672 (1.1); 2.667 (0.8); 2.525 (2.7); 2.507 (123.1); 2.503 (161.9); 2.498 (119.3);
2.334 (0.7); 2.329 (1.0); 2.325 (0.7); 1.234 (0.7); 0.146 (0.8); 0.008 (6.1); 0.000 (171.0); −0.008
(7.4); −0.150 (0.8)
Example 249: $^1$H-NMR (400.0 MHz, d$_6$-DMSO):
δ = 10.443 (3.3); 8.593 (1.6); 8.589 (1.8); 8.581 (1.8); 8.577 (1.8); 8.126 (4.5); 7.874 (1.6); 7.870
(1.7); 7.855 (1.8); 7.851 (1.8); 7.823 (0.5); 7.816 (4.7); 7.811 (1.7); 7.799 (1.7); 7.794 (5.6); 7.787
(0.7); 7.524 (4.3); 7.502 (3.8); 7.389 (1.4); 7.376 (1.4); 7.370 (1.4); 7.357 (1.3); 3.331 (30.7); 2.690
(2.4); 2.585 (16.0); 2.525 (0.7); 2.512 (16.8); 2.507 (35.1); 2.503 (46.7); 2.498 (34.3); 2.494 (17.0);
0.008 (1.7); 0.000 (49.8); −0.009 (1.9)
Example 250: $^1$H-NMR (300.2 MHz, d$_6$-DMSO):
δ = 10.445 (7.0); 8.697 (5.7); 8.692 (5.4); 8.110 (16.0); 8.015 (5.4); 7.791 (9.8); 7.785 (3.4);
7.769 (4.1); 7.762 (14.6); 7.753 (1.9); 7.640 (14.3); 7.632 (3.9); 7.617 (3.2); 7.610 (9.5); 7.476
(0.4); 7.345 (2.8); 7.164 (6.6); 6.984 (3.0); 4.519 (14.7); 3.396 (0.5); 3.348 (360.0); 3.296 (1.6);
3.267 (54.7); 3.223 (0.7); 3.030 (0.5); 3.007 (0.4); 2.822 (0.4); 2.752 (0.6); 2.744 (0.6); 2.579 (0.4);
2.537 (27.1); 2.531 (58.9); 2.525 (82.0); 2.519 (59.8); 2.513 (28.7); 2.470 (20.4); 2.341 (0.5); 2.294
(0.6); 1.257 (0.4); 0.034 (2.1); 0.023 (64.9); 0.012 (2.6)
Example 251: $^1$H-NMR (300.2 MHz, d$_6$-DMSO):
δ = 10.486 (6.7); 9.756 (0.3); 8.867 (3.6); 8.862 (4.1); 8.851 (3.8); 8.846 (3.8); 8.206 (3.2); 8.181
(3.5); 8.131 (15.9); 8.081 (0.4); 7.793 (9.8); 7.786 (5.2); 7.763 (16.0); 7.741 (2.7); 7.648 (1.7);
7.639 (14.0); 7.632 (3.8); 7.617 (3.2); 7.610 (9.8); 7.600 (1.1); 7.397 (3.0); 7.217 (6.8); 7.037 (3.2);
4.520 (14.5); 4.477 (0.4); 4.442 (0.4); 4.064 (0.6); 4.040 (0.6); 3.394 (0.5); 3.347 (246.3); 3.271
(54.8); 3.103 (0.3); 3.035 (0.4); 2.751 (0.5); 2.744 (0.4); 2.537 (22.7); 2.531 (50.3); 2.525 (70.9);
2.519 (51.9); 2.513 (25.2); 2.394 (0.5); 2.289 (0.7); 2.012 (2.7); 1.221 (0.6); 1.198 (1.5); 1.174
(0.7); 0.939 (0.3); 0.219 (0.4); 0.034 (1.5); 0.023 (56.0); 0.013 (2.3); −0.175 (0.3)
Example 252: $^1$H-NMR (400.0 MHz, d$_6$-DMSO):
δ = 10.636 (7.7); 8.846 (3.8); 8.842 (4.1); 8.834 (4.1); 8.830 (4.0); 8.212 (16.0); 8.179 (3.5);
8.159 (3.8); 7.982 (7.6); 7.976 (7.9); 7.881 (7.2); 7.860 (7.8); 7.750 (2.8); 7.738 (2.8); 7.730 (2.7);
7.718 (2.5); 7.694 (5.0); 7.687 (4.8); 7.672 (4.1); 7.666 (4.1); 7.328 (2.9); 7.193 (6.8); 7.058 (3.3);
3.332 (47.5); 2.676 (0.4); 2.672 (0.6); 2.668 (0.4); 2.525 (1.4); 2.507 (62.8); 2.503 (82.1); 2.499
(60.5); 2.494 (30.5); 2.334 (0.4); 2.330 (0.5); 2.325 (0.4); 1.990 (0.7); 1.175 (0.4); 0.008 (1.4);
0.000 (41.7); −0.008 (1.9)
Example 253: $^1$H-NMR (400.0 MHz, d$_6$-DMSO):
δ = 10.639 (3.4); 8.845 (3.7); 8.841 (4.1); 8.833 (4.0); 8.829 (4.0); 8.215 (16.0); 8.175 (3.4);
8.156 (3.7); 8.142 (0.4); 7.808 (0.3); 7.799 (0.7); 7.788 (4.1); 7.772 (4.6); 7.767 (4.6); 7.750 (6.2);
7.737 (3.1); 7.730 (2.9); 7.718 (2.5); 7.327 (2.9); 7.192 (6.6); 7.057 (3.2); 3.332 (34.2); 2.690 (0.6);
2.672 (0.4); 2.667 (0.3); 2.525 (1.1); 2.512 (24.5); 2.507 (50.2); 2.503 (66.4); 2.498 (49.2); 2.494
(24.8); 2.330 (0.4); 1.990 (0.5); 0.008 (1.3); 0.000 (37.2); −0.008 (1.6)
Example 254: $^1$H-NMR (300.2 MHz, d$_6$-DMSO):
δ = 12.356 (0.4); 10.610 (12.1); 8.884 (5.6); 8.879 (5.9); 8.868 (6.0); 8.863 (5.6); 8.176 (4.7);
8.149 (5.3); 8.078 (14.5); 7.795 (4.1); 7.779 (4.0); 7.769 (3.8); 7.753 (3.4); 7.732 (0.4); 7.441
(10.8); 7.411 (13.3); 7.394 (5.1); 7.214 (10.4); 7.133 (16.0); 7.103 (13.2); 7.034 (5.1); 6.893 (1.2);
6.663 (0.8); 4.461 (2.8); 4.447 (2.4); 4.432 (1.4); 4.064 (1.0); 4.040 (1.0); 4.017 (0.4); 3.397 (0.4);
3.341 (123.4); 3.317 (1.3); 2.750 (0.5); 2.536 (25.4); 2.530 (51.6); 2.524 (69.4); 2.518 (49.8); 2.512
(23.1); 2.294 (0.5); 2.286 (0.4); 2.207 (1.8); 2.055 (0.4); 2.012 (7.4); 1.980 (5.1); 1.932 (0.7); 1.770
(4.1); 1.753 (3.8); 1.599 (1.8); 1.586 (2.0); 1.547 (2.7); 1.505 (3.9); 1.474 (8.1); 1.444 (8.6); 1.404
(4.0); 1.379 (15.5); 1.316 (1.9); 1.285 (1.6); 1.259 (1.9); 1.221 (1.3); 1.198 (2.7); 1.174 (1.4); 0.879
(0.3); 0.218 (0.5); 0.034 (3.6); 0.023 (83.9); 0.012 (3.1); −0.177 (0.3)
Example 255: $^1$H-NMR (300.2 MHz, d$_6$-DMSO):
δ = 10.645 (2.6); 8.886 (1.3); 8.881 (1.3); 8.870 (1.4); 8.865 (1.3); 8.180 (1.1); 8.154 (1.3); 8.110
(3.3); 7.798 (0.9); 7.782 (1.0); 7.772 (0.9); 7.756 (0.8); 7.449 (16.0); 7.398 (1.1); 7.218 (2.4); 7.038
(1.2); 3.341 (21.9); 2.775 (0.9); 2.750 (2.8); 2.725 (2.9); 2.700 (0.9); 2.536 (3.6); 2.530 (7.4); 2.524

(10.1); 2.518 (7.3); 2.512 (3.5); 1.379 (2.3); 1.287 (3.6); 1.261 (8.1); 1.236 (3.4); 0.034 (0.5); 0.023 (11.8); 0.012 (0.5)

EXPERIMENTAL SECTION

Process (a)

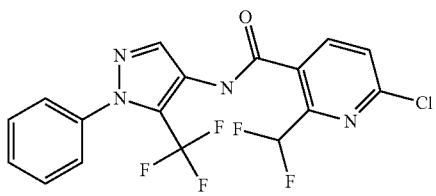 [SMILES: O=C(Nc1cnn(-c2ccccc2)c1C(F)(F)F)c1ccc(Cl)nc1C(F)F]

6-chloro-2-(difluoromethyl)-N-[1-phenyl-5-(trifluoromethyl)-1H-pyrazol-4-yl]nicotinamide Example 1

In a microwave sealable tube, propanephosphonic anhydride (50% in AcOEt, 0.79 ml, 1.32 mmol, 3 eq) is added to a solution of 2-(difluoromethyl)-6-chloronicotinic acid (109 mg, 0.52 mmol, 1.2 eq) and 1-phenyl-5-(trifluoromethyl)-1H-pyrazol-4-amine (100 mg, 0.44 mmol, 1 eq.) in 10 ml of THF. The tube is sealed and the reaction is microwaved 10 min at 150° C. The resulting solution is quenched with aq. sat. $K_2CO_3$, extracted with AcOEt, washed with aq. Sat. $NH_4Cl$ and filtered through alumina. The solvent is evaporated to give pure material (55%)

Process (b)

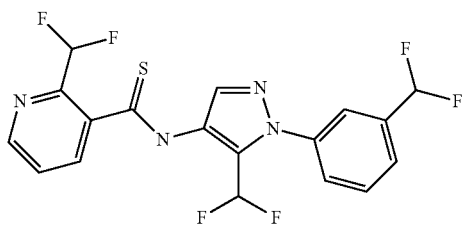 [SMILES: FC(F)c1cccc(-n2ncc(NC(=S)c3cccnc3C(F)F)c2C(F)F)c1]

2-(difluoromethyl)-N-{5-(difluoromethyl)-1-[3-(difluoromethyl)phenyl]-1H-pyrazol-4-yl}pyridine-3-carbothioamide (Example 34)

In a microwave sealable tube, Lawesson's reagent (97 mg, 0.241 mmol, 1 eq) is added to a solution of 2-(difluoromethyl)-N-{5-(difluoromethyl)-1-[3-(difluoromethyl)phenyl]-1H-pyrazol-4-yl}nicotinamide (100 mg, 0.241 mmol, 1 eq) in 5 ml of toluene. The tube is sealed and the reaction is microwaved 30 min at 130° C. The resulting solution is quenched with an aq. solution of NaOH 1N and is filtered through a chem elut cartridge and washed with toluene. The solvent is evaporated and the residue purified by chromatography on silica gel to give pure material (60%)

B. Biological Examples

Example: In Vivo Preventive Test on *Puccinia recondita* (Brown Rust on Wheat)

Solvent: 5% by volume of Dimethyl sulfoxide
10% by volume of Acetone
Emulsifier: 1 µl of Tween® 80 per mg of active ingredient The active ingredients are made soluble and homogenized in a mixture of Dimethyl sulfoxide/Acetone//Tween® 80 and then diluted in water to the desired concentration.

The young plants of wheat are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Puccinia recondita* spores. The contaminated wheat plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test the following compounds according to the invention showed efficacy between 80% and 89% at a concentration of 500 ppm of active ingredient: 7

In this test the following compounds according to the invention showed efficacy between 90% and 100% at a concentration of 500 ppm of active ingredient: 2; 12; 20

In this test the following compounds according to the invention showed efficacy between 70% and 79% at a concentration of 100 ppm of active ingredient: 70; 91; 131; 136; 144; 155; 216

In this test the following compounds according to the invention showed efficacy between 80% and 89% at a concentration of 100 ppm of active ingredient: 3; 28; 29; 31; 32; 34; 58; 72; 98; 129; 130; 132; 134; 135; 137; 147; 148; 152; 158; 162; 163; 165; 168; 176; 184; 185; 186; 189; 191; 193; 194; 195; 196; 197; 198; 199; 200; 201; 202; 203; 215; 217; 218; 219; 220; 221; 225; 235; 236; 237; 253

In this test the following compounds according to the invention showed efficacy between 90% and 100% at a concentration of 100 ppm of active ingredient: 5; 9; 10; 13; 14; 21; 22; 23; 24; 26; 27; 30; 33; 46; 47; 48; 49; 50; 53; 54; 55; 56; 57; 60; 61; 62; 63; 64; 73; 74; 77; 78; 79; 80; 81; 82; 83; 84; 85; 86; 87; 88; 89; 90; 92; 93; 94; 95; 96; 97; 128; 146; 149; 150; 153; 182; 183; 187; 188; 190; 192; 222; 226; 229; 230; 231; 232; 233; 234; 242; 243; 244; 245; 246; 247; 248; 249; 251; 252

Example: In Vivo Preventive Test on *Uromyces Appendiculatus* (Bean Rust)

Solvent: 5% by volume of Dimethyl sulfoxide
10% by volume of Acetone
Emulsifier: 1 µl of Tween® 80 per mg of active ingredient The active ingredients are made soluble and homogenized in a mixture of Dimethyl sulfoxide/Acetone//Tween® 80 and then diluted in water to the desired concentration.

The young plants of bean are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Uromyces appendiculatus* spores. The contaminated bean plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test the following compounds according to the invention showed efficacy between 90% and 100% at a concentration of 500 ppm of active ingredient: 2; 7; 12; 20

In this test the following compounds according to the invention showed efficacy between 70% and 79% at a concentration of 100 ppm of active ingredient: 29; 34; 99; 129; 131; 147; 152; 182; 195

In this test the following compounds according to the invention showed efficacy between 80% and 89% at a concentration of 100 ppm of active ingredient: 13; 22; 23; 32; 47; 79; 100; 110; 112; 113; 114; 118; 121; 148; 196; 199; 203; 231; 234; 236; 248

In this test the following compounds according to the invention showed efficacy between 90% and 100% at a concentration of 100 ppm of active ingredient: 3; 5; 9; 10; 14; 21; 24; 28; 30; 33; 46; 48; 49; 50; 53; 54; 55; 56; 57; 58; 60; 61; 62; 63; 64; 73; 74; 77; 78; 80; 81; 82; 83; 84; 85; 86; 87; 88; 89; 92; 93; 94; 95; 96; 105; 107; 117; 128; 130; 132; 134; 135; 137; 146; 149; 150; 153; 183; 187; 188; 189; 190; 191; 192; 193; 194; 197; 200; 202; 217; 221; 222; 229; 230; 233; 235; 237; 242; 243; 244; 246; 247; 251; 252; 253

Example: In Vivo Preventive Test on *Phakopsora* Test (Soybeans)

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of the causal agent of soybean rust (*Phakopsora pachyrhizi*) and stay for 24 h without light in an incubation cabinet at approximately 24° C. and a relative atmospheric humidity of 95%.

The plants remain in the incubation cabinet at approximately 24° C. and a relative atmospheric humidity of approximately 80% and a day/night interval of 12 h.

The test is evaluated 7 days after the inoculation. 0% means an efficacy which corresponds to that of the untreated control, while an efficacy of 100% means that no disease is observed.

In this test the following compounds according to the invention showed efficacy between 70% and 79% at a concentration of 10 ppm of active ingredient: 73; 85; 94; 128

In this test the following compounds according to the invention showed efficacy between 80% and 89% at a concentration of 10 ppm of active ingredient: 46; 64; 77; 84; 95

In this test the following compounds according to the invention showed efficacy between 90% and 100% at a concentration of 10 ppm of active ingredient: 5; 9; 10; 50; 60; 61; 62; 63; 74; 87; 88; 89; 93; 134; 150; 183; 190

The invention claimed is:
1. A compound of formula (I)

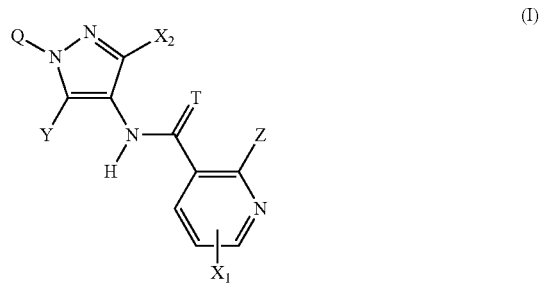

in which the radicals are each defined as follows:
Z is selected from halogen, CN, $NH_2$, $NO_2$, $C_1$-$C_6$-alkyl, $C_1$-$C_6$-haloalkyl, $C_3$-$C_8$-cycloalkyl, $C_3$-$C_7$-halocycloalkyl, $C_1$-$C_6$-alkyloxy, $C_1$-$C_6$-haloalkyloxy, $C_1$-$C_6$-alkylsulfanyl, $C_1$-$C_6$-haloalkylsulfanyl, $C_1$-$C_6$-alkylsulfonyl, $C_1$-$C_6$-haloalkylsulfonyl, $C_1$-$C_8$-alkylamino, di-$C_1$-$C_8$-alkylamino, $C_2$-$C_6$-alkenyl, $C_2$-$C_6$-haloalkenyl, $C_2$-$C_6$-alkynyl;
$X_1$ is selected from H, halogen, CN, $NH_2$, $NO_2$, $C_1$-$C_6$-alkyl, $C_1$-$C_6$-haloalkyl, $C_3$-$C_8$-cycloalkyl, $C_3$-$C_7$-halocycloalkyl, $C_1$-$C_6$-alkyloxy, $C_1$-$C_6$-haloalkyloxy, tri($C_1$-$C_8$)alkylsilyl, $C_1$-$C_6$-alkylsulfanyl, $C_1$-$C_6$-haloalkylsulfanyl, $C_1$-$C_6$-alkylsulfonyl, $C_1$-$C_6$-haloalkylsulfonyl, $C_1$-$C_8$-alkylamino, di-$C_1$-$C_8$-alkylamino, $C_2$-$C_6$-alkenyl, $C_2$-$C_6$-haloalkenyl, $C_2$-$C_6$-alkynyl;
$X_2$ is selected from H, halogen, CN, $NH_2$, $NO_2$, $C_1$-$C_6$-alkyl, $C_1$-$C_6$-haloalkyl, $C_3$-$C_8$-cycloalkyl, $C_3$-$C_7$-halocycloalkyl, $C_1$-$C_6$-alkyloxy, $C_1$-$C_6$-haloalkyloxy, $C_1$-$C_6$-alkylsulfanyl, $C_1$-$C_6$-haloalkylsulfanyl, $C_1$-$C_6$-alkylsulfonyl, $C_1$-$C_6$-haloalkylsulfonyl, $C_2$-$C_6$-alkenyl, $C_2$-$C_6$-haloalkenyl, $C_2$-$C_6$-alkynyl;
Y is selected from halogen, CN, $NH_2$, $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, $C_1$-$C_6$-alkylsulfanyl, $C_1$-$C_6$-haloalkylsulfanyl, $C_1$-$C_6$-alkylsulfonyl, $C_1$-$C_6$-haloalkylsulfonyl, $C_1$-$C_8$-alkylamino, di-$C_1$-$C_8$-alkylamino, $C_2$-$C_6$-alkenyl, $C_2$-$C_6$-haloalkenyl, $C_2$-$C_6$-alkynyl, phenyl or thiophene which may be substituted by one or more $R^a$ group;
Q is a phenyl or a thiophene which may be substituted by one or more $R^a$ groups, a linear or branched carbon chain having 1 to 9 carbon atoms, wherein 1 to 3 non adjacent —$CH_2$— groups may be independently from each other replaced by a group selected from O, $NR^5$, S, SO, $SO_2$, CO, and wherein 1 to 5 hydrogen atoms may be independently from each other replaced by $C_3$-$C_7$-cycloalkyl, halogen or wherein 1 to 5 hydrogen atoms may be independently from each other replaced phenyl or thiophene which may be substituted by one or more $R^a$ groups;
$R^a$ represents hydrogen, halogen, nitro, $NH_2$, cyano, $C_1$-$C_6$-alkyl, $C_1$-$C_6$-haloalkyl, $C_3$-$C_7$-cycloalkyl; $C_1$-$C_6$-alkoxy, $C_1$-$C_6$-haloalkoxy, $C_3$-$C_7$-cycloalkyloxy, $C_1$-$C_6$-alkylsulfanyl, $C_1$-$C_6$-haloalkylsulfanyl, $C_3$-$C_7$-cycloalkylsulfanyl, $C_1$-$C_6$-alkylsulfonyl, $C_1$-$C_6$-haloalkylsulfonyl, $C_3$-$C_7$-cycloalkylsulfonyl, $C_2$-$C_6$-alkenyl, $C_2$-$C_6$-haloalkenyl, $C_2$-$C_6$-alkynyl, tri($C_1$-$C_8$)alkylsilyl, $C_2$-$C_8$-alkynyloxy, aryloxy, $C_1$-$C_6$-alkylamino, di-$C_1$-$C_6$-alkylamino or two vicinal substituents $R^a$ together with the consecutive carbon atoms to which they are linked form a 5- or 6-membered, saturated or unsaturated, carbo- or heterocycle comprising up to 3 heteroatoms;

T is O or S;

$R^5$ represents hydrogen, $C_1$-$C_6$-alkyl, $C_1$-$C_6$-haloalkyl and $C_3$-$C_7$-cycloalkyl;

provided that

Q does not represent methyl and

Y and $X_2$ represent methyl simultaneously only when Z represents a $C_1$-$C_6$-haloalkyl and provided that formula (I) does not represent 2-chloro-N-[1-(3-chlorophenyl)-3-methyl-5-phenyl-1H-pyrazol-4-yl]-3-pyridine carboxamide or 2-chloro-N-[3-methyl-1-(3-methylphenyl)-5-phenyl-1H-pyrazol-4-yl]-3-pyridine carboxamide and one or more salts, solvates, N-oxides, solvates of the salts and N-oxides thereof.

2. A compound of formula (I) according to claim 1, in which the symbols are each defined as follows:

Z is selected from bromine, iodine, fluorine, chlorine, cyclopropyl, cyclobutyl, cyclopentyl, cyclohexyl, cycloheptyl, cyclooctyl, methyl, ethyl, propyl, 1-methylethyl (iso-propyl), n-butyl, 1-methylpropyl (iso-butyl), 2-methylpropyl (sec-butyl), 1,1-dimethylethyl (tert.-butyl), n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoromethylbutyl;

$X_1$ is selected from H, bromine, iodine, fluorine, chlorine, cyclopropyl, cyclobutyl, cyclopentyl, cyclohexyl, cycloheptyl, cyclooctyl, methyl, ethyl, propyl, 1-methylethyl (iso-propyl), n-butyl, 1-methylpropyl (iso-butyl), 2-methylpropyl (sec-butyl), 1,1-dimethylethyl (tert.-butyl), n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoromethylbutyl, CN, $NO_2$, methyloxy, Ethyloxy, methylsulfanyl, ethylsulfanyl, trifluoromethoxy, difluoromethoxy;

$X_2$ is selected from H, bromine, iodine, fluorine, chlorine, cyclopropyl, cyclobutyl, cyclopentyl, cyclohexyl, cycloheptyl, cyclooctyl, methyl, ethyl, propyl, 1-methylethyl (isopropyl), n-butyl, 1-methylpropyl (iso-butyl), 2-methylpropyl (sec-butyl), 1,1-dimethylethyl (tert.-butyl), n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoromethylbutyl, CN, $NO_2$;

Y is selected from halogen, $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, phenyl which may be substituted by one or more Ra group;

Q is selected from phenyl or thiophene which may be substituted by one or more $R^a$ groups; $C_2$-$C_9$-alkyl, $C_1$-$C_9$-haloalkyl, $C_3$-$C_9$-cycloalkyl, ($C_3$-$C_8$-cycloalkyl)-$C_1$-$C_9$-alkyl, ($C_3$-$C_8$-cycloalkyl)-$C_1$-$C_9$-alkyloxy, ($C_1$-$C_8$-alkyl)-$C_1$-$C_9$-alkyloxy, $C_1$-$C_6$-alkylphenyl which may be substituted by one or more $R^a$ groups;

$R^a$ represents hydrogen, halogen, cyano, $C_1$-$C_6$-alkyl; $C_1$-$C_6$-haloalkyl; $C_3$-$C_7$-cycloalkyl; $C_1$-$C_6$-alkoxy; $C_1$-$C_6$-haloalkoxy; $C_3$-$C_7$-cycloalkyloxy; $C_1$-$C_6$-alkylsulfanyl; $C_1$-$C_6$-haloalkylsulfanyl; $C_3$-$C_7$-cycloalkylsulfanyl; $C_1$-$C_6$-alkylsulfonyl; $C_1$-$C_6$-haloalkylsulfonyl; $C_3$-$C_7$-cycloalkylsulfonyl; $C_2$-$C_8$-alkynyloxy;

T is O or S;

provided that

Y and $X_2$ represent methyl simultaneously only when Z represents a $C_1$-$C_6$-haloalkyl and provided that formula (I) does not represent 2-chloro-N-[1-(3-chlorophenyl)-3-methyl-5-phenyl-1H-pyrazol-4-yl]-3-pyridine carboxamide or 2-chloro-N-[3-methyl-1-(3-methylphenyl)-5-phenyl-1H-pyrazol-4-yl]-3-pyridine carboxamide and one or more salts, solvates, N-oxides, solvates of the salts and N-oxides thereof.

3. A compound of formula (I) according to claim 1, in which the symbols are each defined as follows:

Z is selected from fluorine, chlorine, cyclopropyl, cyclobutyl, cyclopentyl, cyclohexyl, methyl, ethyl, propyl, 1-methylethyl (iso-propyl), n-butyl, 1-methylpropyl (iso-butyl), 2-methylpropyl (sec-butyl), 1,1-dimethylethyl (tert.-butyl), n-pentyl, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl;

$X_1$ is selected from H, bromine, iodine, fluorine, chlorine, cyclopropyl, methyl, ethyl, propyl, 1-methylethyl (iso-propyl), n-butyl, 1-methylpropyl (iso-butyl), 2-methylpropyl (sec-butyl), 1,1-dimethylethyl (tert.-butyl), n-pentyl, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, CN, NO$_2$, methyloxy, ethyloxy;

$X_2$ is selected from H, bromine, iodine, fluorine, chlorine, cyclopropyl, methyl, ethyl, propyl, 1-methylethyl (iso-propyl), n-butyl, 1-methylpropyl (iso-butyl), 2-methylpropyl (sec-butyl), 1,1-dimethylethyl (tert.-butyl), n-pentyl, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, CN;

Y is selected from halogen, $C_1$-$C_6$-alkyl, $C_1$-$C_6$-haloalkyl, $C_3$-$C_8$-cycloalkyl, $C_3$-$C_8$-halocycloalkyl, phenyl which may be substituted by one or more $R^a$ group;

Q is selected from phenyl which may be substituted by one or more $R^a$ groups $R^a$ is selected from hydrogen, halogen, nitro, cyano, $C_1$-$C_6$-alkyl; $C_1$-$C_6$-haloalkyl; $C_1$-$C_6$-alkoxy; $C_1$-$C_6$-haloalkoxy;

T is O;

provided that

Y and $X_2$ represent methyl simultaneously only when Z represents a $C_1$-$C_6$-haloalkyl and provided that formula (I) does not represent 2-chloro-N-[1-(3-chlorophenyl)-3-methyl-5-phenyl-1H-pyrazol-4-yl]-3-pyridine carboxamides or 2-chloro-N-[3-methyl-1-(3-methylphenyl)-5-phenyl-1H-pyrazol-4-yl]-3-pyridine carboxamide and one or more salts, solvates, N-oxides, solvates of the salts and N-oxides thereof.

4. A compound of formula (I) according to claim 1,
in which the symbols are each defined as follows:
Z is selected from difluoromethyl, trifluoromethyl, methyl, ethyl, bromine;
$X_1$ is H, F, Cl, methyl;
$X_2$ is H;
Y is selected from chlorine, bromine, trifluoromethyl, difluoromethyl, ethyl, isopropyl, methyl, phenyl, 2-chlorophenyl, 3-chlorophenyl, 4-chlorophenyl, 2-fluorophenyl, 3-fluorophenyl, 4-fluorophenyl, 2-methylphenyl, 3-methylphenyl, 4-methylphenyl, 2-trifluoromethylphenyl, 3-trifluoromethylphenyl, 4-trifluoromethylphenyl;

Q is selected from phenyl, 2-chlorophenyl, 3-chlorophenyl, 4-chlorophenyl, 2-fluorophenyl, 3-fluorophenyl, 4-fluorophenyl, 2-methylphenyl, 3-methylphenyl, 4-methylphenyl, 2-trifluoromethylphenyl, 3-trifluoromethylphenyl, 4-trifluoromethylphenyl, 2-difluoromethylphenyl, 3-difluoromethylphenyl, 4-difluoromethylphenyl, 2,3-difluorophenyl, 2,4-difluorophenyl, 2,5-difluorophenyl, 2,6-difluorophenyl, 3,4-difluorophenyl, 3,5-difluorophenyl, 2,3-dichlorophenyl, 2,4-dichlorophenyl, 2,5-dichlorophenyl, 2,6-dichlorophenyl, 3,4-dichlorophenyl, 3,5-dichlorophenyl;

T is O;

and one or more salts, solvates, N-oxides, solvates of the salts and N-oxides thereof.

5. A method for controlling phytopathogenic harmful fungi, comprising applying a compound according to claim 1 to the phytopathogenic harmful fungi and/or a habitat thereof.

6. A composition for controlling phytopathogenic harmful fungi, comprising a content of at least one compound according to claim 1, in addition to one or more extenders and/or surfactants.

7. At least one compound according to claim 1 for controlling phytopathogenic harmful fungi.

8. A process for producing a composition for controlling phytopathogenic harmful fungi according to claim 6, comprising mixing a compound of claim 1 with one or more extenders and/or surfactants.

9. A compound according to claim 1 for treatment of seed.

10. A compound of according to claim 1 for treatment of one or more transgenic plants.

* * * * *